(12) United States Patent
Hirata et al.

(10) Patent No.: US 8,389,073 B2
(45) Date of Patent: Mar. 5, 2013

(54) FOUR-RING LIQUID CRYSTAL COMPOUND HAVING TETRAHYDROPYRAN AND 2,2',3,3'-TETRAFLUOROBIPHENYL, LIQUID CRYSTAL COMPOSITION AND LIQUID CRYSTAL DISPLAY DEVICE

(75) Inventors: Kenji Hirata, Chiba (JP); Tokifumi Masukawa, Chiba (JP); Junichi Yamashita, Chiba (JP); Maiko Ito, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

(21) Appl. No.: 13/201,626

(22) PCT Filed: Feb. 1, 2010

(86) PCT No.: PCT/JP2010/051356
§ 371 (c)(1),
(2), (4) Date: Aug. 16, 2011

(87) PCT Pub. No.: WO2010/095506
PCT Pub. Date: Aug. 26, 2010

(65) Prior Publication Data
US 2011/0297881 A1    Dec. 8, 2011

(30) Foreign Application Priority Data
Feb. 19, 2009  (JP) ................. 2009-036436

(51) Int. Cl.
C09K 19/34 (2006.01)
C09K 19/30 (2006.01)
C09K 19/32 (2006.01)
C09K 19/12 (2006.01)
C09K 19/20 (2006.01)
C07D 309/02 (2006.01)
C07D 407/02 (2006.01)

(52) U.S. Cl. ............... 428/1.1; 252/299.61; 252/299.62; 252/299.63; 252/299.66; 252/299.67; 549/356; 549/414; 549/415; 549/416; 549/427

(58) Field of Classification Search .............. 549/356, 549/414, 415, 416, 427; 252/299.61, 299.62, 252/299.63, 299.66, 299.67; 428/1.1
See application file for complete search history.

(56) References Cited

U.S. PATENT DOCUMENTS

| 6,217,953 | B1 | 4/2001 | Heckmeier et al. | |
| 6,558,758 | B1* | 5/2003 | Yanai et al. | 428/1.1 |
| 8,124,197 | B2* | 2/2012 | Saito et al. | 428/1.1 |
| 8,158,219 | B2* | 4/2012 | Hattori et al. | 428/1.1 |
| 2002/0038858 | A1 | 4/2002 | Kato et al. | |
| 2008/0063814 | A1 | 3/2008 | Shimada | |
| 2008/0075891 | A1 | 3/2008 | Goto et al. | |

FOREIGN PATENT DOCUMENTS

| EP | 0959060 | 11/1999 |
| EP | 0967261 | 12/1999 |
| EP | 0969071 | 1/2000 |
| JP | 02-004725 | 1/1990 |
| JP | 02-503441 | 10/1990 |
| JP | 10-237448 | 9/1998 |
| JP | 2005-200501 | 7/2005 |

OTHER PUBLICATIONS

F. M. Leslie, "Distortion of Twisted Orientation Patterns in Liquid Crystals by Magnetic Fields", Molecular Crystals and Liquid Crystals, 1970, pp. 57-72, vol. 12.

* cited by examiner

Primary Examiner — Shean C Wu
(74) Attorney, Agent, or Firm — Jianq Chyun IP Office

(57) ABSTRACT

The invention provides a liquid crystal compound that has a large negative dielectric anisotropy ($\Delta\epsilon$) and also has at least one of characteristics such as the stability to heat, light or the like, a high clearing point, a suitable refractive index anisotropy ($\Delta n$), a large negative dielectric anisotropy ($\Delta\epsilon$) and an excellent compatibility with other liquid crystal compounds. An excellent effect in which especially the value of the dielectric anisotropy ($\Delta\epsilon$) is increased negatively is achieved by use of the compound having two moieties of
1) a tetrahydropyran ring and

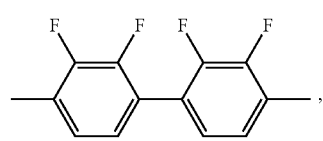

2)

and thus the effect is utilized.

23 Claims, No Drawings

FOUR-RING LIQUID CRYSTAL COMPOUND HAVING TETRAHYDROPYRAN AND 2,2',3,3'-TETRAFLUOROBIPHENYL, LIQUID CRYSTAL COMPOSITION AND LIQUID CRYSTAL DISPLAY DEVICE

CROSS-REFERENCE TO RELATED APPLICATION

This application is a 371 of international application of PCT application serial no. PCT/JP2010/051356, filed on Feb. 1, 2010, which claims the priority benefit of Japan application no. 2009-036436, filed on Feb. 19, 2009. The entirety of each of the above-mentioned patent applications is hereby incorporated by reference herein and made a part of this specification.

TECHNICAL FIELD

The invention relates to a liquid crystal compound and a liquid crystal composition. More specifically, the invention relates to a liquid crystal compound in which the dielectric anisotropy ($\Delta\varepsilon$) is negative, a liquid crystal composition including this compound, and a liquid crystal display device containing this liquid crystal composition.

TECHNICAL BACKGROUND

A display device utilizing a liquid crystal compound (in this patent application, a liquid crystal compound is used as a generic term for a compound that exhibits a liquid crystal phase and a compound that exhibits no liquid crystal phases but useful as a component of a liquid crystal composition) has been widely used for the display of a watch, a calculator, a word processor or the like. The display device utilizes the refractive index anisotropy, the dielectric anisotropy and so forth of the liquid crystal compound.

A liquid crystal phase includes a nematic liquid crystal phase, a smectic liquid crystal phase and a cholestric liquid crystal phase, and the nematic liquid crystal phase is most widely applied. A display mode includes a DS (dynamic scattering) mode, a DAP (deformation of aligned phases) mode, a GH (guest-host) mode, a TN (twisted nematic) mode, a STN (super twisted nematic) mode, a TFT (thin film transistor) mode, a VA (vertical alignment) mode, an IPS (in-plane switching) mode and a PSA (polymer sustained alignment) mode.

A liquid crystal compound used for these display modes is required to exhibit a liquid crystal phase in a wide temperature range, centering at room temperature, to be sufficiently stable under conditions that the display device is used, and also to have sufficient characteristics for driving the display device. However, no single liquid crystal compound that satisfies these conditions has been found until now.

The actual situation is that a liquid crystal composition is prepared by mixing from several to several tens of liquid crystal compounds in order to satisfy the required characteristics. It is required that the liquid crystal composition is stable to moisture, light, heat and air, which are normally present under conditions that the display device is used, and is stable to an electric field or electromagnetic radiation, and is also stable chemically to a compound that will be mixed. It is required that the liquid crystal composition has suitable values of a variety of physical properties such as refractive index anisotropy ($\Delta n$) and dielectric anisotropy ($\Delta\varepsilon$), depending on the display mode or the shape of the display device. Furthermore, it is important that each component in the liquid crystal composition has an excellent solubility in each other.

In recent years, modes such as IPS, VA, OCB and PSA among the display modes have been receiving attention as a display mode capable of overcoming a narrow viewing angle of a liquid crystal display device, which is the greatest subject to be solved. In liquid crystal display devices having these modes, especially a liquid crystal display device having the VA mode or the IPS mode has been studied earnestly, since it has an excellent responsivity in addition to a wide viewing angle, and is capable of providing a high-contrast display. The liquid crystal composition used in the liquid crystal display devices having these display modes is characterized by the negative dielectric anisotropy ($\Delta\varepsilon$). It is known that a liquid crystal composition having a large negative dielectric anisotropy ($\Delta\varepsilon$) can decrease the driving voltage of a liquid crystal display device containing the liquid crystal composition. See the none-patent document No. 1. Accordingly, liquid crystal compounds as the components of the liquid crystal composition are also required to have a larger negative dielectric anisotropy ($\Delta\varepsilon$).

A variety of liquid crystal compounds in which lateral hydrogen on the benzene ring had been replaced by fluorine have conventionally been studied as a component of a liquid crystal composition having negative dielectric anisotropy (the patent documents No. 1 and No. 2). For example, the compound (a) has been reported. However, the compound (a) did not always have a large value although it has negative dielectric anisotropy ($\Delta\varepsilon$) and there were cases where the value was not sufficiently large for decreasing the driving voltage of a liquid crystal display device having a VA mode, an IPS mode or the like.

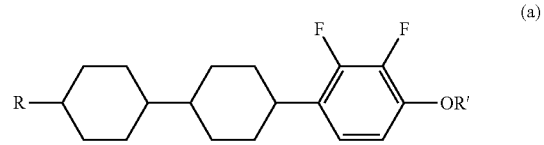
(a)

In the formula, R and R' are alkyl.

Accordingly, in a compound having a 2,3-difluorophenylene moiety, an increase in the absolute value of negative dielectric anisotropy ($\Delta\varepsilon$) has been attempted. For example, a compound having the 2,3-difluorophenylene moiety in which a tetrahydropyran-2,5-diyl moiety is introduced has been reported (Patent document No. 3). The compound (b) has a large negative dielectric anisotropy ($\Delta\varepsilon$) in comparison with the compound (a).

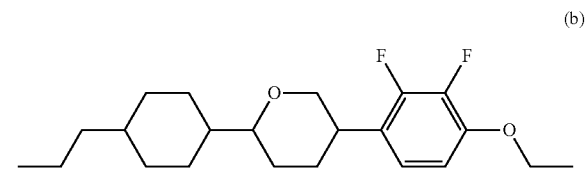 [SMILES: CCCC1CCC(C2CCC(c3ccc(OCC)c(F)c3F)CO2)CC1]
(b)

A compound having two 2,3-difluorophenylene moieties has been reported (Patent document No. 4). The compound (c) has a large negative dielectric anisotropy ($\Delta\varepsilon$) in comparison with the compound (a) or (b). However, a large amount of the compound can not be added to a liquid crystal composition since the compatibility at low temperature is small, and thus the dielectric anisotropy (Δε) of the liquid crystal composition is not necessarily large negatively.

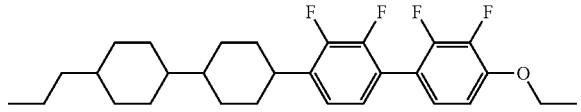 [SMILES: CCCC1CCC(C2CCC(c3ccc(-c4ccc(OCC)c(F)c4F)c(F)c3F)CO2)CC1]

(c)

A liquid crystal compound in which the dielectric anisotropy (Δε) is much larger and negative, its liquid crystal composition and its liquid crystal display device have been expected in order to reduce the driving voltage of a liquid crystal display device having a VA mode, an IPS mode or the like.

PRIOR ART

Patent Document

Patent document No. 1: JP 2811342 B (1998).
Patent document No. 2: JP H02-004725 A (1990).
Patent document No. 3: JP 2000-008040 A (2000).
Patent document No. 4: JP 2000-038585 A (2000).

Non-Patent Document

Non-patent document No. 1: Mol. Cryst. Liq. Cryst., 12, 57 (1970).

OUTLINE OF THE INVENTION

Subject to be Solved by the Invention

The first aim of the invention is to provide a liquid crystal compound having a large negative dielectric anisotropy (Δε) and also having at least one of characteristics such as the stability to heat, light or the like, a high clearing point, a suitable refractive index anisotropy (Δn) and an excellent compatibility with other liquid crystal compounds.

The second aim of the invention is to provide a liquid crystal composition including the compound and having at least one of characteristics such as a small viscosity, a suitable refractive index anisotropy (Δn), a suitable negative dielectric anisotropy (Δε), a low threshold voltage, a high maximum temperature of a nematic phase (the phase transition temperature between a nematic phase and an isotropic phase) and a low minimum temperature of a nematic phase, or having a suitable balance between at least two of the characteristics.

The third aim of the invention is to provide a liquid crystal display device containing the composition and having at least one of characteristics such as a short response time, a small power consumption, a low driving voltage, a large contrast and a wide temperature range in which the device can be used, or having a suitable balance between at least two of the characteristics.

Means for Solving the Subject

As a result of research on the subject described above, we have found that a synergistic effect caused by two factors of
1) a tetrahydropyran ring and

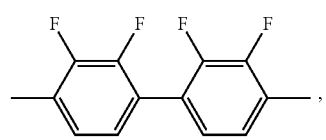

2)

increased especially the value of the dielectric anisotropy (Δε), which was an excellent effect. Moreover, it was found that the subjects could be solved by applying the effect, and thus the invention has completed.

The invention includes Item 1 to Item 32.

Item 1. A compound represented by formula (1):

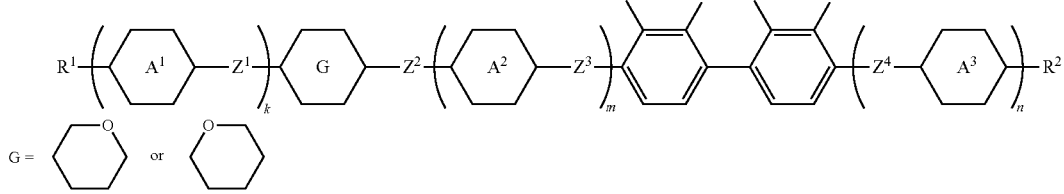

(1)

in formula (1), $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and in the alkyl, alkenyl, alkoxy, alkoxyalkyl and alkenyloxy, arbitrary hydrogen may be replaced by fluorine;

the ring $A^1$, the ring $A^2$ and the ring $A^3$ are independently 1,4-cyclohexylene, 1,4-cyclohexenylene, 1,4-phenylene, tetrahydropyran-2,5-diyl, tetrahydropyran-3,6-diyl, 1,3-dioxane-2,5-diyl, 1,3-dioxane-3,6-diyl, pyrimidine-2,5-diyl, pyrimidine-3,6-diyl, pyridine-2,5-diyl or pyridine-3,6-diyl, and in these rings, arbitrary hydrogen may be replaced by fluorine;

the ring G is tetrahydropyran-2,5-diyl or tetrahydropyran-3,6-diyl;

$Z^1$, $Z^2$, $Z^3$ and $Z^4$ are independently a single bond or —(CH$_2$)$_2$—; and k, m and n are independently 0 or 1, and the sum of k, m and n is 1.

Item 2. The compound according to item 1, wherein in formula (1), $R^1$ and $R^2$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and the ring $A^1$, the ring $A^2$ and the ring $A^3$ are independently 1,4-cyclohexylene, 1,4-cyclohexenylene, 1,4-phenylene, tetrahydropyran-2,5-diyl, tetrahydropyran-3,6-diyl, 2-fluoro-1,4-phenylene, 3-fluoro-1,4-phenylene or 2,3-difluoro-1,4-phenylene.

Item 3. The compound according to item 2, wherein in formula (1), $R^1$ and $R^2$ are independently alkyl having 1 to 10 carbons, alkenyl having 2 to 10 carbons or alkoxy having 1 to 9 carbons.

Item 4. The compound according to item 1 or 3, wherein in formula (1), at least one of $Z^1$, $Z^2$, $Z^3$ and $Z^4$ is a single bond.

Item 5. The compound according to item 1 or 3, wherein in formula (1), $Z^1$, $Z^2$, $Z^3$ and $Z^4$ are a single bond.

Item 6. A compound represented by formula (1-1):

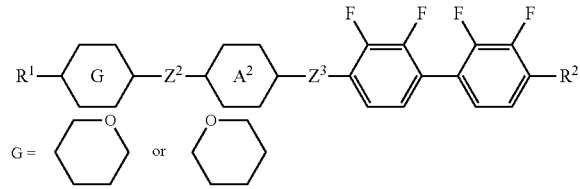

(1-1)

in formula (1-1), $R^1$ and $R^2$ are independently alkyl having 1 to 10 carbons, alkenyl having 2 to 10 carbons or alkoxy having 1 to 9 carbons;

the ring $A^2$ is 1,4-cyclohexylene, 1,4-cyclohexenylene, 1,4-phenylene, tetrahydropyran-2,5-diyl, tetrahydropyran-3,6-diyl, 2-fluoro-1,4-phenylene, 3-fluoro-1,4-phenylene or 2,3-difluoro-1,4-phenylene;

the ring G is tetrahydropyran-2,5-diyl or tetrahydropyran-3,6-diyl; and $Z^2$ and $Z^3$ are independently a single bond or —$(CH_2)_2$—.

Item 7. The compound according to item 6, wherein in formula (1-1), at least one of $Z^2$ and $Z^3$ is a single bond.

Item 8. The compound according to item 6, wherein in formula (1-1), $Z^2$ and $Z^3$ are a single bond.

Item 9. The compound according to item 6, wherein in formula (1-1), the ring $A^2$ is 1,4-cyclohexylene, and $Z^2$ and $Z^3$ are a single bond.

Item 10. The compound according to item 6, wherein in (1-1), $R^1$ is alkyl having 1 to 10 carbons, $R^2$ is alkoxy having 1 to 9 carbons, the ring $A^2$ is 1,4-cyclohexylene, and $Z^2$ and $Z^3$ are a single bond.

Item 11. A compound represented by formula (1-2):

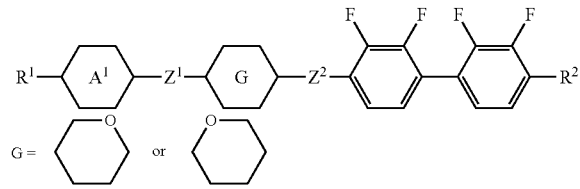

(1-2)

in formula (1-2), $R^1$ and $R^2$ are independently alkyl having 1 to 10 carbons, alkenyl having 2 to 10 carbons or alkoxy having 1 to 9 carbons;

the ring $A^1$ is 1,4-cyclohexylene, 1,4-cyclohexenylene, 1,4-phenylene, tetrahydropyran-2,5-diyl, tetrahydropyran-3,6-diyl, 2-fluoro-1,4-phenylene, 3-fluoro-1,4-phenylene or 2,3-difluoro-1,4-phenylene;

the ring G is tetrahydropyran-2,5-diyl or tetrahydropyran-3,6-diyl; and $Z^1$ and $Z^2$ are independently a single bond or —$(CH_2)_2$—.

Item 12. The compound according to item 11, wherein in formula (1-2), at least one of $Z^1$ and $Z^2$ is a single bond.

Item 13. The compound according to item 11, wherein in formula (1-2), $Z^1$ and $Z^2$ are a single bond.

Item 14. The compound according to item 11, wherein in formula (1-2), the ring $A^1$ is 1,4-cyclohexylene, and $Z^1$ and $Z^2$ is a single bond.

Item 15. The compound according to item 11, wherein in formula (1-2), $R^1$ is alkyl having 1 to 10 carbons, $R^2$ is alkoxy having 1 to 9 carbons, the ring $A^1$ is 1,4-cyclohexylene, and $Z^1$ and $Z^2$ are a single bond.

Item 16. A compound represented by formula (1-3):

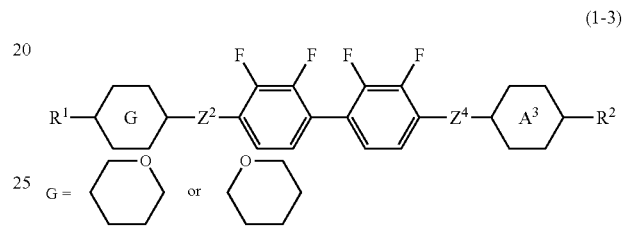

(1-3)

in formula (1-3), $R^1$ and $R^2$ are independently alkyl having 1 to 10 carbons, alkenyl having 2 to 9 carbons or alkoxy having 1 to 9 carbons;

the ring $A^3$ is 1,4-cyclohexylene, 1,4-cyclohexenylene, 1,4-phenylene, tetrahydropyran-2,5-diyl, tetrahydropyran-3,6-diyl, 2-fluoro-1,4-phenylene, 3-fluoro-1,4-phenylene or 2,3-difluoro-1,4-phenylene;

the ring G is tetrahydropyran-2,5-diyl or tetrahydropyran-3,6-diyl; and $Z^2$ and $Z^4$ are independently a single bond or —$(CH_2)_2$—.

Item 17. The compound according to item 16, wherein in formula (1-3), at least one of $Z^2$ and $Z^4$ is a single bond.

Item 18. The compound according to item 16, wherein in formula (1-3), $Z^2$ and $Z^4$ are a single bond.

Item 19. The compound according to item 16, wherein in formula (1-3), the ring $A^3$ is 1,4-cyclohexylene, and $Z^2$ and $Z^4$ are a single bond.

Item 20. The compound according to item 16, wherein in formula (1-3), $R^1$ is alkyl having 1 to 10 carbons, $R^2$ is alkoxy having 1 to 9 carbons, the ring $A^3$ is 1,4-cyclohexylene, and $Z^2$ and $Z^4$ are a single bond.

Item 21. A liquid crystal composition including at least two compounds and one of them is the compound according to any one of items 1 to 20.

Item 22. The liquid crystal composition according to item 21, including at least one compound selected from the group of compounds represented by formulas (2), (3) and (4):

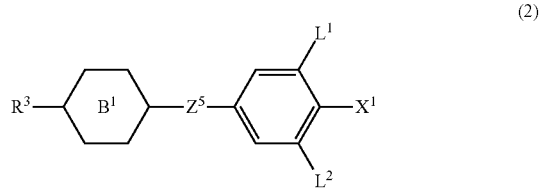

(2)

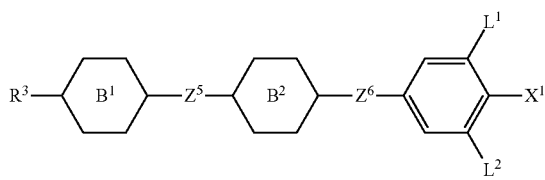

(3)

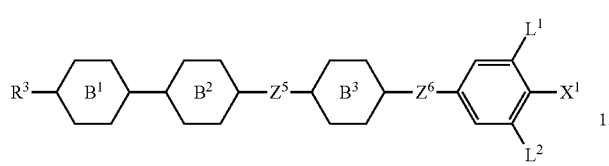

(4)

in formulas (2) to (4),

R³ is independently alkyl having 1 to 10 carbons or alkenyl having 2 to 10 carbons, and in the alkyl and alkenyl, arbitrary hydrogen may be replaced by fluorine, and arbitrary —CH₂— may be replaced by —O—;

X¹ is fluorine, chlorine, —OCF₃, —OCHF₂, —CF₃, —CHF₂, —CH₂F, —OCF₂CHF₂ or —OCF₂CHFCF₃;

the ring B¹, the ring B² and the ring B³ are independently 1,4-cyclohexylene, 1,3-dioxane-2,5-diyl, pyrimidine-2,5-diyl, 1-pyran-2,5-diyl or 1,4-phenylene in which arbitrary hydrogen may be replaced by fluorine;

Z⁵ and Z⁶ are independently —(CH₂)₂—, —(CH₂)₄—, —COO—, —CF₂O—, —OCF₂—, —CH═CH—, —C≡C—, —CH₂O— or a single bond; and L¹ and L² are independently hydrogen or fluorine;

where in in formula (4), the ring B³ is not 1-pyran-2,5-diyl, when both the ring B¹ and the ring B² are 2,3-difluoro-1,4-phenylene; and the ring B¹ is not 1-pyran-2,5-diyl, when both the ring B² and the ring B³ are 2,3-difluoro-1,4-phenylene and Z⁵ is a single bond.

Item 23. The liquid crystal composition according to item 21, including at least one compound selected from the group of compounds represented by formula (5):

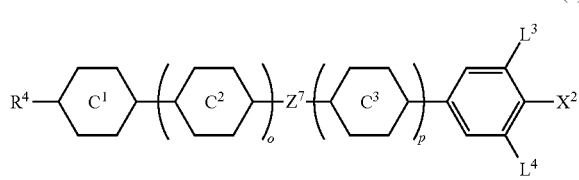

(5)

in formula (5),

R⁴ is alkyl having 1 to 10 carbons or alkenyl having 2 to carbons, and in the alkyl and alkenyl, arbitrary hydrogen may be replaced by fluorine, and arbitrary —CH₂— may be replaced by —O—;

X² is —C≡N or —C≡C—C≡N;

the ring C¹, the ring C² and the ring C³ are independently 1,4-cyclohexylene, 1,4-phenylene in which arbitrary hydrogen may be replaced by fluorine, 1,3-dioxane-2,5-diyl, 1-pyran-2,5-diyl or pyrimidine-2,5-diyl;

Z⁷ is —(CH₂)₂—, —COO—, —CF₂O—, —OCF₂—, —C≡C—, —CH₂O— or a single bond;

L³ and L⁴ are independently hydrogen or fluorine; and o is 0, 1 or 2, and p is 0 or 1.

Item 24. The liquid crystal composition according to item 21, including at least one compound selected from the group of compounds represented by formulas (6), (7), (8), (9), (10) and (11):

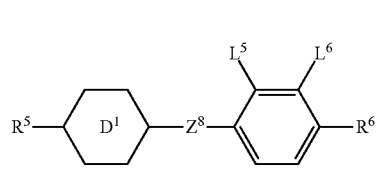

(6)

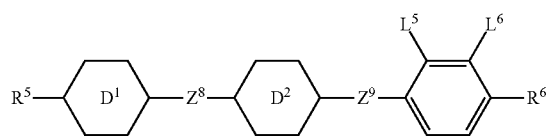

(7)

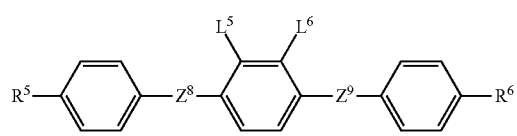

(8)

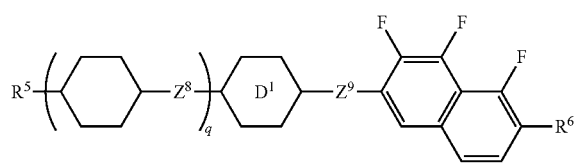

(9)

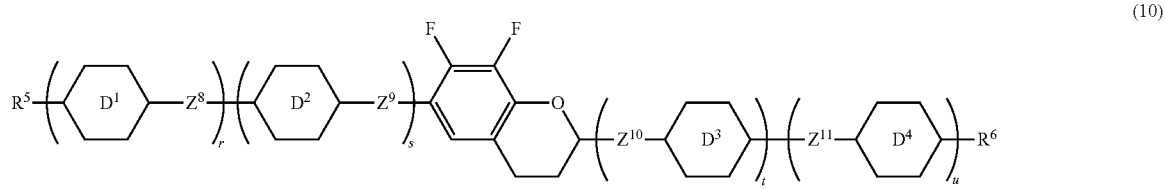

(10)

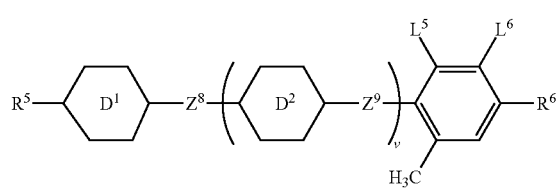

(11)

in formulas (6) to (11), $R^5$ and $R^6$ are independently alkyl having 1 to 10 carbons or alkenyl having 2 to 10 carbons, and in the alkyl and alkenyl, arbitrary hydrogen may be replaced by fluorine, and arbitrary —$CH_2$— may be replaced by —O—;

the ring $D^1$, the ring $D^2$, the ring $D^3$ and the ring $D^4$ are independently 1,4-cyclohexylene, 1,4-cyclohexenylene, 1,4-phenylene in which arbitrary hydrogen may be replaced by fluorine, 6-pyran-2,5-diyl or decahydro-2,6-naphthalene;

$Z^8$, $Z^9$, $Z^{10}$ and $Z^{11}$ are independently —$(CH_2)_2$—, —COO—, —$CH_2O$—, —$OCF_2$—, —$OCF_2(CH_2)_2$— or a single bond;

$L^5$ and $L^6$ are independently fluorine or chlorine; and q, r, s, t, u and v are independently 0 or 1, and the sum of r, s, t and u is 1 or 2.

Item 25. The liquid crystal composition according to item 21, including at least one compound selected from the group of compounds represented by formulas (12), (13) and (14):

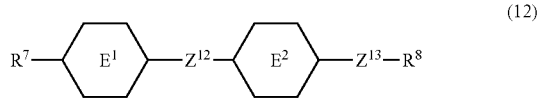
(12)

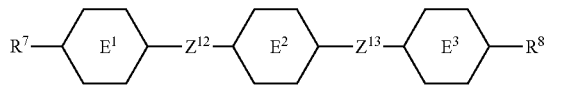
(13)

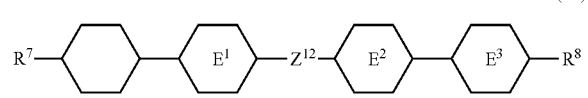
(14)

in formulas (12) to (14), $R^7$ and $R^8$ are independently alkyl having 1 to 10 carbons or alkenyl having 2 to 10 carbons, and in the alkyl and alkenyl, arbitrary —$CH_2$— may be replaced by —O—;

the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{12}$ and $Z^{13}$ are independently —C≡C—, —COO—, —$(CH_2)_2$—, —CH=CH— or a single bond.

Item 26. The liquid crystal composition according to item 22, further including at least one compound selected from the group of compounds represented by formula (5).

Item 27. The liquid crystal composition according to item 22, further including at least one compound selected from the group of compounds represented by formulas (12), (13) and (14).

Item 28. The liquid crystal composition according to item 23, further including at least one compound selected from the group of compounds represented by formulas (12), (13) and (14).

Item 29. The liquid crystal composition according to item 24, further including at least one compound selected from the group of compounds represented by formulas (12), (13) and (14).

Item 30. The liquid crystal composition according to any one of items 21 to 29, further including at least one optically active compound and/or one polymerizable compound.

Item 31. The liquid crystal composition according to any one of items 21 to 30, further including at least one antioxidant and/or one ultraviolet light absorber.

Item 32. A liquid crystal display device containing the liquid crystal composition according to any one of items 21 to 31.

Effect of the Invention

A liquid crystal compound that has a large negative dielectric anisotropy (Δ∈) and also has at least one of characteristics such as the stability to heat, light or the like, a high clearing point, a suitable refractive index anisotropy (Δn), a wide temperature range of a nematic phase and an excellent compatibility with other liquid crystal compounds can be obtained according to the invention.

A liquid crystal composition that has at least one of characteristics such as a small viscosity, a suitable refractive index anisotropy (Δn), a suitable negative dielectric anisotropy (Δ∈), a low threshold voltage, a high maximum temperature of a nematic phase and a low minimum temperature of a nematic phase can be obtained according to the invention.

The liquid crystal display device of the invention has at least one of characteristics such as a short response time, a small power consumption, a low driving voltage, a large contrast and a wide temperature range in which the device can be used, and can be suitably used for a liquid crystal display device having a display mode such as a PC mode, a TN mode, a STN mode, an ECB mode, an OCB mode, an IPS mode, a VA mode, a PSA mode or the like, and can be suitably used especially for a liquid crystal display device having an IPS mode, a VA mode or a PSA mode.

EMBODIMENT TO CARRY OUT THE INVENTION

Usage of the terms in the specification is as follows. The liquid crystal composition of the invention and the liquid crystal display device of the invention may be abbreviated to "the composition" and "the device," respectively. "A liquid crystal display device" is a generic term for a liquid crystal display panel and a liquid crystal display module. "A liquid crystal compound" is a generic term for a compound having a liquid crystal phase such as a nematic phase or a smectic phase, and also for a compound having no liquid crystal phases but being useful as a component of a composition. Such a useful compound has a six-membered ring such as 1,4-cyclohexylene and 1,4-phenylene, and has a rod-like molecular structure. An optically active compound may be added to the composition. Even in the case where this compound is liquid crystalline, the compound is classified as an additive herein. At least one compound selected from the group of compounds represented by formula (1-1) may be abbreviated to "the compound (1-1)." "The compound (1-1)" means one compound, or two or more compounds represented by formula (1-1). The same rules apply to compounds represented by the other formulas. "Arbitrary" is used not only in cases where the position is arbitrary but also in cases where the number is arbitrary. However, it is not used in cases where the number is 0 (zero).

The invention will be explained more specifically as follows.

The liquid crystal compound of the invention is represented by the following formula (1).

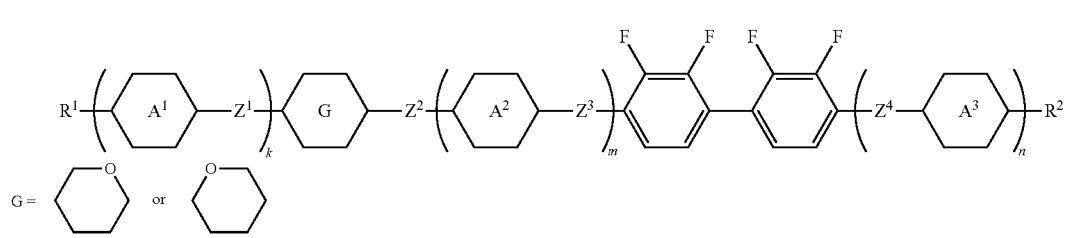

(1)

In formula (1), $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and in the alkyl, alkenyl, alkoxy, alkoxyalkyl and alkenyloxy, arbitrary hydrogen may be replaced by halogen.

$R^1$ includes alkyl having 1 to 10 carbons, alkenyl having 2 to 10 carbons, alkoxy having 1 to 9 carbons, alkoxyalkyl having 2 to 9 carbons and alkenyloxy having 2 to 9 carbons. It is desirable that alkyl chain in these groups is straight. When the alkyl chain is straight, the temperature range of a liquid crystal phase is wide and the viscosity is small. It is desirable that the double bond in the alkenyl is in the odd positions and the configuration is trans. When the alkenyl has a plurality of double bonds, unconjugated double bonds are desirable.

The alkyl is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ and —$C_{10}H_{21}$;

the alkenyl includes —CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —$(CH_2)_3$CH=$CH_2$, —CH=CH$(CH_2)_2$CH=$CH_2$ and —$(CH_2)_2$CH=CH$(CH_2)_2$CH=$CH_2$;

the alkoxy is —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$ and —$OC_9H_{19}$;

the alkoxyalkyl includes —$CH_2OCH_3$, —$CH_2OC_2H_5$, —$(CH_2)_2OCH_3$ and —$(CH_2)_2OC_2H_5$; and the alkenyloxy includes —$OCH_2$CH=$CH_2$, —$OCH_2$CH=$CHCH_3$ and —$OCH_2$CH=$CHC_2H_5$.

Desirable $R^1$ among these is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —$(CH_2)_3$CH=$CH_2$, —CH=CH$(CH_2)_2$CH=$CH_2$ and —$(CH_2)_2$CH=CH$(CH_2)_2$CH=$CH_2$, —$OCH_3$, —$OC_2H_5$, —$OC_3H_7$, —$OC_4H_9$, —$OC_5H_{10}$, —$OC_6H_{13}$, —$OC_7H_{15}$, —$OC_8H_{17}$ and —$OC_9H_{19}$.

More desirable $R^1$ is —$CH_3$, —$C_2H_5$, —$C_3H_7$, —$C_4H_9$, —$C_5H_{11}$, —$C_6H_{13}$—, —CH=$CH_2$, —CH=$CHCH_3$, —CH=$CHC_2H_5$, —$(CH_2)_2$CH=$H_2$, —CH=$CHC_3H_7$, —$(CH_2)_2$CH=$CHCH_3$, —$(CH_2)_3$CH=$CH_2$, —CH=CH$(CH_2)_2$CH=$CH_2$ and —$(CH_2)_2$CH=CH$(CH_2)_2$CH=$CH_2$.

$R^2$ includes alkyl having 1 to 10 carbons, alkenyl having 2 to 10 carbons, alkoxy having 1 to 9 carbons, alkoxyalkyl having 2 to 9 carbons and alkenyloxy having 2 to 9 carbons. It is desirable that alkyl chain in these groups is straight. When the alkyl chain is straight, the temperature range of a liquid crystal phase is wide and the viscosity is small. It is desirable that the configuration of the alkenyl is trans. When the alkenyl has a plurality of double bonds, unconjugated double bonds are desirable.

The alkyl is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ and —$CO_1H_{21}$;

the alkenyl includes —CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —$(CH_2)_3$CH=$CH_2$, —CH=CH$(CH_2)_2$CH=$CH_2$ and —$(CH_2)_2$CH=CH$(CH_2)_2$CH=$CH_2$;

the alkoxy is —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$ and —$OC_9H_{19}$;

the alkoxyalkyl includes —$CH_2OCH_3$, —$CH_2OC_2H_5$, —$(CH_2)_2OCH_3$ and —$(CH_2)_2OC_2H_5$; and the alkenyloxy includes —$OCH_2$CH=$CH_2$, —$OCH_2$CH=$CHCH_3$ and —$OCH_2$CH=$CHC_2H_5$.

Desirable $R^2$ among these includes —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —$(CH_2)_3$CH=$CH_2$, —CH=CH$(CH_2)_2$CH=$CH_2$, —$(CH_2)_2$CH=CH$(CH_2)_2$CH=$CH_2$, —$OCH_3$, —$OC_2H_5$, —$OC_3H_7$, —$OC_4H_9$, —$OC_5H_{10}$, —$OC_6H_{13}$, —$OC_7H_{15}$, —$OC_8H_{17}$ and —$OC_9H_{19}$.

More desirable $R^2$ is —$CH_3$, —$C_2H_5$, —$C_3H_7$, —$C_4H_9$, —$C_5H_{11}$, —$C_6H_{13}$—CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —$(CH_2)_3$CH=$CH_2$, —CH=CH$(CH_2)_2$CH=$CH_2$, —$(CH_2)_2$CH=CH$(CH_2)_2$CH=$CH_2$, —$OCH_3$, —$OC_2H_5$, —$OC_3H_7$, —$OC_4H_9$ and —$OC_5H_{10}$.

In formula (1), the ring $A^1$, the ring $A^2$ and the ring $A^3$ are 1,4-cyclohexylene, 1,4-cyclohexenylene, 1,4-phenylene, tetrahydropyran-2,5-diyl, tetrahydropyran-3,6-diyl, 1,3-dioxane-2,5-diyl, 1,3-dioxane-3,6-diyl, pyrimidine-2,5-diyl, pyrimidine-3,6-diyl, pyridine-2,5-diyl or pyridine-3,6-diyl, and in these ring, arbitrary hydrogen may be replaced by halogen.

When these rings are 1,4-cyclohexylene, the refractive index anisotropy (Δn) is small and the viscosity is small. When the liquid crystal compound is added to a liquid crystal composition, the maximum temperature of a nematic phase is increased.

When these rings are 1,4-phenylene in which hydrogen may be replaced by halogen, the refractive index anisotropy (Δn) is relatively increased and the orientational order parameter is also increased.

Desirable ring $A^1$, ring $A^2$ and ring $A^3$ among these are 1,4-cyclohexylene, 1,4-cyclohexenylene, 1,4-phenylene, 2-fluoro-1,4-phenylene, 3-fluoro-1,4-phenylene, 2,3-difluoro-1,4-phenylene, tetrahydropyran-2,5-diyl and tetrahydropyran-3,6-diyl.

In formula (1), $Z^1$, $Z^2$, $Z^3$ and $Z^4$ are independently a single bond or —$(CH_2)_2$—, and desirable $Z^1$, $Z^2$, $Z^3$ and $Z^4$ are a single bond in view of an increase in the temperature range of a liquid crystal phase and a decrease in the viscosity.

k, m and n are independently 0 or 1, and the sum of k, m and n is 1.

The absolute value of the dielectric anisotropy (Δ∈) is decreased when in formula (1), m is 1, the ring G is tetrahydropyran-2,5-diyl, the ring $A^2$ is 2-fluoro-1,4-phenylene or 2,3-difluoro-1,4-phenylene, and $Z^2$ is a single bond. In the bonding state shown in Figure (A), (A)

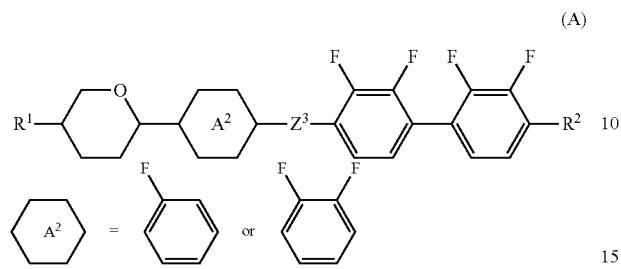

the direction of oxygen in pyran is the reverse of that of fluorine in the ring $A^2$ in a stable conformation, and thus the dielectric anisotropy ($\Delta\varepsilon$) is decreased since the dipole moments are compensated.

Accordingly, desirable $Z^2$ is —$CH_2CH_2$—, when m is 1, the ring G is tetrahydropyran-2,5-diyl, and the ring $A^2$ is 2-fluoro-1,4-phenylene or 2,3-difluoro-1,4-phenylene.

Similarly, desirable $Z^2$ is —$CH_2CH_2$—, when k is 1, and the ring G is tetrahydropyran-2,5-diyl.

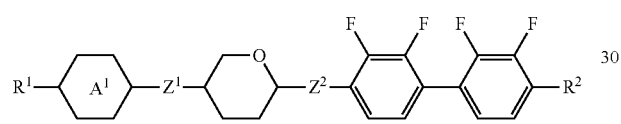

Desirable $Z^1$ is —$CH_2CH_2$—, when k is 1, the ring G is tetrahydropyran-3,6-diyl, and the ring $A^1$ is 3-fluoro-1,4-phenylene or 2,3-difluoro-1,4-phenylene.

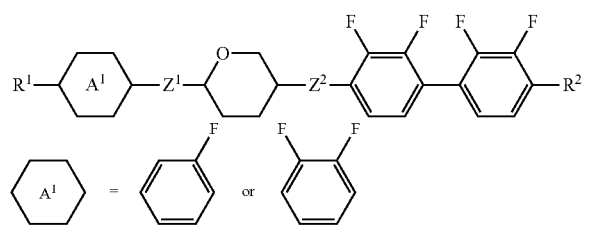

Desirable $Z^4$ is —$CH_2CH_2$—, when n is 1, and the ring $A^3$ is tetrahydropyran-3,6-diyl.

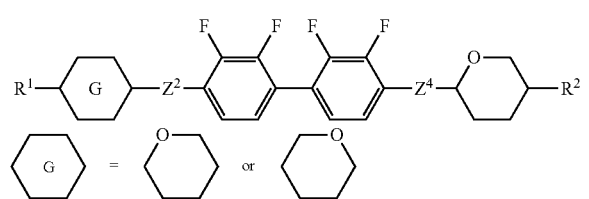

Desirable $Z^2$ is —$CH_2CH_2$—, when the ring G is tetrahydropyran-2,5-diyl.

In the liquid crystal compound represented by formula (1), physical properties such as the refractive index anisotropy ($\Delta n$) and the dielectric anisotropy ($\Delta\varepsilon$) can be adjusted to desired values in the range described above, by a suitable selection of the terminal groups $R^1$ and $R^2$, the ring $A^1$, the ring $A^2$ and the ring $A^3$, and the bonding groups $Z^1$, $Z^2$, $Z^3$ and $Z^4$.

Desirable examples of the liquid crystal compound represented by formula (1) include the compounds represented by formulas (1-1-1) to (1-1-2), (1-2-1) to (1-2-2) and (1-3-1) to (1-3-2).

(1-1-1)

(1-1-2)

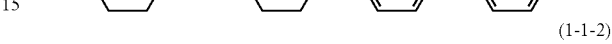

(1-2-1)

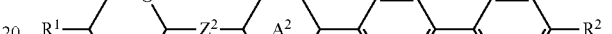

(1-2-2)

(1-3-1)

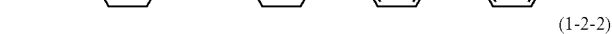

(1-3-2)

In the formulas, $R^1$ is alkyl having 1 to 10 carbons, alkenyl having 2 to 10 carbons or alkoxy having 1 to 9 carbons; $R^2$ is alkyl having 1 to 10 carbons, alkenyl having 2 to 10 carbons or alkoxy having 1 to 9 carbons;

the ring $A^1$, the ring $A^2$ and the ring $A^3$ are independently 1,4-cyclohexylene, 1,4-cyclohexenylene, 1,4-phenylene, 2-fluoro-1,4-phenylene, 3-fluoro-1,4-phenylene, 2,3-difluoro-1,4-phenylene, tetrahydropyran-2,5-diyl, tetrahydropyran-3,6-diyl; and $Z^1$, $Z^2$ and $Z^4$ are independently a single bond or —$CH_2CH_2$—.

The liquid crystal compound represented by formula (1) can be prepared by the introduction of a predetermined group into $R^1$, $R^2$, the ring $A^1$, the ring $A^2$, the ring $A^3$, $Z^1$, $Z^2$, $Z^3$ and $Z^4$ in the formula, and the introduction of such groups can be carried out by known and general synthetic organic methods. Representative examples of the synthesis include the methods described in "Vol. 14: Synthesis and Reaction of Organic Compounds" (1978) in New Experimental Chemistry Course (Shin Jikken Kagaku Kouza, in Japanese; Maruzen Co., Ltd.), or "Vol. 19 to Vol. 26: Organic Synthesis I to VIII" (1991) in Experimental Chemistry Course (Jikken Kagaku Kouza, in Japanese; the fourth edition, Maruzen Co., Ltd.).

One example of the method for the formation of the bonding groups $Z^1$, $Z^2$, $Z^3$ and $Z^4$ will be shown. Schemes for the formation of the bonding groups are as follows. In these schemes, $MSG^1$ or $MSG^2$ is a monovalent organic group. A plurality of $MSG^1$ (or $MSG^2$) used in the schemes may be the same or different. The compounds (1A) and (1B) correspond to the liquid crystal compound represented by (1)

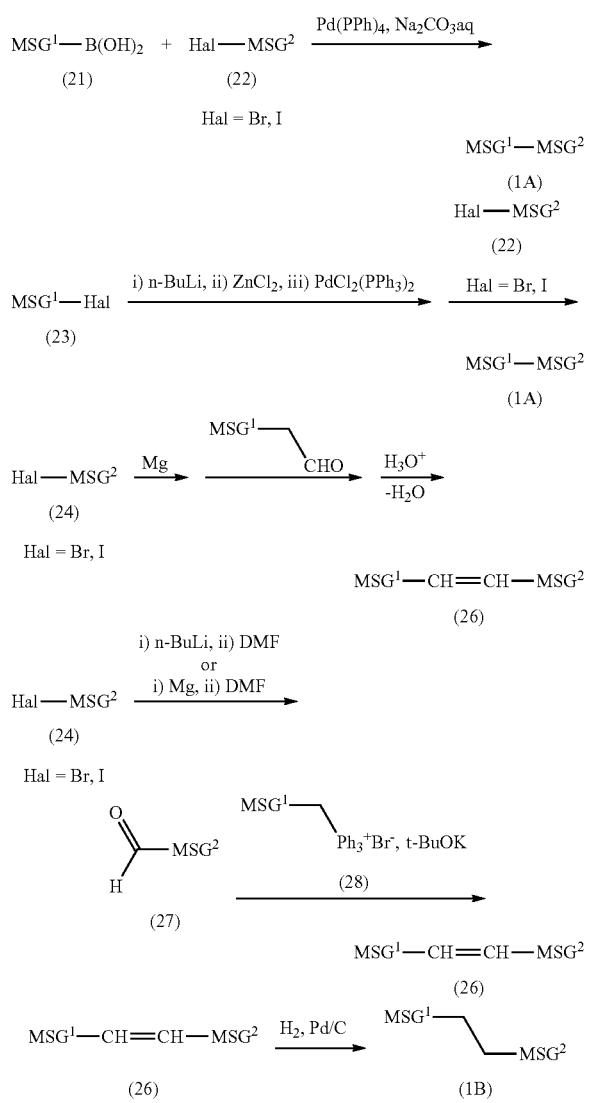

(I) Formation of a Single Bond

The compound (1A) is prepared by the reaction of the arylboronic acid (21) with the compound (22) prepared by known methods, in the presence of a catalyst such as tetrakis(triphenylphosphine)palladium in an aqueous solution of a carbonate. This compound (1A) is also prepared by the reaction of the compound (23) prepared by known methods with n-butyllithium and then with zinc chloride, and then by the reaction with the compound (22) in the presence of a catalyst such as dichlorobis(triphenylphosphine)palladium.

(II) Formation of —$(CH_2)_2$—

The organohalogen compound (24) having a monovalent organic group $MSG^2$ is allowed to react with magnesium to give a Grignard reagent. The reaction of the Grignard reagent thus prepared or a lithium salt with the aldehyde derivative (25) gives the corresponding alcohol derivative. Dehydration of the resulting alcohol derivative in the presence of an acid catalyst such as p-toluenesulfonic acid gives the corresponding compound (26). The compound (1B) is prepared by hydrogenation of the resulting compound (26) in the presence of a catalyst such as palladium on carbon (Pd/C).

A compound, which is formed by the reaction of the organohalogen compound (24) with butyllithium or magnesium, is allowed to react with a formamide such as N,N-dimethylformamide (DMF) to give the aldehyde derivative (27). The sulfonium salt (28) is treated with a base such as potassium t-butoxide to give a ylide, and the ylide is allowed to react with the resulting aldehyde derivative (27) to give the compound (26) having the corresponding double bond. Hydrogenation of the resulting compound (26) in the presence of a catalyst such as palladium on carbon (Pd/C) gives the compound (1B).

Next, one example of a method for the preparation of the tetrahydropyran compound represented by formula (1) is shown in a scheme. A scheme in which the intermediate (30) having an oxetane moiety is prepared is explained first, and then one example of a method for the preparation of the tetrahydropyran-3,6-diyl compound (36) from the synthetic intermediate (30) as a starting material is described.

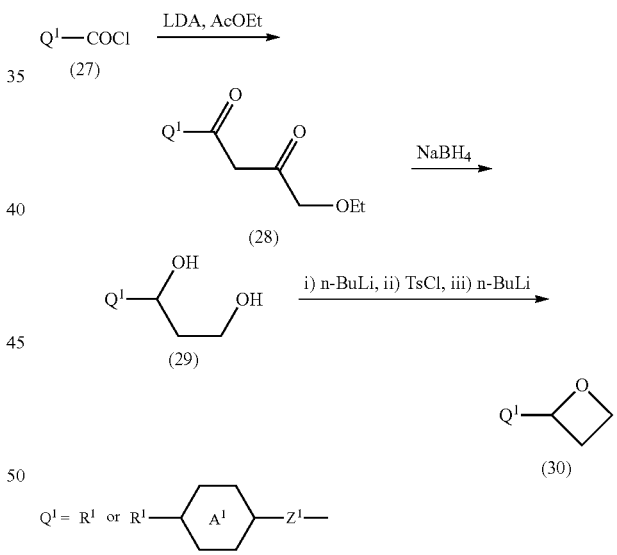

In the compounds (27) to (30), $Q^1$ is a structural unit in formula (1). The structural unit: is shown in the scheme. The meaning of the symbols of $R^1$, $A^1$ and $Z^1$ in these compounds are the same with those of the symbols described in item 1.

That is, the compound (28) is prepared by the reaction of the compound (27) with LDA (lithium diisopropylamide) and then with ethyl acetate. It is desirable that the reaction is carried out at −65° C. or lower in a tetrahydrofuran solvent, and then the reaction mixture was allowed to warm slowly to room temperature. The compound (29) is prepared by the reaction of the compound (28) with sodium borohydride. It is desirable that this reaction is carried out in ethanol solvent at a temperature in the range of room temperature to 50° C. The compound (29) is allowed to react with n-butyllithium in a tetrahydrofuran solvent at a temperature in the range of −5° C. to 5° C., and then with p-toluenesulfonyl chloride. After further addition of n-butyllithium, the reaction mixture is allowed to heat slowly to the boiling point, giving the compound (30). It is desirable that the reactions are carried out at sufficient intervals and just one equivalent of each reagent is used.

The compound (27), which is a starting material, can be easily prepared according to the methods in synthetic organic chemistry.

Next, One example of the method for synthesizing the compound (36) is shown.

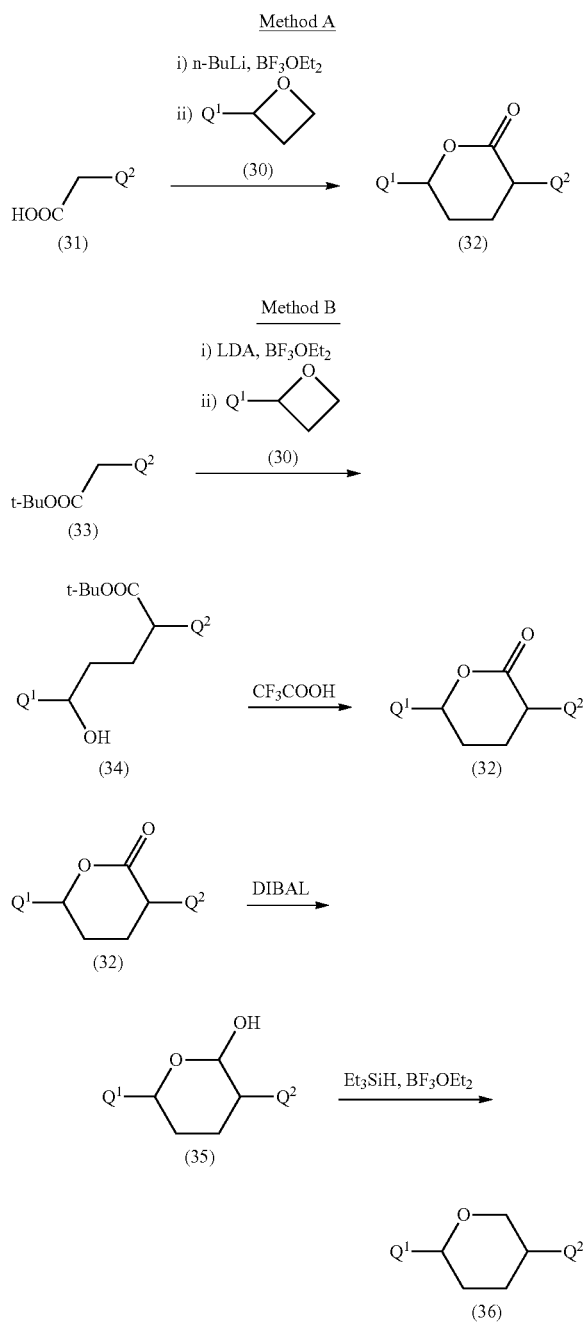

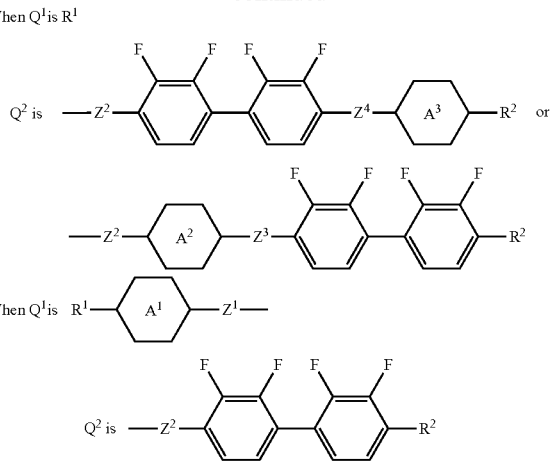

In the compound (30) to the compound (34), $Q^1$ or $Q^2$ is a structural unit in formula (1). The structural unit is shown in the scheme. The meanings of the symbols $R^1$, $R^2$, $A^1$, $A^2$, $A^3$, $Z^1$, $Z^2$, $Z^3$ and $Z^4$ in these compounds are the same with those of the symbols described in item 1.

The method for synthesizing the compound (32) depends on the kind of the bonding group $Z^2$ and the ring $A^2$ as the schemes shows. Two synthetic methods are exemplified.

The method A: the compound (32) is prepared by the reaction of the compound (31) with n-butyllithium, and then with the compound (30) in the presence of a boron trifluoride-diethyl ether complex. Ii is desirable that the reaction is carried out in a tetrahydrofuran solvent at a temperature of −65° C. or lower.

The method B: the compound (34) is prepared by the reaction of the compound (33) with LDA (lithium diisopropylamide), and then with the compound (30) in the presence of a boron trifluoride-diethyl ether complex. It is desirable that the reaction is carried out in a tetrahydrofuran solvent at a temperature of −65° C. or lower. The compound (34) is then allowed to react with trifluoroacetic acid in a dichloromethane solvent at room temperature to give the compound (32).

The compound (35) is prepared by reaction of the compound (32) with DIBAL (diisopropylaluminium hydride). It is desirable that this reaction is carried out in a toluene solvent at a temperature of −50° C. or lower. The compound (36) is prepared by the reaction of the compound (35) in a dichloromethane solvent in the presence of triethylsilane and a boron trifluoride-diethyl ether complex at a temperature of −50° C. or lower.

The compound (31) and the compound (33) are easily prepared according to the methods of synthetic organic chemistry.

The liquid crystal composition of the invention should include the compound represented by formula (1) as a component A. The composition may include the component A only. The composition may include the component A and another component that is not specifically described in this specification. The compositions having a variety of characteristics can be provided by the addition of a component selected from the components B, C, D and E, these of which will be shown below, to the component A.

Desirable components that will be added to the component A are the component B that is at least one compound selected from the group of compounds represented by formulas (2), (3) and (4), and/or the component C that is at least one compound selected from the group of compounds represented by formula (5), and/or the component D that is at least one compound selected from the group of compounds represented by formulas (6), (7), (8), (9), (10) and (11). Further, the threshold voltage, the temperature range of a liquid crystal phase, the refractive index anisotropy, the dielectric anisotropy, the viscosity and so forth can be adjusted by the addition of the component E that is at least one compound selected from the group of compounds represented by formulas (12), (13) and (14).

In each compound included in the liquid crystal composition, there are no major differences in characteristics even if the compound is an analogue composed of any isotope.

In the component B, desirable examples of the compound (2) include the compounds (2-1) to (2-16), desirable examples of the compound (3) include the compounds (3-1) to (3-112), and desirable examples of the compound (4) include the compounds (4-1) to (4-54).

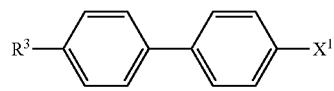
(2-1)

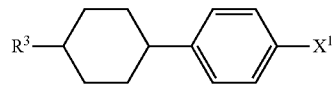
(2-2)

(2-3)

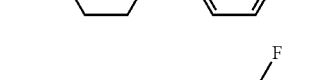
(2-4)

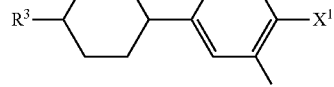
(2-5)

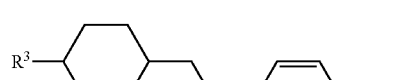
(2-6)

(2-7)

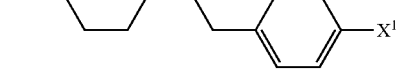
(2-8)

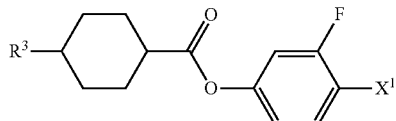
(2-9)

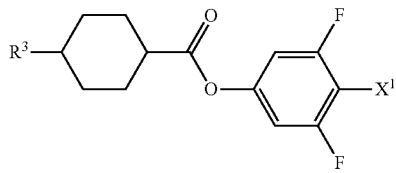
(2-10)

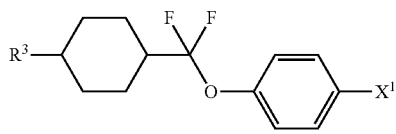
(2-11)

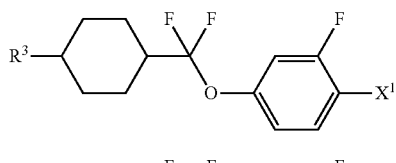
(2-12)

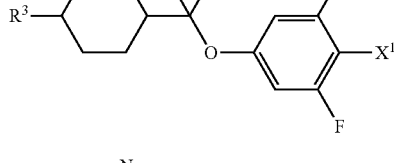
(2-13)

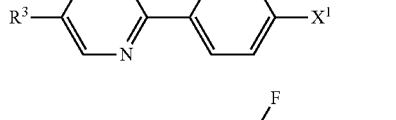
(2-14)

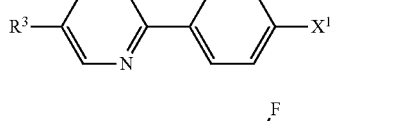
(2-15)

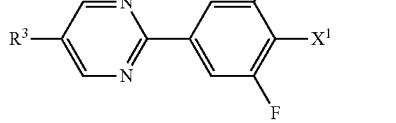
(2-16)

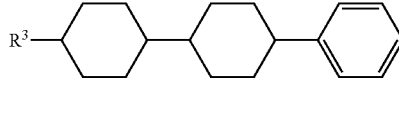
(3-1)

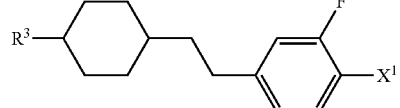

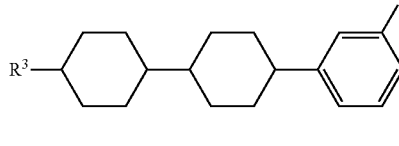
(3-2)

(3-3)

(3-4) through (3-22): chemical structure formulas (3-23) 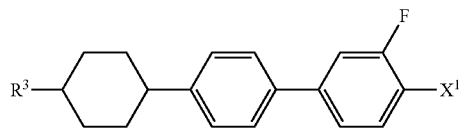
(3-24) 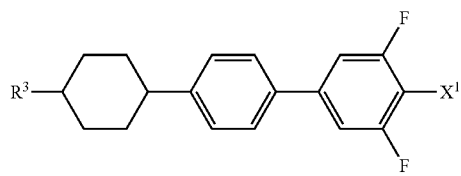
(3-25) 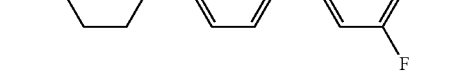
(3-26) 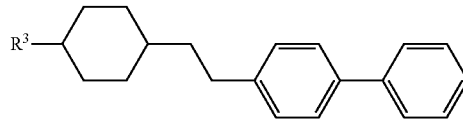
(3-27) 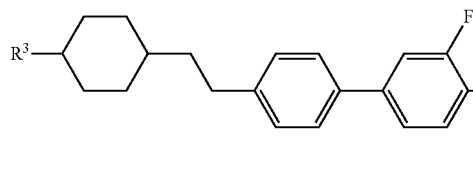
(3-28) 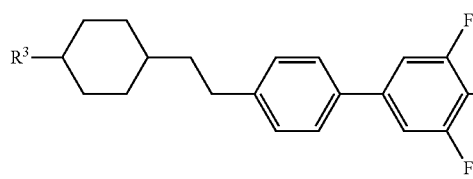
(3-29) 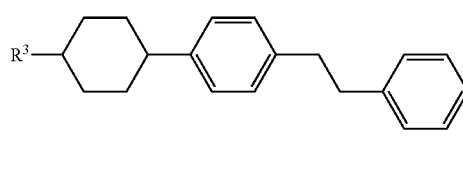
(3-30) 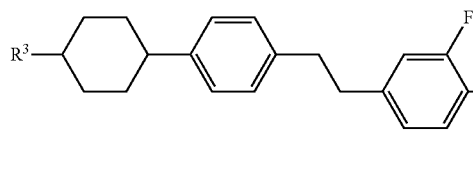
(3-31) 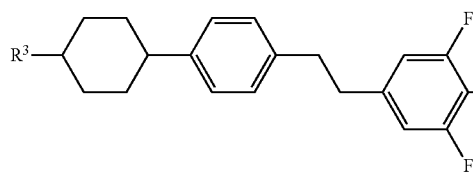
(3-32) 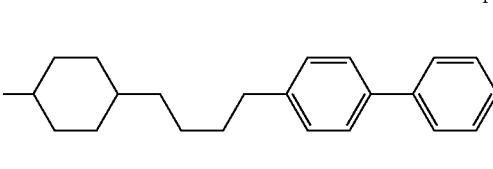
(3-33) 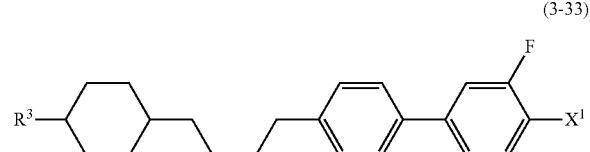
(3-34) 
(3-35) 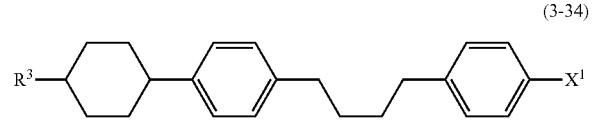
(3-36) 
(3-37) 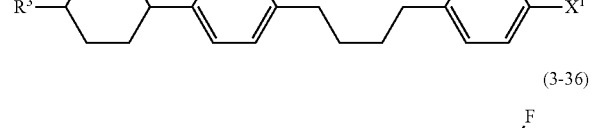
(3-38) 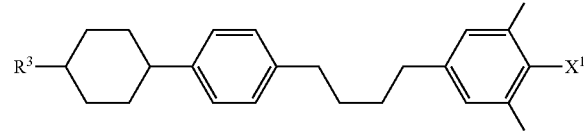
(3-39) 
(3-40) 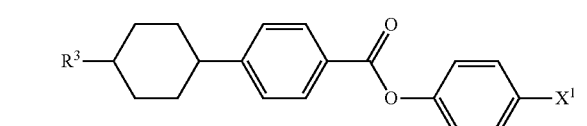
(3-41) 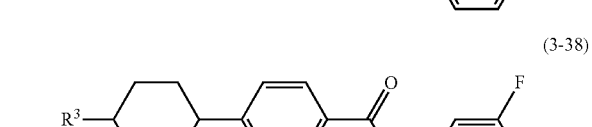

(3-42)
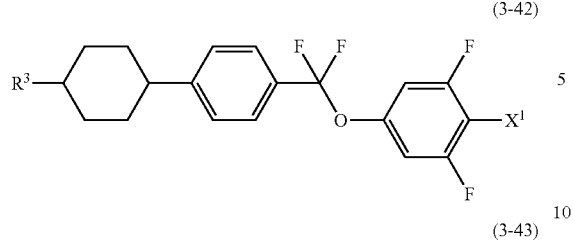
(3-43)
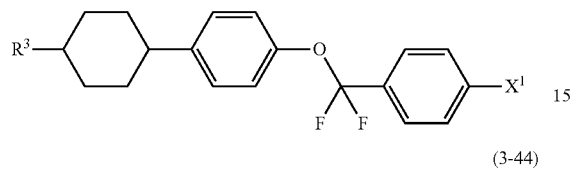
(3-44)
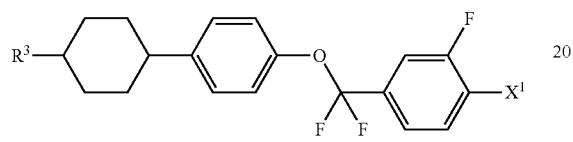
(3-45)
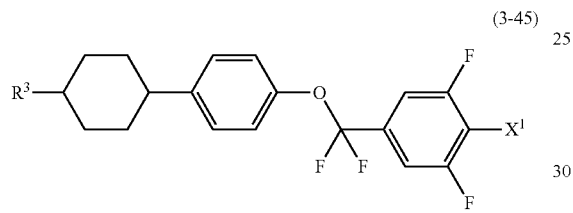
(3-46)
(3-47)
(3-48)
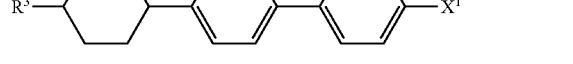
(3-49)
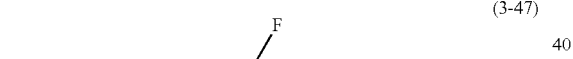
(3-50)
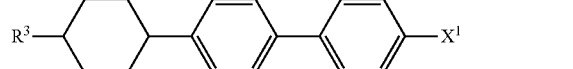
(3-51)
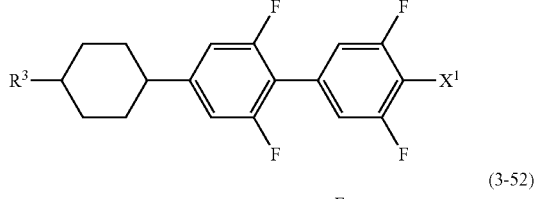
(3-52)
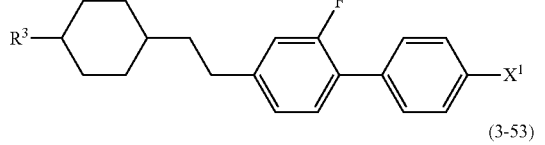
(3-53)
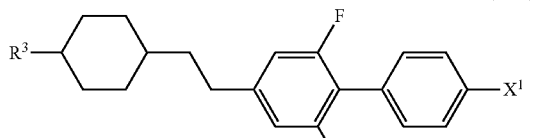
(3-54)
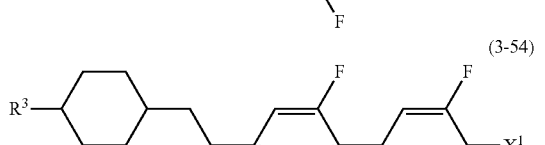
(3-55)
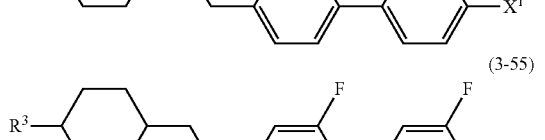
(3-56)
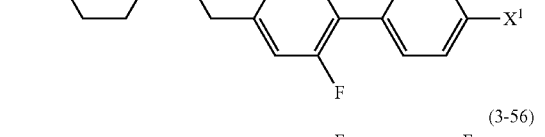
(3-57)
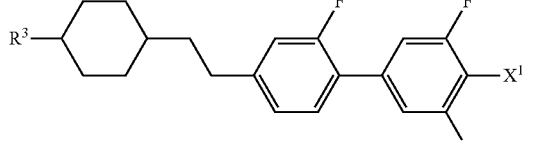
(3-58)
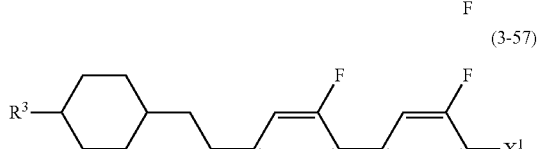
(3-59)
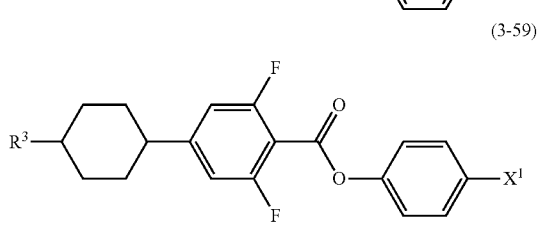

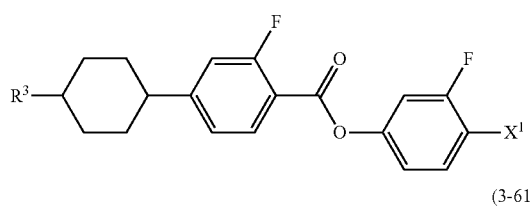
(3-60)
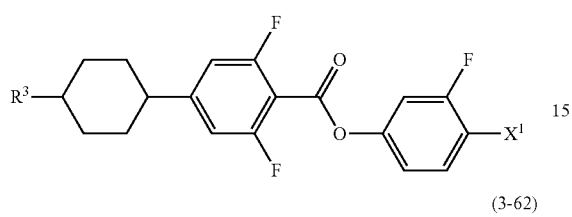
(3-61)
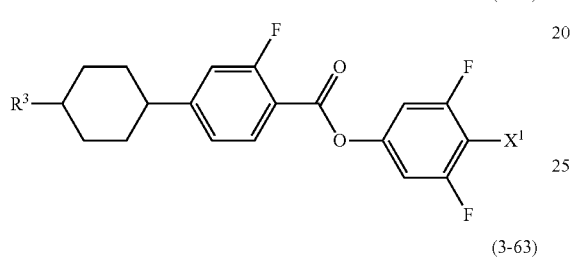
(3-62)
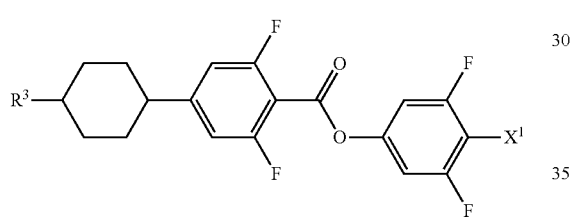
(3-63)
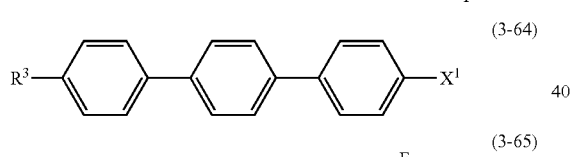
(3-64)
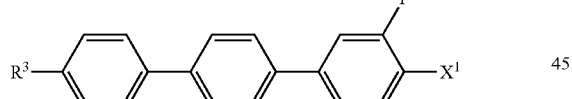
(3-65)
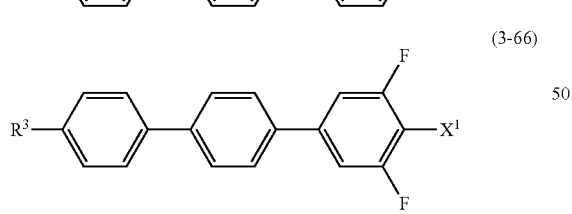
(3-66)
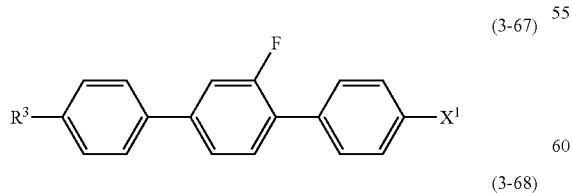
(3-67)
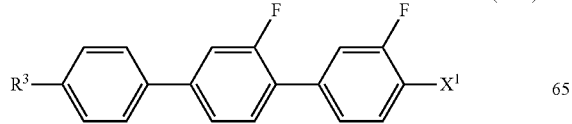
(3-68)
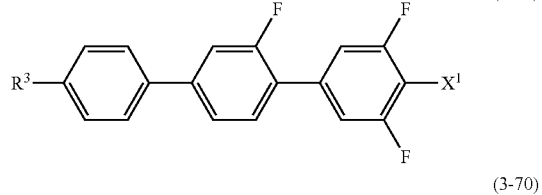
(3-69)
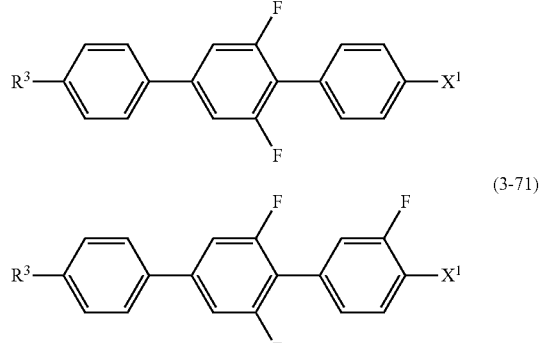
(3-70)
(3-71)
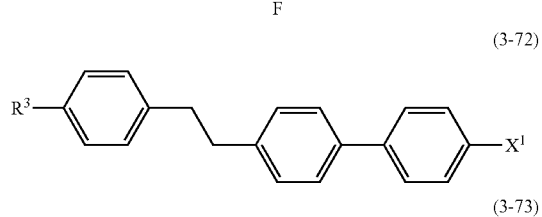
(3-72)
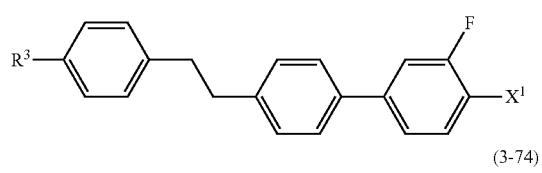
(3-73)
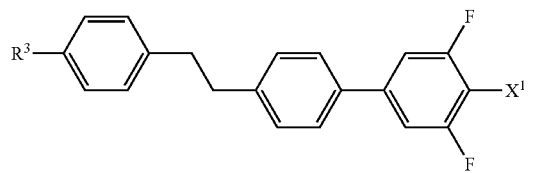
(3-74)
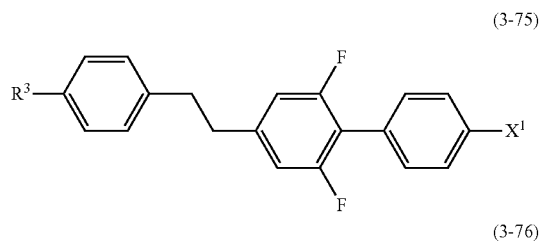
(3-75)
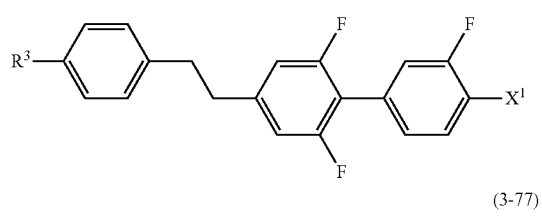
(3-76)
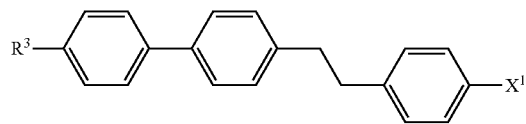
(3-77)

(3-78) 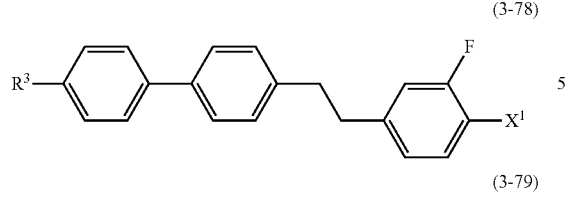
(3-79) 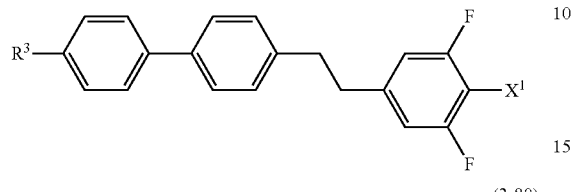
(3-80) 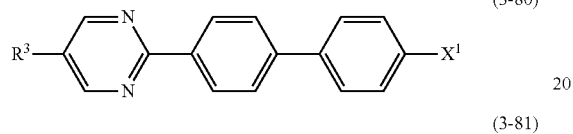
(3-81) 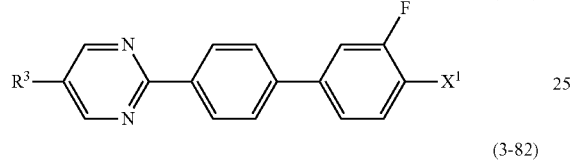
(3-82) 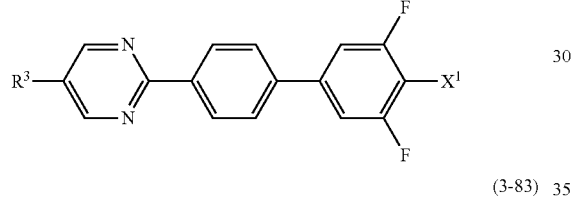
(3-83) 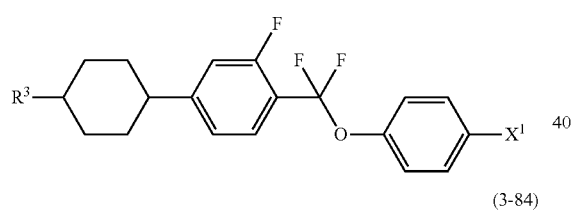
(3-84) 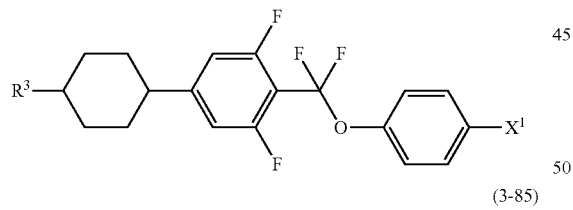
(3-85) 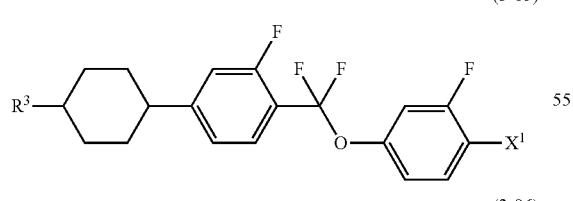
(3-86) 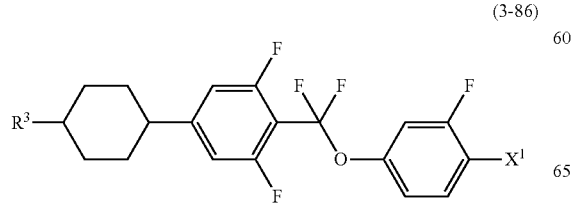
(3-87) 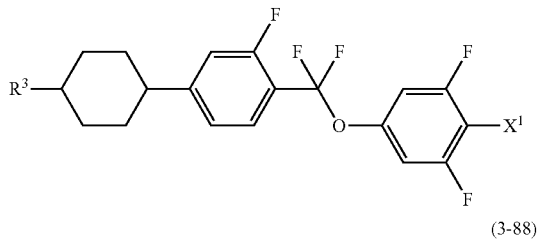
(3-88) 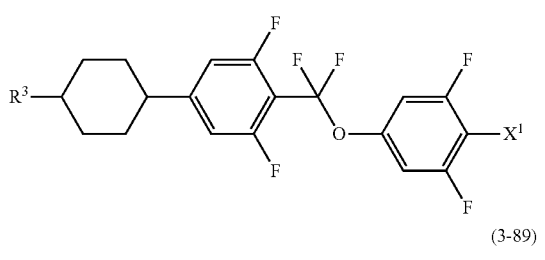
(3-89) 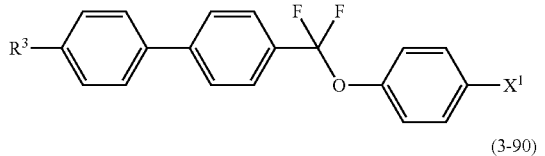
(3-90) 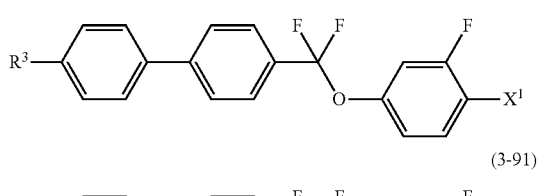
(3-91) 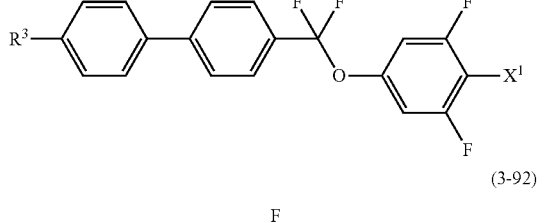
(3-92) 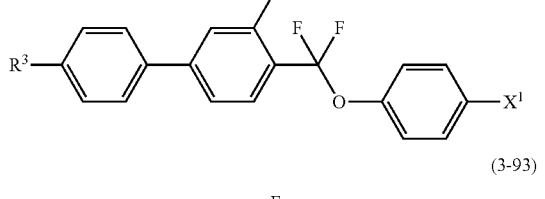
(3-93) 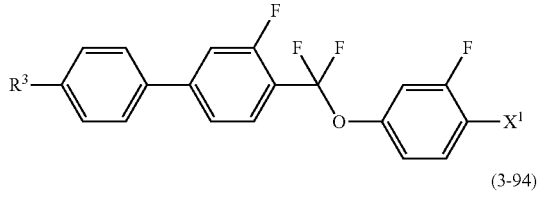
(3-94)

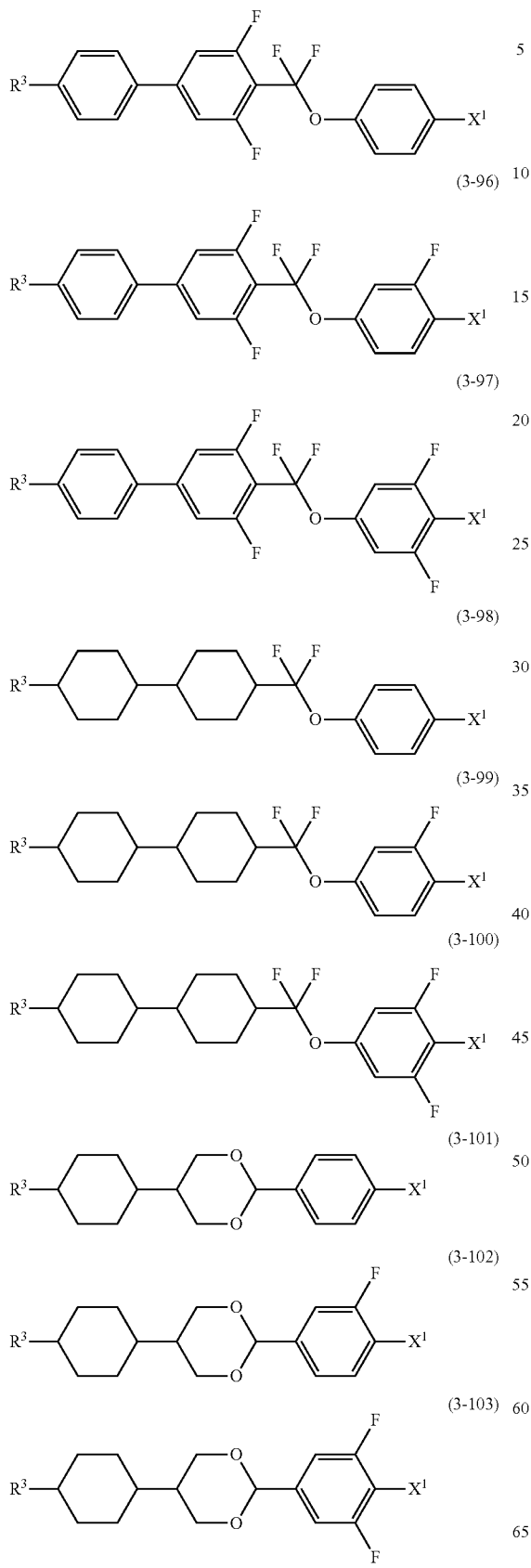
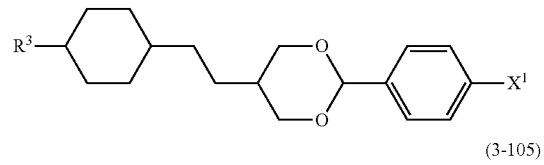
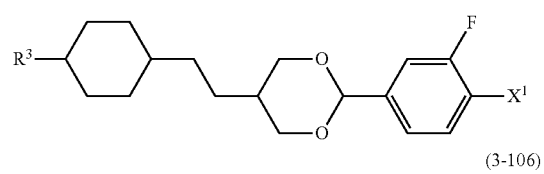
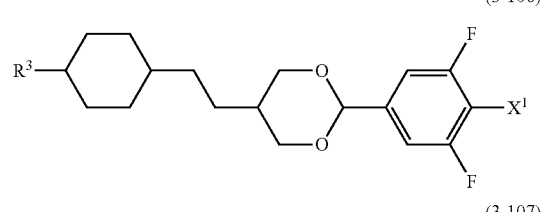
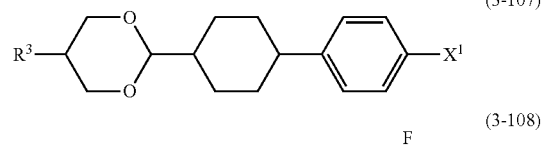
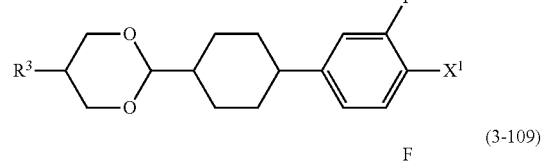
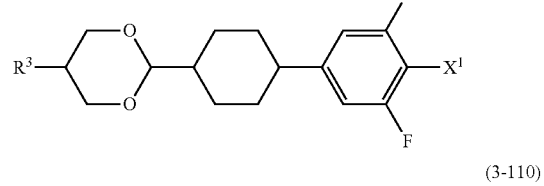
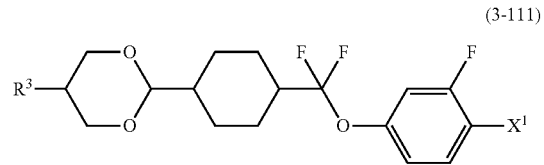
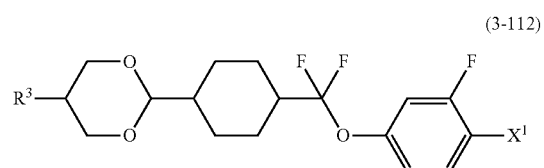
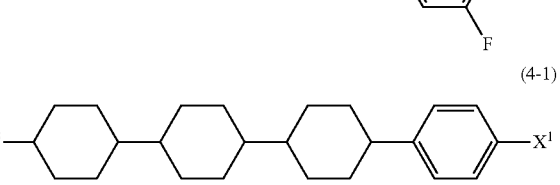

(4-2) 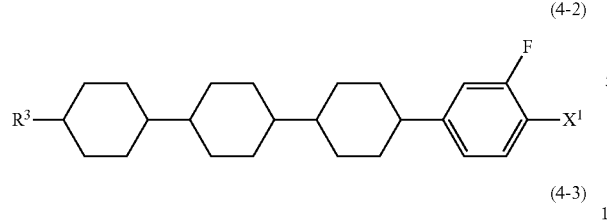
(4-3) 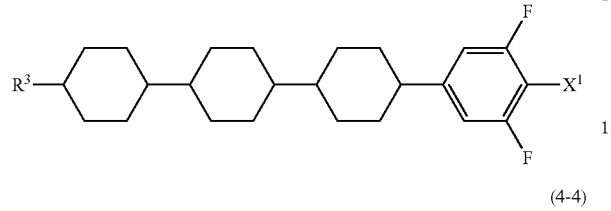
(4-4) 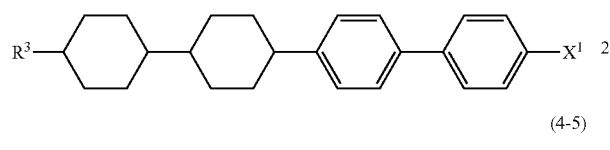
(4-5) 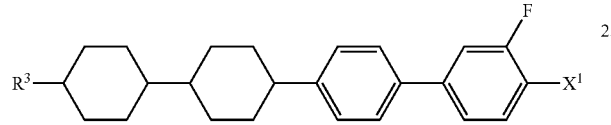
(4-6) 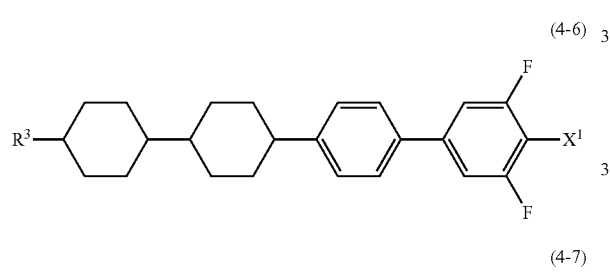
(4-7) 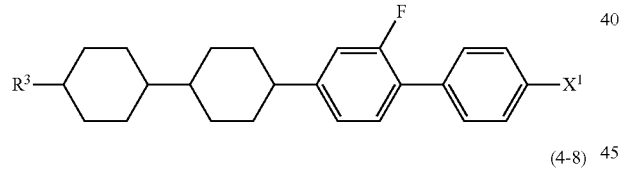
(4-8) 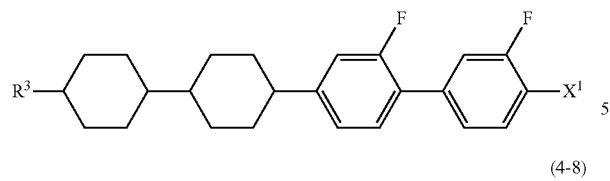
(4-8) 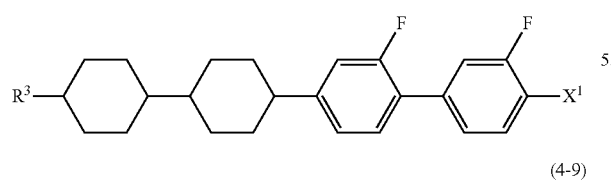
(4-9) 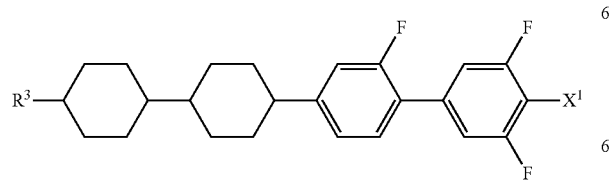
(4-10) 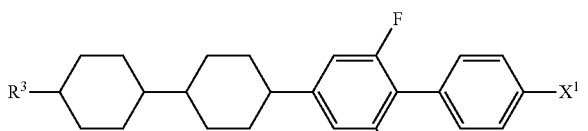
(4-11) 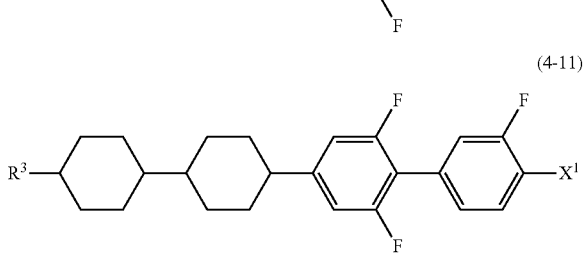
(4-12) 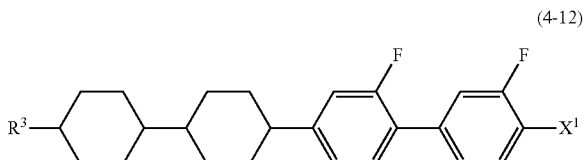
(4-13) 
(4-14) 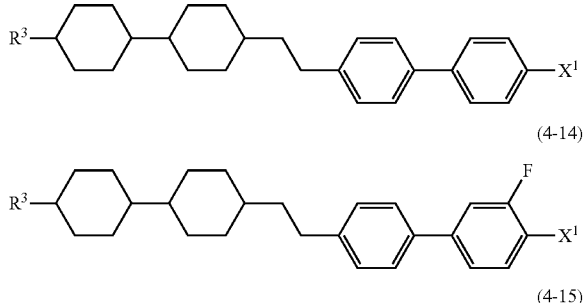
(4-15) 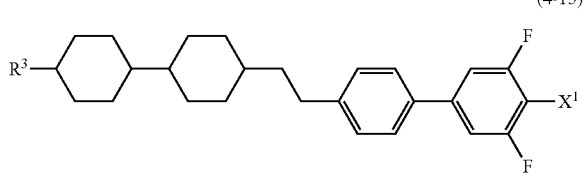
(4-16) 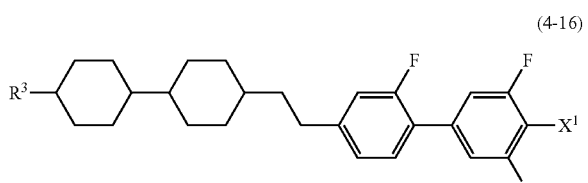
(4-17) 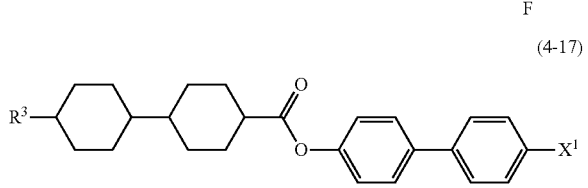
(4-18) 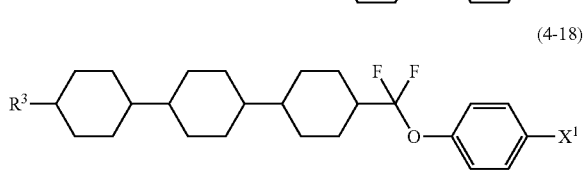

(4-19) 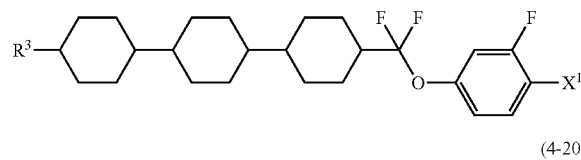
(4-20) 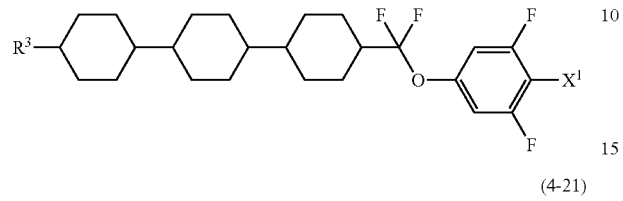
(4-21) 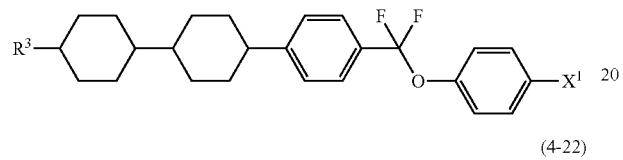
(4-22) 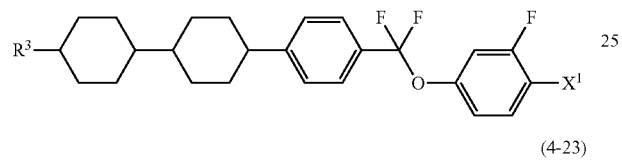
(4-23) 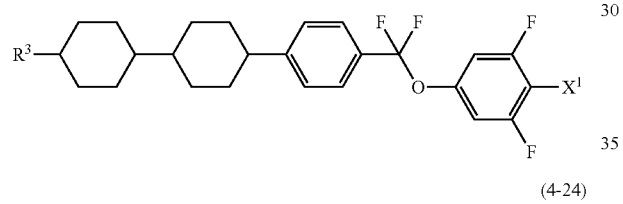
(4-24) 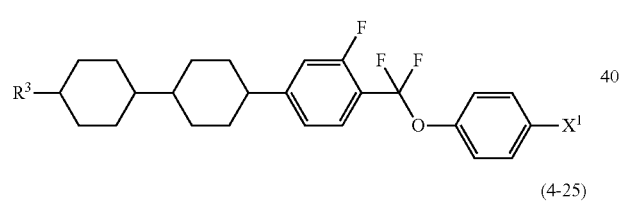
(4-25) 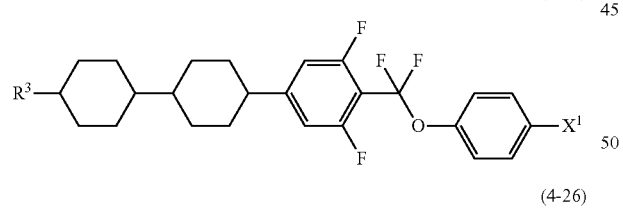
(4-26) 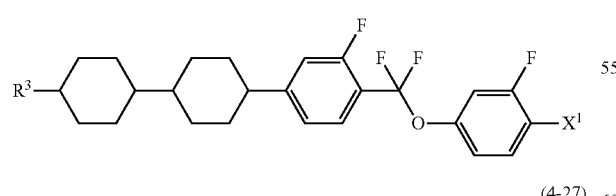
(4-27) 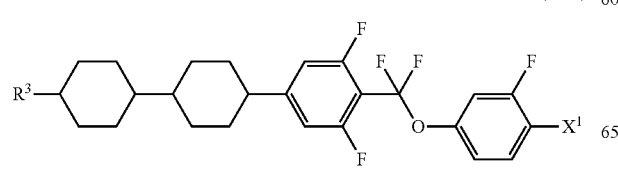
(4-28) 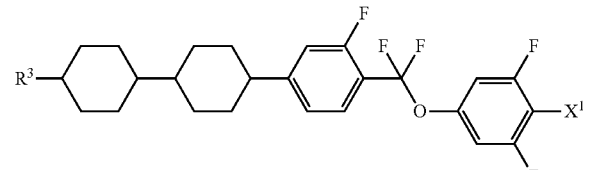
(4-29) 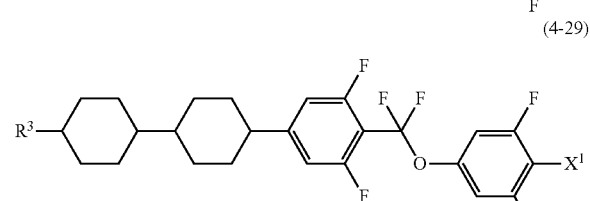
(4-30) 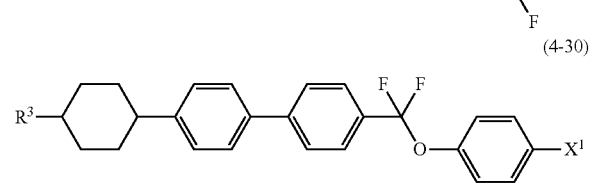
(4-31) 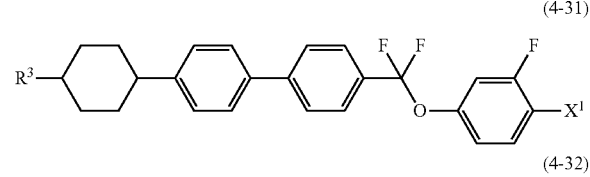
(4-32) 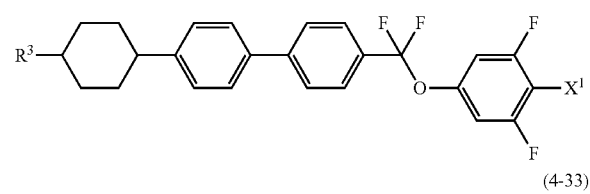
(4-33) 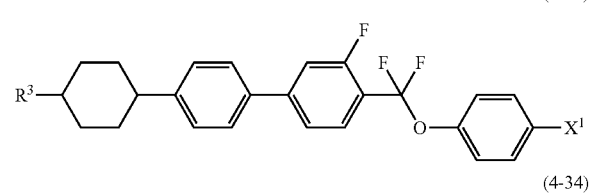
(4-34) 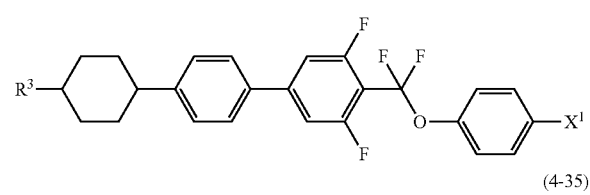
(4-35) 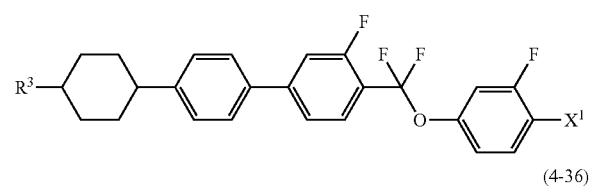
(4-36) 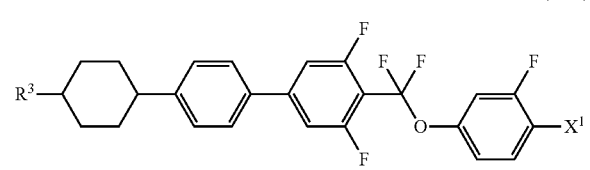

(4-37)
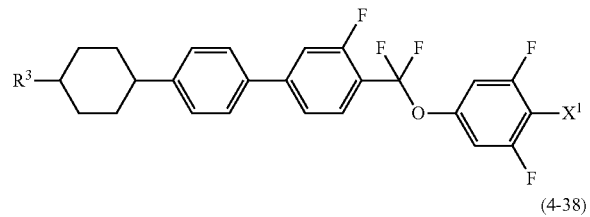
(4-38)
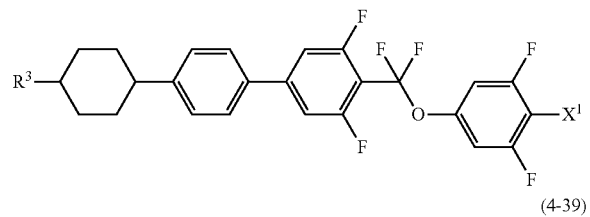
(4-39)
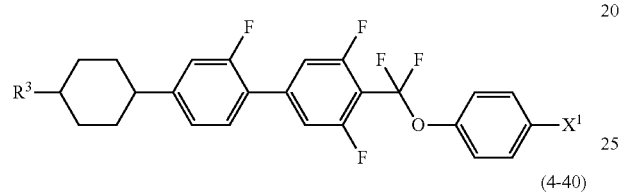
(4-40)
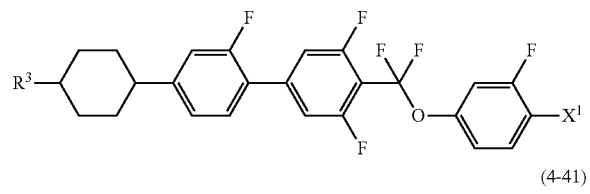
(4-41)
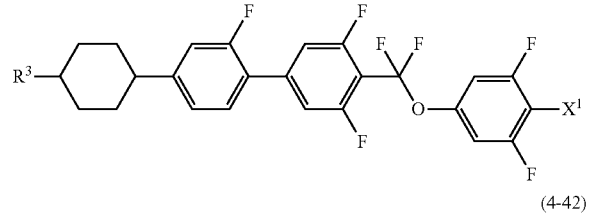
(4-42)
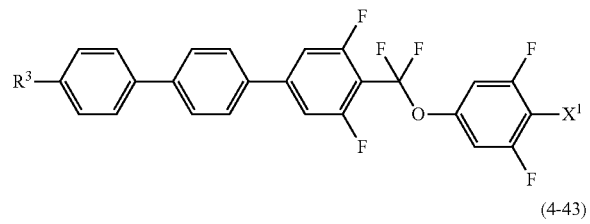
(4-43)
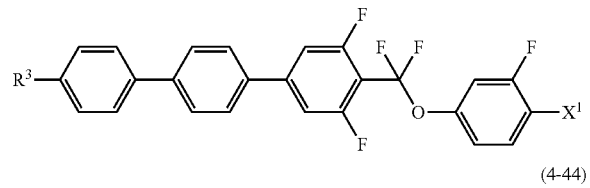
(4-44)
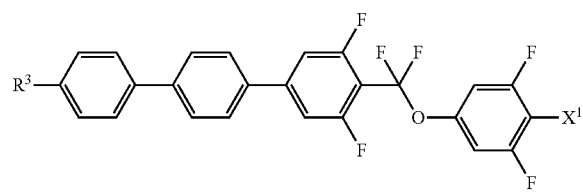
(4-45)
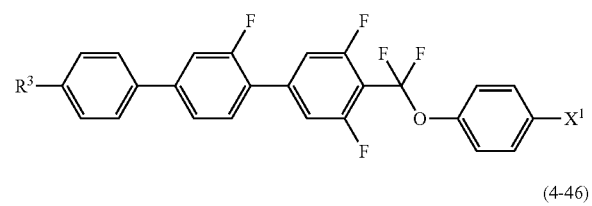
(4-46)
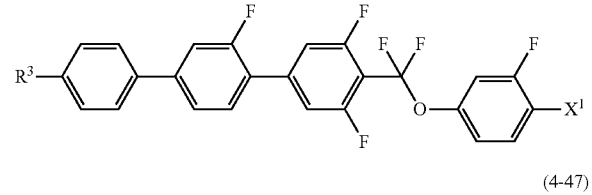
(4-47)
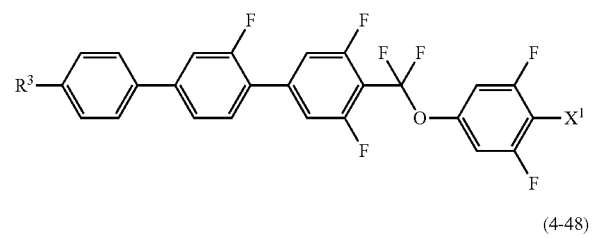
(4-48)
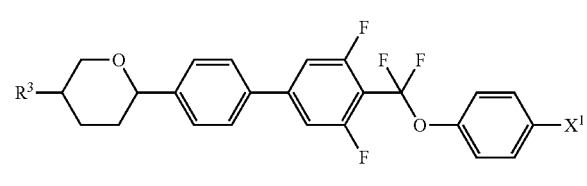
(4-49)
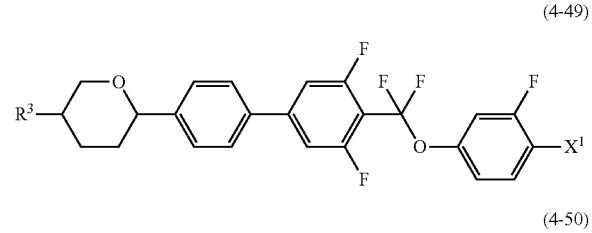
(4-50)
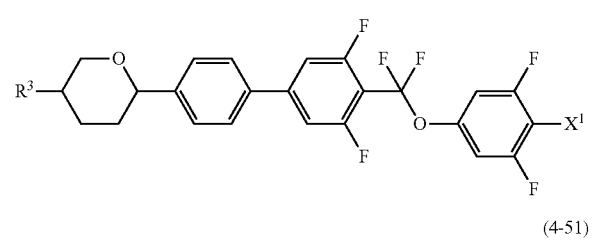
(4-51)
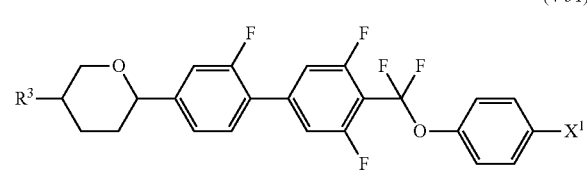
(4-52)
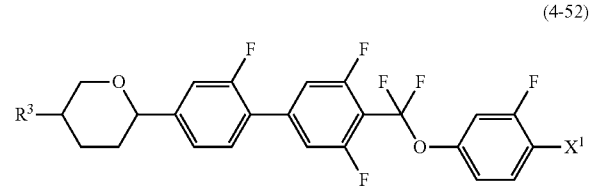

(4-53)

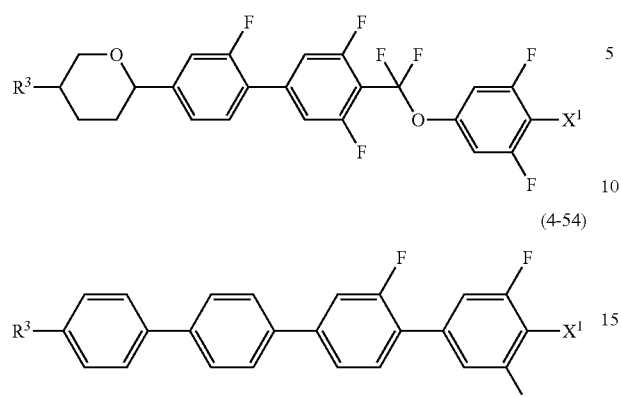

(4-54)

In the formulas, $R^3$ and $X^1$ have the same meanings as described above.

These compounds represented by formulas (2) to (4), that is the component B, are used in the preparation of the liquid crystal composition for use in a TFT mode and a PSA mode, since they have positive dielectric anisotropy and an especially excellent thermal or chemical stability. The content of the component B in the liquid crystal composition is suitably in the range of 1% to 99% by weight, preferably in the range of 10% to 97% by weight, and more preferably 40% to 95% by weight based on the total weight of the liquid crystal composition. The viscosity can be adjusted by a further addition of the compounds (12) to (14) (the component E).

Desirable examples of the compound represented by formula (5), that is the component C, include formulas (5-1) to (5-64).

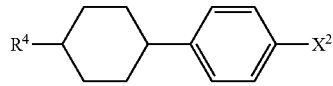
(5-1)

(5-2)

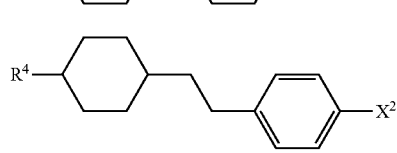
(5-3)

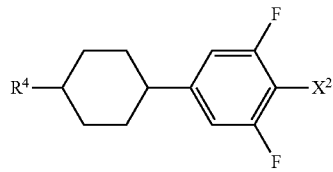
(5-4)

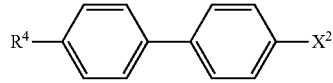
(5-5)

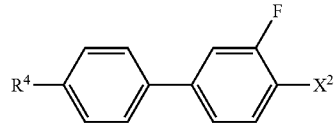
(5-6)

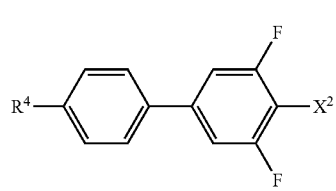
(5-7)

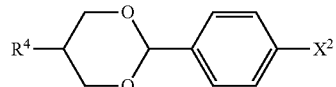
(5-8)

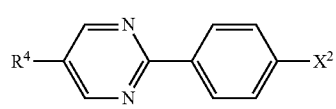
(5-9)

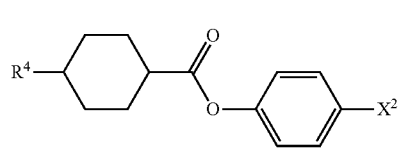
(5-10)

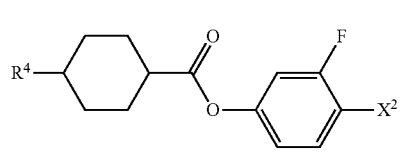
(5-11)

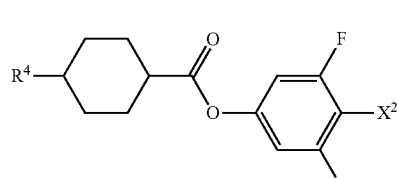
(5-12)

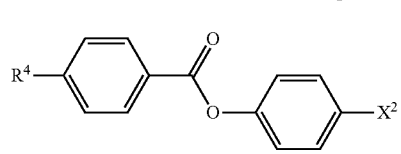
(5-13)

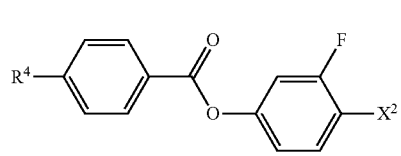
(5-14)

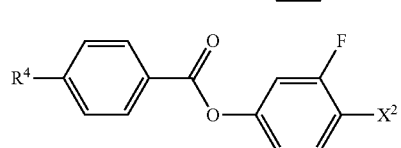
(5-15)

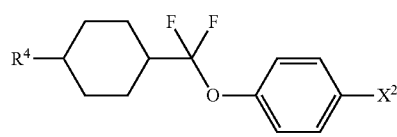
(5-16)

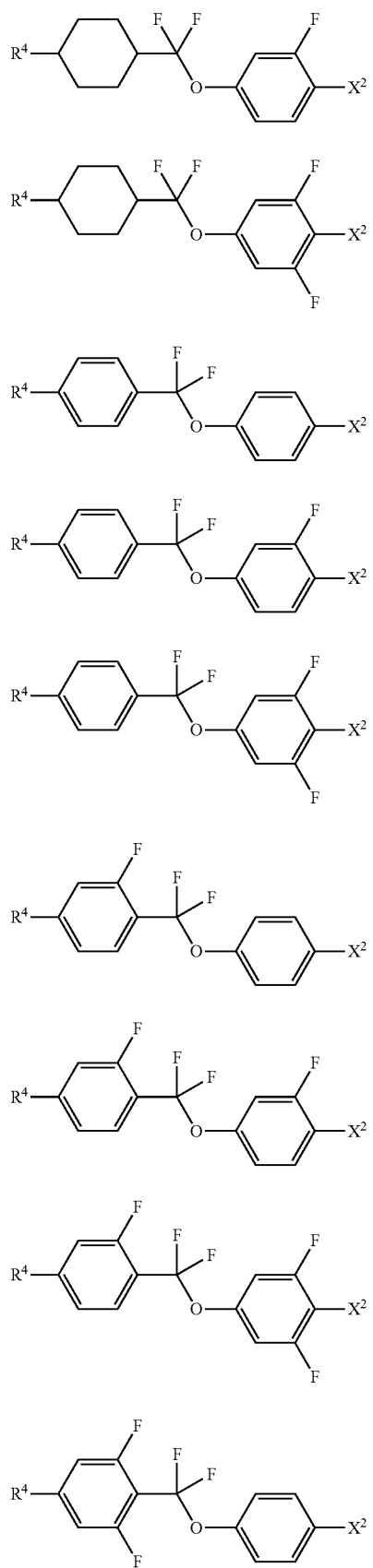
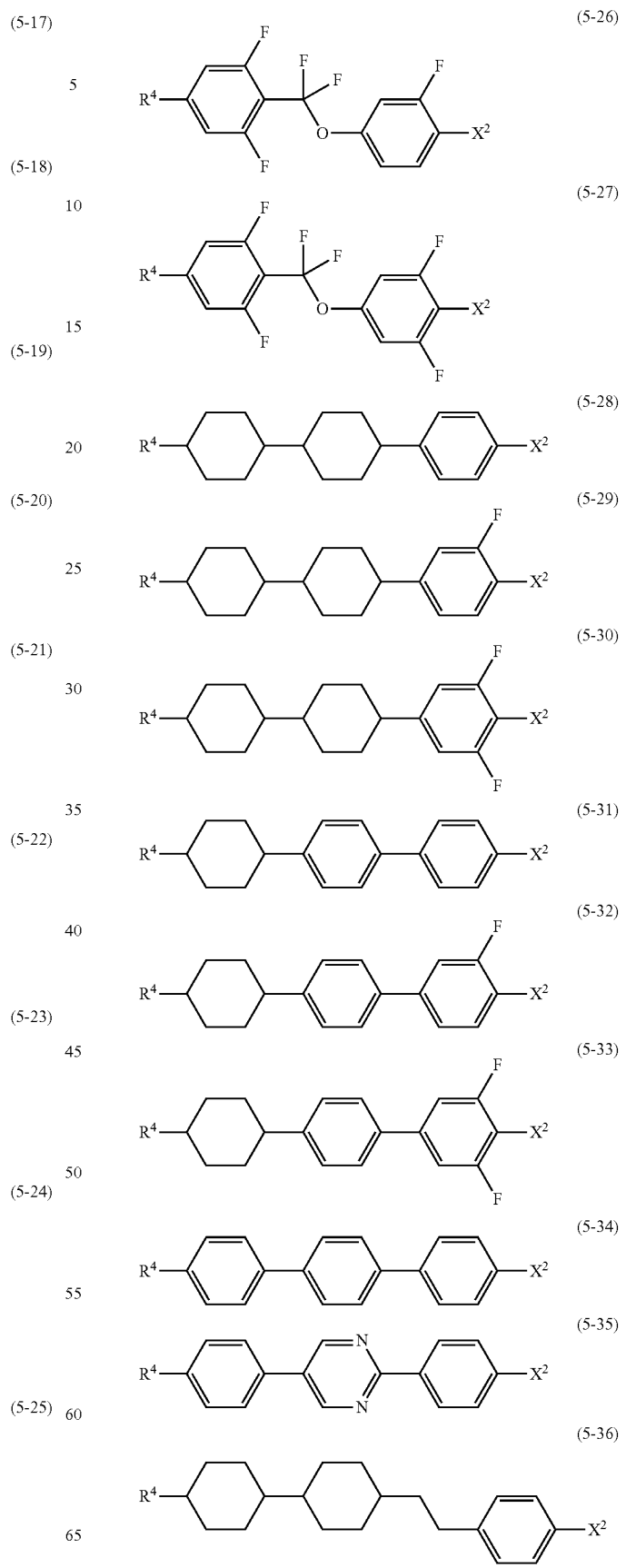

(5-37) 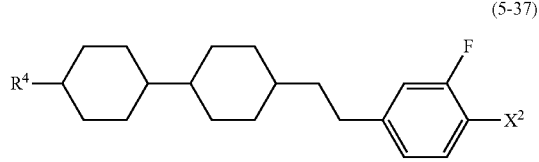
(5-38) 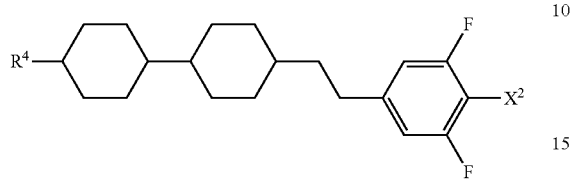
(5-39) 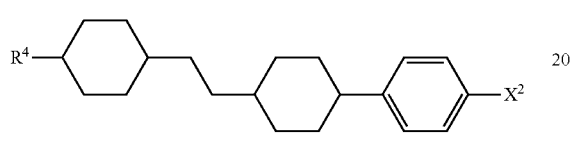
(5-40) 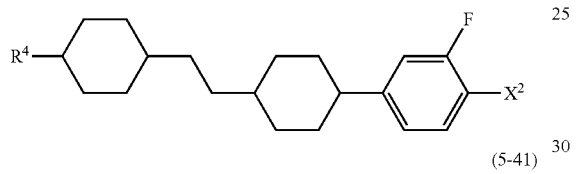
(5-41) 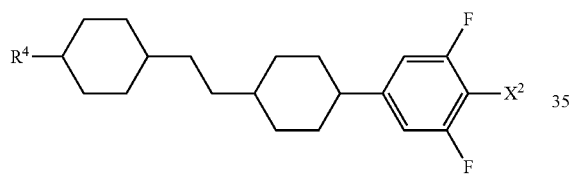
(5-42) 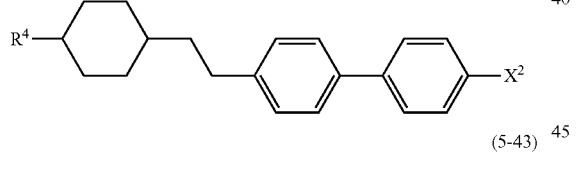
(5-43) 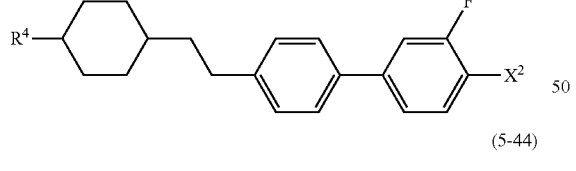
(5-44) 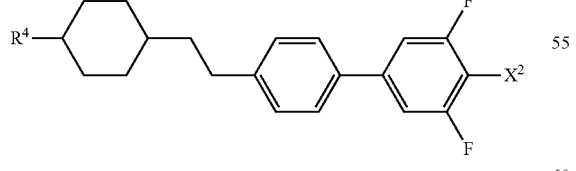
(5-45) 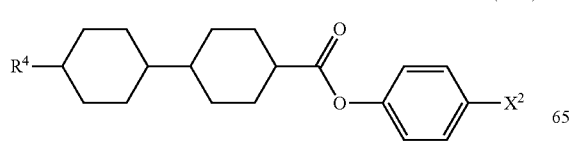
(5-46) 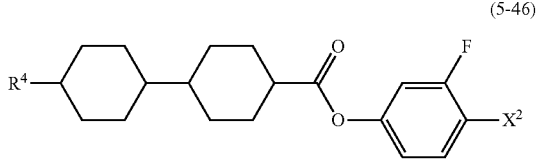
(5-47) 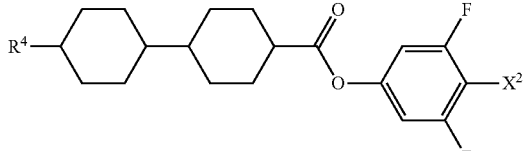
(5-48) 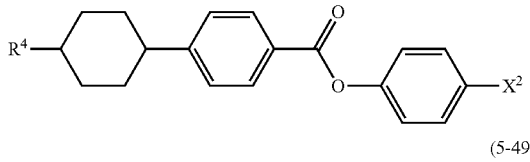
(5-49) 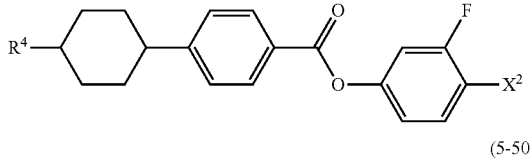
(5-50) 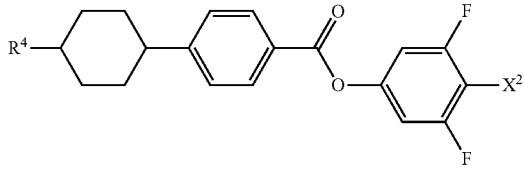
(5-51) 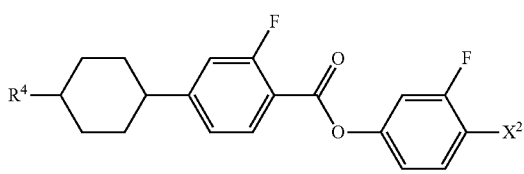
(5-52) 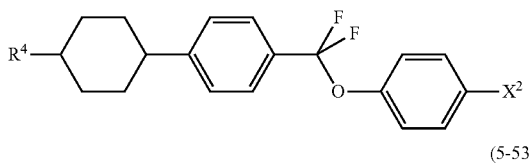
(5-53) 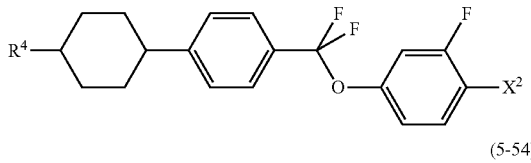
(5-54) 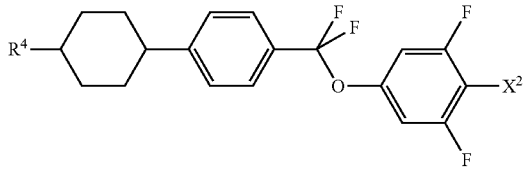

(5-55)
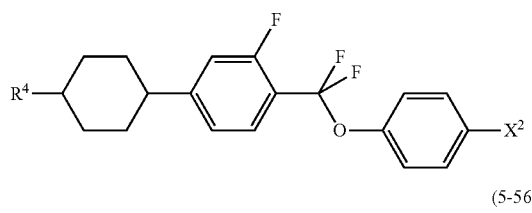

(5-56)
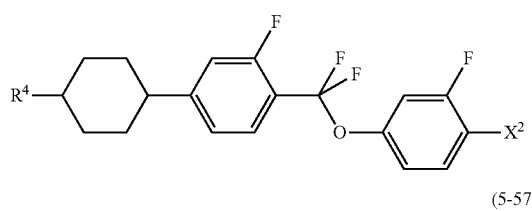

(5-57)

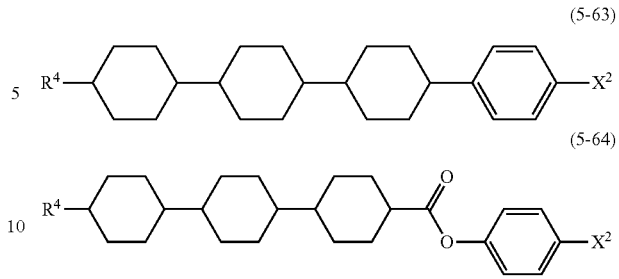
(5-63)

(5-64)

In the formulas, $R^4$ and $X^2$ have the same meanings as described above.

In formula (5), two of the ring $C^2$ may be the same or different when o is 2.

The compound represented by formula (5), that is the component C, is mainly used in the preparation of the liquid crystal composition for use in a STN mode, a TN mode and a PSA mode, since the dielectric anisotropy is positive and the value is quite large. The threshold voltage of the composition can be decreased by the addition of the component C. The viscosity can be adjusted, the refractive index anisotropy can be adjusted, and the temperature range of a liquid crystal phase can be increased. Furthermore, the component C can also be utilized for an improvement of the steepness.

The content of the component C is suitably in the range of 0.1% to 99.9% by weight, preferably in the range of 10% to 97% by weight, and more preferably in the range of 40% to 95% by weight in the preparation of the liquid crystal composition for use in a STN or TN mode. The threshold voltage, the temperature range of a liquid crystal phase, the refractive index anisotropy, the dielectric anisotropy, the viscosity and so forth can be adjusted by the addition of a component which will be described below.

The component D, which is at least one compound selected from the group of compounds represented by formulas (6) to (11), is desirable in the preparation of the liquid crystal composition having negative dielectric anisotropy for use in a VA (vertical alignment) mode, a PSA (polymer sustained alignment) mode and so forth.

Desirable examples of the compounds represented by formulas (6) to (11) (the component D) include formulas (6-1) to (6-6), (7-1) to (7-15), (8-1), (9-1) to (9-3), (10-1) to (10-11) and (11-1) to (11-10).

(5-58)

(5-59)

(5-60)

(5-61)
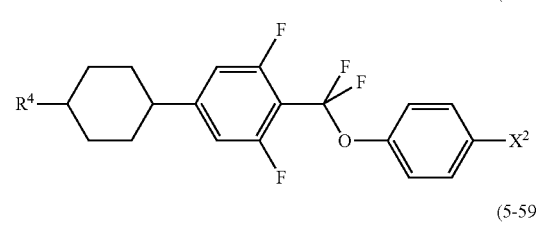

(5-62)
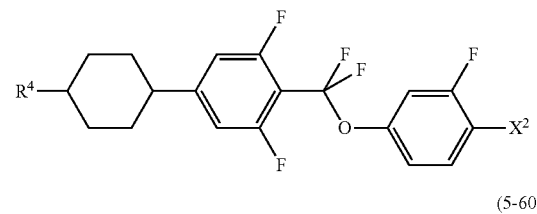

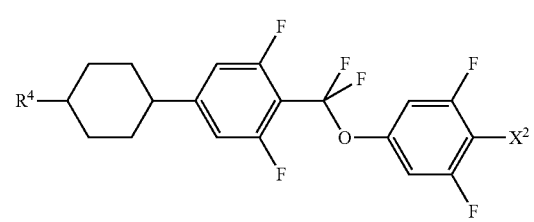

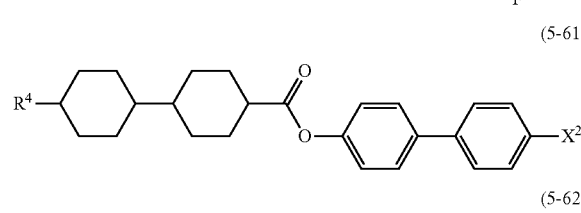

(6-1)

(6-2)

(6-3)

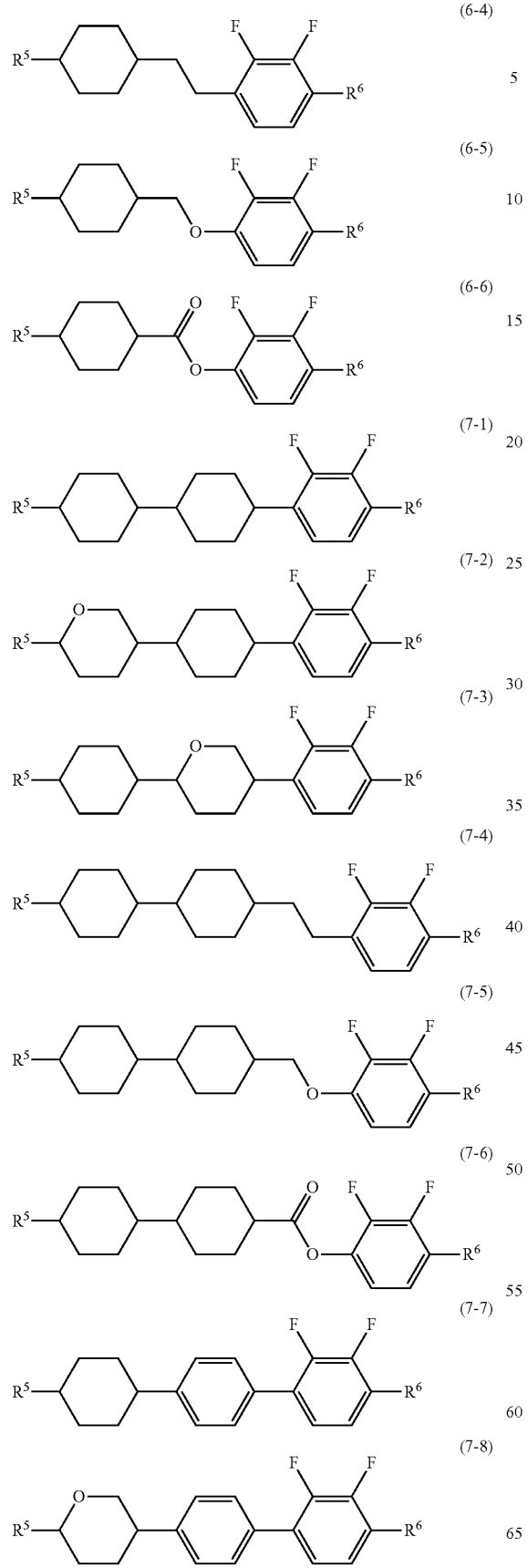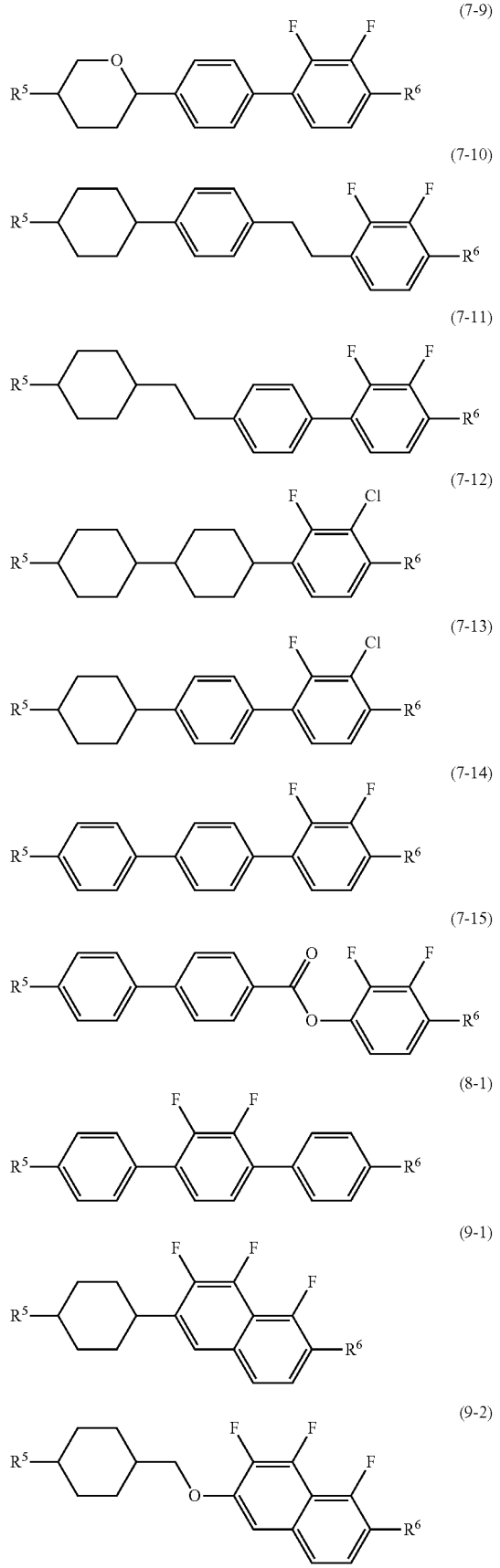

(9-3)
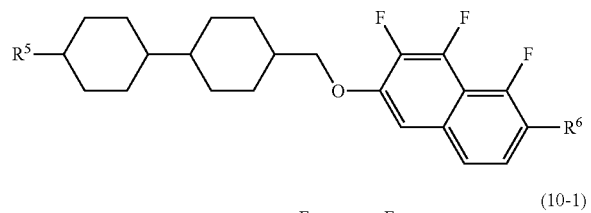
(10-1)
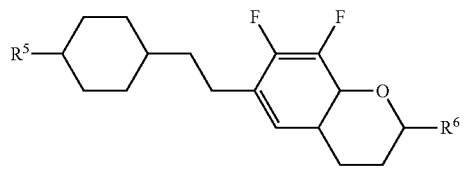
(10-2)
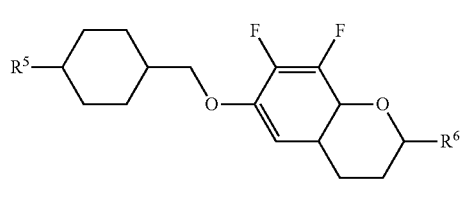
(10-3)
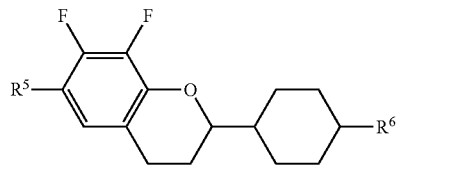
(10-4)
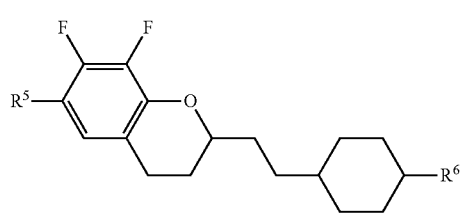
(10-5)
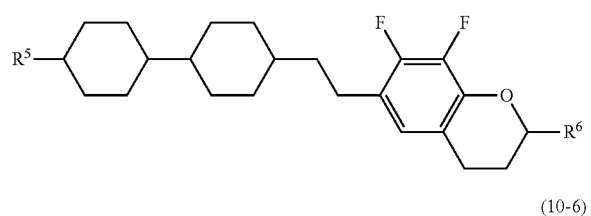
(10-6)
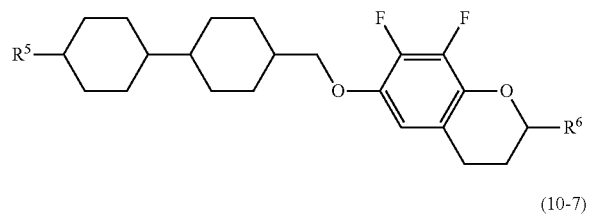
(10-7)
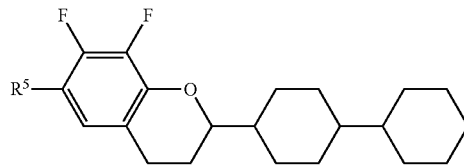
(10-8)
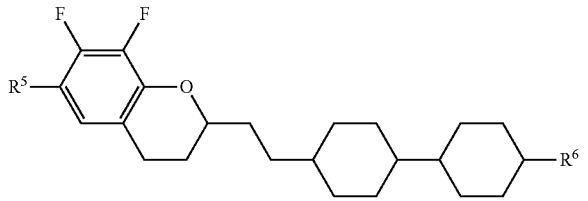
(10-9)
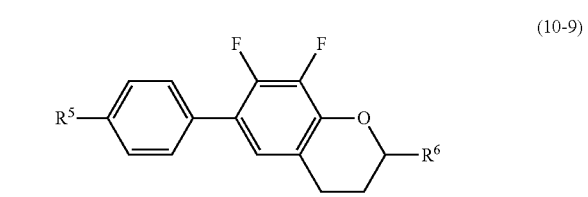
(10-10)
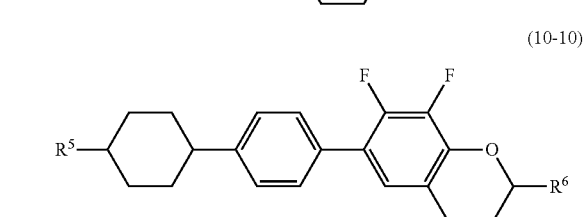
(10-11)
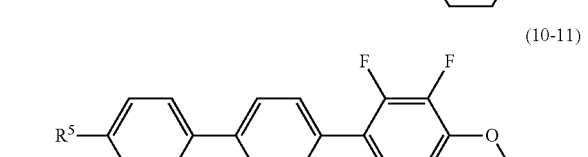
(11-1)
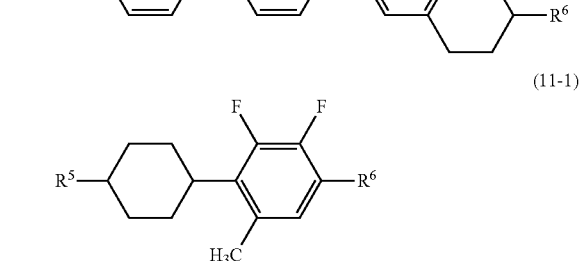
(11-2)
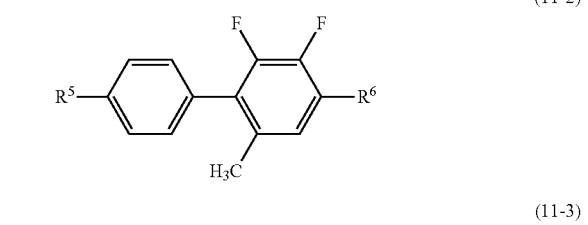
(11-3)
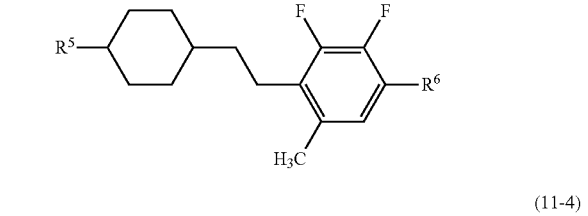
(11-4)

-continued

(11-5)

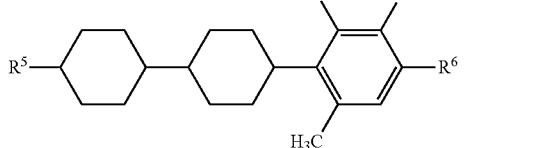
(11-6)

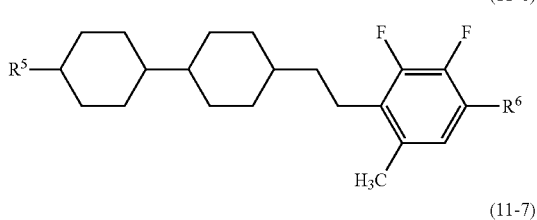
(11-7)

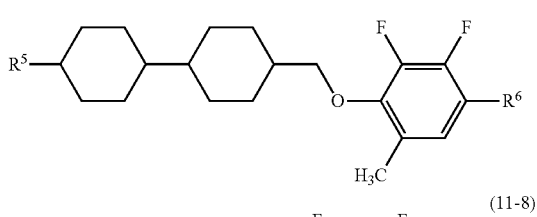
(11-8)

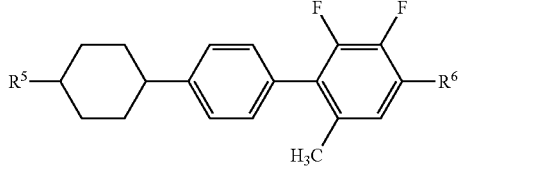
(11-9)

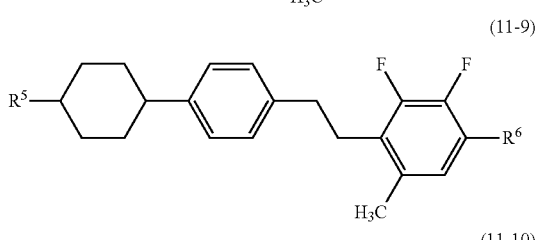
(11-10)

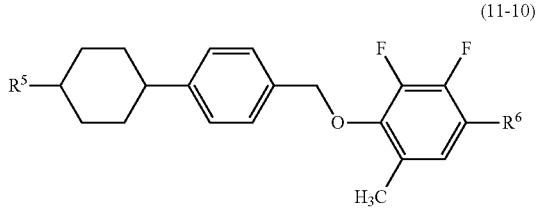

In the formulas, $R^5$ and $R^6$ have the same meanings as described above.

The compounds of the component D are mainly used in the liquid crystal composition having negative dielectric anisotropy for use in a VA mode and a PSA mode. As the content of the component D is increased, the threshold voltage of the composition decreases, however, the viscosity increases. Accordingly, it is desirable that the content of the component D decreases as long as the required value of the threshold is satisfied. On the other hand, there are cases where sufficient voltage drive may not be attained in the content less than 40% by weight, since the absolute value of the dielectric anisotropy is about 5.

The compound represented by formula (6) among the component D is effective mainly in adjusting the threshold voltage, adjusting the viscosity, or adjusting the refractive index anisotropy, since it is a two-ring compound. The compounds represented by formulas (7) and (8) are effective in increasing the clearing point, increasing the temperature range of a nematic phase, decreasing the threshold voltage or increasing the optical anisotropy for instance, since it is a three-ring compound. The compounds represented by formulas (9), (10) and (11) are effective in decreasing the threshold voltage for instance.

The content of the component D is preferably in the range of 40% to 99% by weight, and more preferably in the range of 50% to 95% by weight based on the total amount of the composition, in the preparation of the composition for use in a VA and PSA mode. The elastic constant can be adjusted and the voltage-transmission curve of the composition can be adjusted by the addition of the component D. It is desirable that the content of the component D is 30% by weight or less based on the total amount of the composition when the component D is added to a composition having positive dielectric anisotropy.

Desirable examples of the compounds represented by formulas (12), (13) and (14) (the component E) include formulas (12-1) to (12-11), (13-1) to (13-19) and (14-1) to (14-6), respectively.

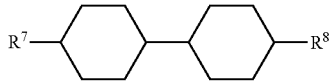
(12-1)

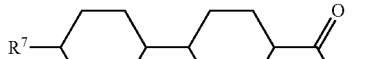
(12-2)

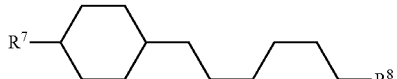
(12-3)

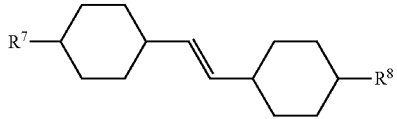
(12-4)

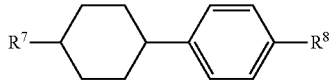
(12-5)

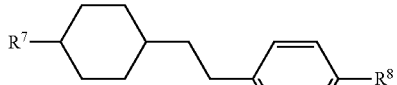
(12-6)

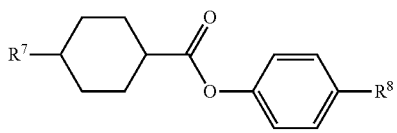
(12-7)

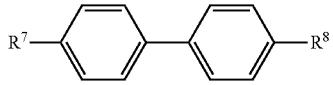
(12-8)

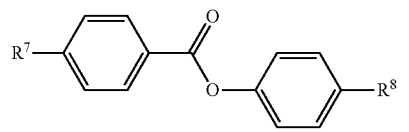
(12-9)
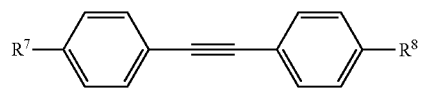
(12-10)
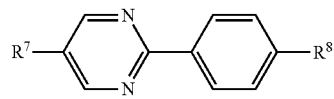
(12-11)
(13-1)
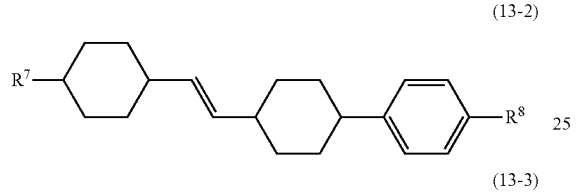
(13-2)
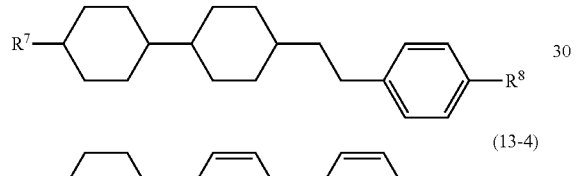
(13-3)
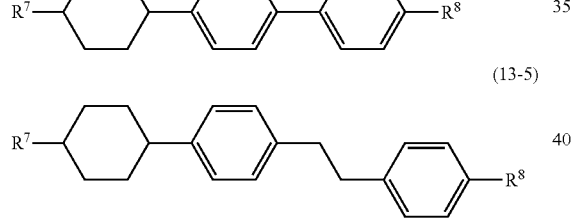
(13-4)
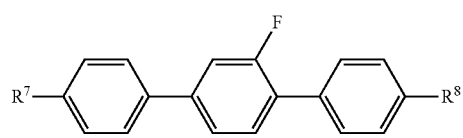
(13-5)
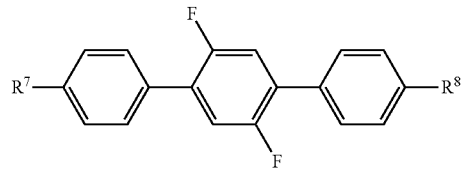
(13-6)
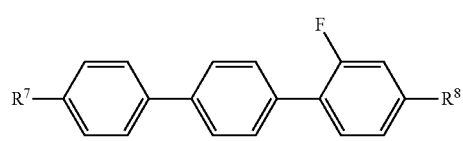
(13-7)
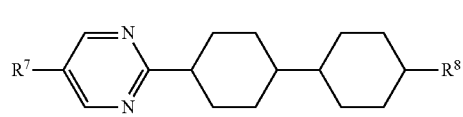
(13-8)
(13-9)
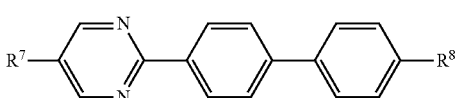
(13-10)
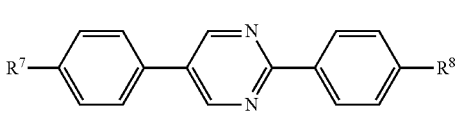
(13-11)
(13-12)
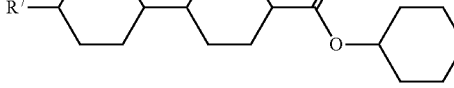
(13-13)
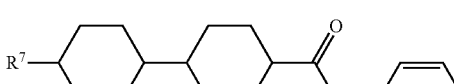
(13-14)
(13-15)
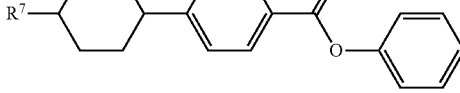
(13-16)
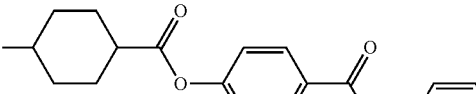
(13-17)
(13-18)
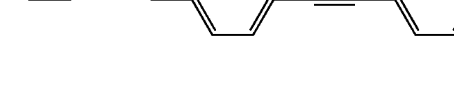
(13-19)
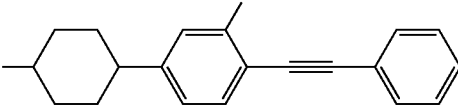
(14-1)
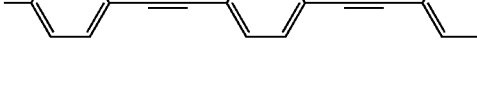
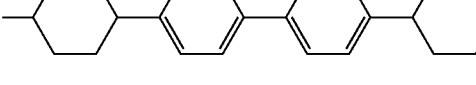

-continued (14-2)
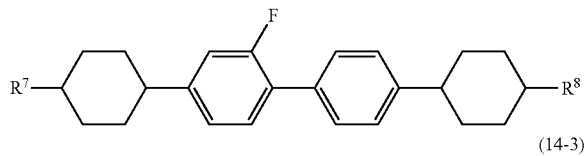

(14-3)
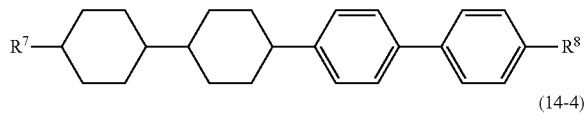

(14-4)
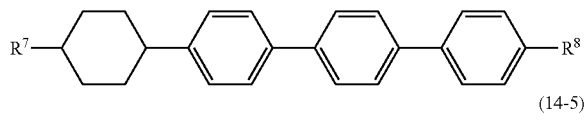

(14-5)
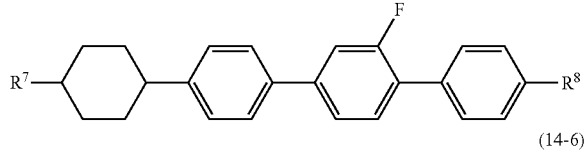

(14-6)
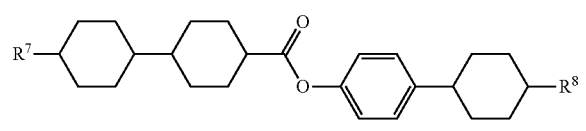

In the formulas, $R^7$ and $R^8$ have the same meanings as described above.

The compounds represented by formulas (12) to (14) (the component E) are close to neutral, since the absolute value of the dielectric anisotropy is small. The compound represented by formula (12) is effective mainly in adjusting the viscosity or adjusting the refractive index anisotropy, and the compounds represented by formulas (13) and (14) are effective in increasing the temperature range of a nematic phase that is caused by an increase in the clearing point for instance, or adjusting the refractive index anisotropy.

As the content of the component E is increased, the threshold voltage of the liquid crystal composition increases and the viscosity decreases. Accordingly, it is desirable that the content increases as long as the required value of the threshold voltage of the liquid crystal composition is satisfied. The content of the component E is preferably 30% by weight or more, and more preferably 50% by weight or more based on the total amount of the composition, in the preparation of the liquid crystal composition for use in a TFT or PSA mode. The content of the component E is preferably 30% by weight or more, and more preferably 40% by weight or more based on the total amount of the composition, in the preparation of the liquid crystal composition for use in a TN mode, a STN mode or a PSA mode.

It is desirable that the liquid crystal composition includes at least one of the compound represented by formula (1) in the range of 0.1% to 99% by weight for exhibiting excellent characteristics.

The liquid crystal composition is generally prepared according to known methods such as the mutual dissolution of necessary components at a high temperature, for example. An additive that is well-known to a person skilled in the art may be added to the composition depending on its intended use. For example, a liquid crystal composition including an optically active compound, or including a polymerizable compound and a polymerization initiator, those of which will be described below, or a liquid crystal composition for use in a GH mode, to which a dye is added, can be prepared. The additive is generally well known to a person skilled in the art, and is described in the literature and so forth in detail.

One or more optically active compounds may be added to the liquid crystal composition of the invention which is descried above.

A known chiral dopant is added as an optically active compound. The chiral dopant is effective in inducing a helical structure in liquid crystals, adjusting a necessary twist angle and thus preventing a reverse twist. Examples of the chiral dopant include the following optically active compounds (Op-1) to (Op-13).

(Op-1)
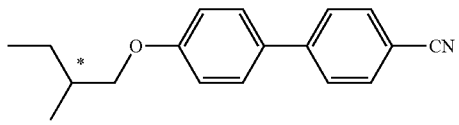

(Op-2)
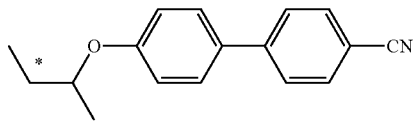

(Op-3)
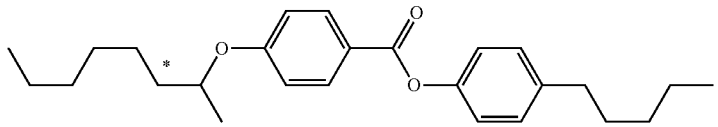

(Op-4)
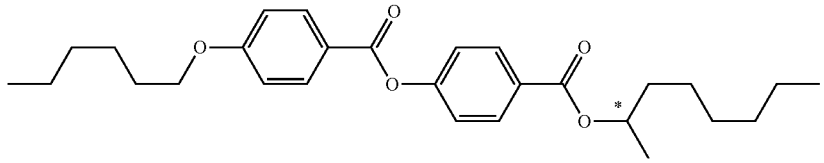

-continued (Op-5)
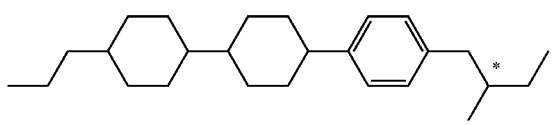

(Op-6)
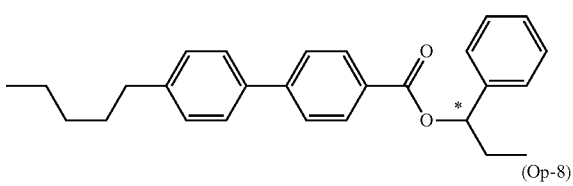

(Op-7)
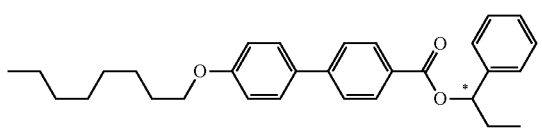

(Op-8)
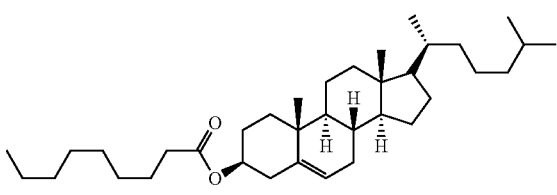

(Op-9)
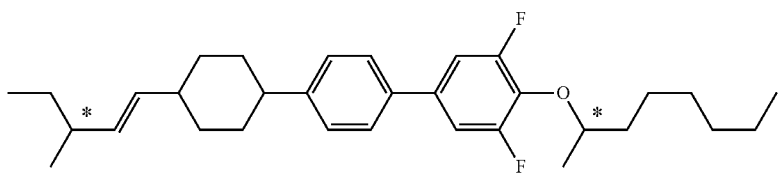

(Op-10)
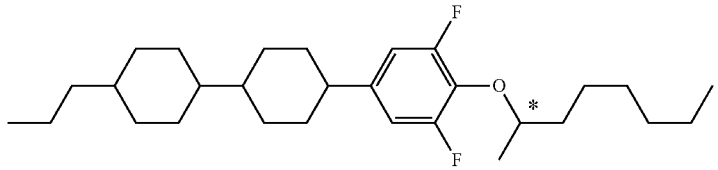

(Op-11)
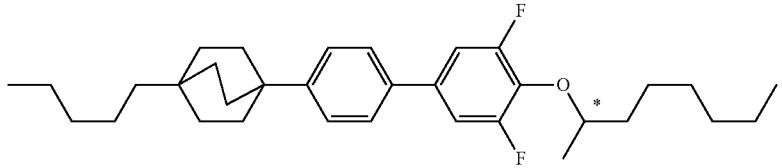

(Op-12)
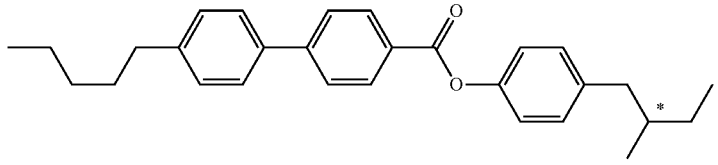

(Op-13)
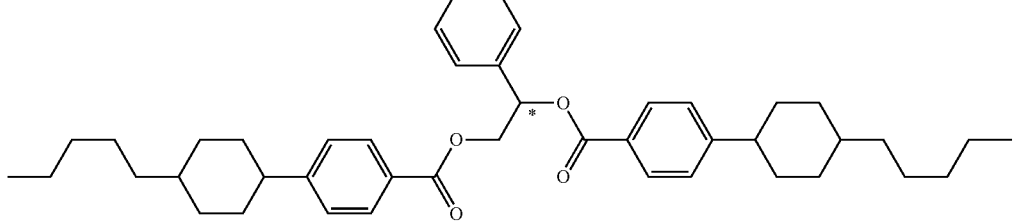

A helical pitch is usually adjusted by the addition of this optically active compound to the liquid crystal composition. It is desirable to adjust the helical pitch to the range of 40 micrometers to 200 micrometers in a liquid crystal composition for use in a TFT mode and a TN mode. It is desirable to adjust the helical pitch to the range of 6 micrometers to 20 micrometers in a liquid crystal composition for use in a STN mode. It is desirable to adjust the helical pitch to the range of 1.5 micrometers to 4 micrometers for use in a BTN (bistable twisted nematic) mode. Two or more optically active compounds may be added for the purpose of adjusting the temperature dependence of the helical pitch.

The liquid crystal composition of can be used for use in a GH mode by the addition of a dichroic dye such as a merocyanine, stylyl, azo, azomethine, azoxy, quinophthalone, anthraquinone or tetrazine compound.

The liquid crystal composition can be used for a NCAP-device prepared by micro-encapsulating nematic liquid crystals, and for a polymer-distributed liquid crystal display device (PDLCD) prepared by forming a three-dimensional network polymer in liquid crystals, such as a polymer network liquid crystal display device (PNLCD), and also for use in an ECB (electrically controlled birefringence) mode or a DS mode.

The liquid crystal composition can be used as a liquid crystal composition for use in a PSA (polymer sustained alignment) mode by the addition of a polymerizable compound. Examples of the polymerizable compound include compounds having polymerizable groups such as acrylates, methacrylates, vinyl compounds, vinyloxy compounds, propenyl ethers, epoxy compounds, vinyl ketones and oxetanes. The polymerizable compound is polymerized on irradiation with ultraviolet light or the like, preferably in the presence of a suitable initiator such as a photopolymerization initiator. Suitable conditions for the polymerization, and a suitable type and a suitable amount of the initiator are known to a person skilled in the art and are described in the literature. For example, Irgacure 651 (registered trademark), Irgacure 184 (registered trademark) or Darocure 1173 (registered trademark) (Ciba Japan K.K.), each of which is a photo-initiator, is suitable for radical polymerization.

The invention will be explained below in more detail by way of examples. In each example, the symbols C, SA, SB, SX, N and I stand for crystals, a smectic A phase, a smectic B phase, a smectic phase which the phase structure is not yet analyzed, a nematic phase and an isotropic phase, respectively. The degree Celsius (° C.) was used for the unit of the phase transition temperature.

EXAMPLES

The invention will be explained below in more detail based on examples. However, the invention is not limited to the examples. The term "%" means "% by weight," unless otherwise noted.

Analytical methods will be explained first, since the resulting compounds herein were identified on the basis of nuclear magnetic resonance spectra obtained by means of $^1$H-NMR analysis, gas chromatograms obtained by means of gas chromatography (GC) analysis and so forth.

$^1$H-NMR Analysis:

A model DRX-500 apparatus (made by Bruker BioSpin Corporation) was used for measurement. Samples prepared in the examples and so forth were dissolved in deuterated solvents such as $CDCl_3$ in which the samples were soluble, and the measurement was carried out under the conditions of room temperature, twenty-four times of accumulation and 500 MHz. Tetramethylsilane (TMS) was used as the standard reference material for the zero point of the chemical shift (δ values).

GC Analysis

A Gas Chromatograph Model GC-14B made by Shimadzu Corporation was used for measurement. A capillary column CBP1-M25-025 (length 25 m, bore 0.22 mm, film thickness 0.25 micrometer; dimethylpolysiloxane as a stationary liquid phase; non-polar) made by Shimadzu Corporation was used. Helium was used as a carrier gas, and its flow rate was adjusted to 1 ml per minute. The temperature of the sample injector was set at 280° C. and the temperature of the detector (FID) was set at 280° C.

A sample was dissolved in toluene to give a 1% by weight solution, and then 1 microliter of the resulting solution was injected into the sample injector.

Chromatopac Model C-R6A made by Shimadzu Corporation or its equivalent was used as a recorder. The obtained gas chromatogram showed the retention time of the peaks and the values of the peak areas corresponding to the component compounds.

Incidentally, chloroform or hexane, for example, may also be used as a solvent for diluting the sample. The following capillary columns may also be used: DB-1 (length 30 m, bore 0.32 mm, film thickness 0.25 micrometer) made by Agilent Technologies Inc., HP-1 (length 30 m, bore 0.32 mm, film thickness 0.25 micrometer) made by Agilent Technologies Inc., Rtx-1 (length 30 m, bore 0.32 mm, film thickness 0.25 micrometer) made by Restek Corporation, BP-1 (length 30 m, bore 0.32 mm, film thickness 0.25 micrometer) made by SGE International Pty. Ltd, and so forth.

The ratio of the peak areas in the gas chromatogram corresponds to the ratio of component compounds. In general, the percentage by weight of each component compound in an analytical sample is not completely the same as the percentage of each peak area in the analytical sample. In the invention, however, the percentage by weight of the component compound in the analytical sample corresponds substantially to the percentage of the peak area in the analytical sample, because the correction coefficient is essentially 1 (one) when the columns described above are used.

Samples for the Measurement of the Physical Properties of Liquid Crystal Compounds and so Forth Two kinds of samples are used for measuring the physical properties of a liquid crystal compound: one is the compound itself, and the other is a mixture of the compound and mother liquid crystals.

In the latter case using a sample in which the compound is mixed with mother liquid crystals, the measurement is carried out according to the following method. First, the sample is prepared by mixing 15% by weight of the liquid crystal compound obtained and 85% by weight of the mother liquid crystals. Then, extrapolated values are calculated from the measured values of the resulting sample by means of an extrapolation method based on the following formula. The extrapolated values are regarded as the physical properties of this compound.

[Extrapolated value]=(100×[Measured value of sample]−[% by weight of mother liquid crystals]×[Measured value of mother liquid crystals])/[% by weight of liquid crystal compound]

When a smectic phase appears at 25° C. or crystals deposit at 25° C. even at this ratio of the liquid crystal compound to the mother liquid crystals, the ratio of the liquid crystal compound to the mother liquid crystals is changed in the order of (10% by weight: 90% by weight), (5% by weight: 95% by weight) and (1% by weight: 99% by weight). The physical properties of the sample are measured at the ratio in which the smectic phase does not appear at 25° C. or the crystals does not deposit at 25° C. Extrapolated values are determined according to the above equation, and are regarded as the physical properties of the liquid crystal compound.

There are a variety of mother liquid crystals used for measurement and, for example, each component (% by weight) of the mother liquid crystals (A) is shown below.

母液晶 A：

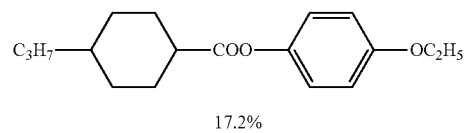

17.2%

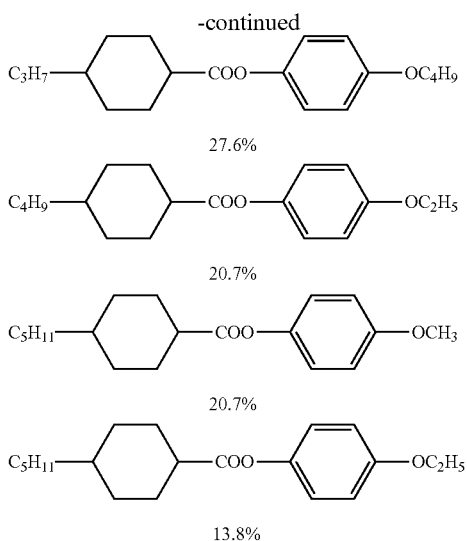

Incidentally, in the case where the physical properties of a liquid crystal composition were measured, the liquid crystal composition itself was used as a sample.

Methods for Measurements of the Physical Properties of Liquid Crystal Compounds and so Forth The physical properties of compounds were measured according to the following methods. Most are measurement methods described in the Standard of Electronic Industries Association of Japan, EIAJ•ED-2521A, or the modified methods. No TFT was attached to a TN device or a VA device used for measurement.

When a liquid crystal compound itself was employed as a sample, measured values was described here as experimental data. When a sample was prepared by mixing the liquid crystal compound with mother liquid crystals, values calculated from measured values according to the extrapolation method was described here as extrapolated values.

Phase Structure and Transition Temperature (° C.)

Measurements were carried out according to the following methods (1) and (2).

(1) A compound was placed on a hot plate of a melting point apparatus (Hot Stage Model FP-52 made by Mettler Toledo International Inc.) equipped with a polarizing microscope, and the phase conditions and their changes were observed with the polarizing microscope, specifying the kind of phase while the compound was heated at the rate of 3° C. per minute.

(2) A sample was heated and then cooled at the rate of 3° C. per minute using a Perkin-Elmer differential scanning calorimeter, a DSC-7 System or a Diamond DSC System. The starting point of an endothermic peak or an exothermic peak caused by the phase change of the sample was obtained by means of the extrapolation, and thus the phase transition temperature was determined.

Hereinafter, the symbol C stood for crystals, which were expressed by $C_1$ or $C_2$ when the kind of crystals were distinguishable. The symbols S and N stood for a smectic phase and a nematic phase, respectively. The symbol Iso stood for a liquid (isotropic). When a smectic B phase or a smectic A were distinguishable in the smectic phases, they were expressed as $S_B$ and $S_A$, respectively. Phase-transition temperatures were expressed as, for example, "C 50.0 N 100.0 Iso", which means that the phase-transition temperature from crystals to a nematic phase (CN) is 50.0° C., and the phase-transition temperature from the nematic phase to a liquid (NI) is 100.0° C. The same applied to the other transition temperatures.

Maximum Temperature of a Nematic Phase ($T_{NI}$; ° C.):

A sample (a liquid crystal composition, or a mixture of a liquid crystal compound and mother liquid crystals) was placed on a hot plate of a melting point apparatus (Hot Stage Model FP-52 made by Mettler Toledo International Inc.) equipped with a polarizing microscope, and was observed with the polarizing microscope while being heated at the rate of 1° C. per minute. A maximum temperature meant a temperature measured when part of the sample began to change from a nematic phase to an isotropic liquid. Hereinafter, the maximum temperature of a nematic phase may simply be abbreviated to "the maximum temperature."

Compatibility at Low Temperature:

Samples were prepared by mixing a liquid crystal compound with mother liquid crystals so that the amount of the liquid crystal compound became 20% by weight, 15% by weight, 10% by weight, 5% by weight, 3% by weight and 1% by weight, and were placed in glass vials. After these glass vials had been kept in a freezer at −10° C. or −20° C. for a certain period of time, they were observed as to whether or not crystals or a smectic phase had been deposited.

Viscosity (Bulk Viscosity; η; Measured at 20° C.; mPa·s)

It is characterized that as viscosity is decreased, response time decreases.

An E-type viscometer was used for measurement.

Viscosity (Rotational Viscosity; γ1; Measured at 25° C.; mPa·s)

It is characterized that as rotational viscosity is decreased, response time decreases.

Rotational viscosity was measured according to the method described in M. Imai, et al., Molecular Crystals and Liquid Crystals, vol. 259, p. 37 (1995). A sample (a liquid crystal composition, or a mixture of a liquid crystal compound and mother liquid crystals) was poured into a VA device in which the distance between two glass substrates (cell gap) was 20 micrometers. A voltage in the range of 30 V to 50 V was applied stepwise with an increment of 1 volt to the device. After a period of 0.2 second with no voltage, a voltage was applied repeatedly under the conditions of only one rectangular wave (rectangular pulse; 0.2 second) and no voltage (2 seconds). The peak current and the peak time of the transient current generated by the applied voltage were measured. The value of rotational viscosity was obtained from the measured values and the calculating equation (8) on page 40 of the paper presented by M. Imai, et al. Incidentally, the value of the dielectric anisotropy ($\Delta\in$) necessary for the present calculation was obtained by the method described below under the heading "Dielectric Anisotropy."

Refractive Index Anisotropy ($\Delta n$; Measured at 25° C.)

Measurement was carried out using an Abbe refractometer with a polarizing plate attached to the ocular, on irradiation with light at a wavelength of 589 nm at a temperature of 25° C. The surface of the main prism was rubbed in one direction, and then a sample (a liquid crystal composition, or a mixture of a liquid crystal compound and mother liquid crystals) was dropped onto the main prism. The refractive index (n∥) was measured when the direction of the polarized light was parallel to that of the rubbing. The refractive index (n⊥) was measured when the direction of polarized light was perpendicular to that of the rubbing. The value of the refractive index anisotropy was calculated from the equation: $\Delta n = n\| - n\bot$.

Dielectric Anisotropy ($\Delta\in$; Measured at 25° C.)

An ethanol (20 mL) solution of octadecyltriethoxysilane (0.16 mL) was applied to a well-washed glass substrate. The glass substrate was rotated with a spinner, and then heated at 150° C. for 1 hour. A VA device in which the distance (cell gap) was micrometers was assembled from the two glass substrates.

A polyimide alignment film was prepared on glass substrates in a similar manner. After a rubbing-treatment to the alignment film formed on the glass substrates, a TN device in which the distance between the two glass substrates was 9 micrometers and the twist angle was 80 degrees was assembled.

A sample (a liquid crystal composition, or a mixture of a liquid crystal compound and mother liquid crystals) was poured into the VA device obtained, a voltage of 0.5 V (1 kHz, sine waves) was applied to the sample, and then the dielectric constant ($\in_\|$) in the major axis direction of the liquid crystal molecules was measured.

The sample (the liquid crystal composition, or the mixture of the liquid crystal compound and the mother liquid crystals) was poured into the TN device obtained, a voltage of 0.5 V (1 kHz, sine waves) was applied to the sample, and then the dielectric constant ($\in_\perp$) in the minor axis direction of the liquid crystal molecules was measured.

The value of the dielectric anisotropy was calculated from the equation of $\Delta\in = \in_\| - \in_\perp$.

Synthetic examples of the liquid crystal compound

Example 1

Preparation of 5-(4'-ethoxy-2,2',3,3'-tetrafluorobiphenyl-4-yl)-2-(4-propylcyclohexyl)tetrahydropyran (No. 1)

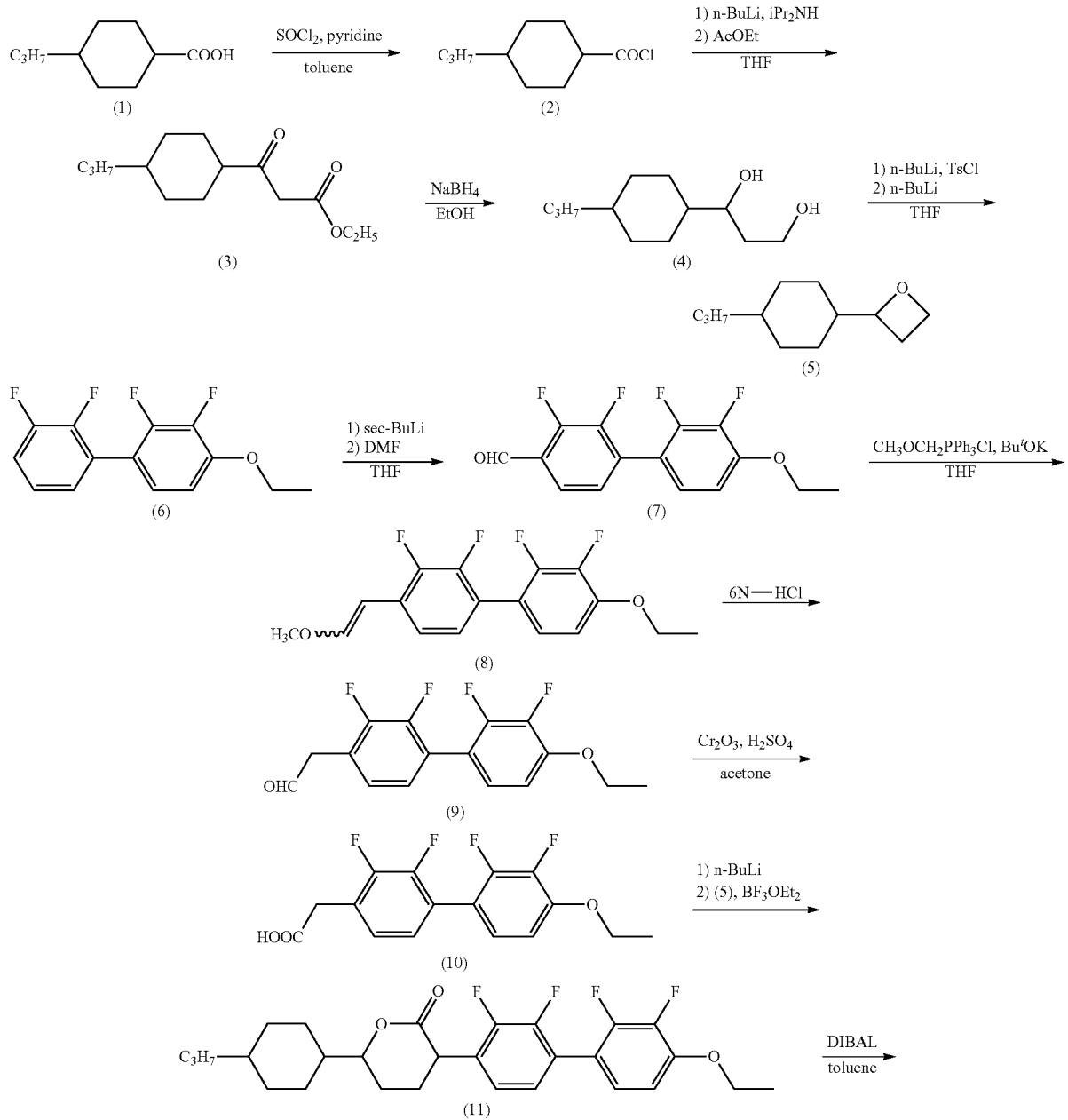

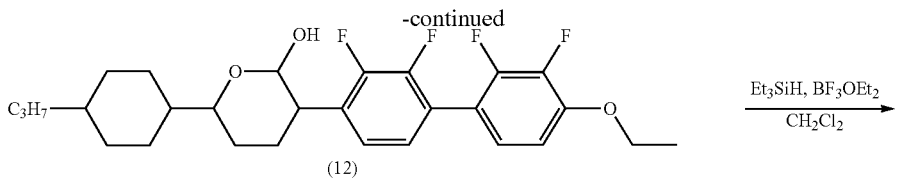

First Step:

Toluene (1,000 ml) was added to trans-4-propylcyclohexanecarboxylic acid (1) (500.0 g) in a reaction vessel under an atmosphere of nitrogen, and the mixture was heated to 50° C. Pyridine (0.70 ml) and thionyl chloride (360.0 g) were then added, and the stirring was continued for 3 hours. The unreacted thionyl chloride and the toluene were distilled off at atmospheric pressure. The residue was distilled under reduced pressure (83° C., 3 mmHg) to give trans-4-propylcyclohexanecarboxylic acid chloride (2) (531.7 g) in 98% yield.

Second Step:

THF (1,000 ml) was added to diisopropylamine (162.9 g) in a reaction vessel under an atmosphere of nitrogen. n-Butyllithium was added dropwise, while the solution was kept at −40° C. or lower, and the stirring was continued for 30 minutes. The solution was cooled at −65° C. or lower, and ethyl acetate (141.9 g) and then a THF (200 ml) solution of trans-4-propylcyclohexanecarboxylic acid chloride (2) (189.9 g) prepared in the first step were added dropwise. After the reaction mixture had been slowly warmed up to room temperature with stirring, it was quenched with a saturated aqueous solution of ammonium chloride. Water (1,000 ml) was then added to give two layers. The water layer was extracted with toluene (500 ml) three times, and the combined organic layer was washed with water and then dried over anhydrous magnesium sulfate. The solvent was distilled off under reduced pressure. The residue was purified by silica gel chromatography (silica gel: 300 g, eluent: toluene) to give 3-oxo-3-(trans-4-propyl-cyclohexyl)-propionic acid ethyl ester (3) (220 g) in 90% yield.

Third Step:

An ethanol (300 ml) solution of (3-oxo-3-(trans-4-propyl-cyclohexyl)-propionic acid ethyl ester (3) (220.0 g) prepared in the second step was added dropwise at 50° C. or lower to a suspension of sodium borohydride (45 g) in ethanol (500 ml), in a reaction vessel under an atmosphere of nitrogen, and the stirring was continued at room temperature for 5 hours. The reaction mixture was quenched with water (1,000 ml), to which ethyl acetate (500 ml) was added to give two layers The water layer was extracted with ethyl acetate (500 ml) twice, and the combined organic layer was washed with water and then dried over anhydrous magnesium sulfate. The solvent was distilled off under reduced pressure. The residue was purified by silica gel chromatography (silica gel: 500 g, eluent: heptane/ethyl acetate=50/50 by volume) to give 1-(trans-4-propyl-cyclohexyl)-propane-1,3-diol (4) (135 g) in 67% yield.

Fourth Step:

THF (1,000 ml) was added to 1-(trans-4-propyl-cyclohexyl)-propane-1,3-diol(4) (229.3 g) prepared in the third step in a reaction vessel under an atmosphere of nitrogen. n-Butyllithium (1.63 M in n-hexane; 702 ml) was added dropwise to the mixture at around −5° C. After 30 minutes of stirring, p-toluenesulfonyl chloride (218.2 g) in a THF (1,000 ml) solution was added dropwise. After the reaction mixture had been stirred for 30 minutes, n-butyllithium (1.63 M in n-hexane; 702 ml) was added dropwise at around −5° C., and then the reaction mixture was heated slowly up to the reflux temperature. After the evolution of gas had ceased, the reaction mixture was cooled to room temperature, and quenched with a saturated aqueous solution of ammonium chloride, and then water (1,000 ml) was added to give two layers. The water layer was extracted with toluene (500 ml) three times, and the combined organic layer was washed with water and then dried over anhydrous magnesium sulfate. The solvent was distilled off under reduced pressure. The residue was treated with silica gel chromatography (silica gel: 200 g, eluent: heptane/ethyl acetate=90/10 by volume) and distilled under reduced pressure (71 to 74° C., 3 mmHg) to give 2-(trans-4-propyl-cyclohexyl)-oxetane (5) (145 g) in 70% yield.

Fifth Step:

THF (400 ml) was added to 4-ethoxy-2,2',3,3'-tetrafluorobiphenyl (6) (39.25 g) prepared by means of a conventional coupling reaction in a reaction vessel under an atmosphere of nitrogen. The solution was cooled to −65° C. or lower, and sec-butyllithium (1.08 M in cyclohexane and n-hexane; 141.3 ml) was added dropwise. After the reaction mixture had been stirred at −65° C. for another 1 hour, N,N,-dimethylformamide (21.2 g) was added dropwise, and the reaction mixture was warmed slowly to room temperature. The reaction mixture was quenched with a saturated aqueous solution of ammonium chloride, and water (500 ml) was added to give two layers. The water layer was extracted with toluene (200 ml) twice, and the combined organic layer was washed with water and then dried over anhydrous magnesium sulfate. The solvent was distilled off under reduced pressure. The residue was treated with silica gel chromatography (silica gel: 30 g, eluent: toluene) to give 4-ethoxy-2,2',3,3'-tetrafluorobiphenyl-4-carboaldehyde (7) (30 g) in 70% yield.

Sixth Step:

THF (150 ml) was added to methoxymethyltriphenylphosphonium chloride (26.8 g) in a reaction vessel under an atmosphere of nitrogen and the solution was cooled to −20° C. Potassium t-butoxide (10.1 g) was added, and the stirring was continued for 1 hour. A THF (100 ml) solution of 4-ethoxy-2,2',3,3'-tetrafluorobiphenyl-4-carboaldehyde (7) (17.9 g) prepared in the fifth step was added dropwise, and the stirring was continued for 1 hour. The reaction mixture was warmed to room temperature and water (200 ml) was added to give two layers. The water layer was extracted with toluene (100 ml) three times, and the combined organic layer was washed with water and then dried over anhydrous magnesium sulfate.

The solvent was distilled off under reduced pressure. The residue was purified by silica gel chromatography (silica gel: 20 g, eluent: toluene) to give 4-ethoxy-2,2',3,3'-tetrafluoro-4'-(2-methoxyvinyl)biphenyl (8) (18.5 g) in 94.5% yield.

Seventh Step:

4-Ethoxy-2,2',3,3'-tetrafluoro-4'-(2-methoxyvinyl)biphenyl (8) (18.5 g) prepared in the sixth step was dissolved in acetone (200 ml) and hydrochloric acid (6M; 200 ml) was added, and the stirring was continued at room temperature for 1 hour. Water (200 ml) was added, and the water layer was extracted with toluene (100 ml) three times. The combined organic layer was washed with water and then dried over anhydrous magnesium sulfate. The solvent was distilled off under reduced pressure to leave 2-(4'-ethoxy-2,2',3,3'-tetrafluorobiphenyl-4-yl)acetoaldehyde (9) (17.2 g) in 97.2% yield.

Eight Step:

2-(4'-Ethoxy-2,2',3,3'-tetrafluorobiphenyl-4-yl)acetoaldehyde (9) (17.2 g) prepared in the seventh step was dissolved in acetone (150 ml) and the solution was cooled on an ice bath. The Jones reagent (2.67M; 35 ml) was added to the solution. After 2 hours of stirring, isopropyl alcohol (10 ml) was added, and the stirring was continued for 30 minutes. The reaction mixture was filtered through Celite, and water (200 ml) and ethyl acetate (100 ml) were added to filtrate to give two layers. The water layer was extracted with ethyl acetate (50 ml) three times, and the combined organic layer was washed with water. The solution was dried over anhydrous magnesium sulfate. The solvent was distilled off under reduced pressure. The residue was purified by means of back-extraction to give 2-(4'-ethoxy-2,2',3,3'-tetrafluorobiphenyl-4-yl)acetic acid (10) (13.6 g) in 75.2% yield.

Ninth Step:

THF (50 ml) was added to 2-(4'-ethoxy-2,2',3,3'-tetrafluorobiphenyl-4-yl)acetic acid (10) (2.0 g) prepared in the eighth step. The solution was cooled to −5° C., and n-butyllithium (1.59 M in n-hexane; 7.66 ml) was added dropwise. After the addition had been completed, the reaction mixture was returned to room temperature, and the stirring was continued for 30 minutes. The solution was then cooled to −65° C., and 2-(trans-4-propyl-cyclohexyl)-oxetane (5) (1.0 g) in a THF (5 ml) solution and a boron trifluoride-diethyl ether complex (0.86 g) were added dropwise. After the addition had been completed, the reaction mixture was returned to room temperature, and a 10% aqueous solution of formic acid (100 ml) was added to give two layers. The water layer was extracted with toluene (20 ml) three times and the combined organic layer was washed with water and then dried over anhydrous magnesium sulfate. The solvent was distilled off under reduced pressure. The residue was purified by silica gel chromatography (silica gel: 200 g, eluent: heptane/ethyl acetate=90/10 by volume) to give 3-(4'-ethoxy-2,2',3,3'-tetrafluorobiphenyl-4-yl)-6-(4-propylcyclohexyl)tetrahydropyran-2-one (11) (2.35 g) in 86.1% yield.

Tenth Step:

Toluene (20 ml) was added to 3-(4'-ethoxy-2,2',3,3'-tetrafluorobiphenyl-4-yl)-6-(4-propylcyclohexyl)tetrahydropyran-2-one (11) (2.35 g) prepared in the ninth step. A toluene solution of diisobutylaluminum hydride (0.99 M; 9.6 ml) was added dropwise at −50° C. or lower, and the stirring was continued for 3 hours. The reaction mixture was poured into a 10% aqueous solution of formic acid (50 ml) to give two layers. The water layer was extracted with toluene (20 ml) twice and the combined organic layer was washed with water, and then dried over anhydrous magnesium sulfate. The solvent was distilled off under reduced pressure to leave 3-(4'-ethoxy-2,2',3,3'-tetrafluorobiphenyl-4-yl)-6-(4-propylcyclohexyl)tetrahydropyran-2-ol (12) (2.29 g) in 99% yield.

Eleventh Step:

Dichloromethane (30 ml) was added to 3-(4'-ethoxy-2,2',3,3'-tetrafluorobiphenyl-4-yl)-6-(4-propylcyclohexyl)tetrahydropyran-2-ol (12) (2.29 g) prepared in the tenth step. Triethylsilane (1.93 g) and a boron trifluoride-diethyl ether complex (2.37 g) were added dropwise to the solution at −30° C. After 3 hours of stirring, water (30 ml) was added to give two layers. The organic layer was washed with water, dried over anhydrous magnesium sulfate. The solvent was distilled off under reduced pressure. The residue was purified by silica gel chromatography (silica gel: 200 g, eluent: heptane/ethyl acetate=80/20 by volume) and then by recrystallization (heptane/ethyl acetate=90/10 by volume) to give 5-(4'-ethoxy-2,2',3,3'-tetrafluorobiphenyl-4-yl)-2-(4-propylcyclohexyl)tetrahydropyran (13) (0.8 g) in 36% yield.

The chemical shift (δ, ppm) in $^1$H-NMR analysis was described below, and the resulting compound was identified as 5-(4'-ethoxy-2,2',3,3'-tetrafluorobiphenyl-4-yl)-2-(4-propylcyclohexyl)tetrahydropyran (13). The solvent for measurement was $CDCl_3$.

Chemical shift δ (ppm): 7.1-6.9 (m, 3H), 6.80 (t, 1H), 4.17 (q, 2H), 4.09-4.05 (m, 1H), 3.46 (t, 1H), 3.19 (tt, 1H), 3.13-3.08 (m, 1H), 2.09-2.03 (m, 1H), 2.00-1.93 (m, 1H), 1.85-1.7 (m, 5H), 1.55-1.45 (m, 4H), 1.43-0.97 (m, 8H), 0.95-0.83 (m, 5H).

The phase transition temperature of the resulting compound (13), that is to say, the compound No. 1 was as follows.

Transition temperature: C 100.3 N 263.9 Iso.

Example 2

Preparation of 5-(4'-ethoxy-2,2',3,3'-tetrafluorobiphenyl-4-yl)-2-(4-pentylcyclohexyl)tetrahydropyran (No. 573)

5-(4'-Ethoxy-2,2',3,3'-tetrafluorobiphenyl-4-yl)-2-(4-pentylcyclohexyl)tetrahydropyran (No. 573) (1.9 g) was prepared in 16.2% overall yield, using 2-(trans-4-pentyl-cyclohexyl)-oxetane (3.8 g) instead of 2-(trans-4-propyl-cyclohexyl)-oxetane (5) in the ninth step of Example 1, by carrying out a similar reaction and a similar work-up.

The chemical shift (δ, ppm) in $^1$H-NMR analysis was described below, and the resulting compound was identified as 5-(4'-ethoxy-2,2',3,3'-tetrafluorobiphenyl-4-yl)-2-(4-pentylcyclohexyl)tetrahydropyran (No. 573). The solvent for measurement was $CDCl_3$.

Chemical shift δ (ppm): 7.10-6.96 (m, 3H), 6.80 (t, 1H), 4.17 (q, 2H), 4.11-4.04 (m, 1H), 3.46 (t, 1H), 3.19 (tt, 1H), 3.14-3.08 (m, 1H), 2.10-2.03 (m, 1H), 2.01-1.93 (m, 1H), 1.87-1.71 (m, 5H), 1.55-1.45 (m, 4H), 1.43-1.13 (m, 10H), 1.13-0.96 (m, 2H), 0.95-0.83 (m, 5H).

The phase transition temperature of the resultant compound No. 573 was as follows.

Transition temperature: C 98.7 N 256.2 Iso.

Example 3

Preparation of 2-propyl-5-(2,2',3,3'-tetrafluoro-4'-(4-propylcyclohexyl)biphenyl-4-yl)tetrahydro-2H-pyran (No. 217)

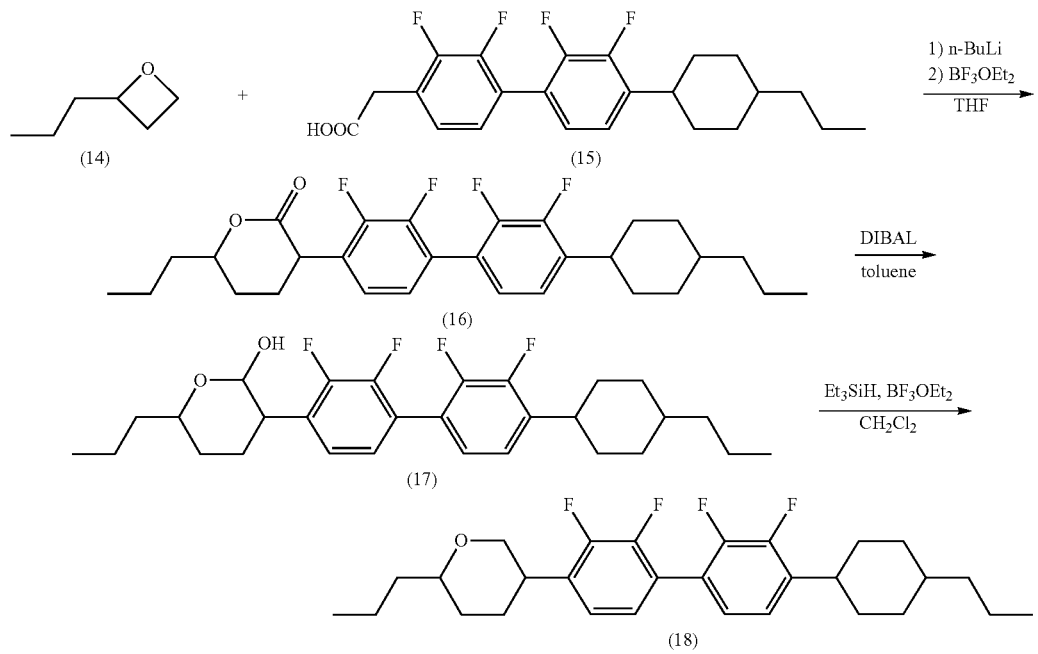

First Step:

THF (40 ml) was added to 2-(2,2'-3,3'-tetrafluoro-4'-(4-propylcyclohexyl)biphenyl-4-yl)acetic acid (15) (4.0 g). The solution was cooled to −5° C. and n-butyllithium (1.65 M n-hexane; 11.87 ml) was added dropwise. After the addition had been completed, the reaction mixture was returned to room temperature, and the stirring was continued for 30 minutes. The mixture was then cooled to −65° C., and 2-propyloxetane (14) (0.89 g) in a THF (2 ml) solution and a boron trifluoride-diethyl ether complex (1.39 g) were added dropwise. After the reaction mixture had been returned to room temperature, a 10% aqueous solution of formic acid (100 ml) was added to give two layers. The water layer was extracted with toluene (20 ml) three times and the combined organic layer was washed with water. The solution was dried over anhydrous magnesium sulfate and the solvent was distilled off under reduced pressure. The residue was purified by silica gel chromatography (silica gel: 20 g, eluent: heptane/ethyl acetate=90/10 by volume) to give 6-propyl-3-(2,2',3,3'-tetrafluoro-4'-(4-propylcyclohexyl)biphenyl-4-yl)tetrahydro-2H-pyran-2-one (16) (4.18 g) in 80.0% yield.

Second Step:

Toluene (50 ml) was added to 6-propyl-3-(2,2',3,3'-tetrafluoro-4'-(4-propylcyclohexyl)biphenyl-4-yl)tetrahydro-2H-pyran-2-one (16) (4.18 g) prepared in the first step. A diisobutylaluminum hydride-toluene solution (0.99 M; 12.5 ml) was added dropwise at −50° C. or lower, and the stirring was continued for 3 hours. The reaction mixture was poured into a 10% aqueous solution of formic acid (50 ml) to give two layers. The water layer was extracted with toluene (20 ml) twice and the combined organic layer was washed with water. The solution was dried over anhydrous magnesium sulfate. The solvent was distilled off under reduced pressure to leave 6-propyl-3-(2,2',3,3'-tetrafluoro-4'-(4-propylcyclohexyl)biphenyl-4-yl)tetrahydro-2H-pyran-2-ol (17) (4.2 g) in 99% yield.

Third Step:

Dichloromethane (40 ml) was added to 6-propyl-3-(2,2',3,3'-tetrafluoro-4'-(4-propylcyclohexyl)biphenyl-4-yl)tetrahydro-2H-pyran-2-ol (17) (4.2 g) prepared in the second step. Triethylsilane (1.01 g) and a boron trifluoride-diethyl ether complex (1.82 g) were added dropwise to the solution at −30° C. After 3 hours of stirring, water (40 ml) was added to give two layers. The organic layer was washed with water and dried over anhydrous magnesium sulfate. The solvent was distilled off under reduced pressure. The residue was purified by silica gel chromatography (silica gel: 200 g, eluent: heptane/ethyl acetate=80/20 by volume), and then by recrystallization (heptane/ethyl acetate=90/10 by volume) to give 2-propyl-5-(2,2',3,3'-tetrafluoro-4'-(4-propylcyclohexyl)biphenyl-4-yl)tetrahydro-2H-pyran (18) (1.8 g) in 44.3% yield.

The chemical shift (δ, ppm) in $^1$H-NMR analysis was described below, and the resulting compound (18) was identified as 2-propyl-5-(2,2',3,3'-tetrafluoro-4'-(4-propylcyclohexyl)biphenyl-4-yl)tetrahydro-2H-pyran (18). The solvent for measurement was CDCl$_3$.

Chemical shift δ (ppm): 7.10-6.88 (m, 4H), 4.10-4.04 (m, 1H), 3.49 (dd, 1H), 3.42-3.34 (m, 1H), 3.26-3.17 (tt, 1H), 2.93-2.83 (tt, 1H), 2.08-2.01 (m, 1H), 1.94-1.77 (m, 6H), 1.64-1.19 (m, 12H), 1.16-1.05 (m, 2H), 0.97-0.88 (m, 6H).

The phase transition temperature of the resulting compound (18), that is to say, the compound No. 217 was as follows.

Transition temperature: C 106.1 N 231.7 Iso.

Example 4

Preparation of 2-pentyl-5-(2,2',3,3'-tetrafluoro-4'-(6-propyltetrahydro-2H-pyran-3-yl)biphenyl-4-yl)tetrahydro-2H-pyran (No. 574)

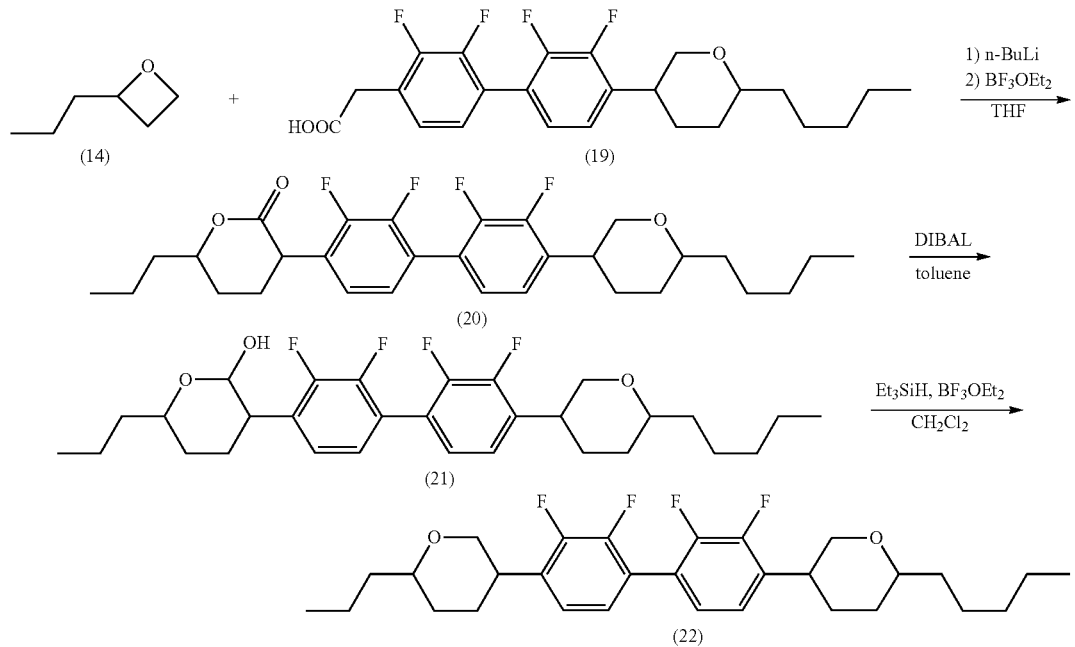

First Step:

THF (20 ml) was added to 2-(2,2'-3,3'-tetrafluoro-4'-(6-pentyltetrahydro-2H-pyran-3-yl)biphenyl-4-yl)acetic acid (19) (1.42 g). The solution was cooled to −5° C., and n-butyllithium (1.57 M in n-hexane; 4.13 ml) was added dropwise. After the addition had been completed, the reaction mixture was returned to room temperature, and the stirring was continued for 30 minutes. The mixture was then cooled to −65° C., and 2-propyloxetane (14) (0.32 g) in a THF (1 ml) solution and a boron trifluoride-diethyl ether complex (0.51 g) were added dropwise. After the reaction mixture had been returned to room temperature, a 10% aqueous solution of formic acid (30 ml) was added to give two layers. The water layer was extracted with toluene (10 ml) three times, and the combined organic layer was washed with water and then dried over anhydrous magnesium sulfate. The solvent was distilled off under reduced pressure. The residue was purified by silica gel chromatography (silica gel: 20 g, eluent: heptane/ethyl acetate=50/50 by volume) to give 6-propyl-3-(2,2',3,3'-tetrafluoro-4'-(6-pentyltetrahydro-2H-pyran-3-yl)biphenyl-4-yl)tetrahydro-2H-pyran-2-one (20) (1.2 g) in 71.2% yield.

Second Step:

Toluene (10 ml) was added to 6-propyl-3-(2,2',3,3'-tetrafluoro-4'-(6-pentyltetrahydro-2H-pyran-3-yl)biphenyl-4-yl)tetrahydro-2H-pyran-2-one (20) (1.2 g) prepared in the first step. A diisobutylaluminum hydride-toluene solution (0.99 M; 3.49 ml) was added dropwise at −50° C. or lower, and the stirring was continued for 3 hours. The reaction mixture was poured into a 10% aqueous solution of formic acid (15 ml) to give two layers. The water layer was extracted with toluene (10 ml) twice, and the combined organic layer was washed with water and then dried over anhydrous magnesium sulfate. The solvent was distilled off under reduced pressure to leave 6-propyl-3-(2,2',3,3'-tetrafluoro-4'-(6-pentyltetrahydro-2H-pyran-3-yl)biphenyl-4-yl)tetrahydro-2H-pyran-2-ol (21) (1.2 g) in 98% yield.

Third Step:

Dichloromethane (10 ml) was added to 6-propyl-3-(2,2',3,3'-tetrafluoro-4'-(6-pentyltetrahydro-2H-pyran-3-yl)biphenyl-4-yl)tetrahydro-2H-pyran-2-ol (21) (1.2 g) prepared in the second step. Tiethylsilane (0.27 g) and a boron trifluoride-diethyl ether complex (0.49 g) were added dropwise to the solution at −30° C. After 3 hours of stirring, water (10 ml) was added to give two layers. The organic layer was washed with water and dried over anhydrous magnesium sulfate. The solvent was distilled off under reduced pressure. The residue was purified by silica gel chromatography (silica gel: 20 g, eluent: heptane/ethyl acetate=50/50 by volume), and then by recrystallization (heptane/ethyl acetate=90/10 by volume) to give 2-pentyl-5-(2,2',3,3'-tetrafluoro-4'-(6-propyltetrahydro-2H-pyran-3-yl)biphenyl-4-yl)tetrahydro-2H-pyran (22) (0.3 g) in 25.8% yield.

The chemical shift (δ, ppm) in $^1$H-NMR analysis was described below, and the resulting compound (22) was identified as 2-butyl-5-(2,2',3,3'-tetrafluoro-4'-(6-propyltetrahydro-2H-pyran-3-yl)biphenyl-4-yl)tetrahydro-2H-pyran (22). The solvent for measurement was $CDCl_3$.

Chemical shift δ (ppm): 7.09-6.99 (m, 4H), 4.10-4.04 (dt, 2H), 3.48 (dd, 2H), 3.42-3.31 (m, 2H), 3.26-3.17 (tt, 2H), 2.09-2.01 (m, 2H), 1.89-1.77 (m, 4H), 1.63-1.24 (m, 14H), 0.97-0.93 (t, 3H), 0.93-0.88 (t, 3H).

The phase transition temperature of the resulting compound (22), that is to say, the compound No. 574 was as follows.

Transition temperature: C 50.0 N 173.0 Iso.

Example 5

Preparation of 2-(4'-ethoxy-2,2',3,3'-tetrafluorobiphenyl-4-yl)-5-(4-propylcyclohexyl)tetrahydro-2H-pyran (No. 43)

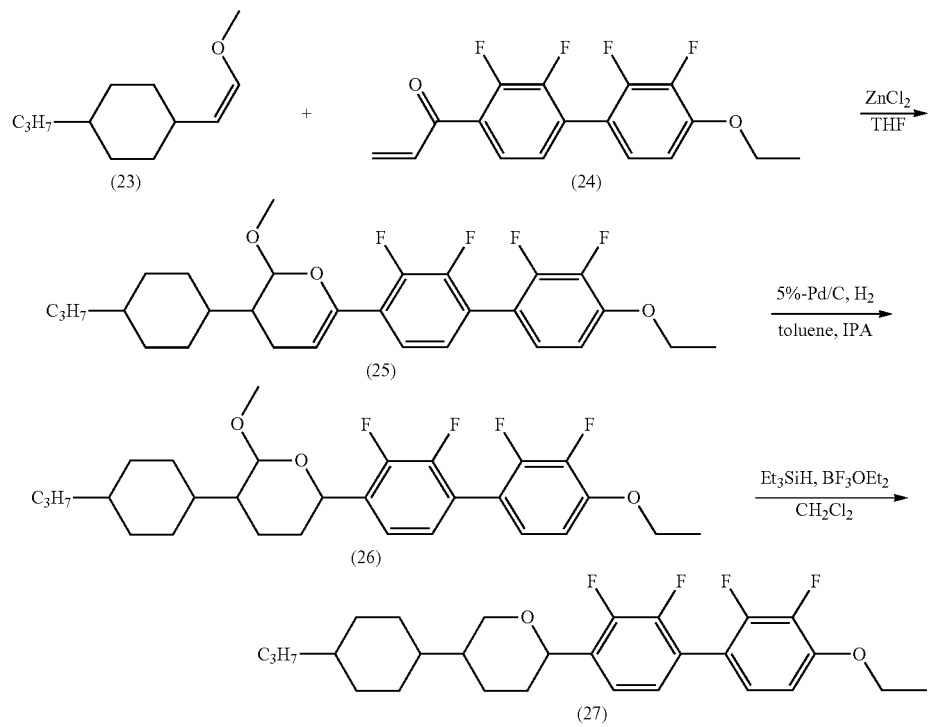

First Step:

1-(2-Methoxyvinyl)-4-propylcyclohexane (23) (5.09 g), 1-(4'-ethoxy-2,2',3,3'-tetrafluorobiphenyl-4-yl)prop-2-ene-1-one (24) (3.65 g) was dissolved in THF (20 ml) in a reaction vessel under an atmosphere of nitrogen, and then zinc chloride (2.73 g) was added, and the stirring was continued at room temperature for 45 hours. Toluene (40 ml) and water (40 ml) were added to give two layers. The organic layer was washed with a 5% aqueous solution of sodium hydrogencarbonate and water, and dried over anhydrous magnesium sulfate. The solvent was distilled off under reduced pressure. The residue was purified by silica gel chromatography (silica gel: 100 g, eluent: heptane/toluene=50/50 by volume) to give 6-(4'-ethoxy-2,2'-3,3'-tetrafluorobiphenyl-4-yl)-2-methoxy-3-(4-propylcyclohexyl)-3,4-dihydro-2H-pyran (25) (5.29 g) in 67% yield.

Second Step:

6-(4'-Ethoxy-2,2'-3,3'-tetrafluorobiphenyl-4-yl)-2-methoxy-3-(4-propylcyclohexyl)-3,4-dihydro-2H-pyran (25) (3.59 g) prepared in the first step was dissolved in a mixture of toluene (18 ml) and isopropyl alcohol (IPA; 18 ml), and 5%-Pd/C (0.18 g) was added, and the stirring was continued under a hydrogen atmosphere at room temperature for 12 hours. 5%-Pd/C was removed by filtration, and the solvent was distilled off under reduced pressure to leave 6-(4'-ethoxy-2,2'-3,3'-tetrafluorobiphenyl-4-yl)-2-methoxy-3-(4-propylcyclohexyl)tetrahydro-2H-pyran (26) (3.60 g) in 99% yield.

Third Step:

6-(4'-Ethoxy-2,2'-3,3'-tetrafluorobiphenyl-4-yl)-2-methoxy-3-(4-propylcyclohexyl)tetrahydro-2H-pyran (26) (16.4 g) prepared in the second step was dissolved in dichloromethane (65 ml). The solution was cooled to 0° C. or lower, and triethylsilane (7.28 g) and a boron trifluoride-diethyl ether complex (8.88 g) were added dropwise. After 3 hours of stirring, water (30 ml) was added to give two layers. The organic layer was washed with water, and dried over anhydrous magnesium sulfate. The solvent was distilled off under reduced pressure. The residue was purified by silica gel chromatography (silica gel: 30 g, eluent: toluene), and then by recrystallization (Solmix A-11) to give 2-(4'-ethoxy-2,2',3,3'-tetrafluorobiphenyl-4-yl)-5-(4-propylcyclohexyl)tetrahydro-2H-pyran (27) (9.93 g) in 65% yield.

The chemical shift ($\delta$, ppm) in $^1$H-NMR analysis was described below, and the resulting compound was identified as 2-(4'-ethoxy-2,2',3,3'-tetrafluorobiphenyl-4-yl)-5-(4-propylcyclohexyl)tetrahydro-2H-pyran (27). The solvent for measurement was $CDCl_3$.

Chemical shift $\delta$ (ppm): 7.32-7.27 (t, 1H), 7.14-7.07 (t, 1H), 7.05-6.99 (dt, 1H), 6.83-6.78 (dt, 1H), 4.61 (d, 1H), 4.21-4.14 (m, 3H), 3.37 (t, 1H), 2.05-1.94 (m, 2H), 1.82-1.70 (m, 4H), 1.60-0.80 (m, 19H).

The phase transition temperature of the resulting compound (27), that is to say, the compound No. 43 was as follows.

Transition temperature: C 112.9 N 273.8 Iso.

Example 6

Preparation of 2-(2-(4'-ethoxy-2,2',3,3'-tetrafluorobiphenyl-4-yl)ethyl)-5-(4-propylcyclohexyl)tetrahydro-2H-pyran (No. 72)

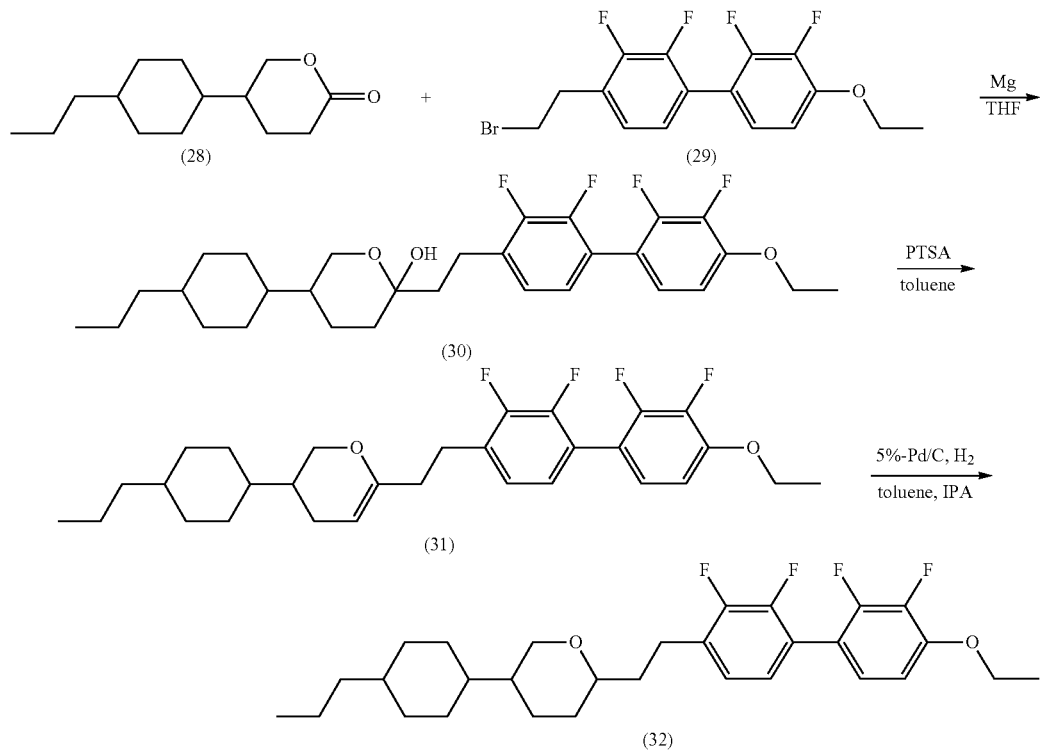

First Step:

THF (5 ml) was added to magnesium turnings (0.30 g) in a reaction vessel under an atmosphere of nitrogen, and a minute amount of iodine was added. 4-(2-Bromoethyl)-4'-ethoxy-2,2',3,3'-tetrafluorobiphenyl (29) (4.60 g) in a THF (5 ml) solution was slowly added dropwise at a temperature 50° C. or lower. After the addition had been completed, the stirring was continued at room temperature for 30 minutes. The reaction mixture was then cooled to −30° C. or lower, and 5-(4-propylcyclohexyl)tetrahydro-2H-pyran-2-one (20) (2.46 g) in a THF (5 ml) solution was added dropwise. After the reaction mixture had been stirred at room temperature for 5 hours, it was quenched with a saturated aqueous solution of ammonium chloride, and water (20 ml) was added to give two layers. The water layer was extracted with toluene (10 ml) twice, and the combined organic layer was washed with water and then dried over anhydrous magnesium sulfate. The solvent was distilled off under reduced pressure. The residue was purified by silica gel chromatography (silica gel: 20 g, eluent: toluene/ethyl acetate=70/30 by volume) to give 2-(2-(4'-ethoxy-2,2',3,3'-tetrafluorobiphenyl-4-yl)ethyl)-5-(4-propylcyclohexyl)tetrahydro-2H-pyran-2-ol (30) (2.7 g) in 47.1% yield.

Second Step:

2-(2-(4'-Ethoxy-2,2',3,3'-tetrafluorobiphenyl-4-yl)ethyl)-5-(4-propylcyclohexyl)tetrahydro-2H-pyran-2-ol (30) (2.7 g) prepared in the first step was dissolved in toluene (20 ml), and p-toluenesulfonyl chloride (25 mg) was added. A reaction vessel was equipped with a Dean-Stark condenser, and the mixture was refluxed for 3 hours. After the reaction mixture had been cooled, it was washed with a saturated aqueous solution of sodium hydrogencarbonate and water, and dried over anhydrous magnesium sulfate. The solvent was distilled off under reduced pressure to leave 6-(2-(4'-ethoxy-2,2',3,3'-tetrafluorobiphenyl-4-yl)ethyl)-3-(4-propylcyclohexyl)-3,4-dihydro-2H-pyran (31) (2.5 g) in 95.9% yield.

Third Step:

6-(2-(4'-Ethoxy-2,2',3,3'-tetrafluorobiphenyl-4-yl)ethyl)-3-(4-propylcyclohexyl)-3,4-dihydro-2H-pyran (31) (2.5 g) prepared in the second step was dissolved in a mixture of toluene (5 ml) and IPA (5 ml), and 5%-Pd/C 125 mg) was added. The stirring was continued under a hydrogen atmosphere at room temperature for 12 hours. 5%-Pd/C was removed by filtration, and the solvent was distilled off under reduced pressure. The residue was purified by silica gel chromatography (silica gel: 20 g, eluent: toluene), and then by recrystallization (heptane/toluene=50/50 by volume) to give 2-(2-(4'-ethoxy-2,2',3,3'-tetrafluorobiphenyl-4-yl)ethyl)-5-(4-propylcyclohexyl)tetrahydro-2H-pyran (32) (0.7 g) in 30.1% yield.

The chemical shift (δ, ppm) in H-NMR analysis was described below, and the resulting compound was identified as 2-(2-(4'-ethoxy-2,2',3,3'-tetrafluorobiphenyl-4-yl)ethyl)-5-(4-propylcyclohexyl)tetrahydro-2H-pyran (32). The solvent for measurement was $CDCl_3$.

Chemical shift δ (ppm): 7.06-6.98 (m, 3H), 6.83-6.77 (dt, 1H), 4.17 (q, 2H), 4.08-4.03 (m, 1H), 3.22-3.10 (m, 2H), 2.91-2.82 (m, 1H), 2.80-2.71 (m, 1H), 1.92-1.85 (m, 1H), 1.84-1.63 (m, 7H), 1.49 (t, 3H), 1.40-1.08 (m, 8H), 1.04-0.76 (m, 8H).

The phase transition temperature of the resulting compound (32), that is to say, the compound No. 72 was as follows.

Transition temperature: C 67.2 N 193.5 Iso.

The following compounds No. 1 to No. 574 can be produced according to the synthetic methods described in Example 1 to Example 6.

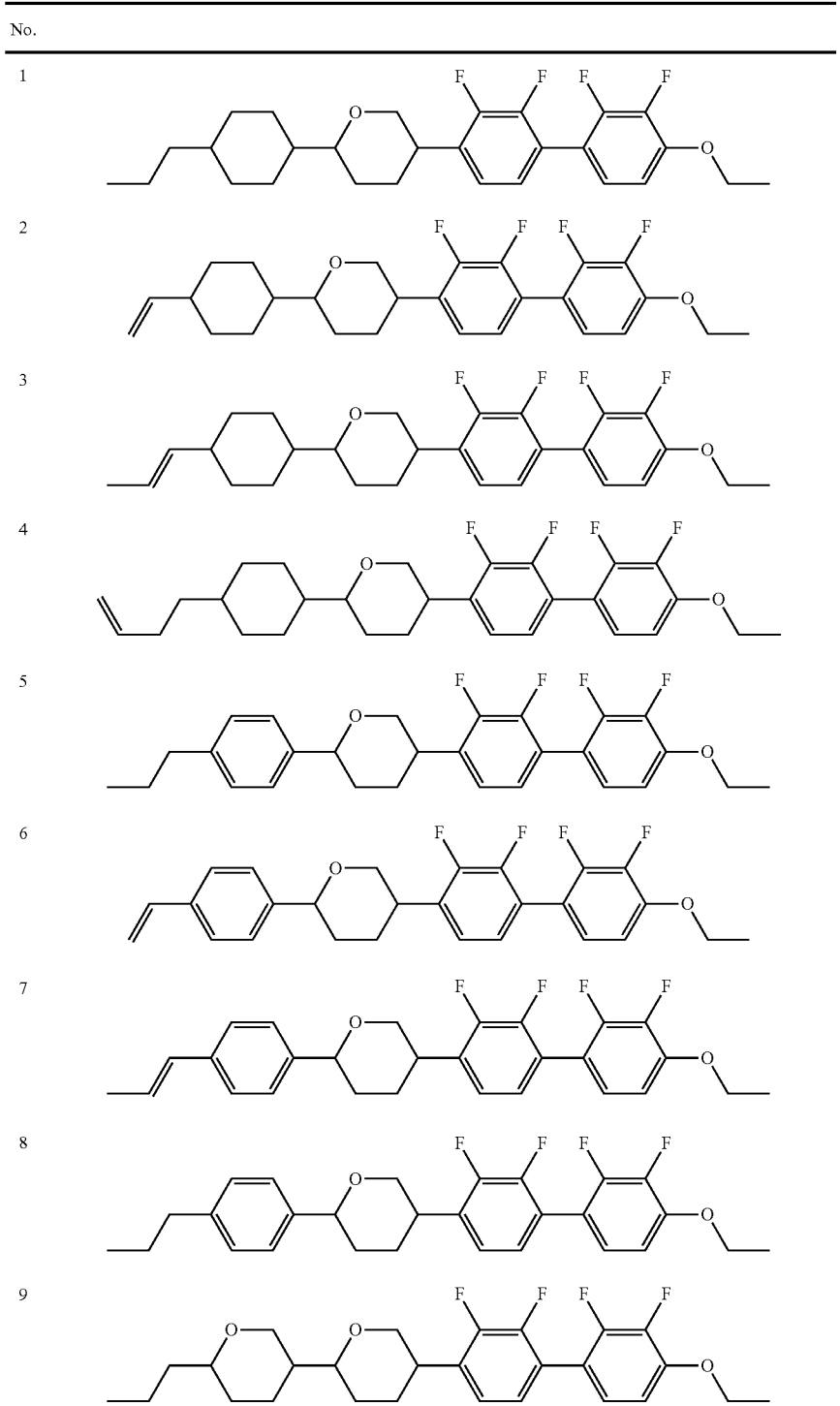

| No. | |
|---|---|
| 10 | 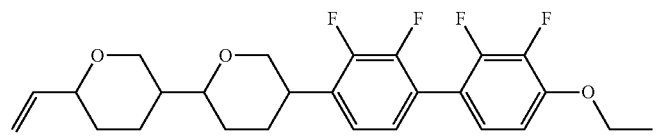 |
| 11 | 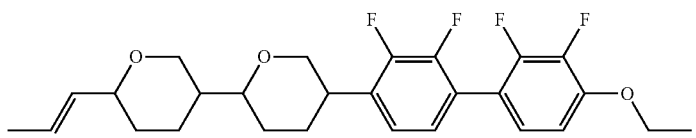 |
| 12 | 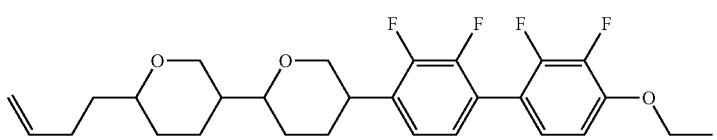 |
| 13 | 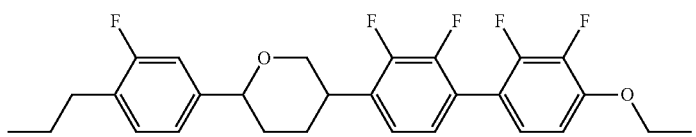 |
| 14 | 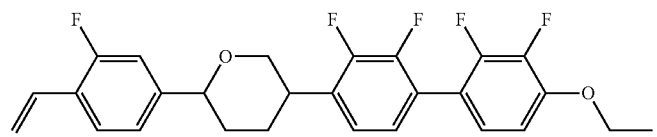 |
| 15 | 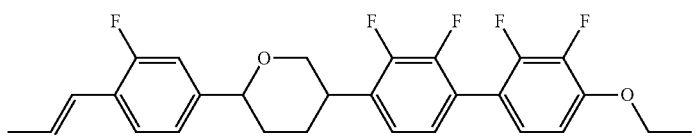 [SMILES: C/C=C/c1ccc(C2CCC(c3ccc(-c4ccc(OCC)c(F)c4F)c(F)c3F)CO2)cc1F] |
| 16 | 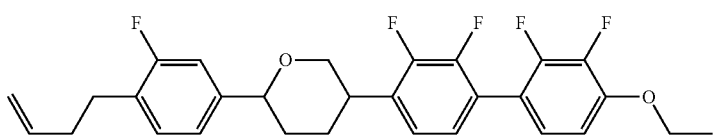 [SMILES: C=CCCc1ccc(C2CCC(c3ccc(-c4ccc(OCC)c(F)c4F)c(F)c3F)CO2)cc1F] |
| 17 | 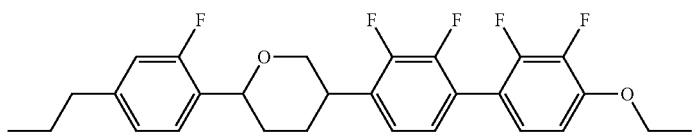 |
| 18 | 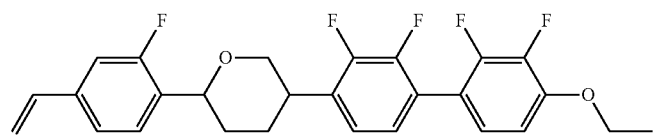 |
| 19 | 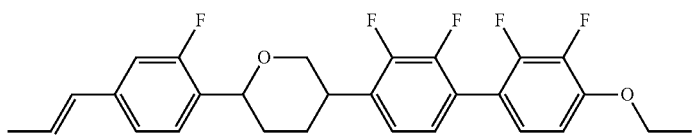 |
| 20 | 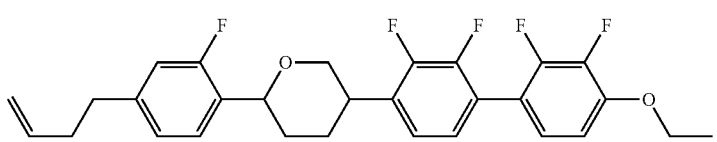 [SMILES: C=CCCc1ccc(C2CCC(c3ccc(-c4ccc(OCC)c(F)c4F)c(F)c3F)CO2)c(F)c1] |

-continued
| No. | |
|---|---|
| 21 | 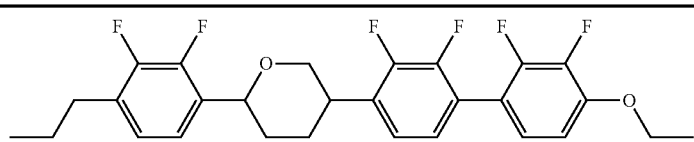 |
| 22 | 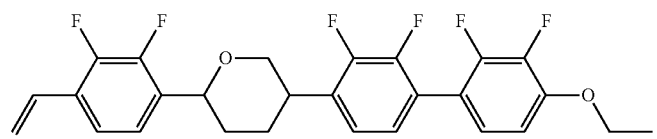 |
| 23 | 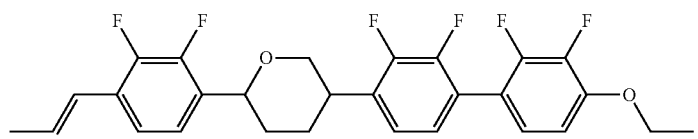 [SMILES: C/C=C/c1ccc(C2CCC(c3ccc(-c4ccc(OCC)c(F)c4F)c(F)c3F)CO2)c(F)c1F] |
| 24 | 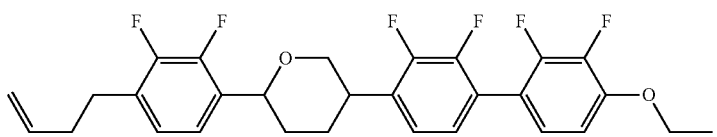 [SMILES: C=CCCc1ccc(C2CCC(c3ccc(-c4ccc(OCC)c(F)c4F)c(F)c3F)CO2)c(F)c1F] |
| 25 | 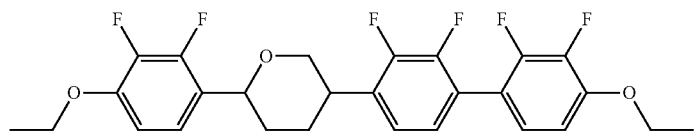 |
| 26 | 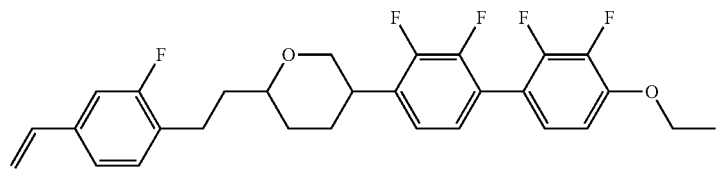 |
| 27 | 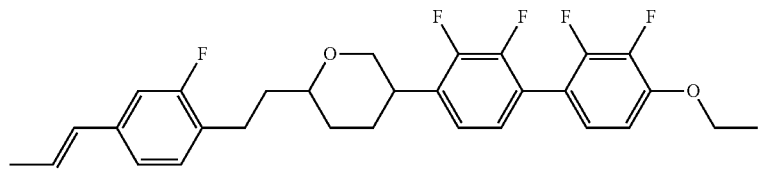 [SMILES: C/C=C/c1ccc(CCC2CCC(c3ccc(-c4ccc(OCC)c(F)c4F)c(F)c3F)CO2)c(F)c1] |
| 28 | 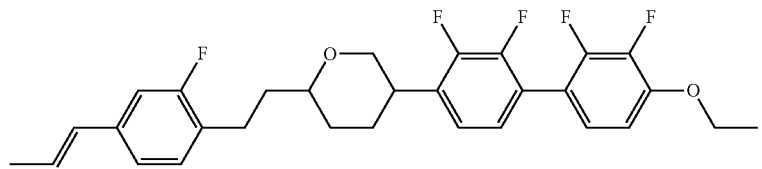 |
| 29 | 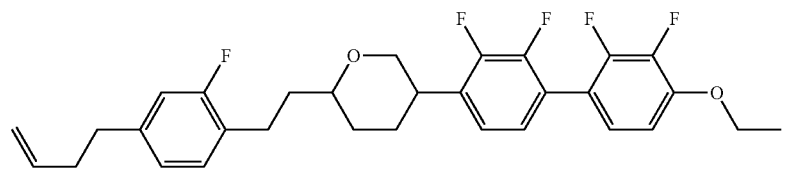 |
| 30 | 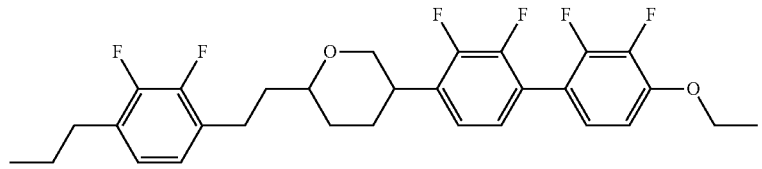 |

-continued
| No. | |
|---|---|
| 31 | 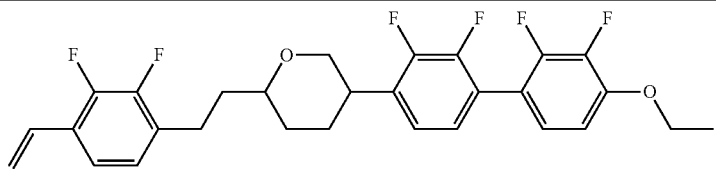 |
| 32 | 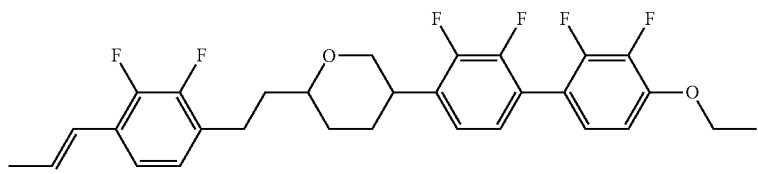 |
| 33 | 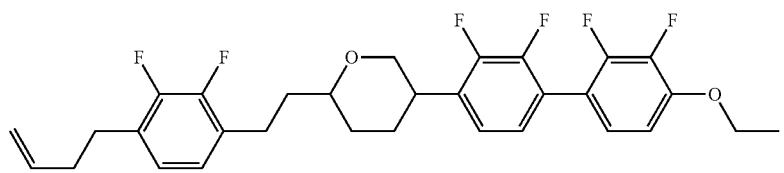 |
| 34 | 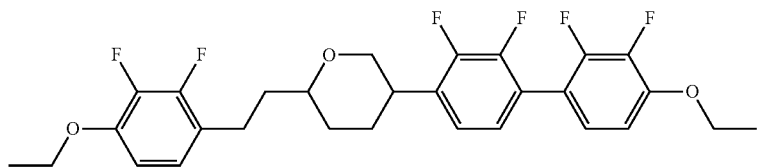 |
| 35 | 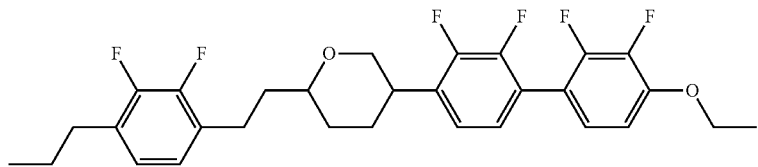 [SMILES: CCCc1ccc(CCC2CCC(c3ccc(-c4ccc(OCC)c(F)c4F)c(F)c3F)CO2)c(F)c1F] |
| 36 | 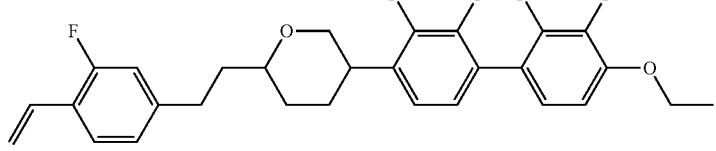 |
| 37 | 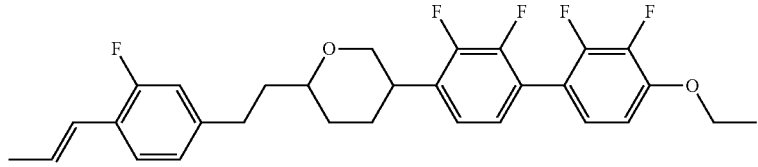 [SMILES: C/C=C/c1ccc(CCC2CCC(c3ccc(-c4ccc(OCC)c(F)c4F)c(F)c3F)CO2)c(F)c1F] |
| 38 | 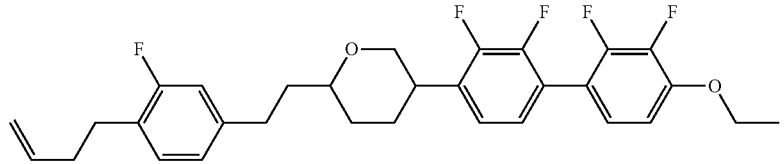 [SMILES: C=CCCc1ccc(CCC2CCC(c3ccc(-c4ccc(OCC)c(F)c4F)c(F)c3F)CO2)c(F)c1F] |
| 39 | 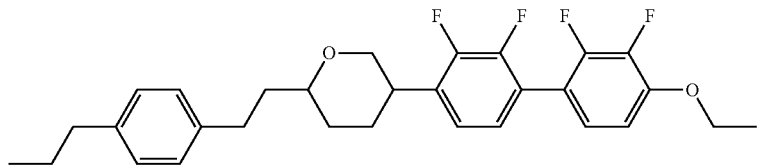 [SMILES: CCCc1ccc(CCC2CCC(c3ccc(-c4ccc(OCC)c(F)c4F)c(F)c3F)CO2)cc1] |

| No. | |
|---|---|
| 40 | 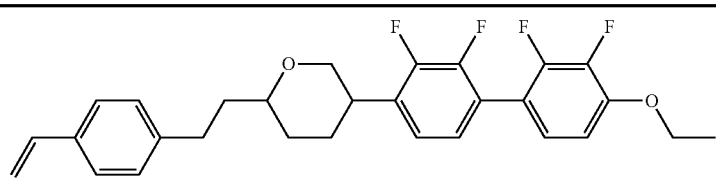 |
| 41 | 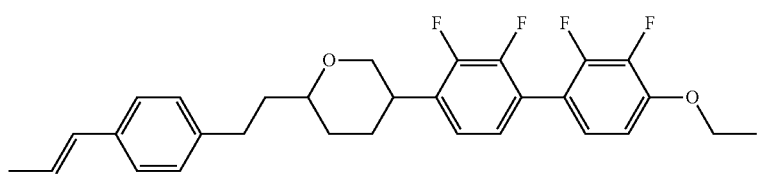 |
| 42 | 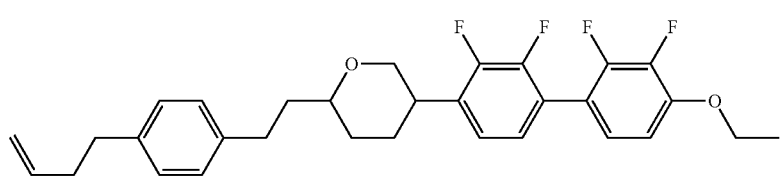 [SMILES: C=CCCc1ccc(CCC2CCC(c3ccc(-c4ccc(OCC)c(F)c4F)c(F)c3F)CO2)cc1] |
| 43 | 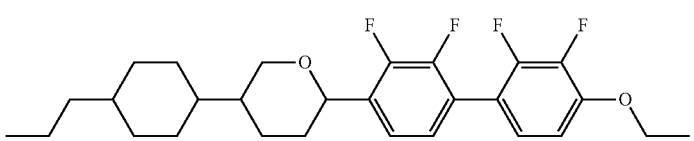 |
| 44 | 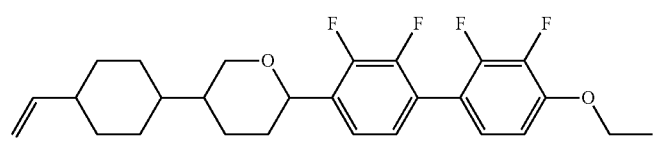 [SMILES: C=CC1CCC(C2CCC(c3ccc(-c4ccc(OCC)c(F)c4F)c(F)c3F)OC2)CC1] |
| 45 | 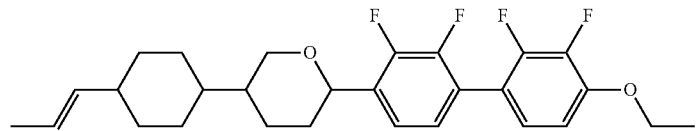 |
| 46 | 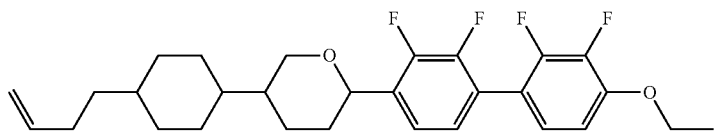 [SMILES: C=CCCC1CCC(C2CCC(c3ccc(-c4ccc(OCC)c(F)c4F)c(F)c3F)OC2)CC1] |
| 47 | 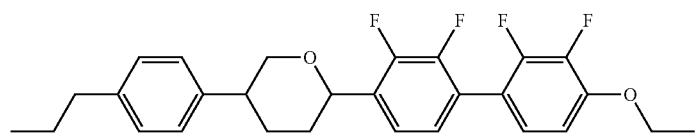 [SMILES: CCCc1ccc(C2CCC(c3ccc(-c4ccc(OCC)c(F)c4F)c(F)c3F)OC2)cc1F] |
| 48 | 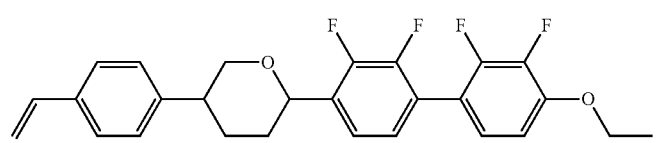 [SMILES: C=Cc1ccc(C2CCC(c3ccc(-c4ccc(OCC)c(F)c4F)c(F)c3F)OC2)c(F)c1] |
| 49 | 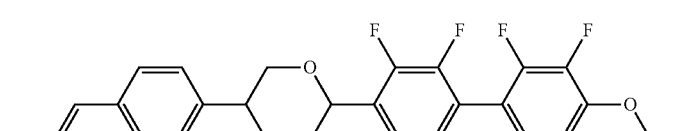 |

-continued
| No. | |
|---|---|
| 50 | 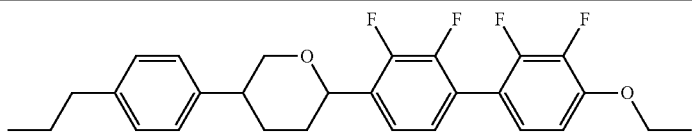 |
| 51 | 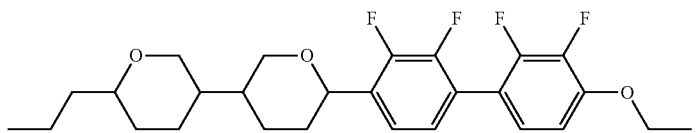 |
| 52 | 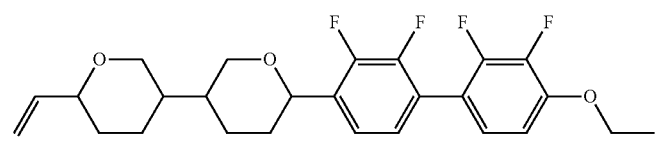 |
| 53 | 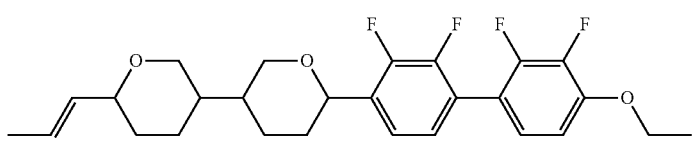 |
| 54 | 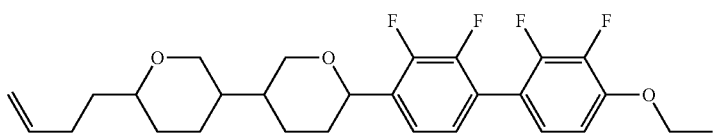 |
| 55 | 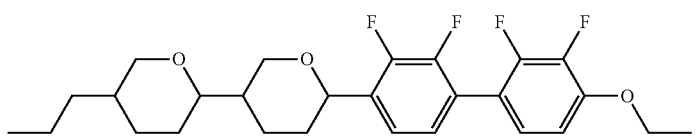 |
| 56 | 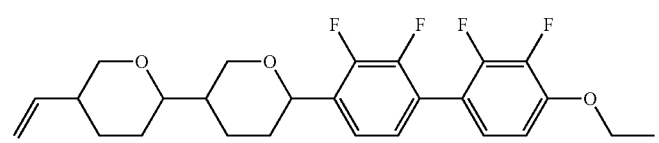 |
| 57 | 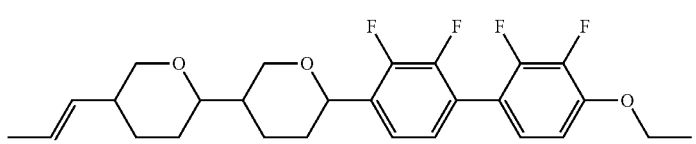 |
| 58 | 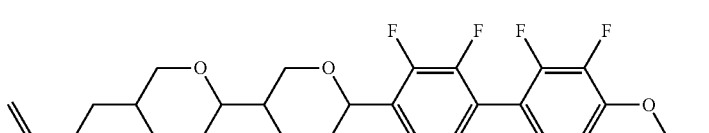 |
| 59 | 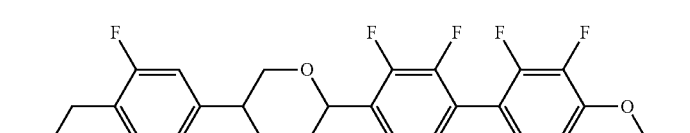 |
| 60 | 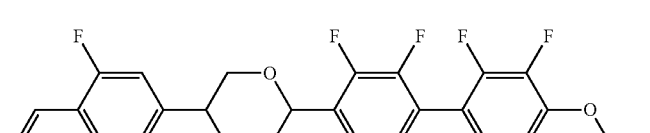 |

-continued
| No. | |
|---|---|
| 61 | 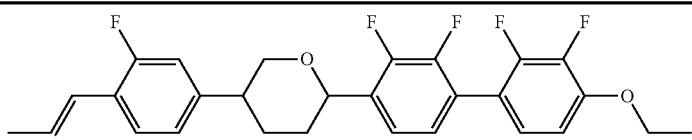 |
| 62 | 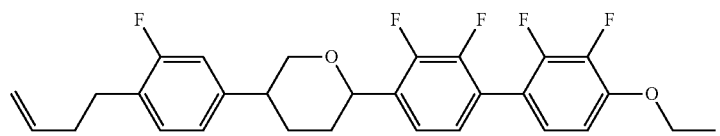 |
| 63 | 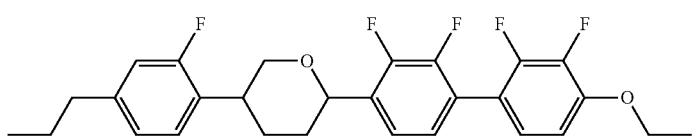 |
| 64 | 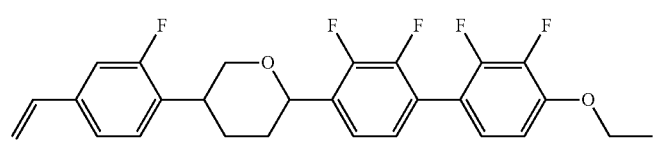 |
| 65 | 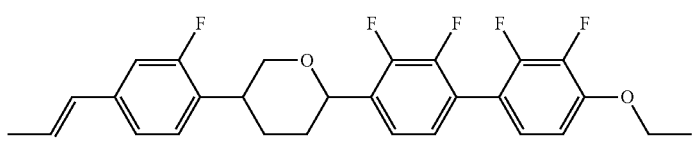 [SMILES: C/C=C/c1ccc(C2CCC(c3ccc(-c4ccc(OCC)c(F)c4F)c(F)c3F)OC2)c(F)c1F] |
| 66 | 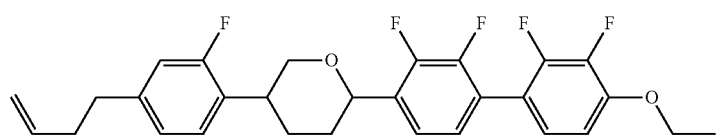 [SMILES: C=CCCc1ccc(C2CCC(c3ccc(-c4ccc(OCC)c(F)c4F)c(F)c3F)OC2)c(F)c1F] |
| 67 | 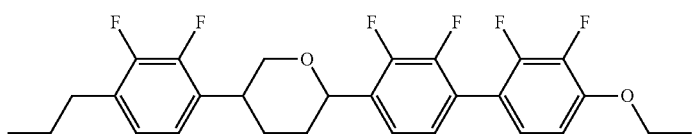 |
| 68 | 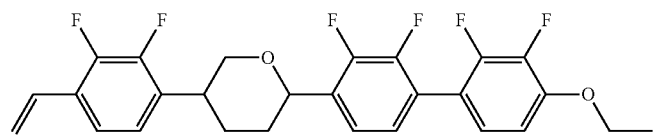 |
| 69 | 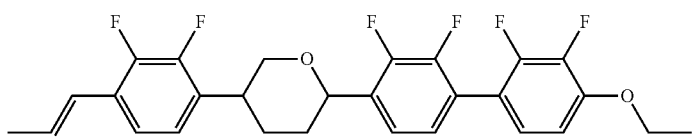 |
| 70 | 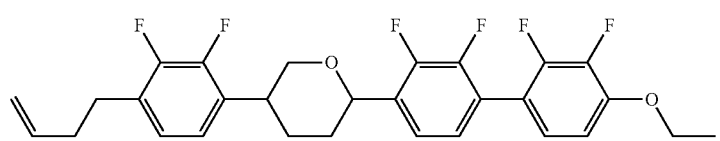 |
| 71 | 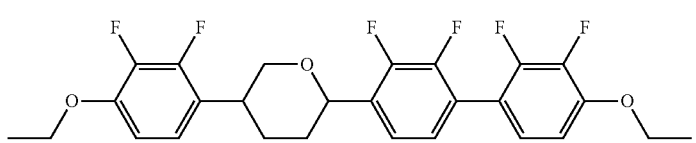 |

-continued
| No. | |
|---|---|
| 72 | 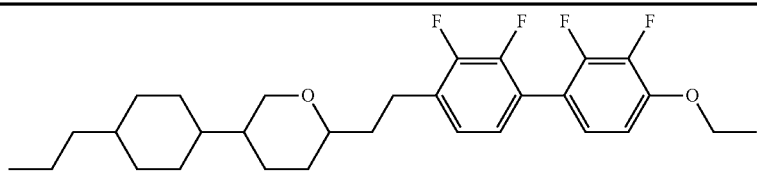 |
| 73 | 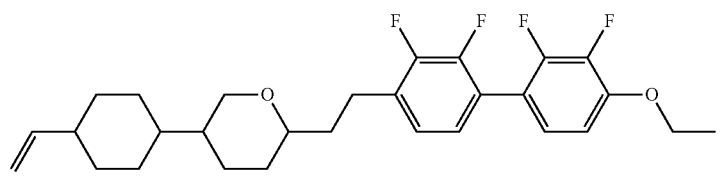 [SMILES: C=CC1CCC(C2CCC(CCc3ccc(-c4ccc(OCC)c(F)c4F)c(F)c3F)OC2)CC1] |
| 74 | 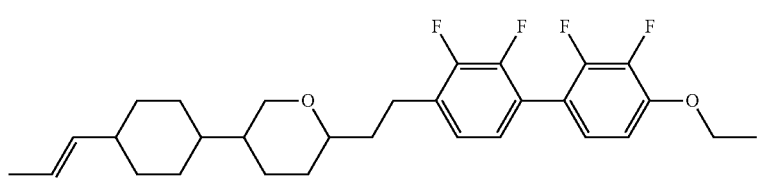 |
| 75 | 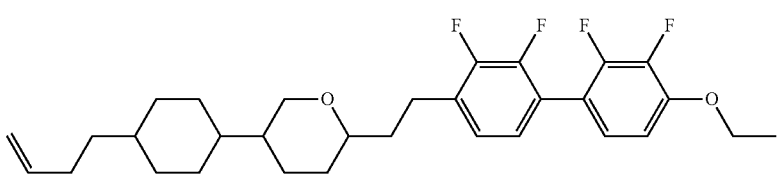 |
| 76 | 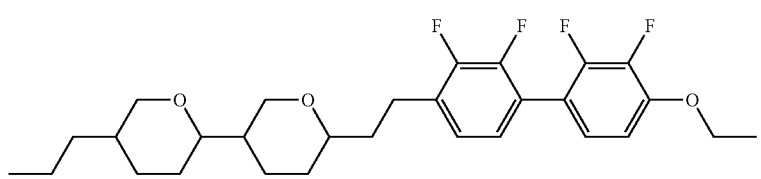 |
| 77 | 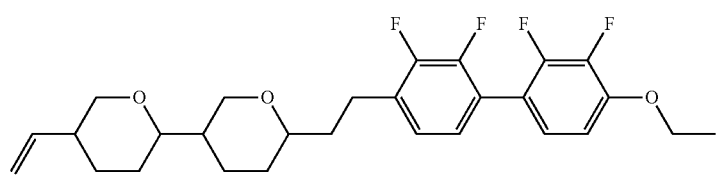 |
| 78 | 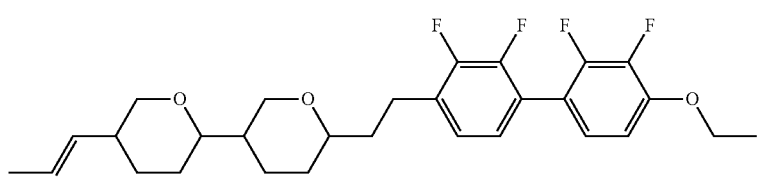 |
| 79 | 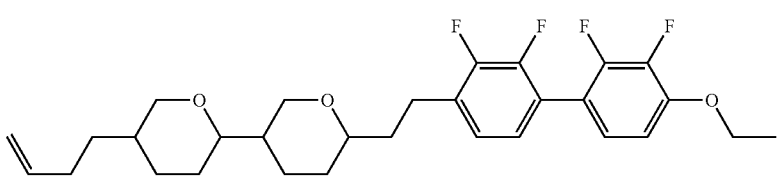 |
| 80 | 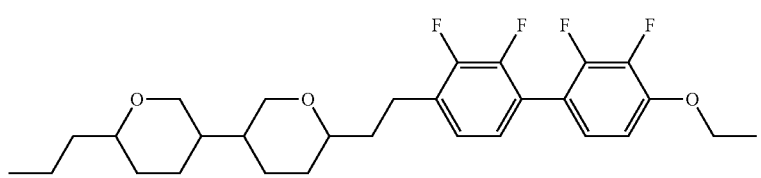 |

-continued
| No. | |
|---|---|
| 81 | 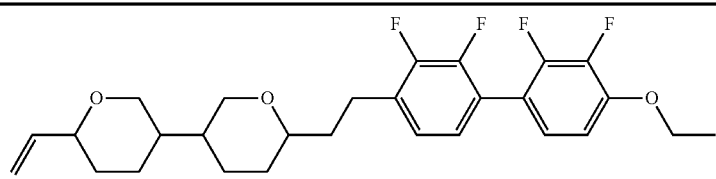 |
| 82 | 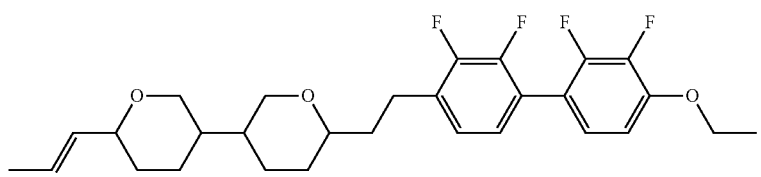 |
| 83 | 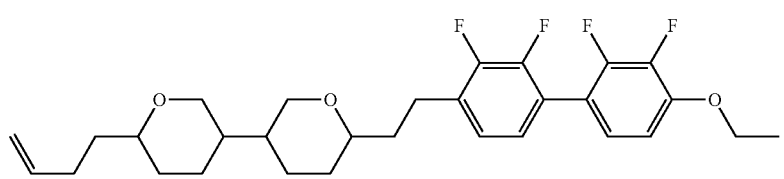 [SMILES: C=CCCC1CCC(C2CCC(CCc3ccc(-c4ccc(OCC)c(F)c4F)c(F)c3F)OC2)CC1] |
| 84 | 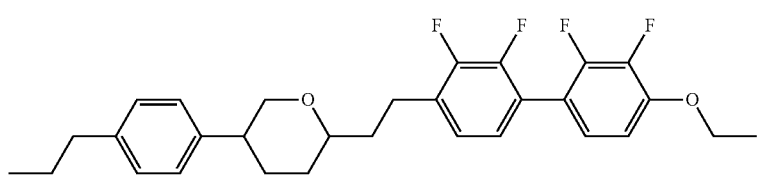 |
| 85 | 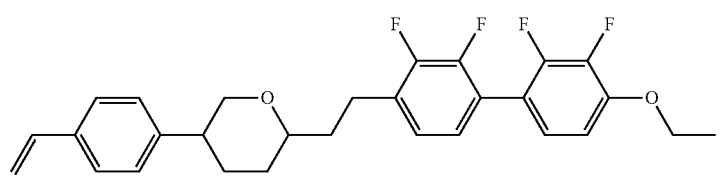 |
| 86 | 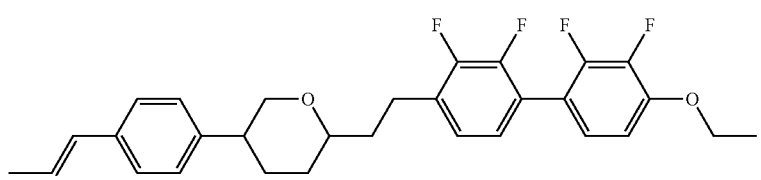 [SMILES: C/C=C/c1ccc(C2CCC(CCc3ccc(-c4ccc(OCC)c(F)c4F)c(F)c3F)OC2)cc1] |
| 87 | 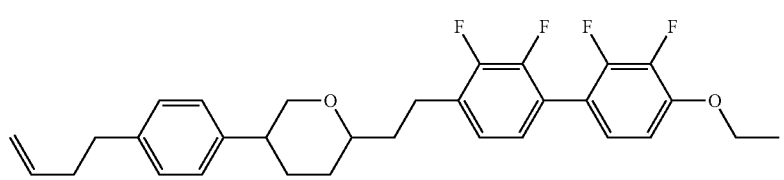 [SMILES: C=CCCc1ccc(C2CCC(CCc3ccc(-c4ccc(OCC)c(F)c4F)c(F)c3F)OC2)cc1] |
| 88 | 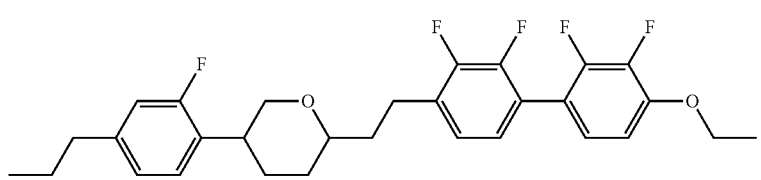 |
| 89 | 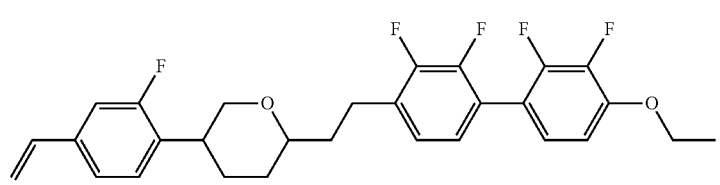 [SMILES: C=Cc1ccc(C2CCC(CCc3ccc(-c4ccc(OCC)c(F)c4F)c(F)c3F)OC2)c(F)c1] |

-continued
| No. | |
|---|---|
| 90 | 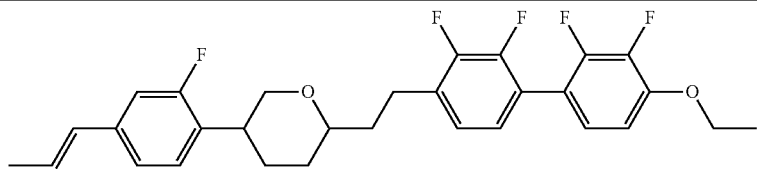 |
| 91 | 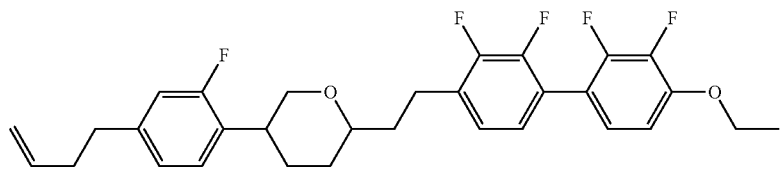 [SMILES: C=CCCc1ccc(C2CCC(CCc3ccc(-c4ccc(OCC)c(F)c4F)c(F)c3F)OC2)c(F)c1] |
| 92 | 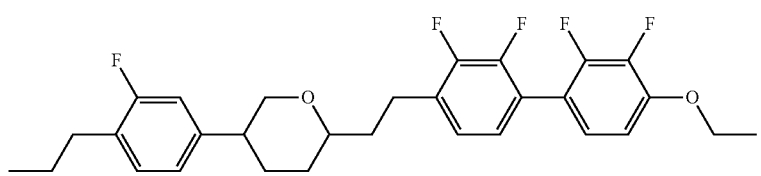 |
| 93 | 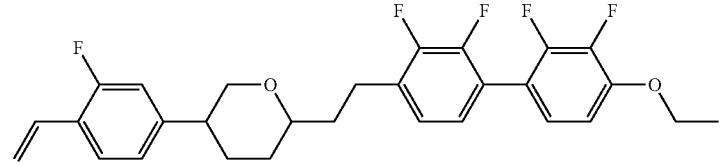 |
| 94 | 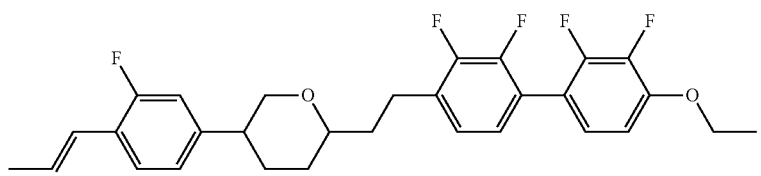 [SMILES: C/C=C/c1ccc(C2CCC(CCc3ccc(-c4ccc(OCC)c(F)c4F)c(F)c3F)OC2)cc1F] |
| 95 | 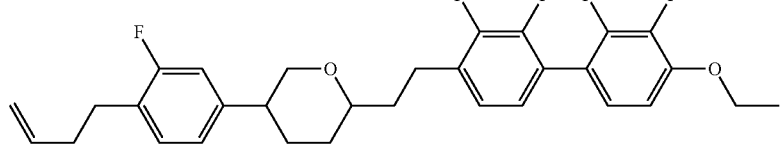 |
| 96 | 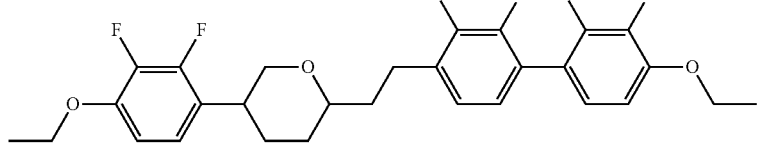 |
| 97 | 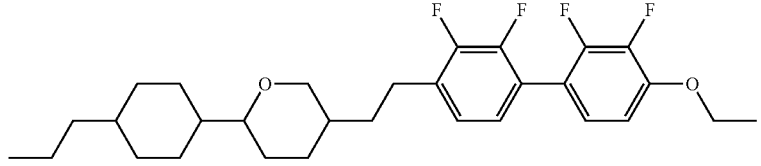 [SMILES: CCCC1CCC(C2CCC(CCc3ccc(-c4ccc(OCC)c(F)c4F)c(F)c3F)CO2)CC1] |
| 98 | 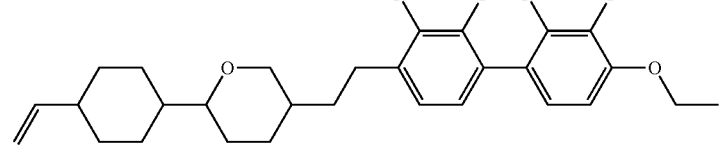 |

| No. | |
|---|---|
| 99 | 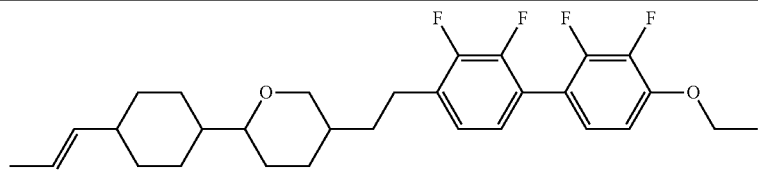 |
| 100 | 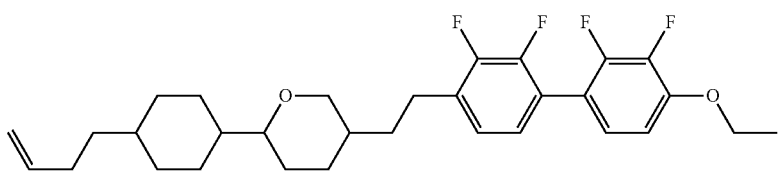 |
| 101 | 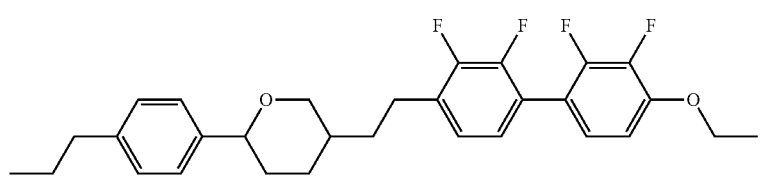 |
| 102 | 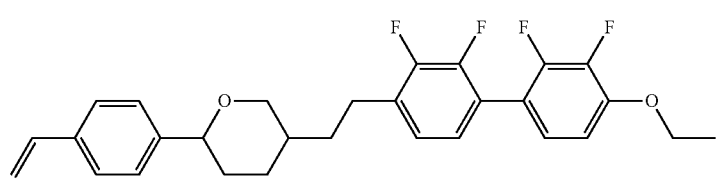 |
| 103 | 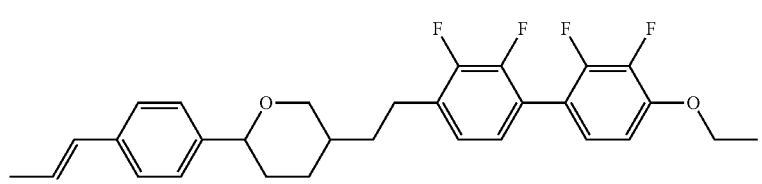 [SMILES: C/C=C/c1ccc(C2CCC(CCc3ccc(-c4ccc(OCC)c(F)c4F)c(F)c3F)CO2)cc1] |
| 104 | 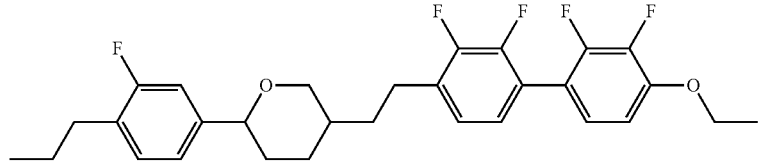 [SMILES: CCCc1ccc(C2CCC(CCc3ccc(-c4ccc(OCC)c(F)c4F)c(F)c3F)CO2)cc1F] |
| 105 | 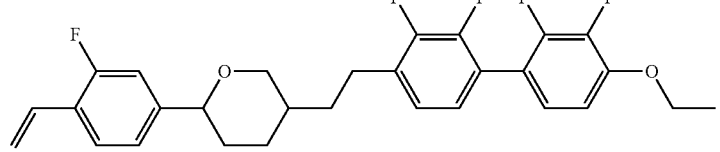 |
| 106 | 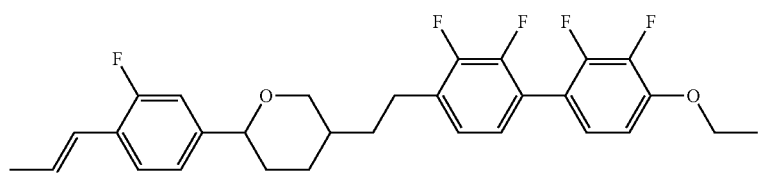 [SMILES: C/C=C/c1ccc(C2CCC(CCc3ccc(-c4ccc(OCC)c(F)c4F)c(F)c3F)CO2)cc1F] |
| 107 | 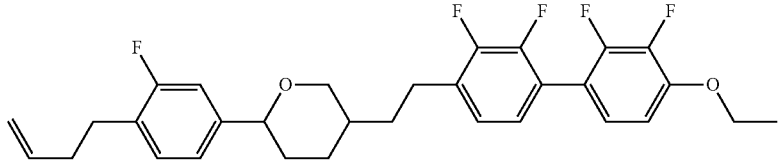 |

-continued
| No. | |
|---|---|
| 108 | 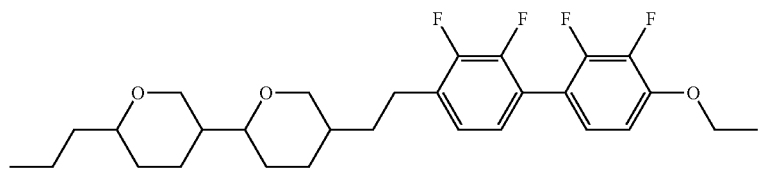 [SMILES: CCCC1CCC(C2CCC(CCc3ccc(-c4ccc(OCC)c(F)c4F)c(F)c3F)CO2)CO1] |
| 109 | 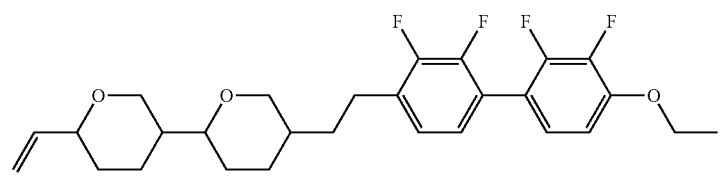 [SMILES: C=CC1CCC(C2CCC(CCc3ccc(-c4ccc(OCC)c(F)c4F)c(F)c3F)CO2)CO1] |
| 110 | 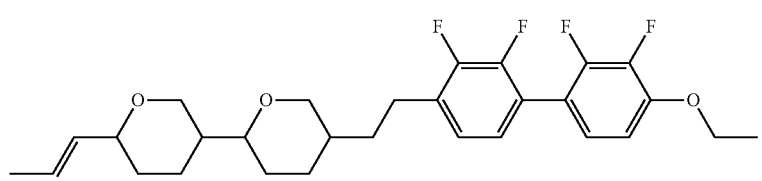 |
| 111 | 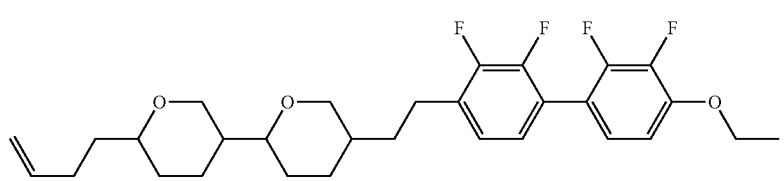 [SMILES: C=CCCC1CCC(C2CCC(CCc3ccc(-c4ccc(OCC)c(F)c4F)c(F)c3F)CO2)CO1] |
| 112 | 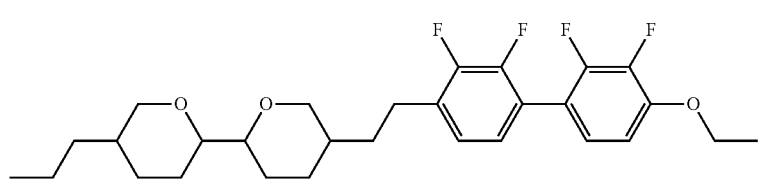 |
| 113 | 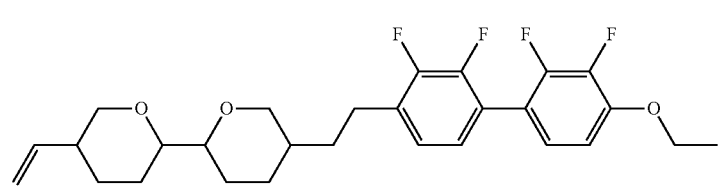 |
| 114 | 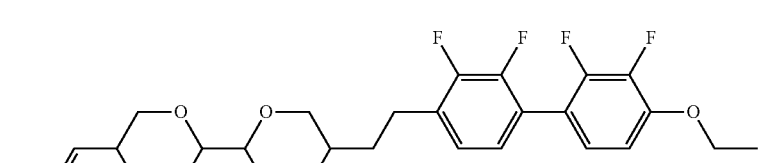 |
| 115 | 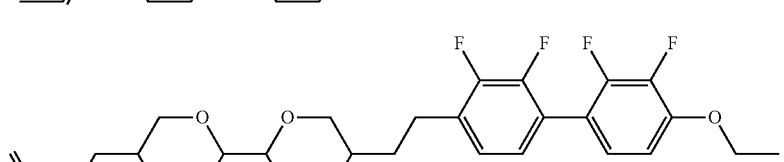 |
| 116 | 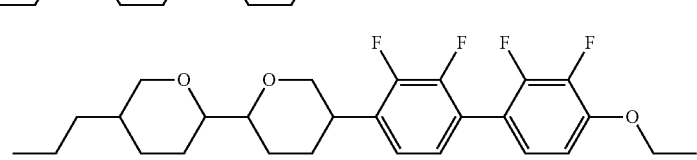 |

-continued
| No. | |
|---|---|
| 117 | 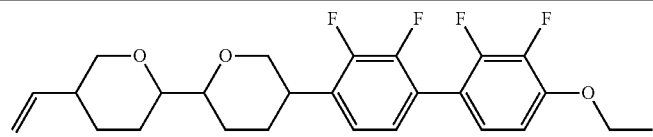 |
| 118 | 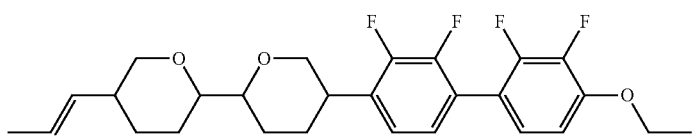 |
| 119 | 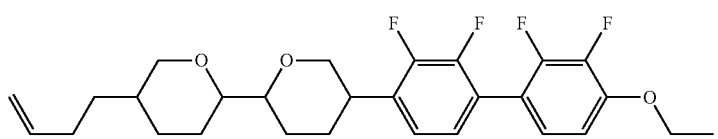 [SMILES: C=CCCC1CCC(C2CCC(c3ccc(-c4ccc(OCC)c(F)c4F)c(F)c3F)CO2)OC1] |
| 120 | 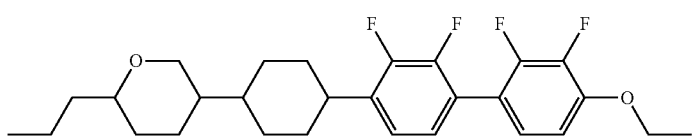 |
| 121 | 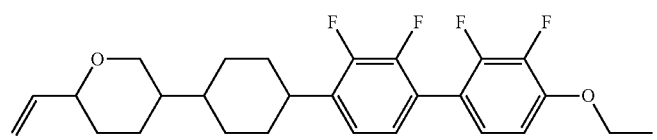 [SMILES: C=CC1CCC(C2CCC(c3ccc(-c4ccc(OCC)c(F)c4F)c(F)c3F)CC2)CO1] |
| 122 | 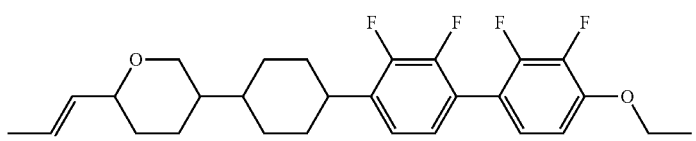 |
| 123 | 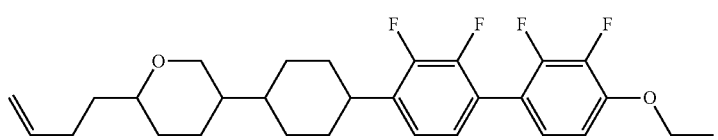 [SMILES: C=CCCC1CCC(C2CCC(c3ccc(-c4ccc(OCC)c(F)c4F)c(F)c3F)CC2)CO1] |
| 124 | 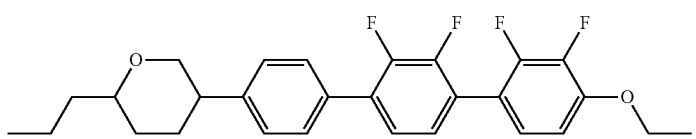 [SMILES: CCCC1CCC(c2ccc(-c3ccc(-c4ccc(OCC)c(F)c4F)c(F)c3F)cc2)CO1] |
| 125 | 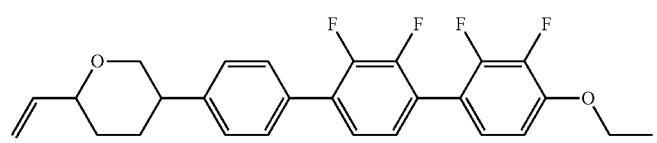 |
| 126 | 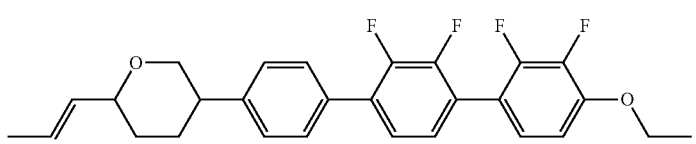 [SMILES: C/C=C/C1CCC(c2ccc(-c3ccc(-c4ccc(OCC)c(F)c4F)c(F)c3F)cc2)CO1] |
| 127 | 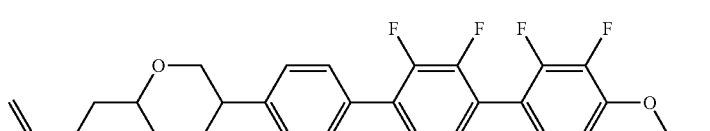 |

-continued
| No. | |
|---|---|
| 128 | 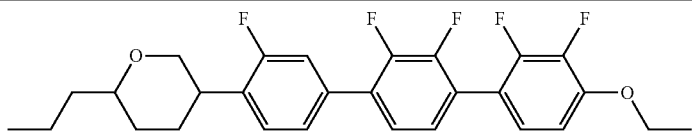 |
| 129 | 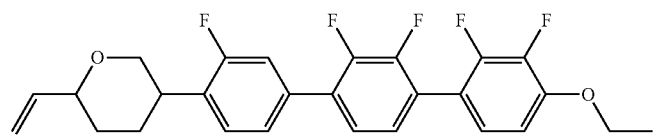 |
| 130 | 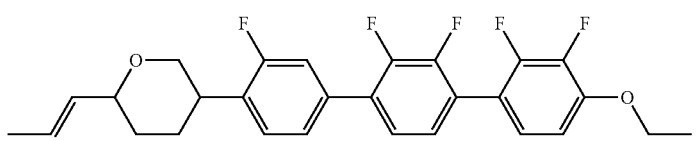 [SMILES: C/C=C/C1CCC(c2ccc(-c3ccc(-c4ccc(OCC)c(F)c4F)c(F)c3F)cc2F)CO1] |
| 131 | 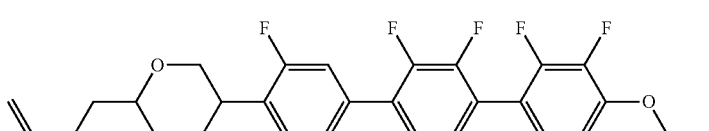 |
| 132 | 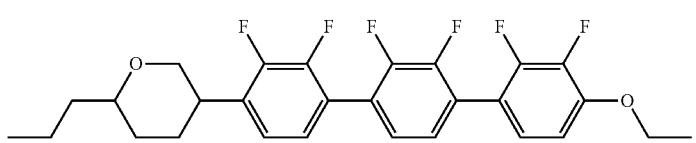 |
| 133 | 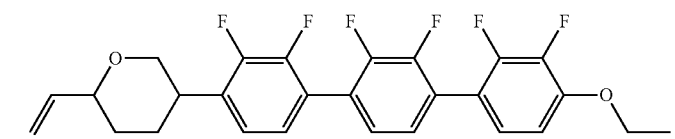 [SMILES: C=CC1CCC(c2ccc(-c3ccc(-c4ccc(OCC)c(F)c4F)c(F)c3F)c(F)c2F)CO1] |
| 134 | 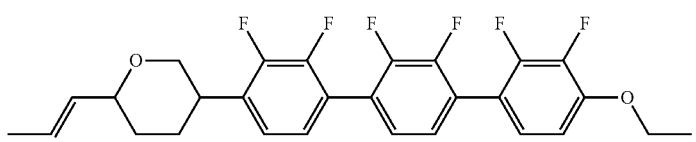 |
| 135 | 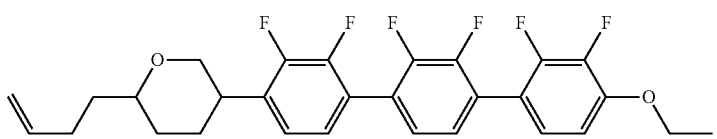 |
| 136 | 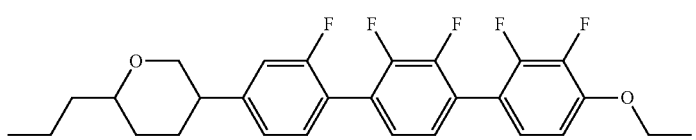 |
| 137 | 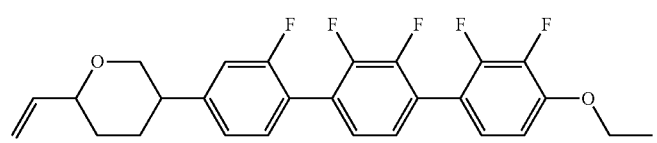 |
| 138 | 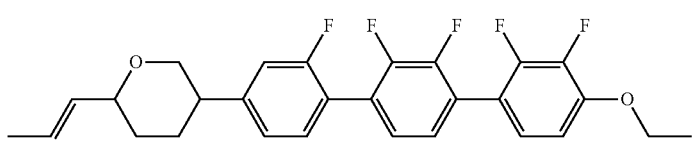 |

-continued
| No. |
|---|
| 139 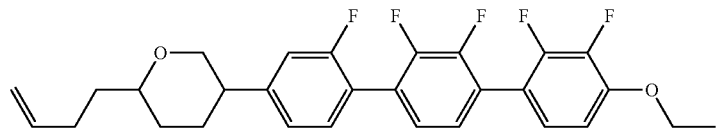 [SMILES: C=CCCC1CCC(c2ccc(-c3ccc(-c4ccc(OCC)c(F)c4F)c(F)c3F)c(F)c2)CO1] |
| 140 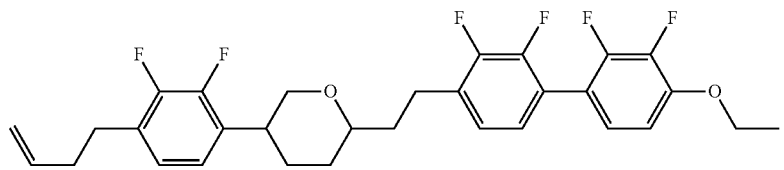 [SMILES: C=CCCc1ccc(C2CCC(CCc3ccc(-c4ccc(OCC)c(F)c4F)c(F)c3F)OC2)c(F)c1F] |
| 141 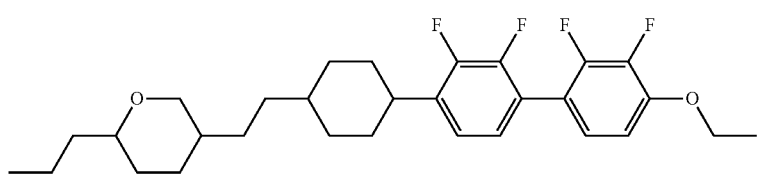 |
| 142 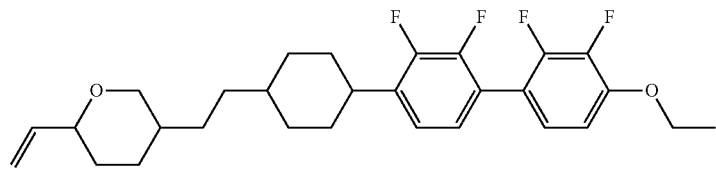 [SMILES: C=CC1CCC(CCC2CCC(c3ccc(-c4ccc(OCC)c(F)c4F)c(F)c3F)CC2)CO1] |
| 143 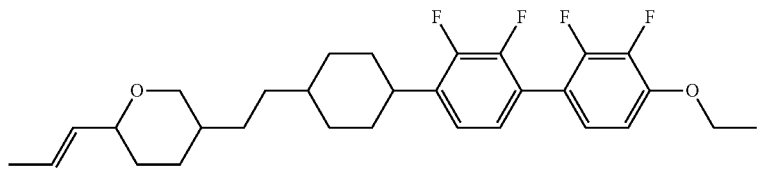 [SMILES: C/C=C/C1CCC(CCC2CCC(c3ccc(-c4ccc(OCC)c(F)c4F)c(F)c3F)CC2)CO1] |
| 144 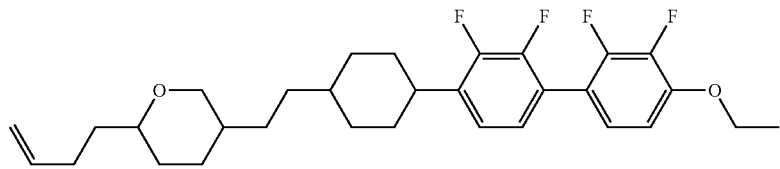 |
| 145 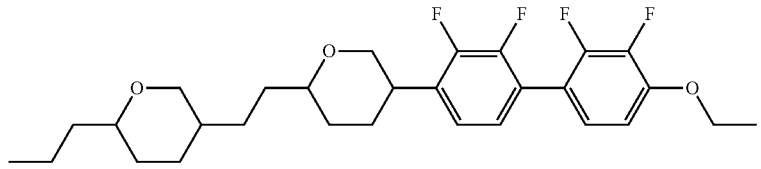 [SMILES: CCCC1CCC(CCC2CCC(c3ccc(-c4ccc(OCC)c(F)c4F)c(F)c3F)CO2)CO1] |
| 146 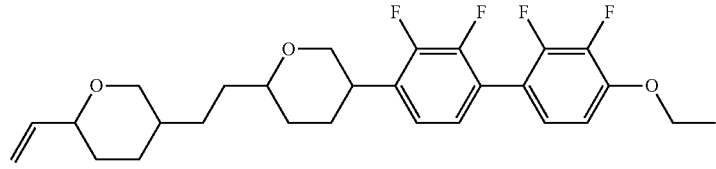 |
| 147 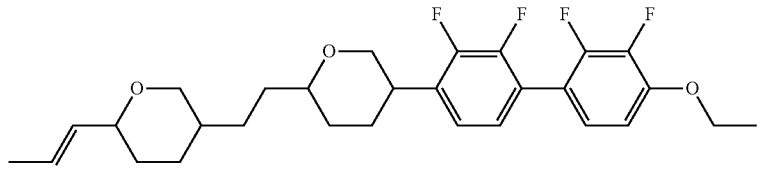 [SMILES: C/C=C/C1CCC(CCC2CCC(c3ccc(-c4ccc(OCC)c(F)c4F)c(F)c3F)CO2)CO1] |

-continued
| No. | |
|---|---|
| 148 | 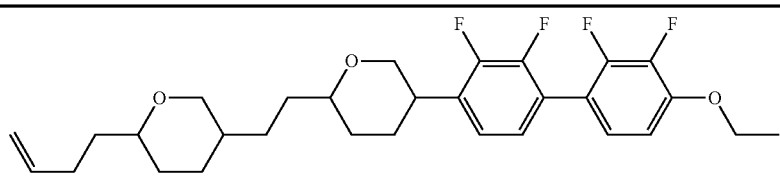 |
| 149 | 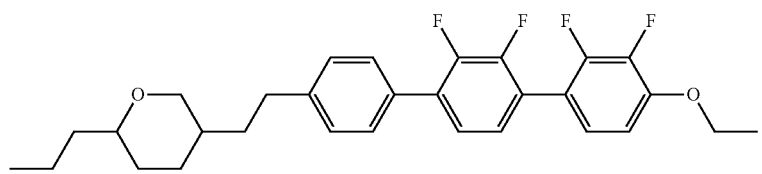 |
| 150 | 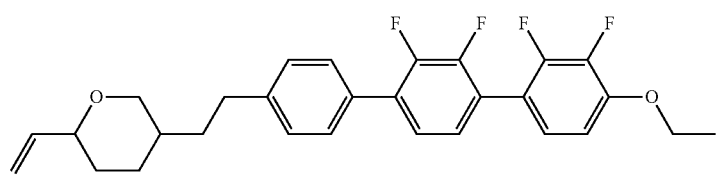 |
| 151 | 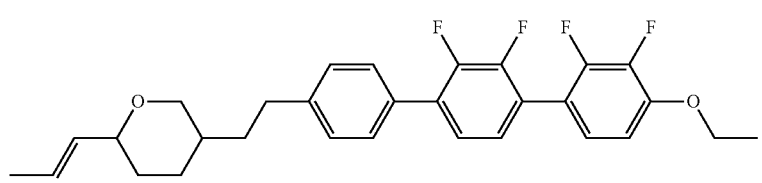 |
| 152 | 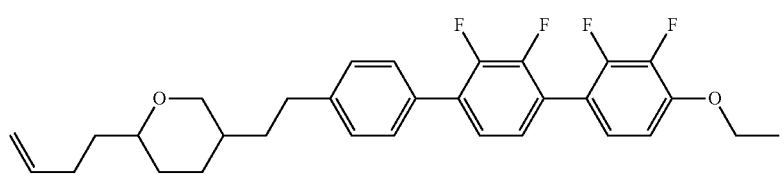 |
| 153 | 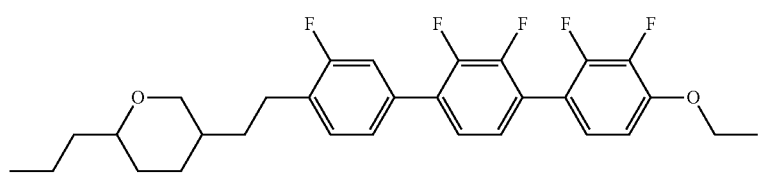 |
| 154 | 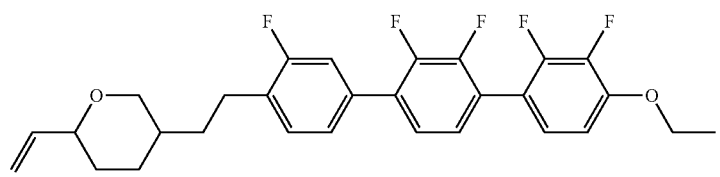 [SMILES: C=CC1CCC(CCc2ccc(-c3ccc(-c4ccc(OCC)c(F)c4F)c(F)c3F)cc2F)CO1] |
| 155 | 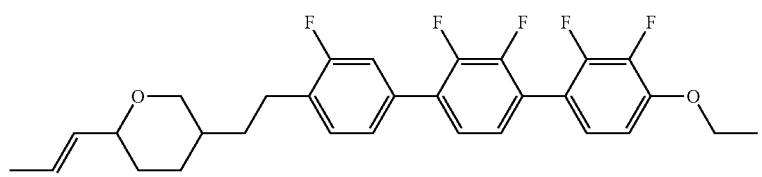 [SMILES: C/C=C/C1CCC(CCc2ccc(-c3ccc(-c4ccc(OCC)c(F)c4F)c(F)c3F)cc2F)CO1] |
| 156 | 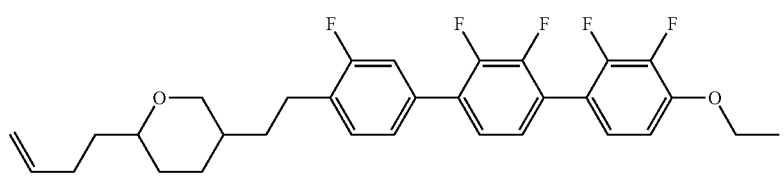 |

-continued
| No. |
|---|
| 157 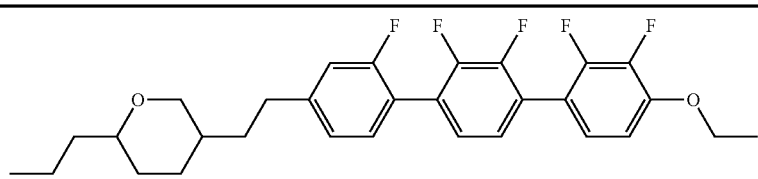 |
| 158 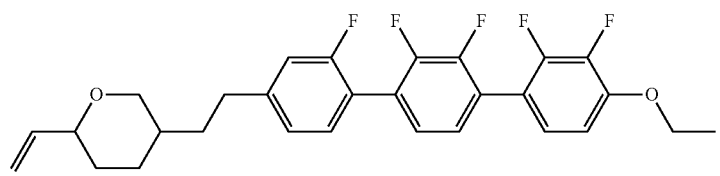 |
| 159 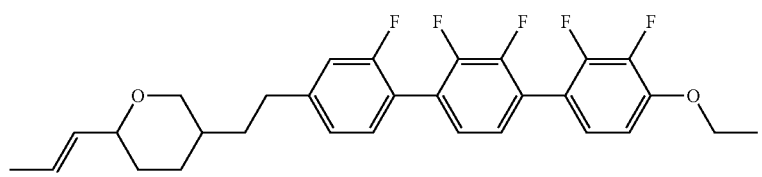 [SMILES: C/C=C/C1CCC(CCc2ccc(-c3ccc(-c4ccc(OCC)c(F)c4F)c(F)c3F)c(F)c2)CO1] |
| 160 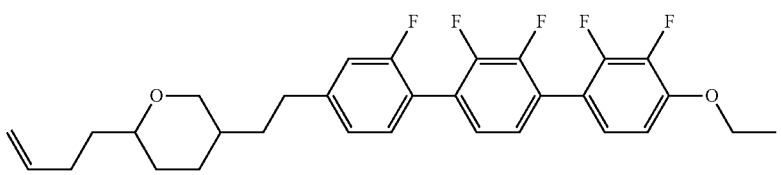 [SMILES: C=CCCC1CCC(CCc2ccc(-c3ccc(-c4ccc(OCC)c(F)c4F)c(F)c3F)c(F)c2)CO1] |
| 161 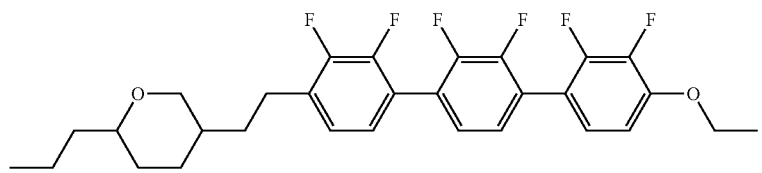 |
| 162 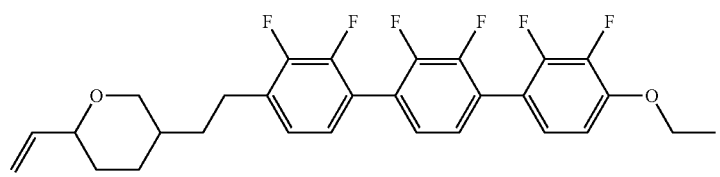 [SMILES: C=CC1CCC(CCc2ccc(-c3ccc(-c4ccc(OCC)c(F)c4F)c(F)c3F)c(F)c2F)CO1] |
| 163 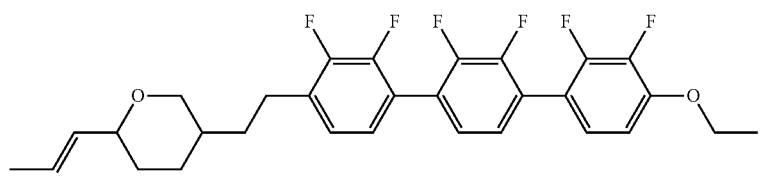 |
| 164 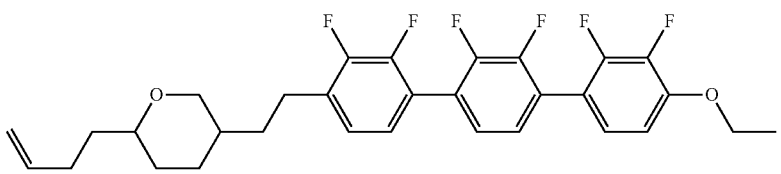 |
| 165 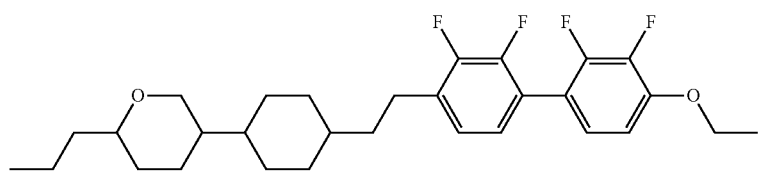 |

-continued
| No. | |
|---|---|
| 166 | 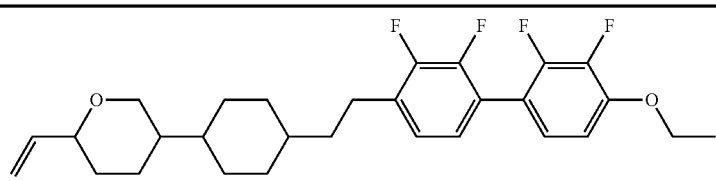 |
| 167 | 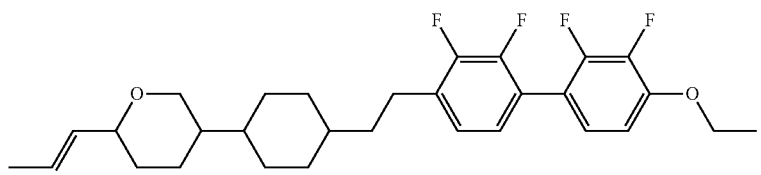 |
| 168 | 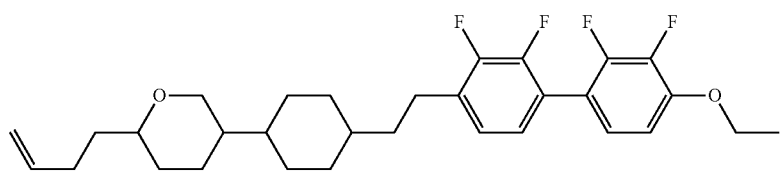 |
| 169 | 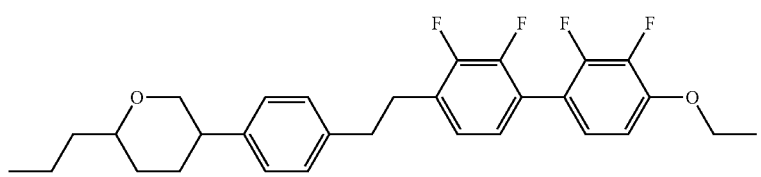 [SMILES: CCCC1CCC(c2ccc(CCc3ccc(-c4ccc(OCC)c(F)c4F)c(F)c3F)cc2)CO1] |
| 170 | 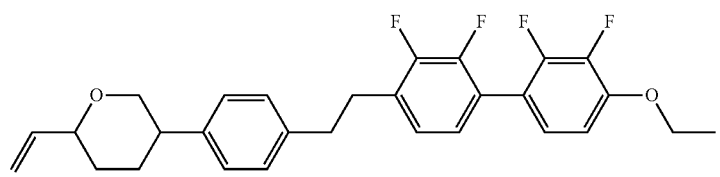 |
| 171 | 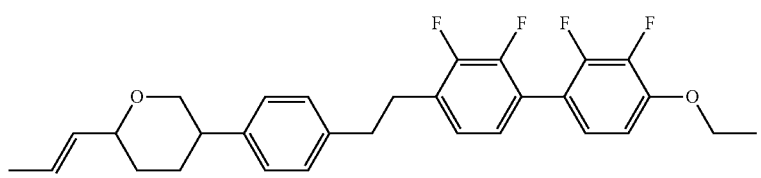 |
| 172 | 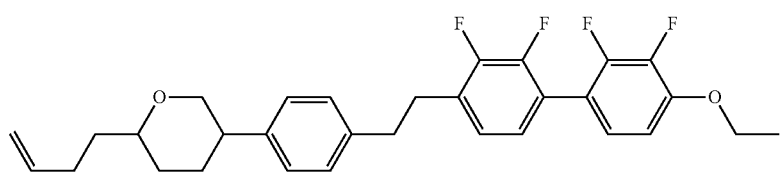 [SMILES: C=CCCC1CCC(c2ccc(CCc3ccc(-c4ccc(OCC)c(F)c4F)c(F)c3F)cc2)CO1] |
| 173 | 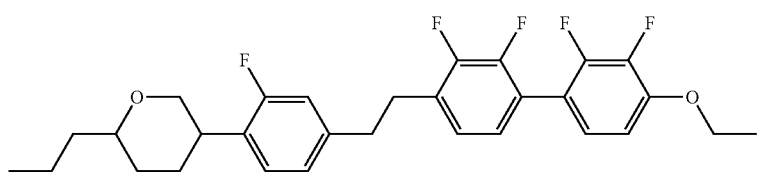 [SMILES: CCCC1CCC(c2ccc(CCc3ccc(-c4ccc(OCC)c(F)c4F)c(F)c3F)c(F)c2)CO1] |
| 174 | 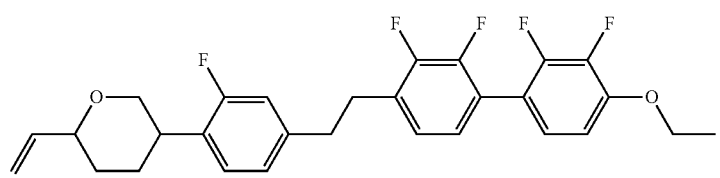 |

-continued
| No. |
|---|
| 175 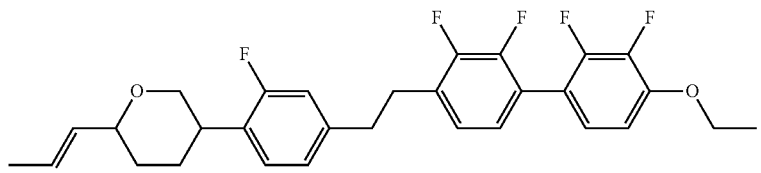 |
| 176 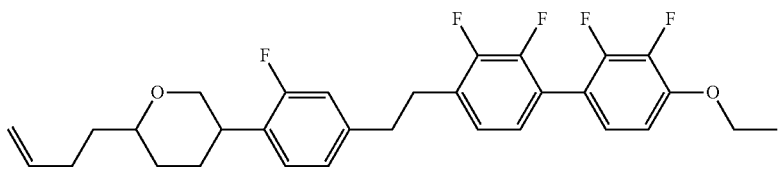 |
| 177 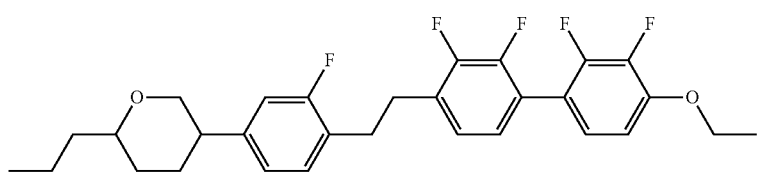 |
| 178 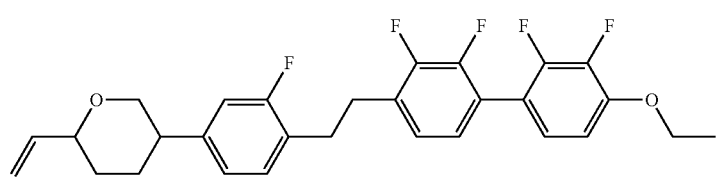 [SMILES: C=CC1CCC(c2ccc(CCc3ccc(-c4ccc(OCC)c(F)c4F)c(F)c3F)c(F)c2)CO1] |
| 179 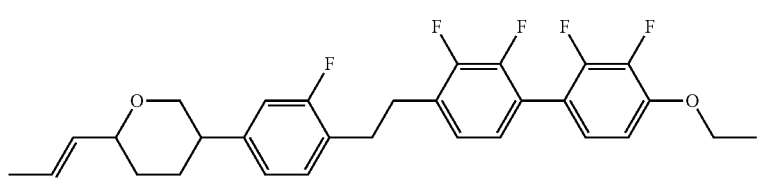 |
| 180 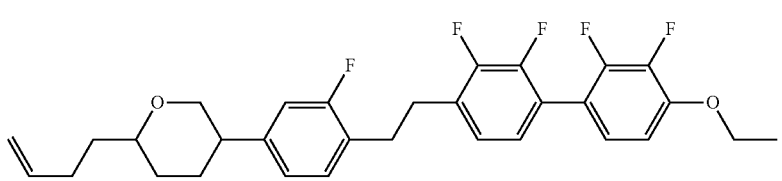 |
| 181 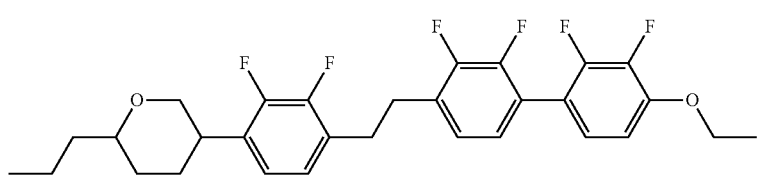 |
| 182 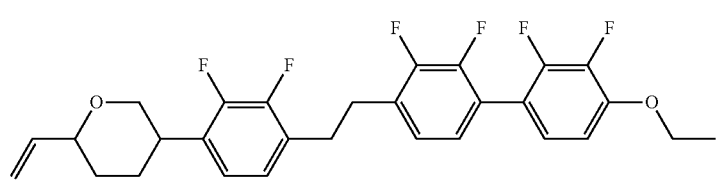 |
| 183 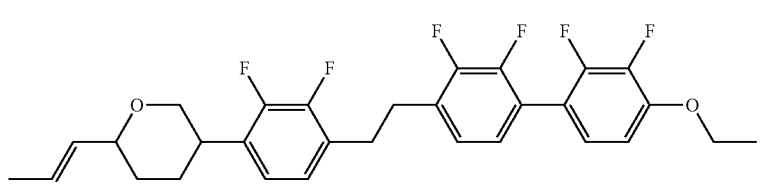 |

| No. |
|---|
| 184 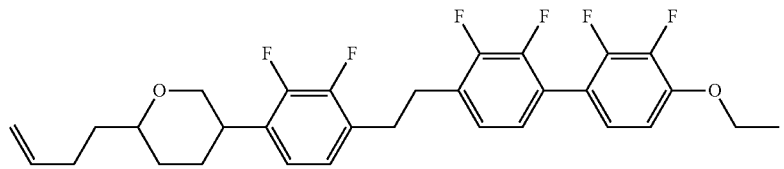 [SMILES: C=CCCC1CCC(c2ccc(CCc3ccc(-c4ccc(OCC)c(F)c4F)c(F)c3F)c(F)c2)CO1] |
| 185 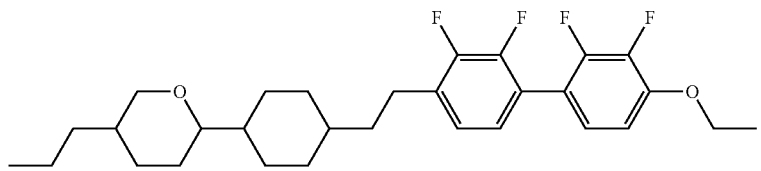 |
| 186 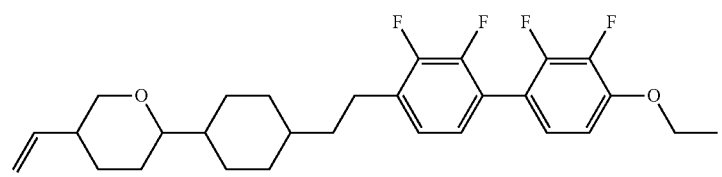 |
| 187 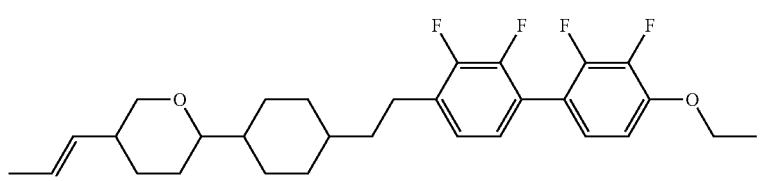 |
| 188 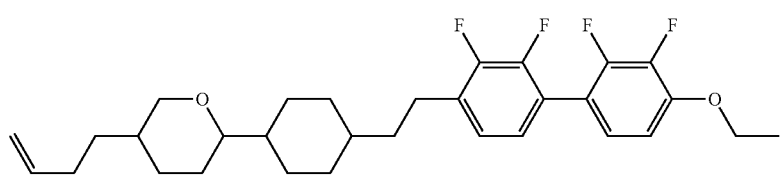 [SMILES: C=CCCC1CCC(C2CCC(CCc3ccc(-c4ccc(OCC)c(F)c4F)c(F)c3F)CC2)OC1] |
| 189 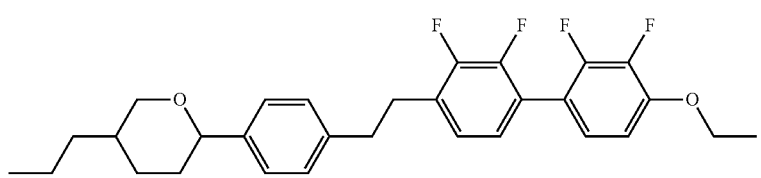 |
| 190 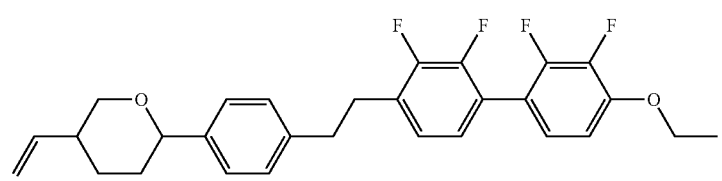 [SMILES: C=CC1CCC(c2ccc(CCc3ccc(-c4ccc(OCC)c(F)c4F)c(F)c3F)cc2)OC1] |
| 191 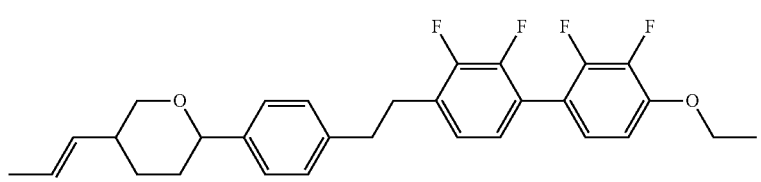 |
| 192 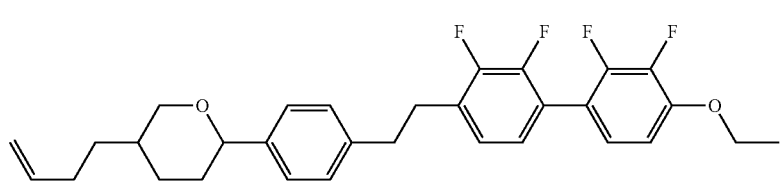 |

-continued
| No. | |
|---|---|
| 193 | 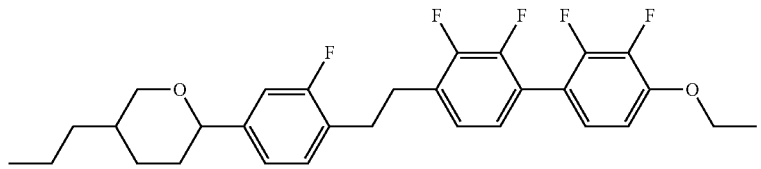 |
| 194 | 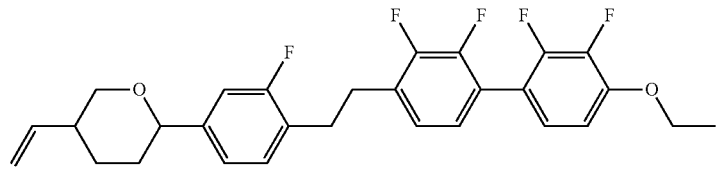 |
| 195 | 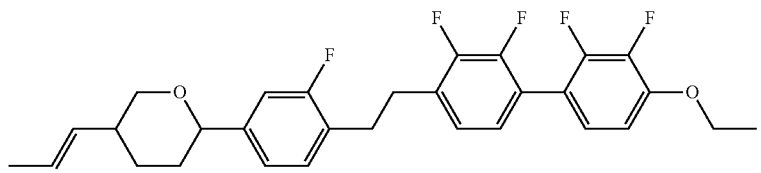 [SMILES: C/C=C/C1CCC(c2ccc(CCc3ccc(-c4ccc(OCC)c(F)c4F)c(F)c3F)cc2)OC1] |
| 196 | 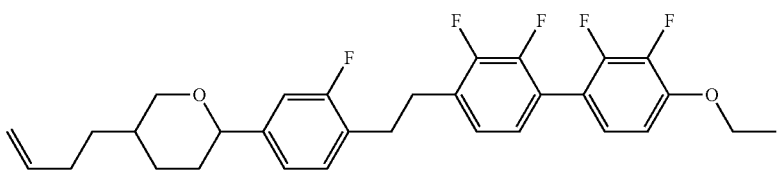 [SMILES: C=CCCC1CCC(c2ccc(CCc3ccc(-c4ccc(OCC)c(F)c4F)c(F)c3F)c(F)c2)OC1] |
| 197 | 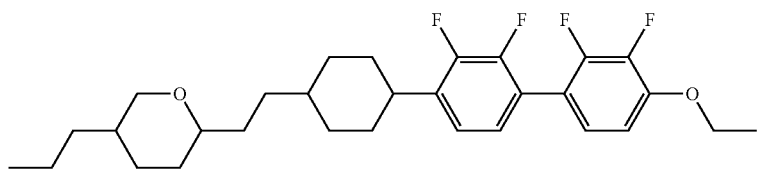 |
| 198 | 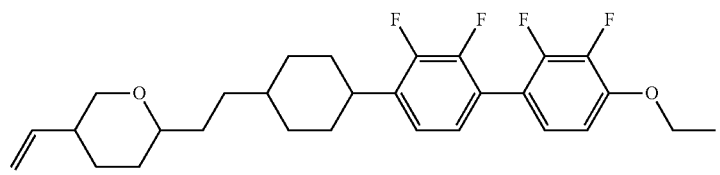 [SMILES: C=CC1CCC(CCC2CCC(c3ccc(-c4ccc(OCC)c(F)c4F)c(F)c3F)CC2)OC1] |
| 199 | 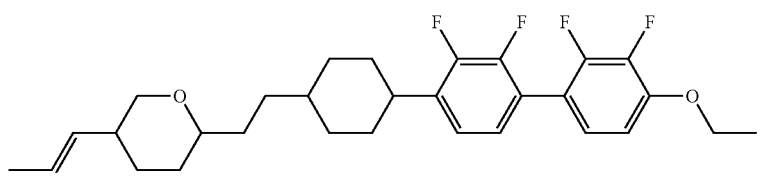 [SMILES: C/C=C/C1CCC(CCC2CCC(c3ccc(-c4ccc(OCC)c(F)c4F)c(F)c3F)CC2)OC1] |
| 200 | 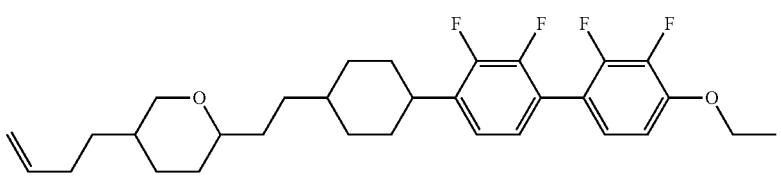 |
| 201 | 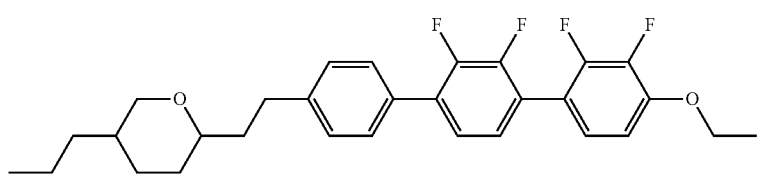 |

| No. |
|---|
| 202 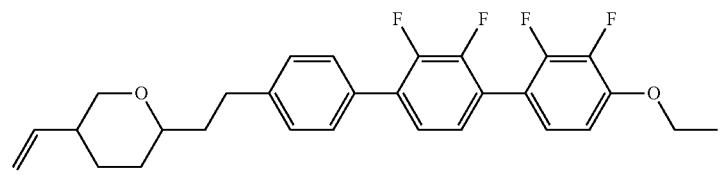 [SMILES: C=CC1CCC(CCc2ccc(-c3ccc(-c4ccc(OCC)c(F)c4F)c(F)c3F)cc2)OC1] |
| 203 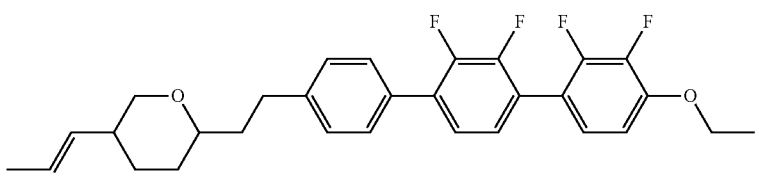 [SMILES: C/C=C/C1CCC(CCc2ccc(-c3ccc(-c4ccc(OCC)c(F)c4F)c(F)c3F)cc2)OC1] |
| 204 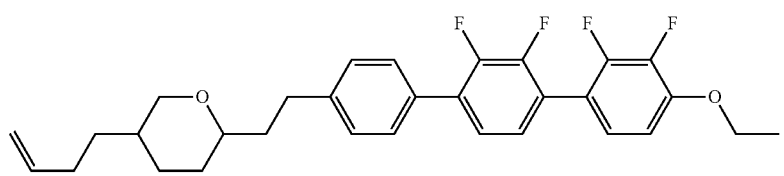 [SMILES: C=CCCC1CCC(CCc2ccc(-c3ccc(-c4ccc(OCC)c(F)c4F)c(F)c3F)cc2)OC1] |
| 205 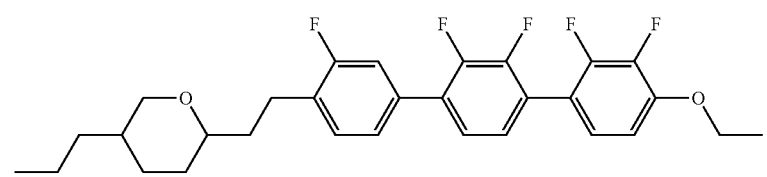 |
| 206 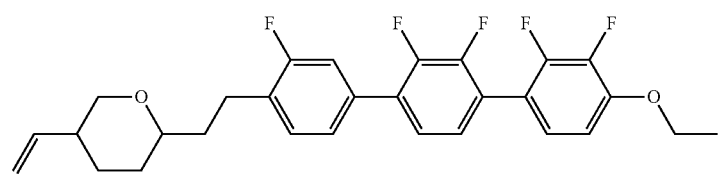 [SMILES: C=CC1CCC(CCc2ccc(-c3ccc(-c4ccc(OCC)c(F)c4F)c(F)c3F)cc2F)OC1] |
| 207 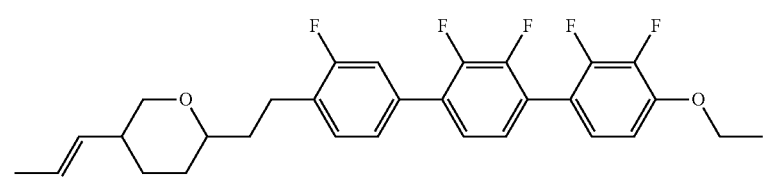 |
| 208 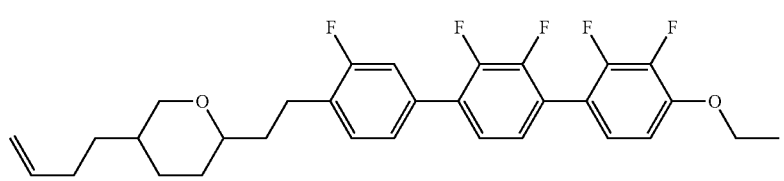 [SMILES: C=CCCC1CCC(CCc2ccc(-c3ccc(-c4ccc(OCC)c(F)c4F)c(F)c3F)cc2F)OC1] |
| 209 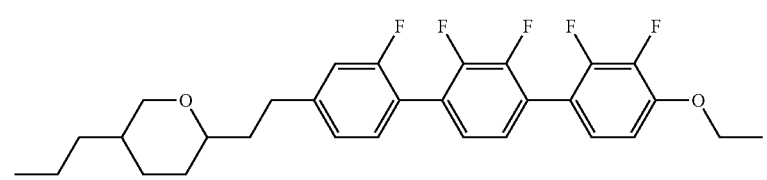 [SMILES: CCCC1CCC(CCc2ccc(-c3ccc(-c4ccc(OCC)c(F)c4F)c(F)c3F)c(F)c2)OC1] |
| 210 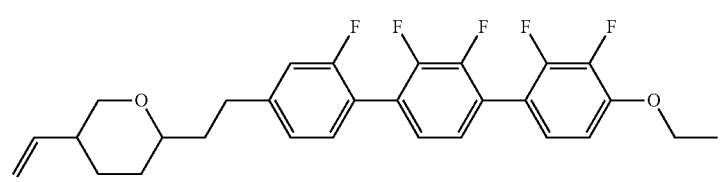 |

-continued
| No. |
|---|
| 211 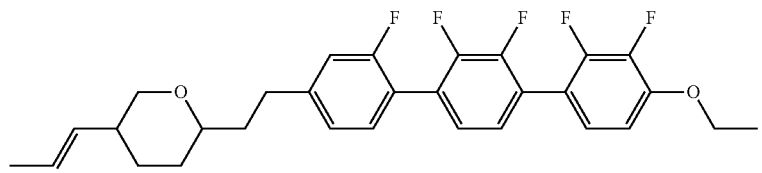 [SMILES: C/C=C/C1CCC(CCc2ccc(-c3ccc(-c4ccc(OCC)c(F)c4F)c(F)c3F)c(F)c2)OC1] |
| 212 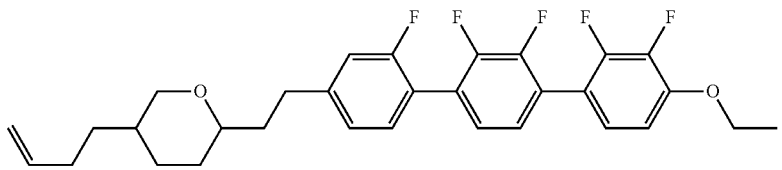 [SMILES: C=CCCC1CCC(CCc2ccc(-c3ccc(-c4ccc(OCC)c(F)c4F)c(F)c3F)c(F)c2)OC1] |
| 213 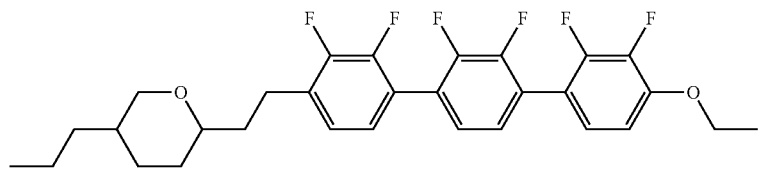 [SMILES: CCCC1CCC(CCc2ccc(-c3ccc(-c4ccc(OCC)c(F)c4F)c(F)c3F)c(F)c2F)OC1] |
| 214 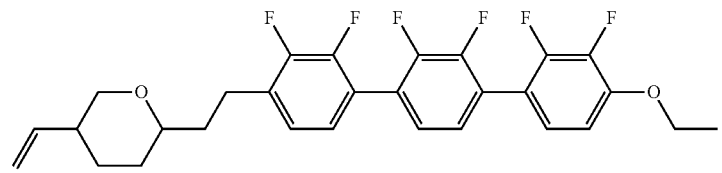 [SMILES: C=CC1CCC(CCc2ccc(-c3ccc(-c4ccc(OCC)c(F)c4F)c(F)c3F)c(F)c2F)OC1] |
| 215 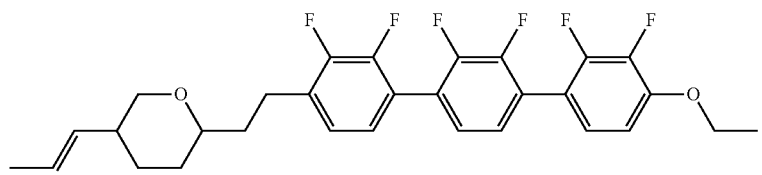 [SMILES: C/C=C/C1CCC(CCc2ccc(-c3ccc(-c4ccc(OCC)c(F)c4F)c(F)c3F)c(F)c2F)OC1] |
| 216 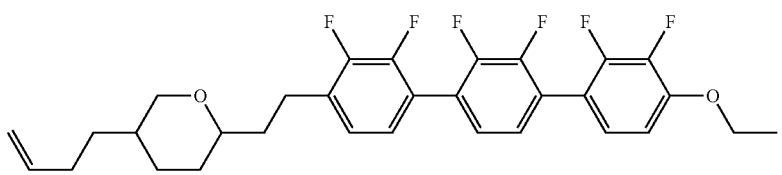 [SMILES: C=CCCC1CCC(CCc2ccc(-c3ccc(-c4ccc(OCC)c(F)c4F)c(F)c3F)c(F)c2F)OC1] |
| 217 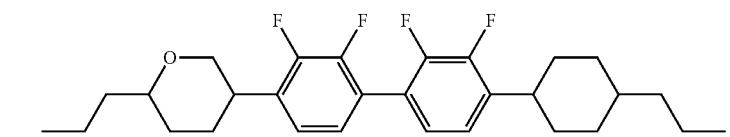 |
| 218 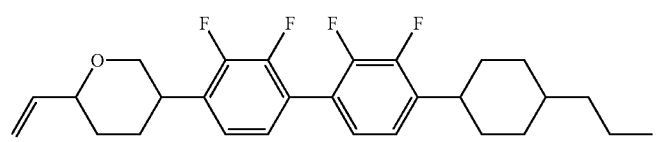 |
| 219 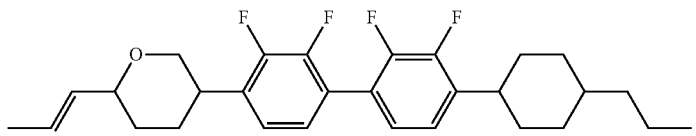 [SMILES: C/C=C/C1CCC(c2ccc(-c3ccc(C4CCC(CCC)CC4)c(F)c3F)c(F)c2F)CO1] |

-continued
| No. | |
|---|---|
| 220 | 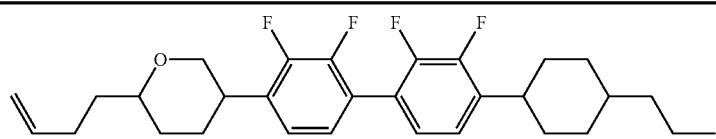 |
| 221 | 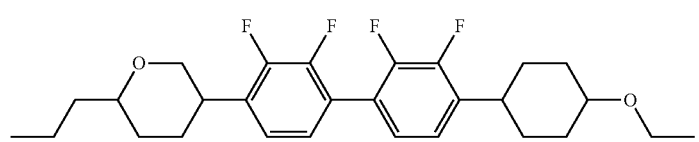 |
| 222 | 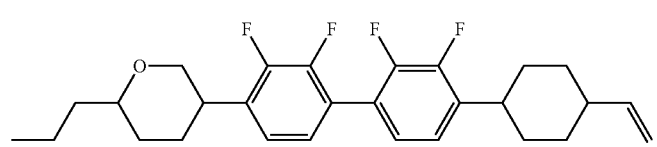 |
| 223 | 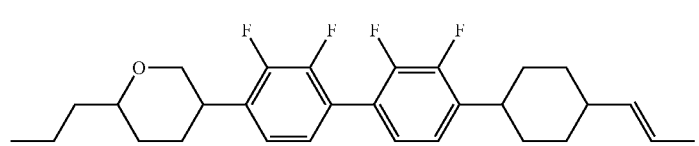 |
| 224 | 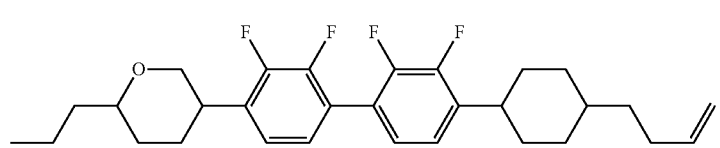 |
| 225 | 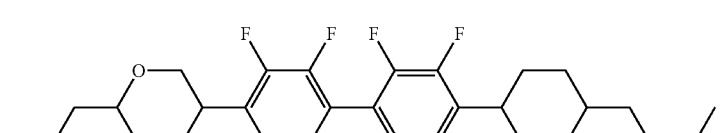 |
| 226 | 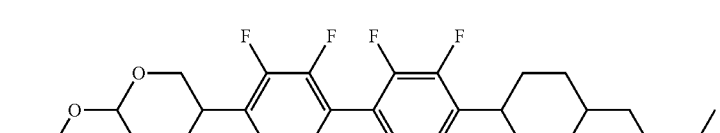 |
| 227 | 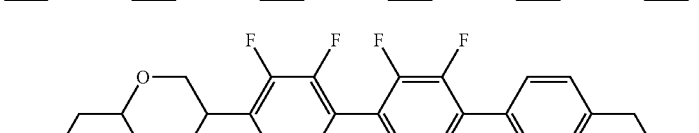 |
| 228 | 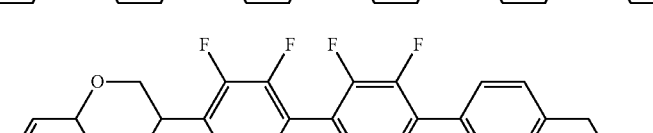 |
| 229 | 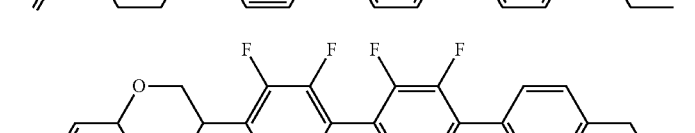 |
| 230 | 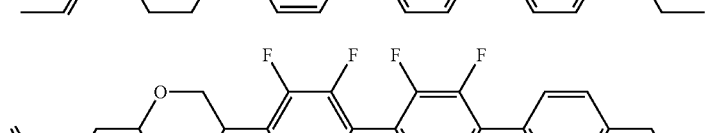 |

-continued
| No. | |
|---|---|
| 231 | 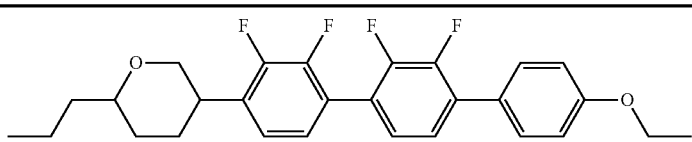 |
| 232 | 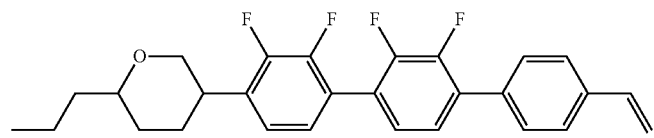 |
| 233 | 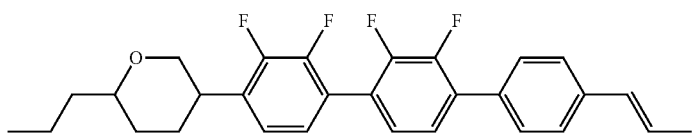 [SMILES: CCCc1ccc(-c2ccc(-c3ccc(C4CCC(CCC)OC4)c(F)c3F)c(F)c2F)cc1] |
| 234 | 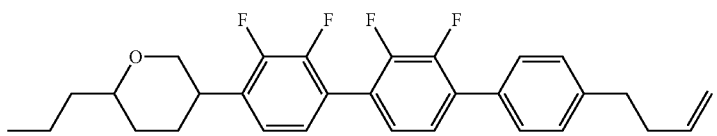 |
| 235 | 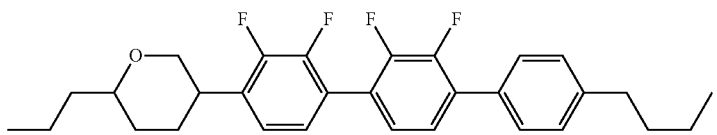 |
| 236 | 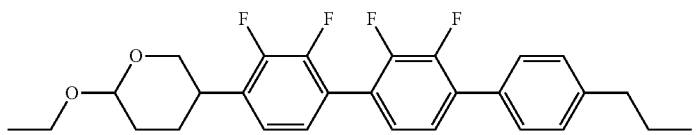 |
| 237 | 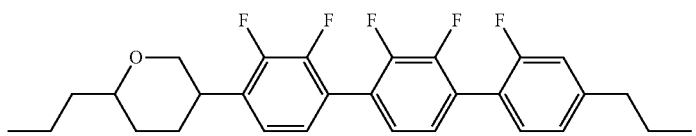 [SMILES: CCCc1ccc(-c2ccc(-c3ccc(C4CCC(CCC)OC4)c(F)c3F)c(F)c2F)c(F)c1] |
| 238 | 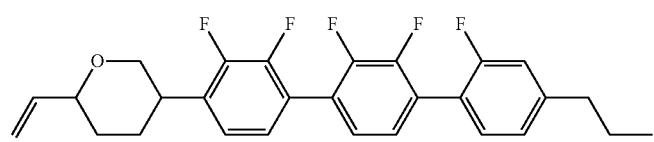 |
| 239 | 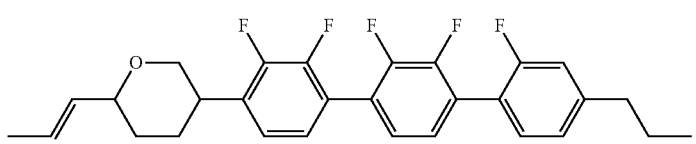 |
| 240 | 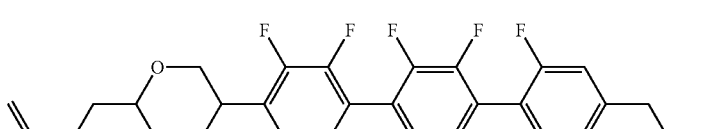 |
| 241 | 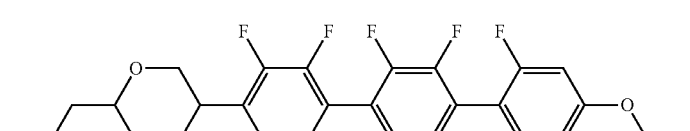 |

| No. | |
|---|---|
| 242 | 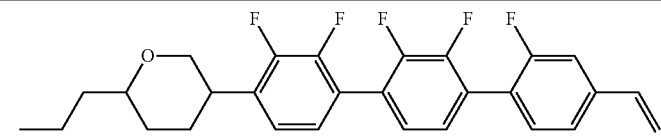 |
| 243 | 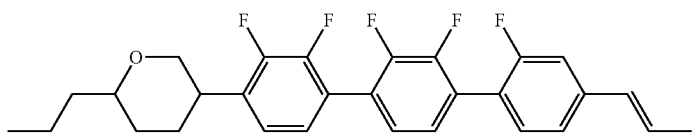 |
| 244 | 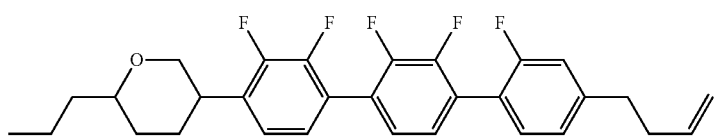 |
| 245 | 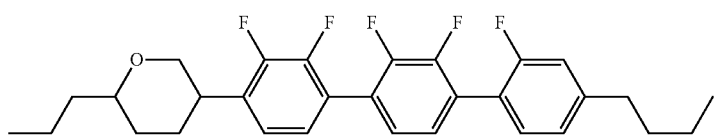 |
| 246 | 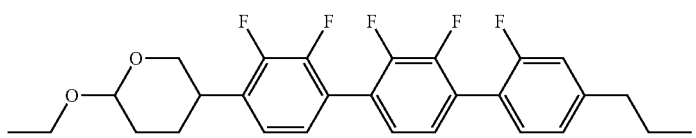 |
| 247 | 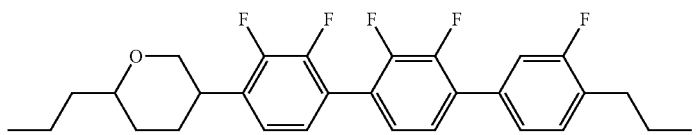 |
| 248 | 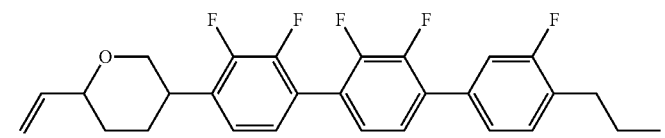 |
| 249 | 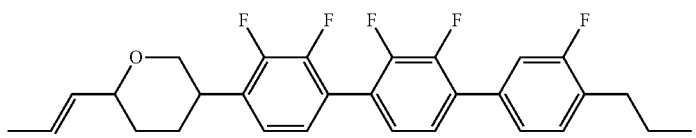 |
| 250 | 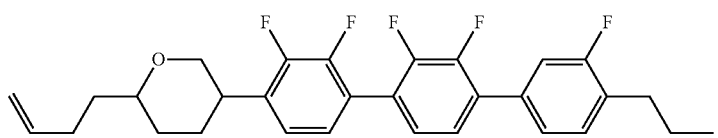 [SMILES: C=CCCC1CCC(c2ccc(-c3ccc(-c4ccc(CCC)c(F)c4)c(F)c3F)c(F)c2F)CO1] |
| 251 | 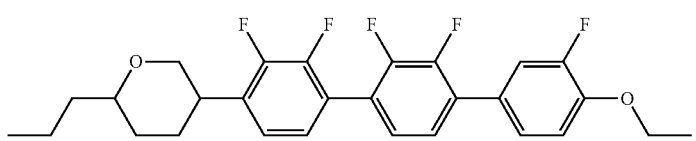 |
| 252 | 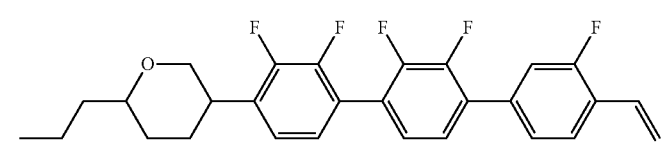 |

| No. | |
|---|---|
| 253 | 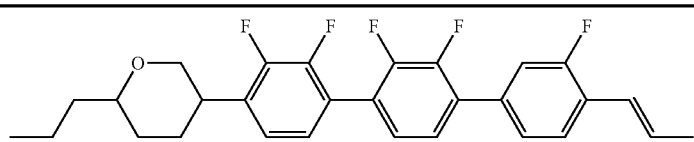 |
| 254 | 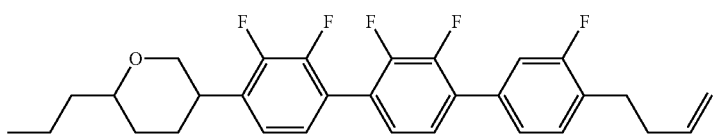 |
| 255 | 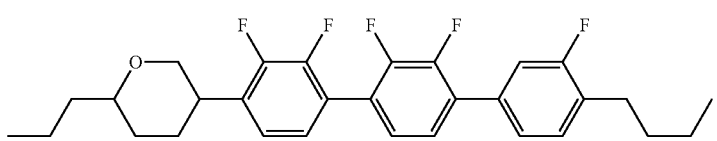 [SMILES: C=CCCc1ccc(-c2ccc(-c3ccc(C4CCC(CCC)OC4)c(F)c3F)c(F)c2F)cc1F] |
| 256 | 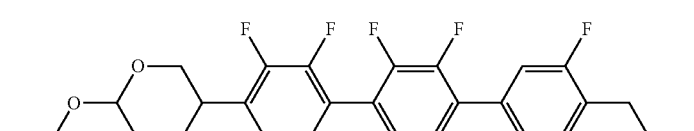 |
| 257 | 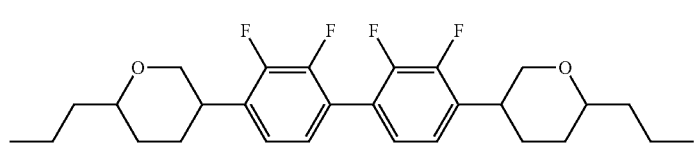 [SMILES: CCCC1CCC(c2ccc(-c3ccc(C4CCC(OCC)OC4)c(F)c3F)c(F)c2F)CO1] |
| 258 | 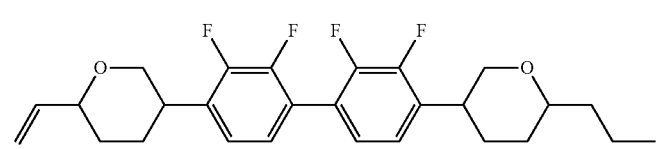 |
| 259 | 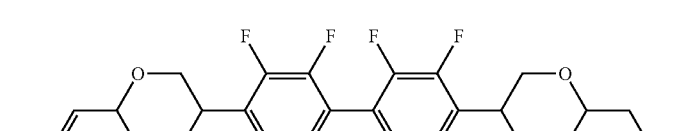 |
| 260 | 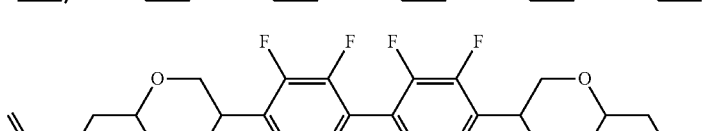 |
| 261 | 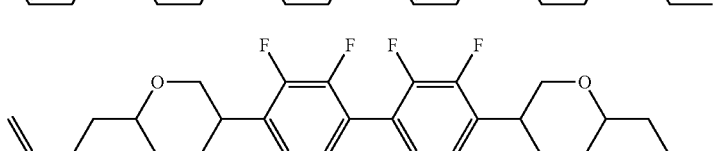 |
| 262 | 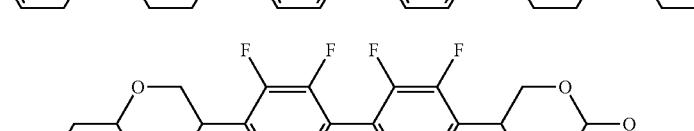 |
| 263 | 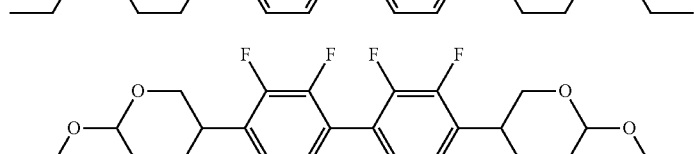 |

| No. |
|---|
| 264 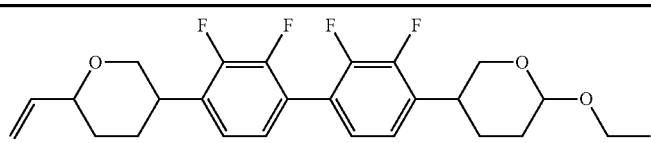 |
| 265 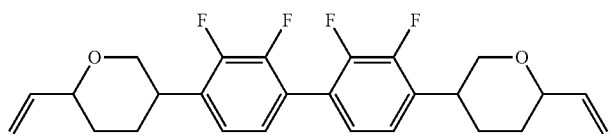 [SMILES: C=CC1CCC(c2ccc(-c3ccc(C4CCC(C=C)OC4)c(F)c3F)c(F)c2F)CO1] |
| 266 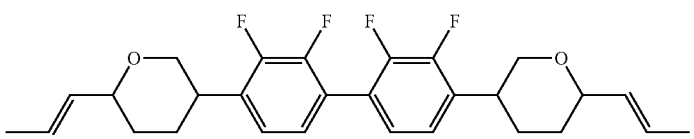 [SMILES: C/C=C/C1CCC(c2ccc(-c3ccc(C4CCC(/C=C/C)OC4)c(F)c3F)c(F)c2F)CO1] |
| 267 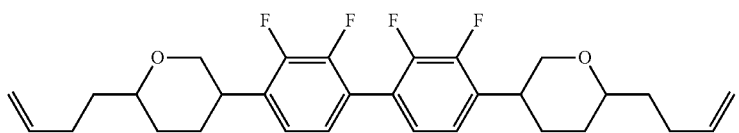 |
| 268 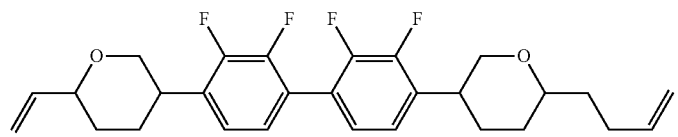 [SMILES: C=CCCC1CCC(c2ccc(-c3ccc(C4CCC(C=C)OC4)c(F)c3F)c(F)c2F)CO1] |
| 269 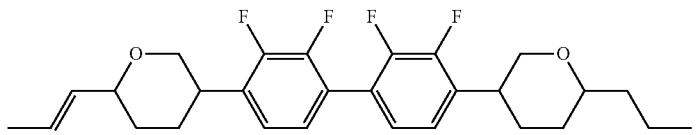 |
| 270 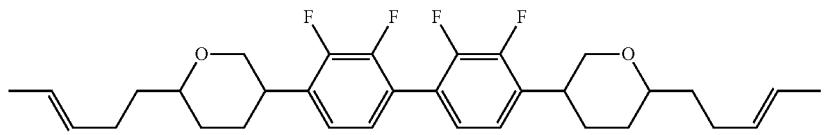 [SMILES: C/C=C/CCC1CCC(c2ccc(-c3ccc(C4CCC(CC/C=C/C)OC4)c(F)c3F)c(F)c2F)CO1] |
| 271 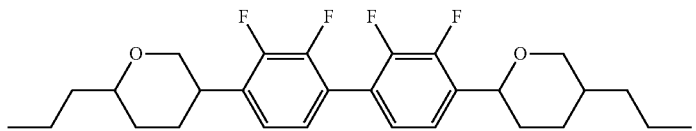 |
| 272 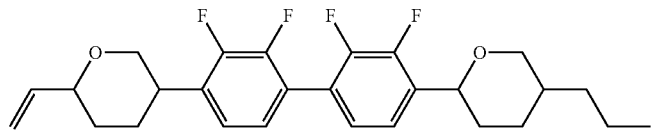 |
| 273 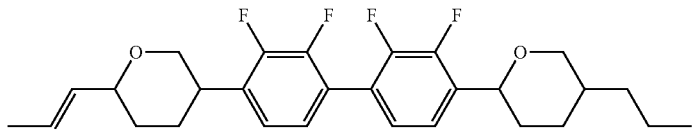 |
| 274 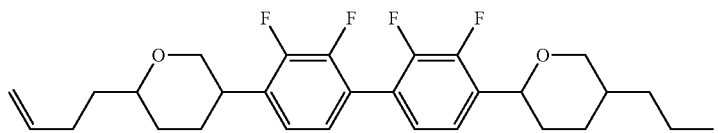 |

-continued
| No. |
|---|
| 275 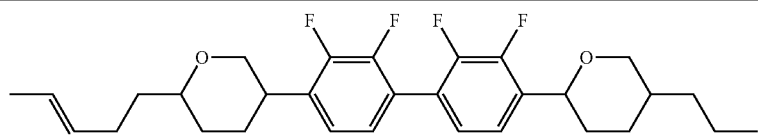 |
| 276 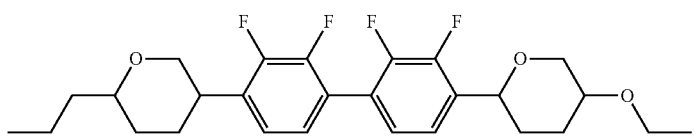 |
| 277 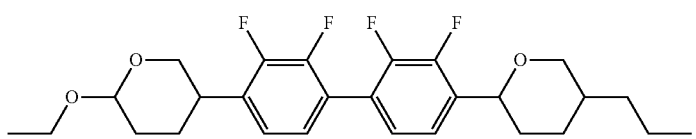 [SMILES: CCCC1CCC(c2ccc(-c3ccc(C4CCC(OCC)OC4)c(F)c3F)c(F)c2F)OC1] |
| 278  |
| 279 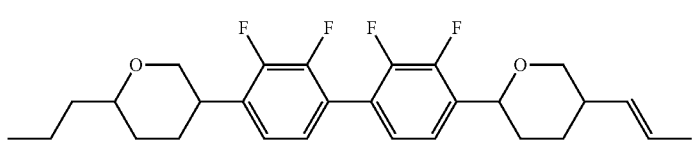 [SMILES: C/C=C/C1CCC(c2ccc(-c3ccc(C4CCC(CCC)OC4)c(F)c3F)c(F)c2F)OC1] |
| 280 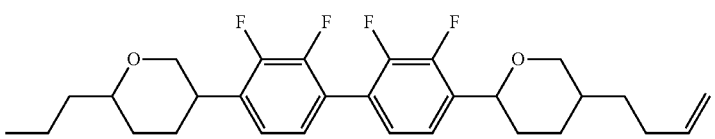 [SMILES: C=CCCC1CCC(c2ccc(-c3ccc(C4CCC(CCC)OC4)c(F)c3F)c(F)c2F)OC1] |
| 281 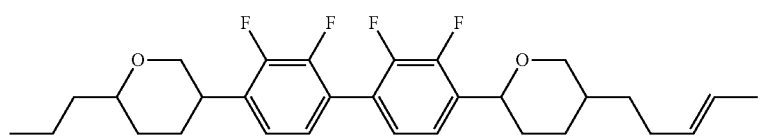 [SMILES: C/C=C/CCC1CCC(c2ccc(-c3ccc(C4CCC(CCC)OC4)c(F)c3F)c(F)c2F)OC1] |
| 282 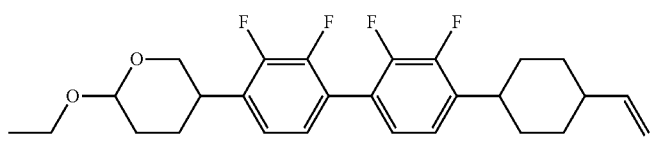 [SMILES: C=CC1CCC(c2ccc(-c3ccc(C4CCC(OCC)OC4)c(F)c3F)c(F)c2F)CC1] |
| 283 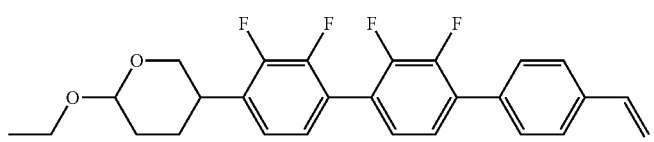 [SMILES: C=Cc1ccc(-c2ccc(-c3ccc(C4CCC(OCC)OC4)c(F)c3F)c(F)c2F)cc1] |
| 284 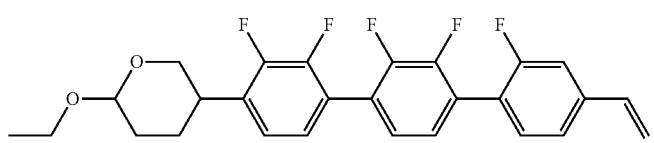 [SMILES: C=Cc1ccc(-c2ccc(-c3ccc(C4CCC(OCC)OC4)c(F)c3F)c(F)c2F)cc1F] |
| 285 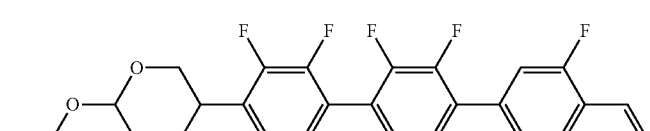 |

| No. | |
|---|---|
| 286 | 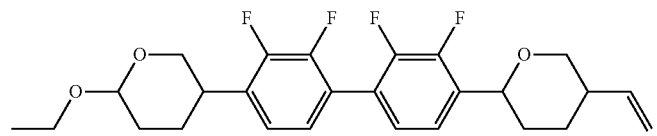 |
| 287 | 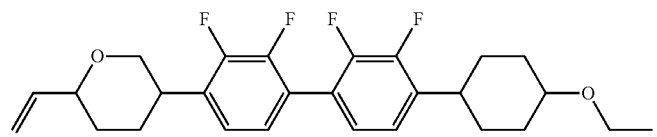 [SMILES: C=CC1CCC(c2ccc(-c3ccc(C4CCC(OCC)CC4)c(F)c3F)c(F)c2F)CO1] |
| 288 | 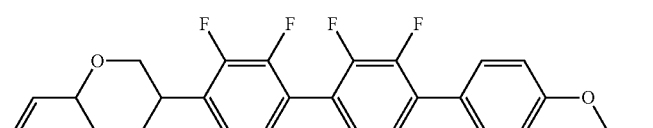 |
| 289 | 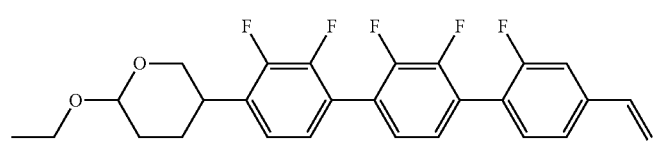 [SMILES: C=Cc1ccc(-c2ccc(-c3ccc(C4CCC(OCC)OC4)c(F)c3F)c(F)c2F)c(F)c1] |
| 290 | 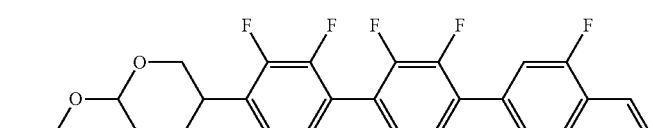 |
| 291 | 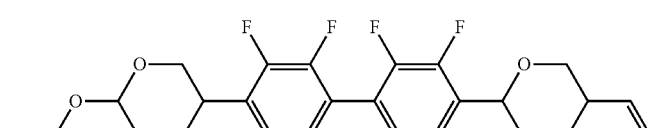 |
| 292 | 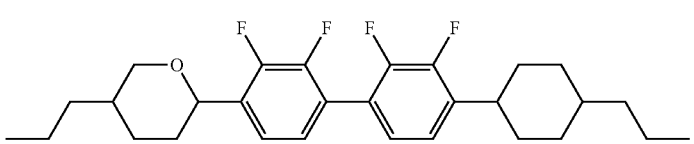 |
| 293 | 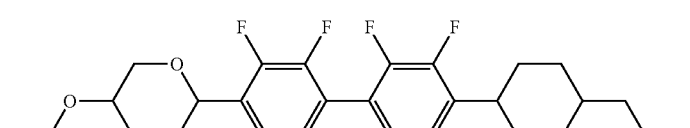 |
| 294 | 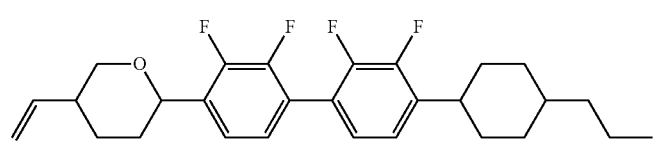 |
| 295 | 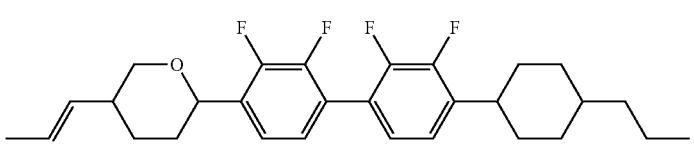 [SMILES: C/C=C/C1CCC(c2ccc(-c3ccc(C4CCC(CCC)CC4)c(F)c3F)c(F)c2F)OC1] |
| 296 | 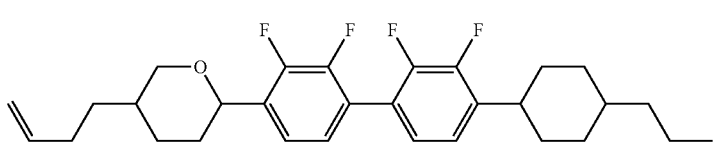 [SMILES: C=CCCC1CCC(c2ccc(-c3ccc(C4CCC(CCC)CC4)c(F)c3F)c(F)c2F)OC1] |

| No. | |
|---|---|
| 297 | 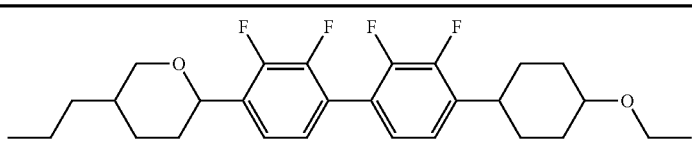 |
| 298 | 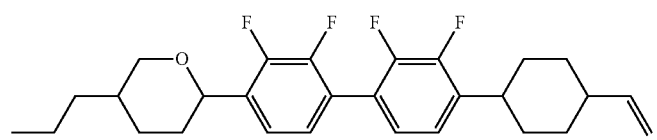 [SMILES: C=CC1CCC(c2ccc(-c3ccc(C4CCC(CCC)CO4)c(F)c3F)c(F)c2F)CC1] |
| 299 | 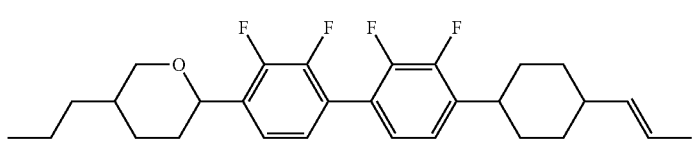 |
| 300 | 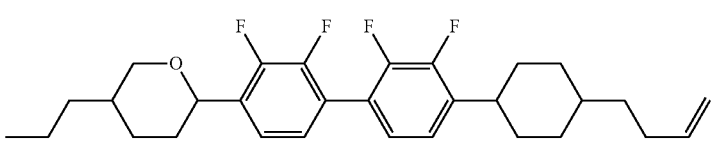 |
| 301 | 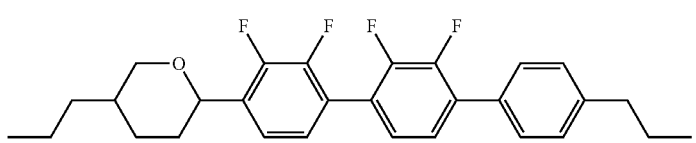 |
| 302 | 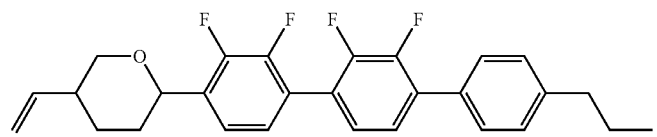 |
| 303 | 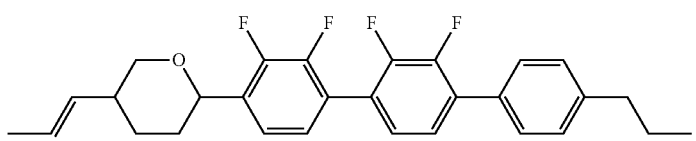 |
| 304 | 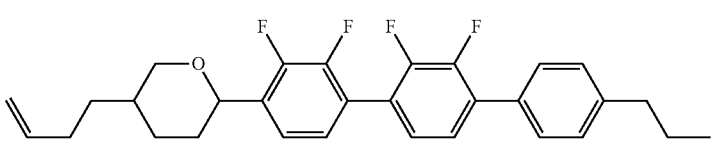 |
| 305 | 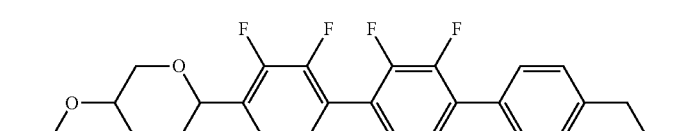 |
| 306 | 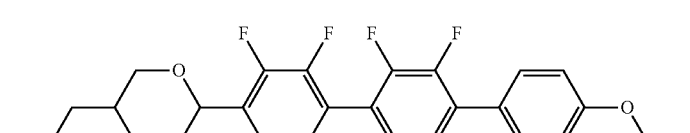 |
| 307 | 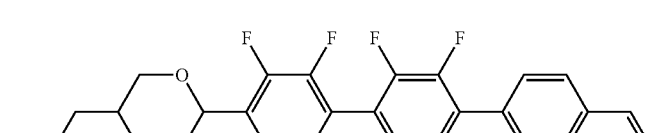 |

-continued
| No. | |
|---|---|
| 308 | 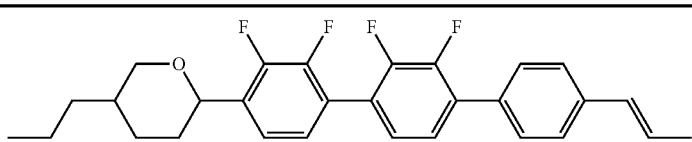 |
| 309 | 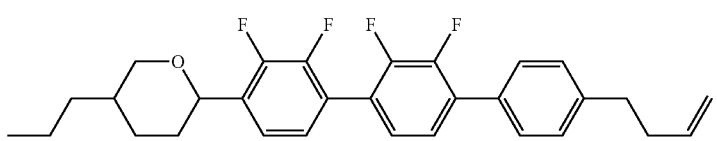 |
| 310 | 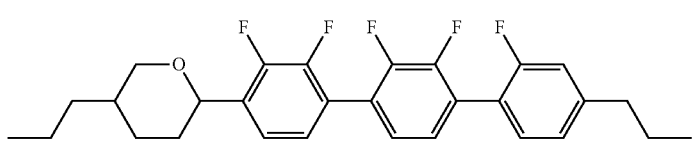 |
| 311 | 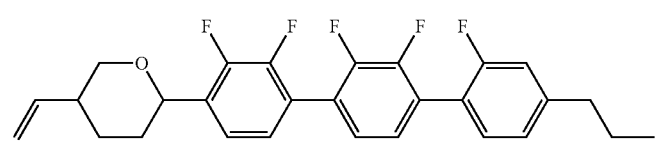 |
| 312 | 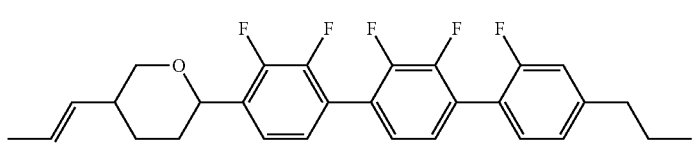 |
| 313 | 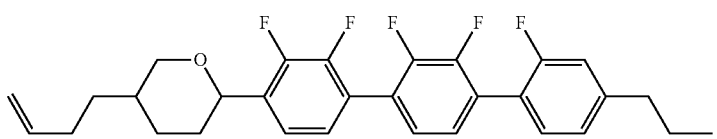 [SMILES: C=CCCC1CCC(c2ccc(-c3ccc(-c4ccc(CCC)cc4)c(F)c3F)c(F)c2F)OC1] |
| 314 | 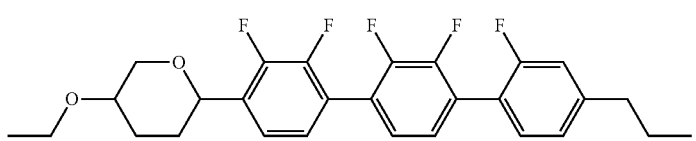 [SMILES: CCCc1ccc(-c2ccc(-c3ccc(C4CCC(CCC)CO4)c(F)c3F)c(F)c2F)c(F)c1] |
| 315 | 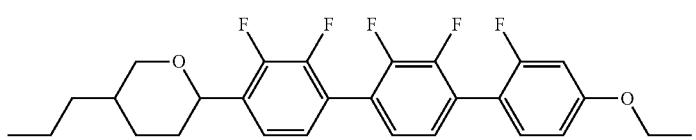 |
| 316 | 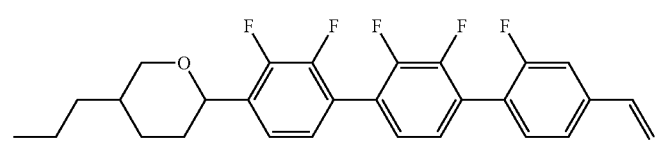 |
| 317 | 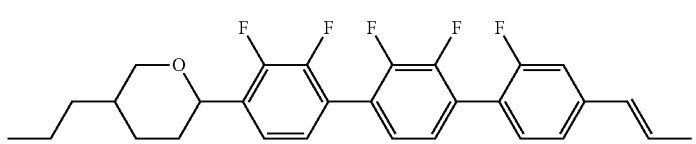 |
| 318 | 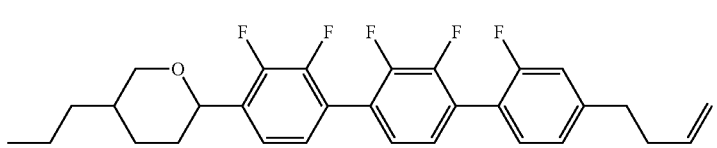 |

-continued
| No. | |
|---|---|
| 319 | 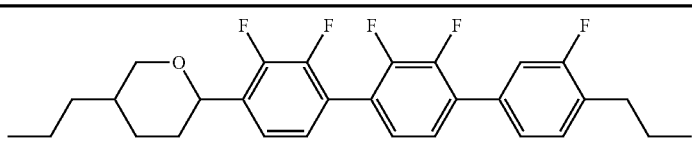 |
| 320 | 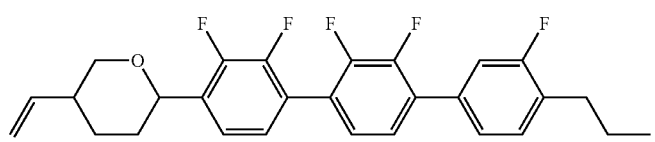 [SMILES: C=CC1CCC(c2ccc(-c3ccc(-c4ccc(CCC)c(F)c4)c(F)c3F)c(F)c2F)OC1] |
| 321 | 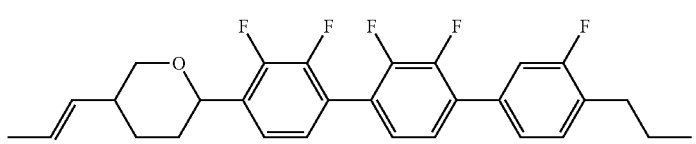 [SMILES: C/C=C/C1CCC(c2ccc(-c3ccc(-c4ccc(CCC)c(F)c4)c(F)c3F)c(F)c2F)OC1] |
| 322 | 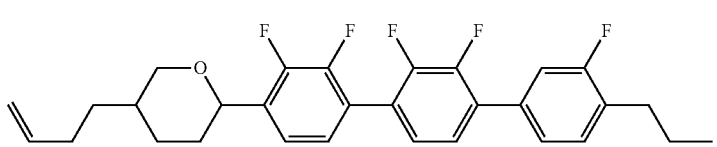 [SMILES: C=CCCC1CCC(c2ccc(-c3ccc(-c4ccc(CCC)c(F)c4)c(F)c3F)c(F)c2F)OC1] |
| 323 | 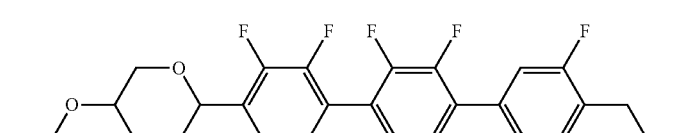 |
| 324 | 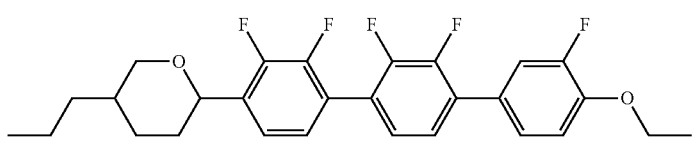 |
| 325 | 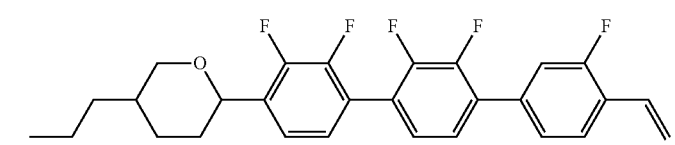 [SMILES: C=Cc1ccc(-c2ccc(-c3ccc(C4CCC(CCC)CO4)c(F)c3F)c(F)c2F)cc1F] |
| 326 | 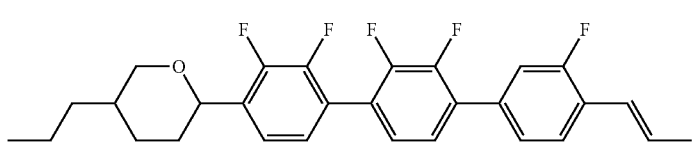 [SMILES: C/C=C/c1ccc(-c2ccc(-c3ccc(C4CCC(CCC)CO4)c(F)c3F)c(F)c2F)cc1F] |
| 327 | 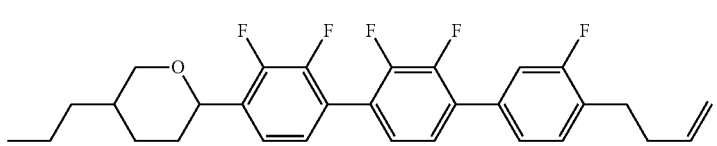 |
| 328 | 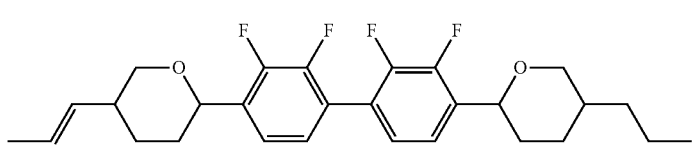 |
| 329 | 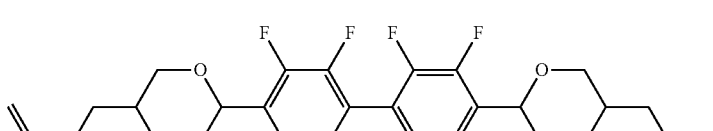 |

-continued
| No. | |
|---|---|
| 330 | 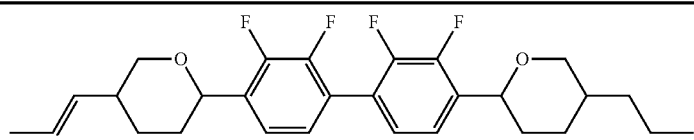 |
| 331 | 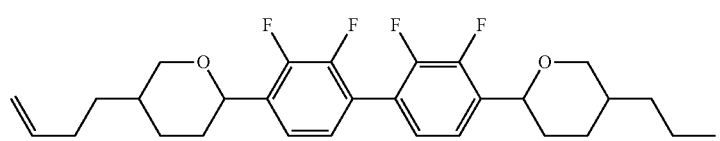 [SMILES: C=CCCC1CCC(c2ccc(-c3ccc(C4CCC(CCC)CO4)c(F)c3F)c(F)c2F)OC1] |
| 332 | 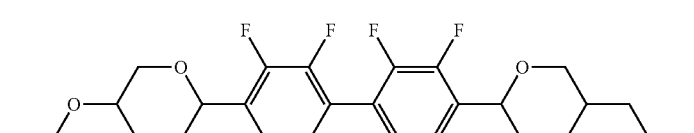 |
| 333 | 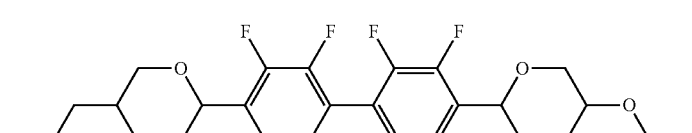 |
| 334 | 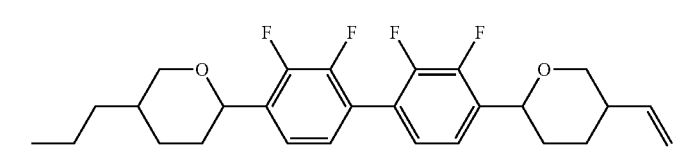 |
| 335 | 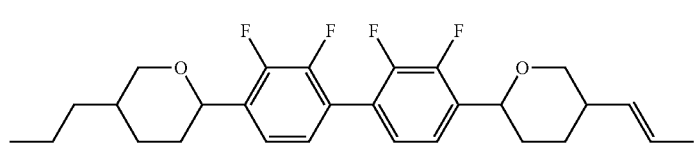 [SMILES: C/C=C/C1CCC(c2ccc(-c3ccc(C4CCC(CCC)CO4)c(F)c3F)c(F)c2F)OC1] |
| 336 | 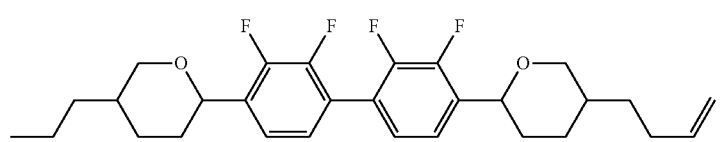 |
| 337 | 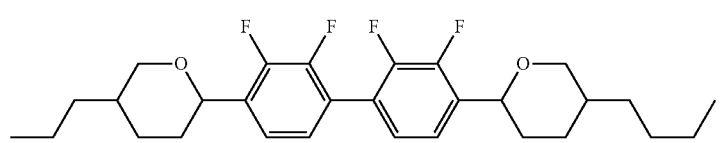 |
| 338 | 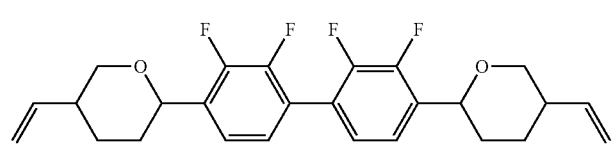 [SMILES: C=CC1CCC(c2ccc(-c3ccc(C4CCC(C=C)CO4)c(F)c3F)c(F)c2F)OC1] |
| 339 | 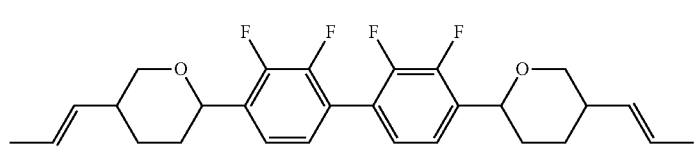 [SMILES: C/C=C/C1CCC(c2ccc(-c3ccc(C4CCC(/C=C/C)CO4)c(F)c3F)c(F)c2F)OC1] |
| 340 | 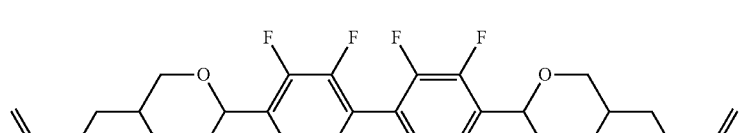 |

| No. | |
|---|---|
| 341 | 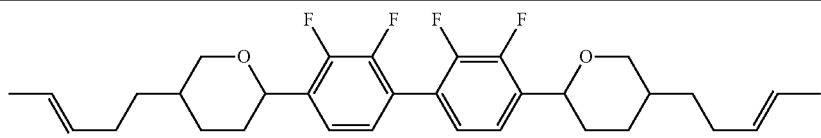 |
| 342 | 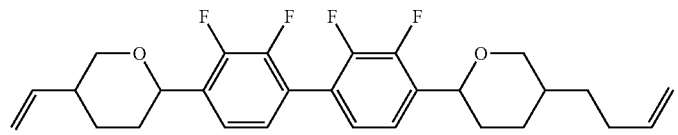 [SMILES: C=CCCC1CCC(c2ccc(-c3ccc(C4CCC(C=C)CO4)c(F)c3F)c(F)c2F)OC1] |
| 343 | 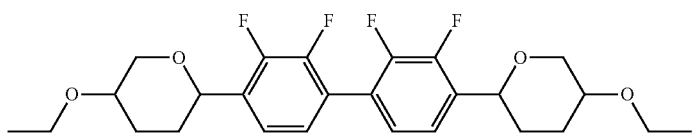 |
| 344 | 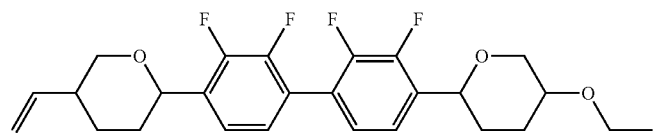 |
| 345 | 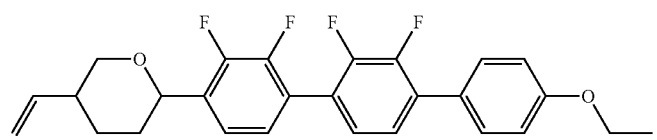 [SMILES: C=CC1CCC(c2ccc(-c3ccc(-c4ccc(OCC)c(F)c4)c(F)c3F)c(F)c2F)OC1] |
| 346 | 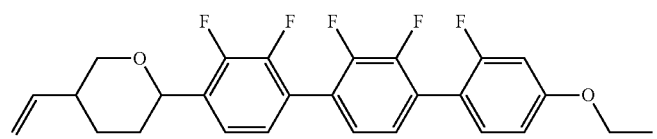 |
| 347 | 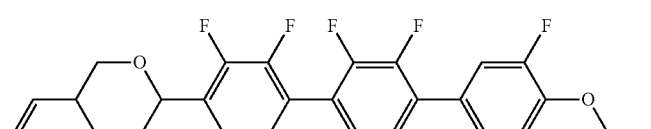 |
| 348 | 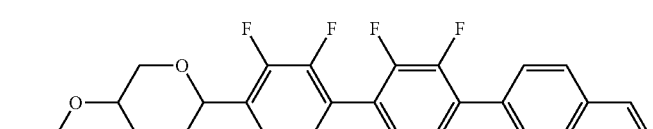 |
| 349 | 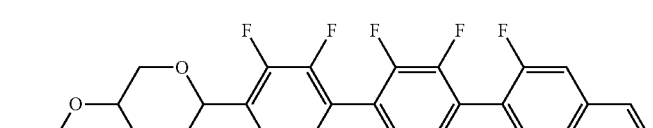 |
| 350 | 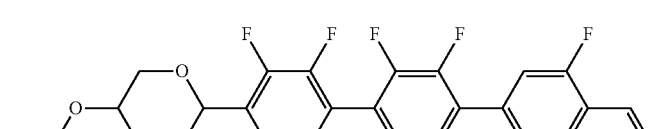 |
| 351 | 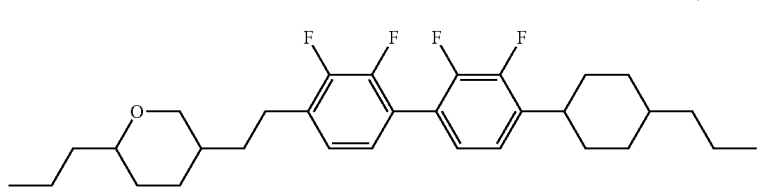 |

-continued
| No. |  |
|---|---|
| 352 | 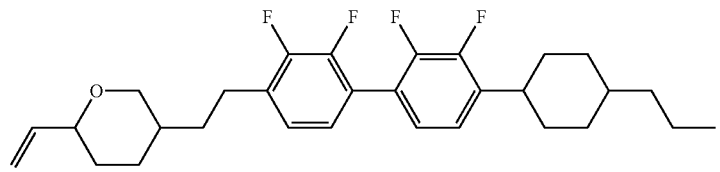 |
| 353 | 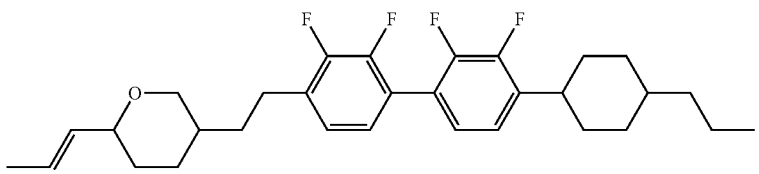 |
| 354 | 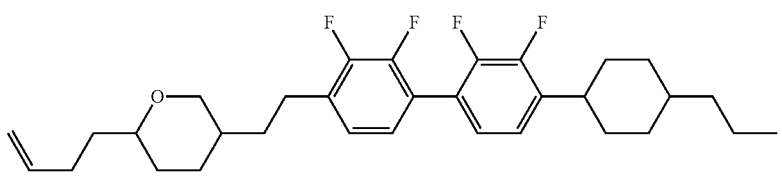 |
| 355 | 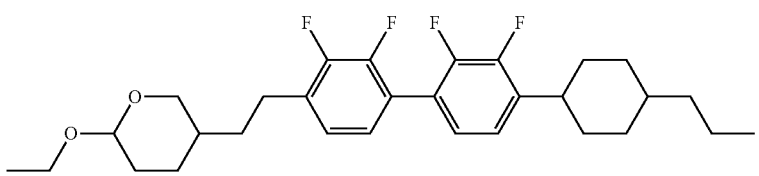 [SMILES: CCCC1CCC(c2ccc(-c3ccc(CCC4CCC(CCC)OC4)c(F)c3F)c(F)c2F)CC1] |
| 356 | 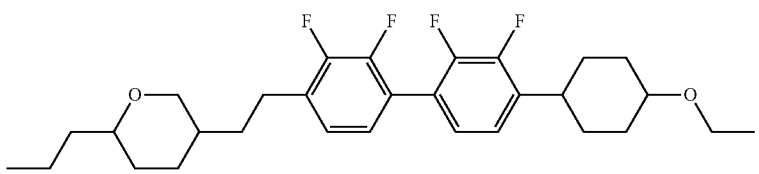 |
| 357 | 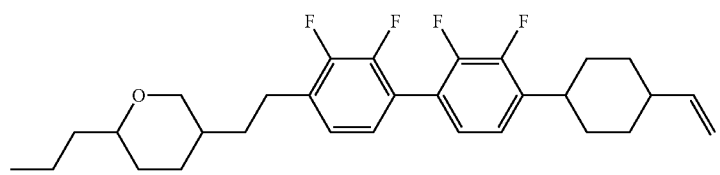 [SMILES: C=CC1CCC(c2ccc(-c3ccc(CCC4CCC(CCC)OC4)c(F)c3F)c(F)c2F)CC1] |
| 358 | 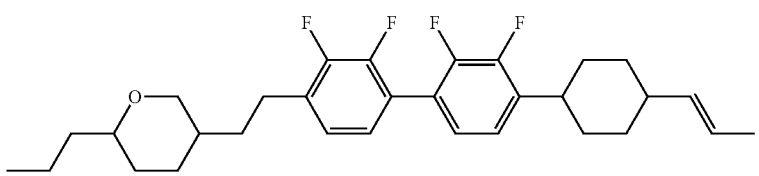 [SMILES: C/C=C/C1CCC(c2ccc(-c3ccc(CCC4CCC(CCC)OC4)c(F)c3F)c(F)c2F)CC1] |
| 359 | 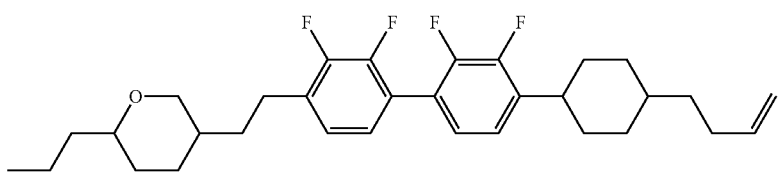 [SMILES: C=CCCC1CCC(c2ccc(-c3ccc(CCC4CCC(CCC)OC4)c(F)c3F)c(F)c2F)CC1] |
| 360 | 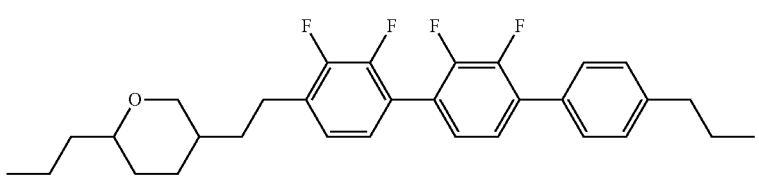 [SMILES: CCCc1ccc(-c2ccc(-c3ccc(CCC4CCC(CCC)OC4)c(F)c3F)c(F)c2F)cc1] |

| No. |
|---|
| 361 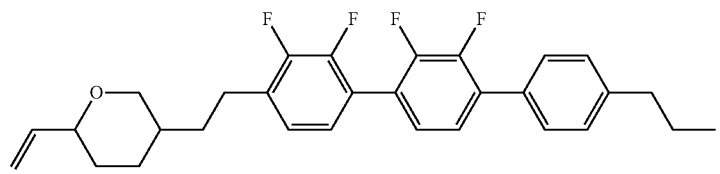 |
| 362 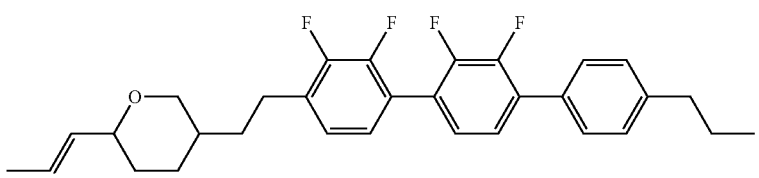 [SMILES: C/C=C/C1CCC(CCc2ccc(-c3ccc(-c4ccc(CCC)cc4)c(F)c3F)c(F)c2F)CO1] |
| 363 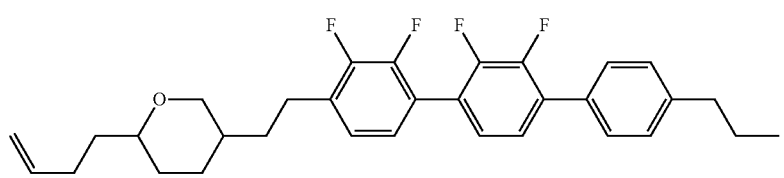 |
| 364 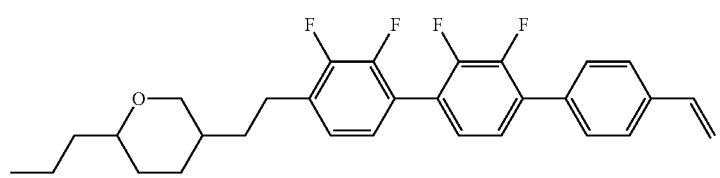 |
| 365 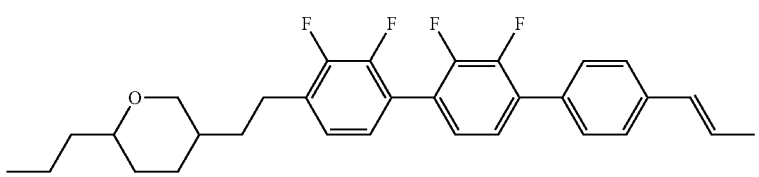 [SMILES: C/C=C/c1ccc(-c2ccc(-c3ccc(CCC4CCC(CCC)OC4)c(F)c3F)c(F)c2F)cc1] |
| 366 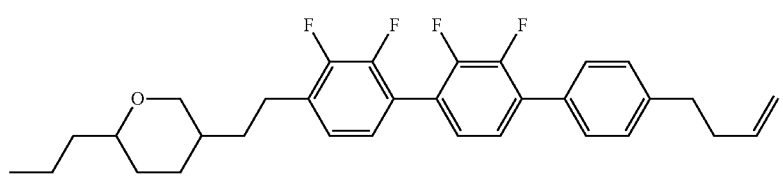 |
| 367 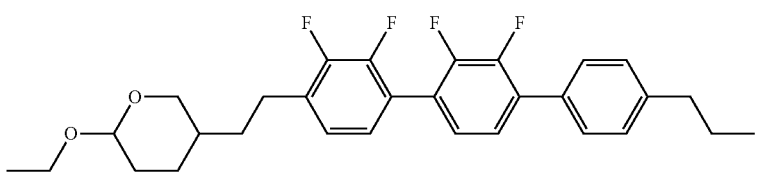 |
| 368 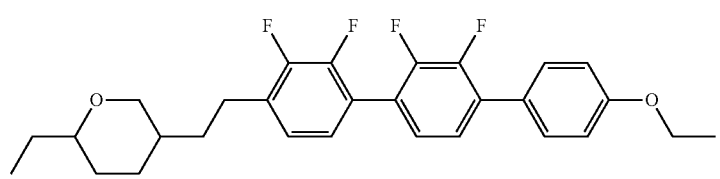 [SMILES: CCOc1ccc(-c2ccc(-c3ccc(CCC4CCC(CC)OC4)c(F)c3F)c(F)c2F)cc1] |
| 369 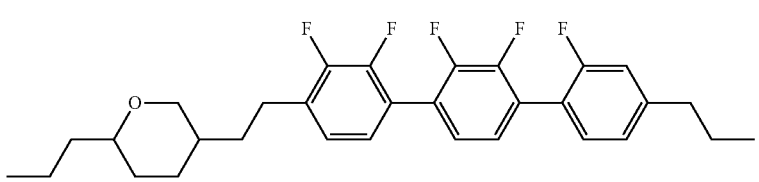 |

-continued
| No. | |
|---|---|
| 370 | 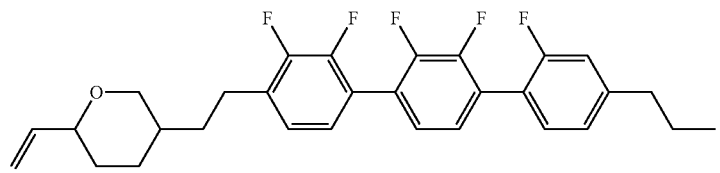 [SMILES: C=CC1CCC(CCc2ccc(-c3ccc(-c4ccc(CCC)cc4F)c(F)c3F)c(F)c2F)CO1] |
| 371 | 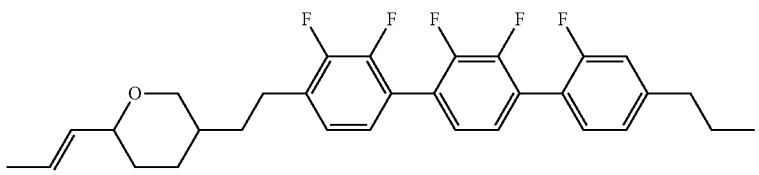 |
| 372 | 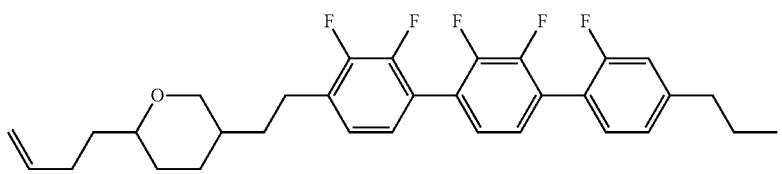 [SMILES: C=CCCC1CCC(CCc2ccc(-c3ccc(-c4ccc(CCC)cc4F)c(F)c3F)c(F)c2F)CO1] |
| 373 | 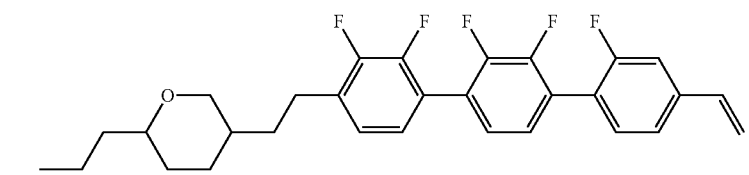 [SMILES: C=Cc1ccc(-c2ccc(-c3ccc(CCC4CCC(CCC)OC4)c(F)c3F)c(F)c2F)c(F)c1] |
| 374 | 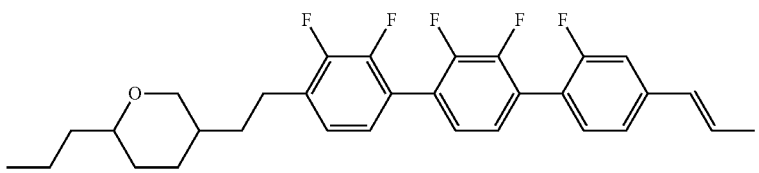 [SMILES: C/C=C/c1ccc(-c2ccc(-c3ccc(CCC4CCC(CCC)OC4)c(F)c3F)c(F)c2F)c(F)c1] |
| 375 | 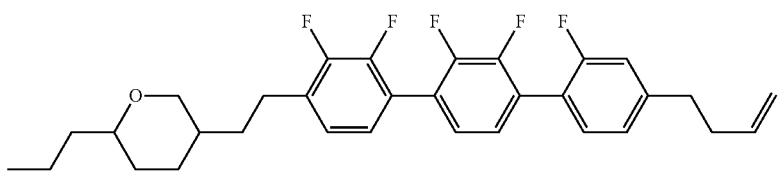 |
| 376 | 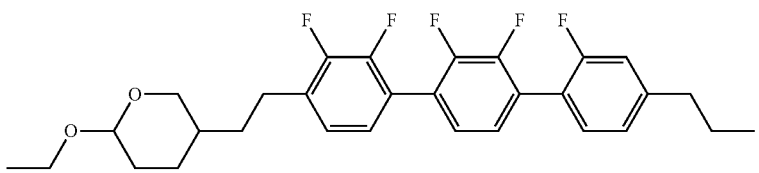 |
| 377 | 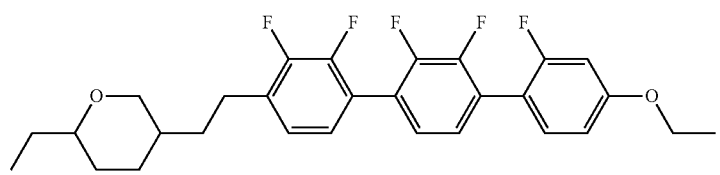 |
| 378 | 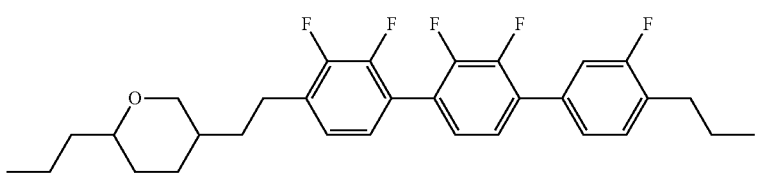 [SMILES: CCCc1ccc(-c2ccc(-c3ccc(CCC4CCC(CCC)OC4)c(F)c3F)c(F)c2F)cc1F] |

| No. |
|---|
| 379 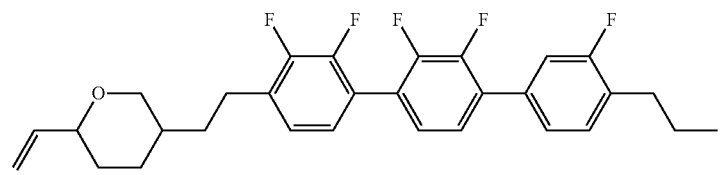 [SMILES: C=CC1CCC(CCc2ccc(-c3ccc(-c4ccc(CCC)c(F)c4)c(F)c3F)c(F)c2F)CO1] |
| 380 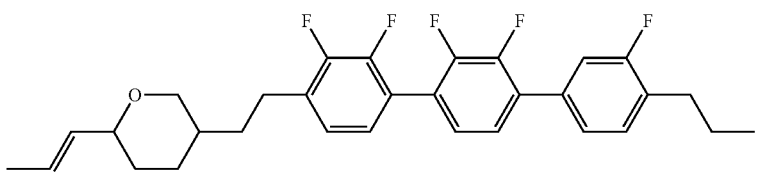 |
| 381 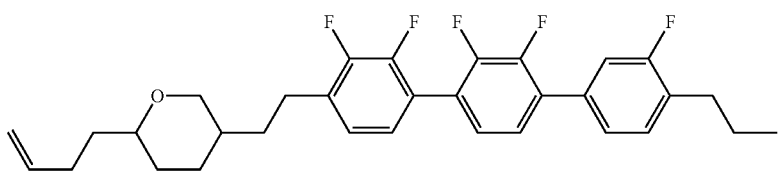 [SMILES: C=CCCC1CCC(CCc2ccc(-c3ccc(-c4ccc(CCC)c(F)c4)c(F)c3F)c(F)c2F)CO1] |
| 382 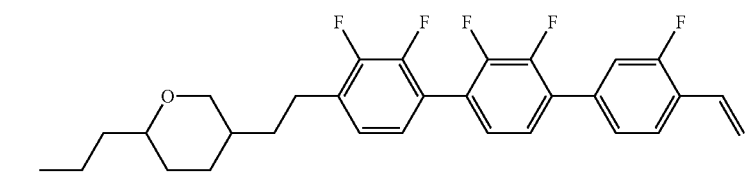 |
| 383 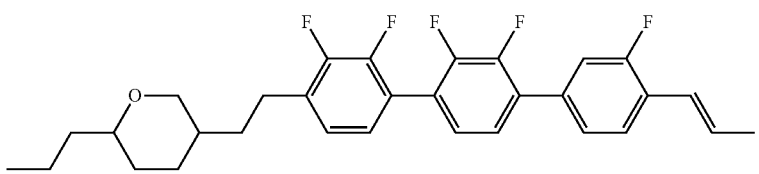 |
| 384 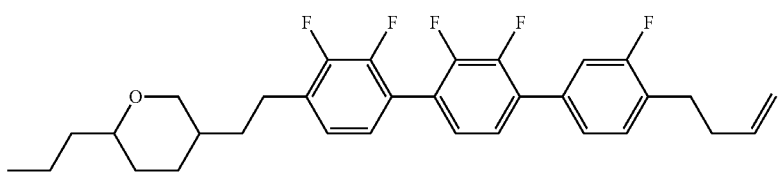 |
| 385 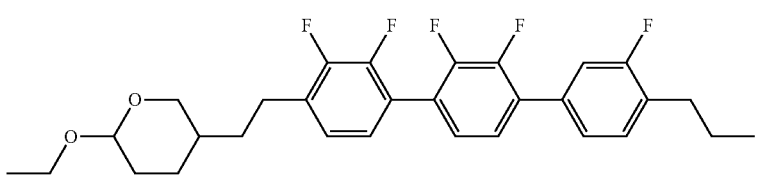 |
| 386 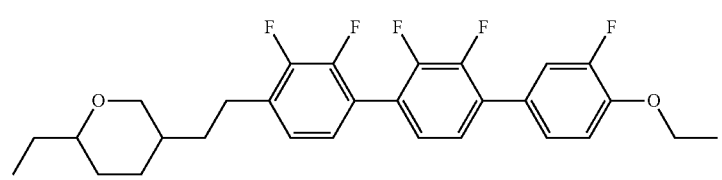 |
| 387 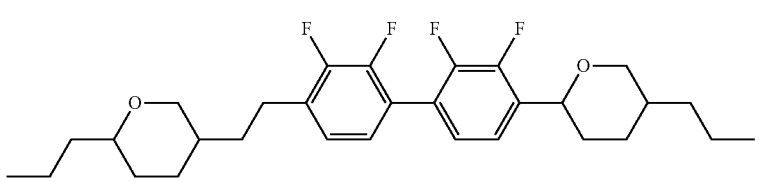 |

-continued
| No. |
|---|
| 388 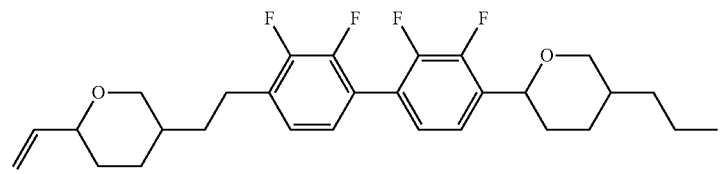 |
| 389 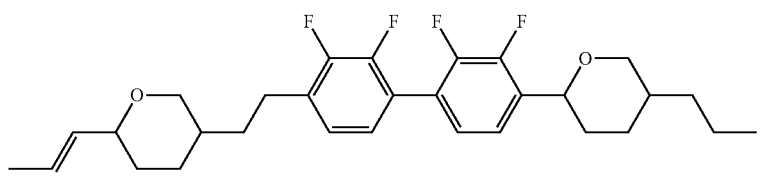 |
| 390 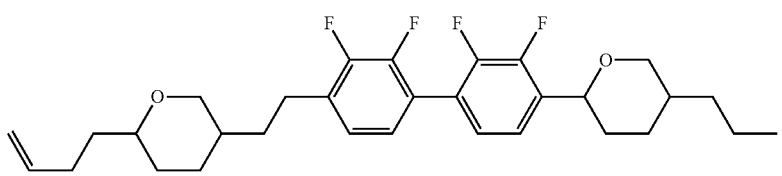 |
| 391 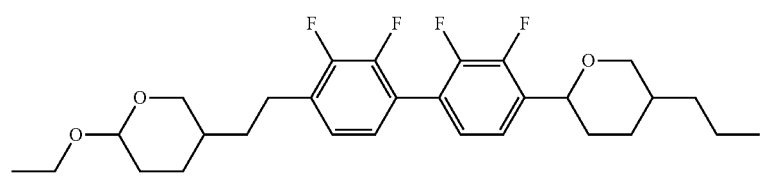 |
| 392 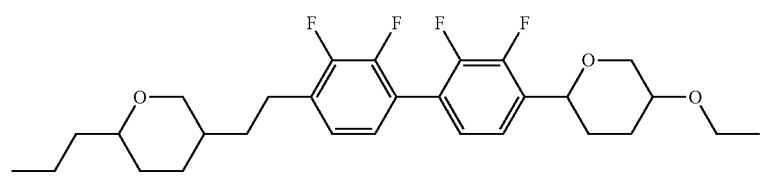 |
| 393 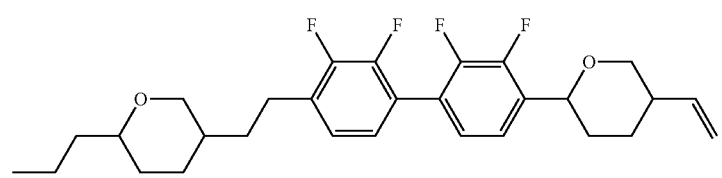 |
| 394 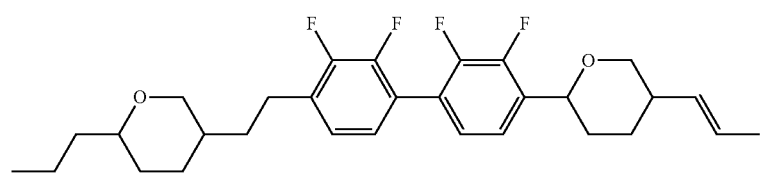 [SMILES: CCCC1CCC(c2ccc(-c3ccc(CCC4CCC(CCC)OC4)c(F)c3F)c(F)c2F)OC1] |
| 395 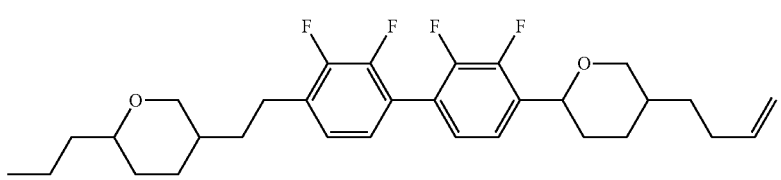 |
| 396 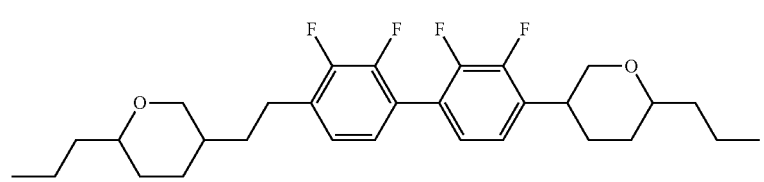 |

| No. |
|---|
| 397 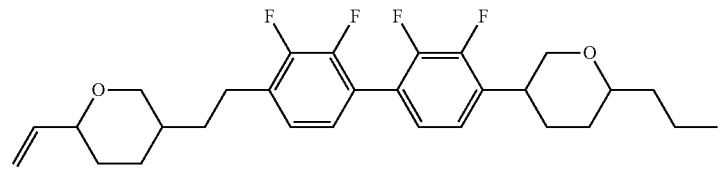 |
| 398 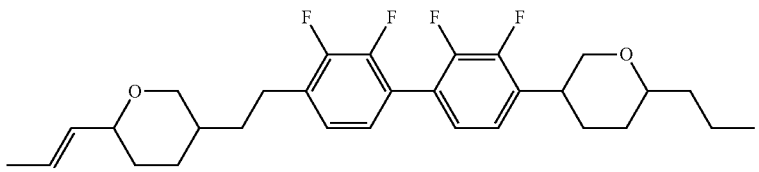 |
| 399 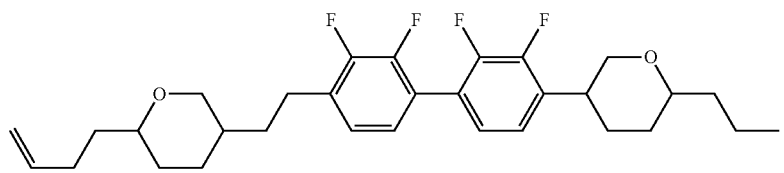 [SMILES: C=CCCC1CCC(CCc2ccc(-c3ccc(C4CCC(CCC)OC4)c(F)c3F)c(F)c2F)CO1] |
| 400 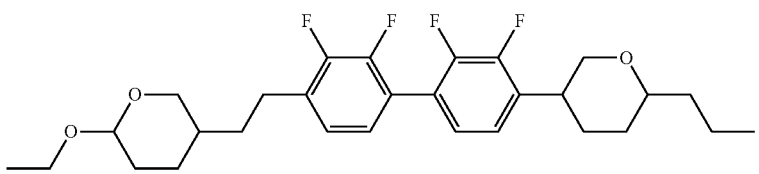 |
| 401 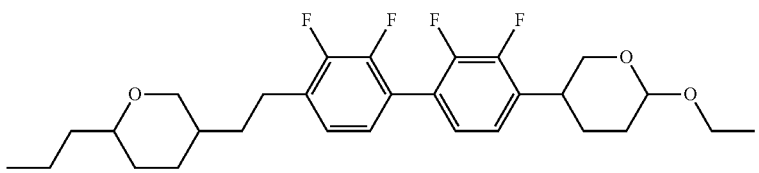 [SMILES: CCCC1CCC(c2ccc(-c3ccc(CCC4CCC(OCC)OC4)c(F)c3F)c(F)c2F)CO1] |
| 402 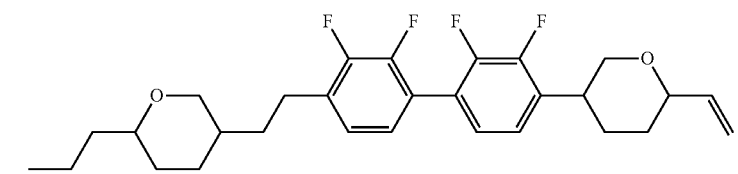 |
| 403 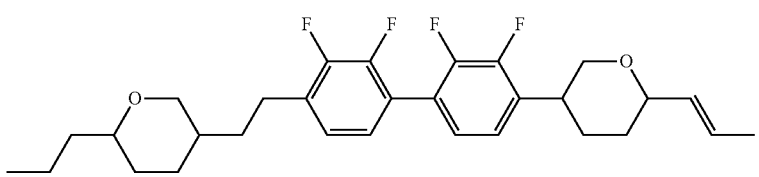 [SMILES: C/C=C/C1CCC(c2ccc(-c3ccc(CCC4CCC(CCC)OC4)c(F)c3F)c(F)c2F)CO1] |
| 404 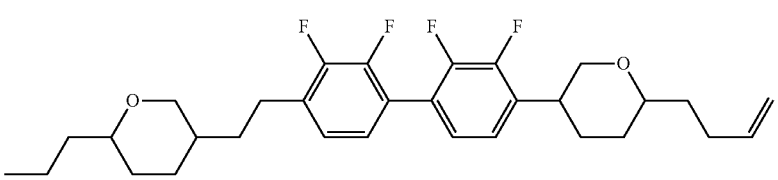 |
| 405 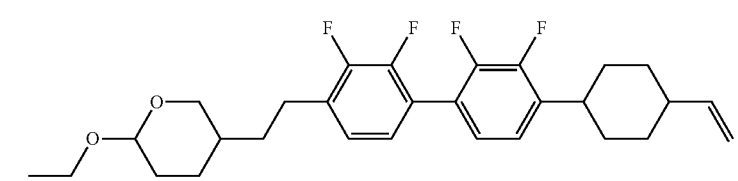 |

-continued
| No. | |
|---|---|
| 406 | 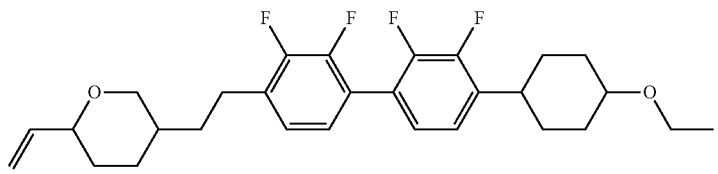 [SMILES: C=CC1CCC(CCc2ccc(-c3ccc(C4CCC(OCC)CC4)c(F)c3F)c(F)c2F)CO1] |
| 407 | 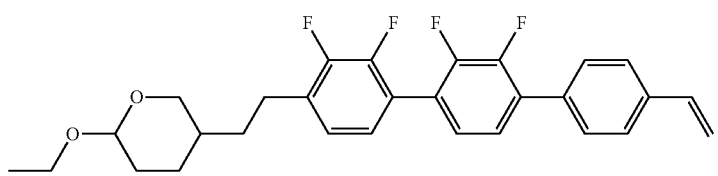 [SMILES: C=Cc1ccc(-c2ccc(-c3ccc(CCC4CCC(OCC)OC4)c(F)c3F)c(F)c2F)cc1] |
| 408 | 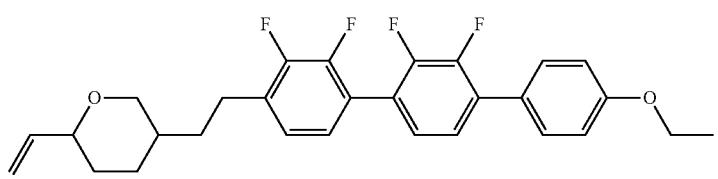 |
| 409 | 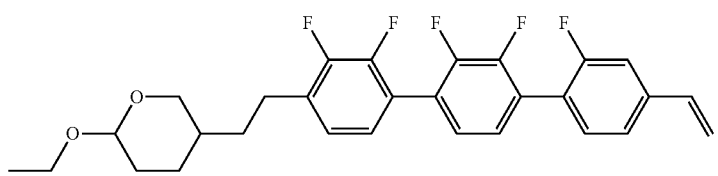 |
| 410 | 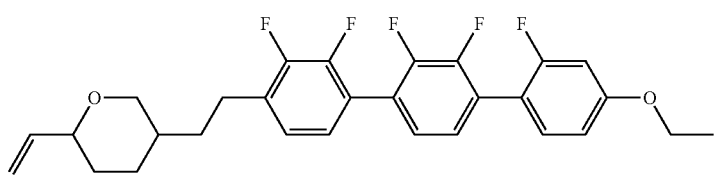 |
| 411 | 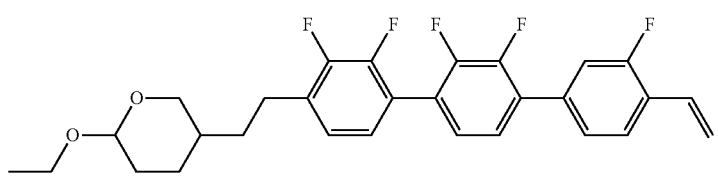 [SMILES: C=Cc1ccc(-c2ccc(-c3ccc(CCC4CCC(OCC)OC4)c(F)c3F)c(F)c2F)cc1F] |
| 412 | 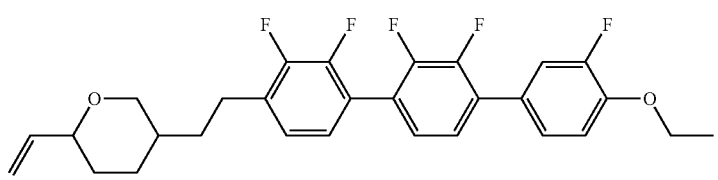 |
| 413 | 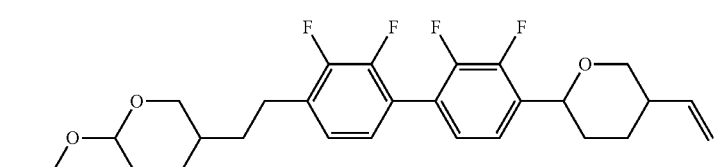 |

| No. |
|---|
| 414 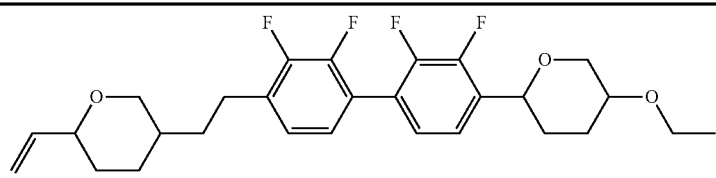 |
| 415 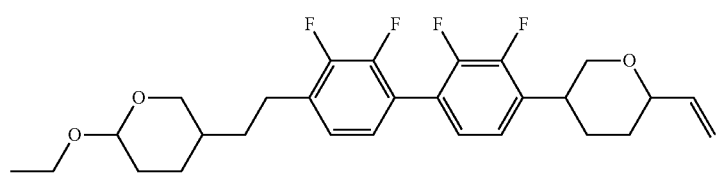 |
| 416 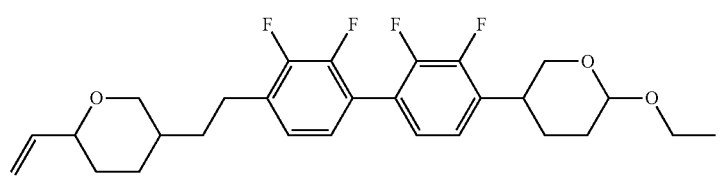 |
| 417 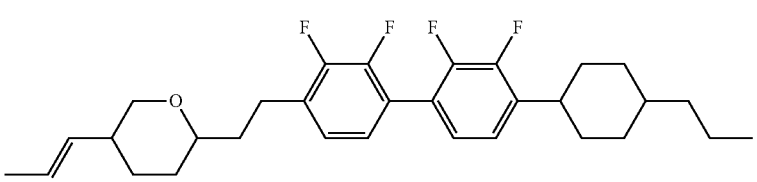 |
| 418 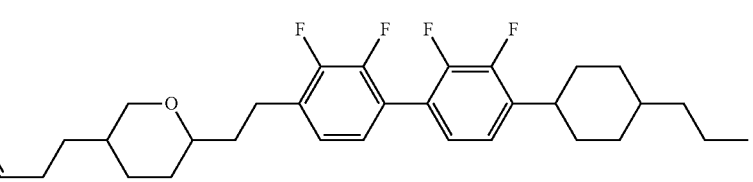 |
| 419 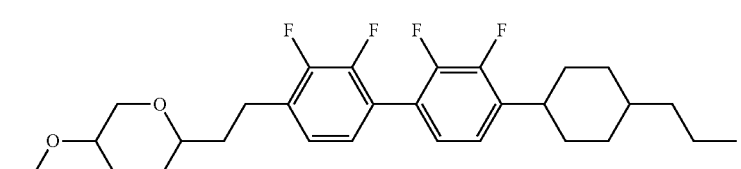 |
| 420 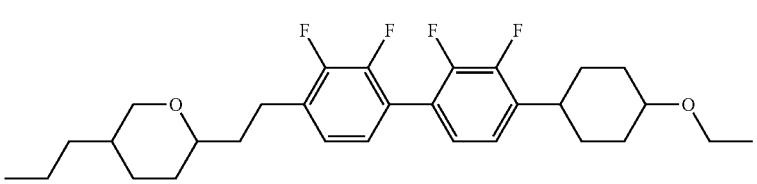 |
| 421 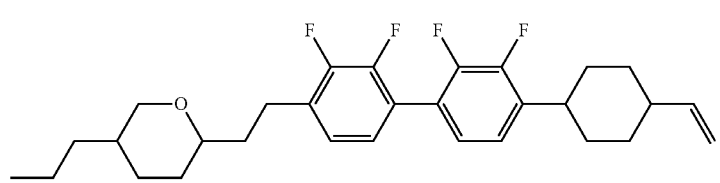 [SMILES: C=CC1CCC(c2ccc(-c3ccc(CCC4CCC(CCC)CO4)c(F)c3F)c(F)c2F)CC1] |
| 422 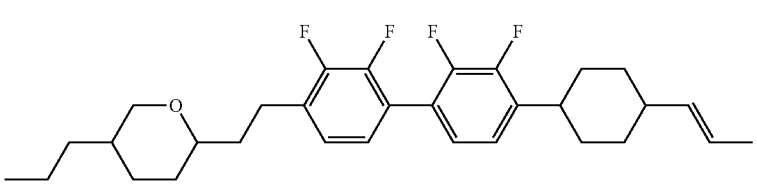 |

| No. | |
|---|---|
| 423 | 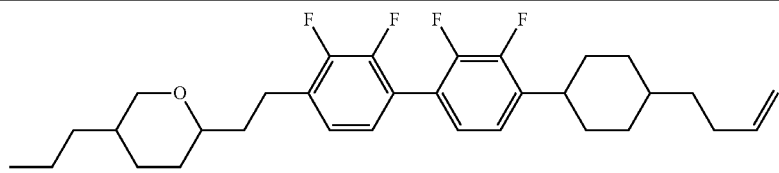 |
| 424 | 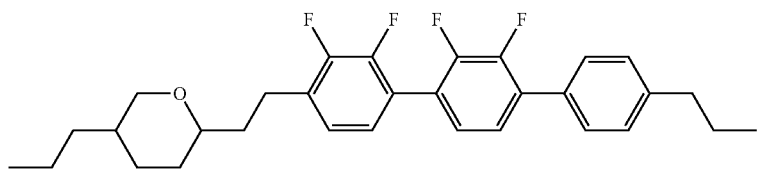 |
| 425 | 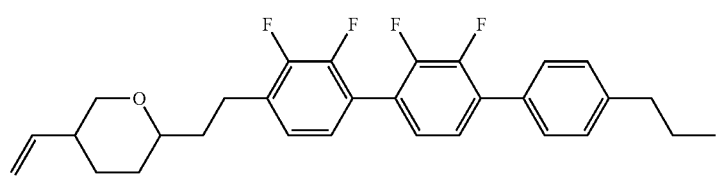 [SMILES: C=CC1CCC(CCc2ccc(-c3ccc(-c4ccc(CCC)cc4)c(F)c3F)c(F)c2F)OC1] |
| 426 | 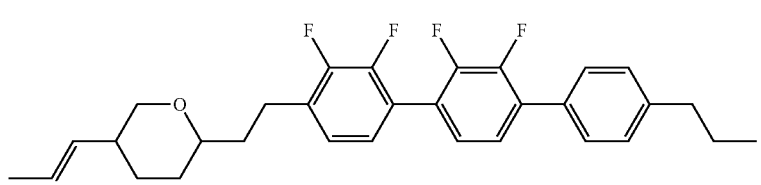 |
| 427 | 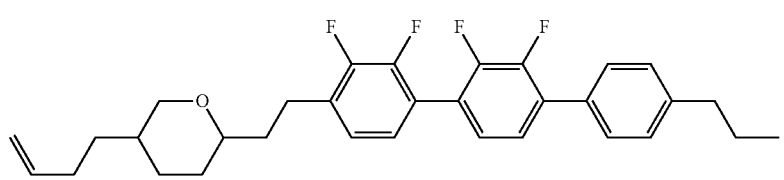 |
| 428 | 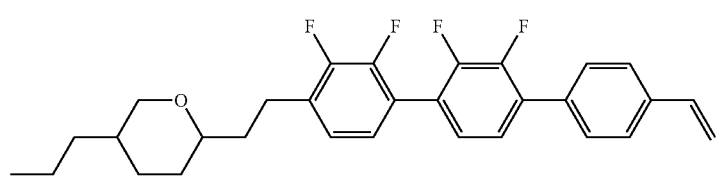 |
| 429 | 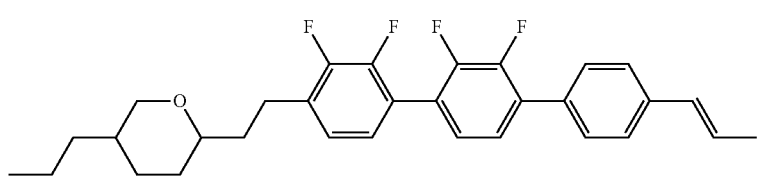 |
| 430 | 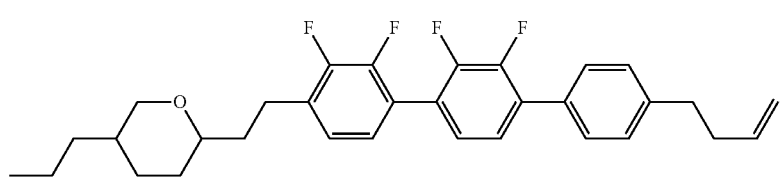 |
| 431 | 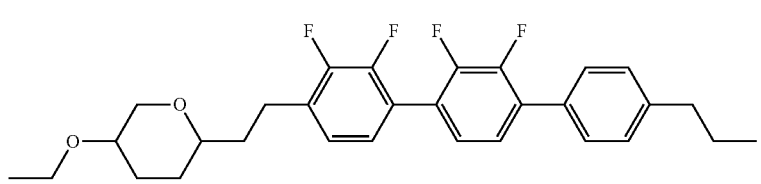 |

| No. | |
|---|---|
| 432 | 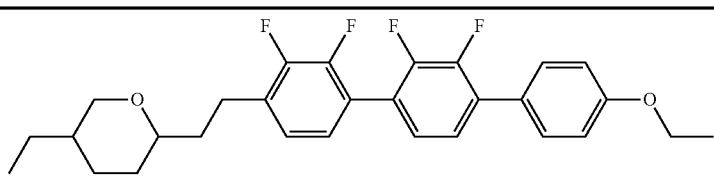 |
| 433 | 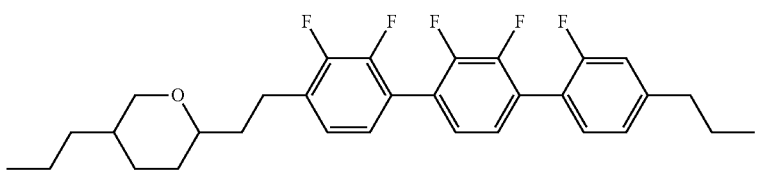 |
| 434 | 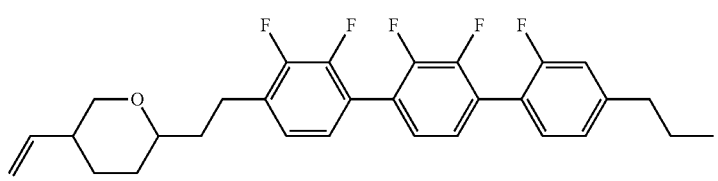 |
| 435 | 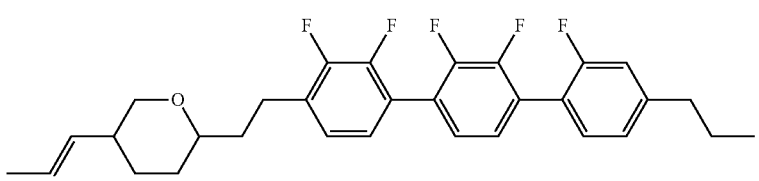 [SMILES: C/C=C/C1CCC(CCc2ccc(-c3ccc(-c4ccc(CCC)cc4)c(F)c3F)c(F)c2F)OC1] |
| 436 | 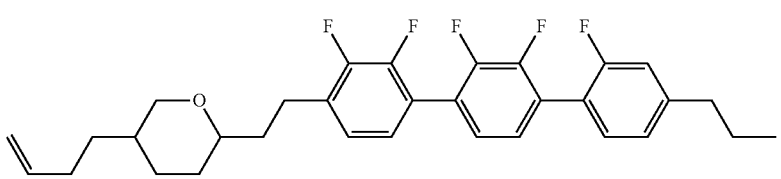 |
| 437 | 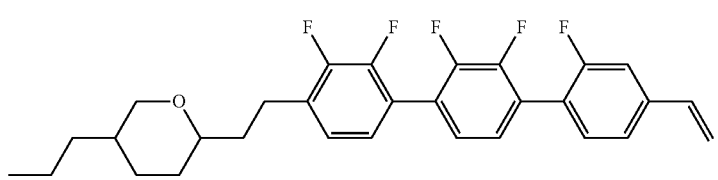 |
| 438 | 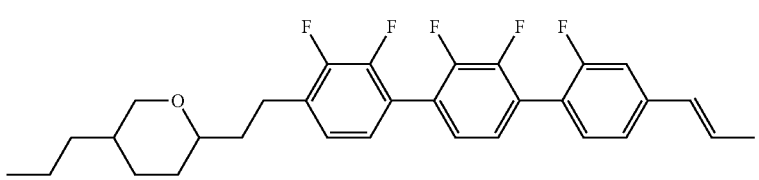 [SMILES: C/C=C/c1ccc(-c2ccc(-c3ccc(CCC4CCC(CCC)CO4)c(F)c3F)c(F)c2F)cc1] |
| 439 | 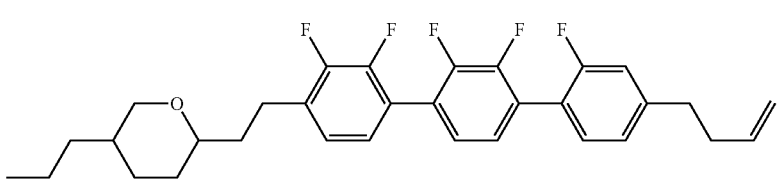 [SMILES: C=CCCc1ccc(-c2ccc(-c3ccc(CCC4CCC(CCC)CO4)c(F)c3F)c(F)c2F)cc1] |
| 440 | 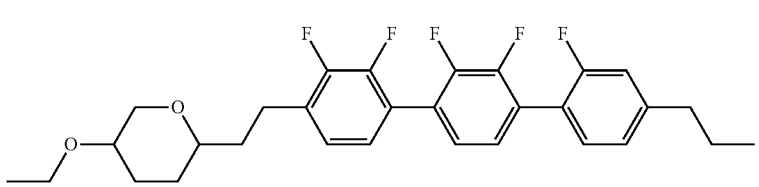 |

| No. | |
|---|---|
| 441 | 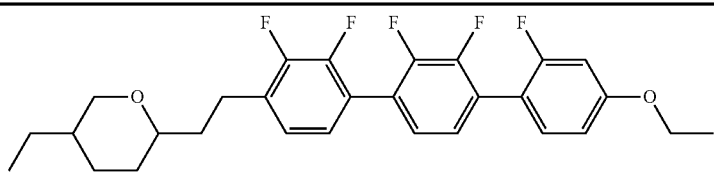 |
| 442 | 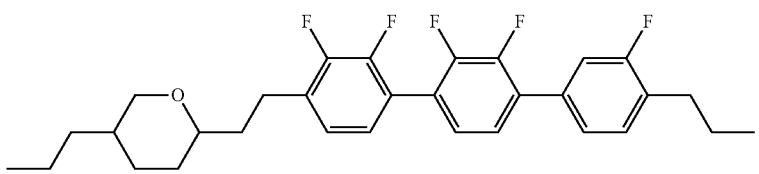 [SMILES: CCCc1ccc(-c2ccc(-c3ccc(CCC4CCC(CCC)CO4)c(F)c3F)c(F)c2F)cc1F] |
| 443 | 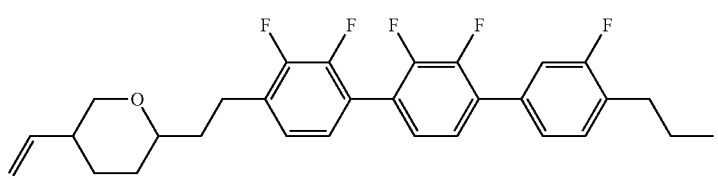 [SMILES: C=CC1CCC(CCc2ccc(-c3ccc(-c4ccc(CCC)c(F)c4)c(F)c3F)c(F)c2F)OC1] |
| 444 | 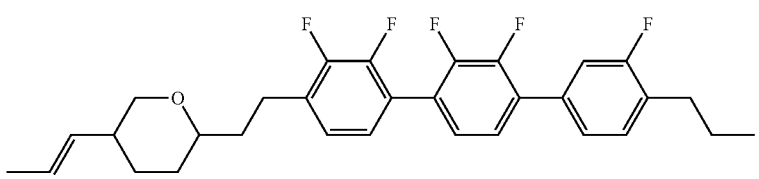 |
| 445 | 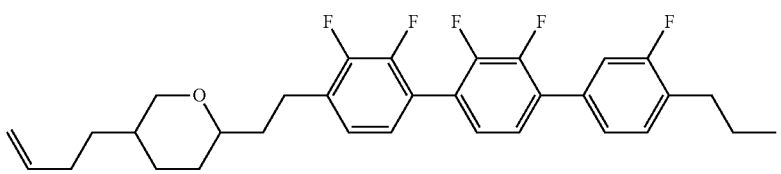 |
| 446 | 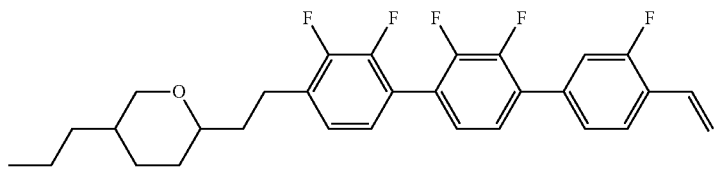 |
| 447 | 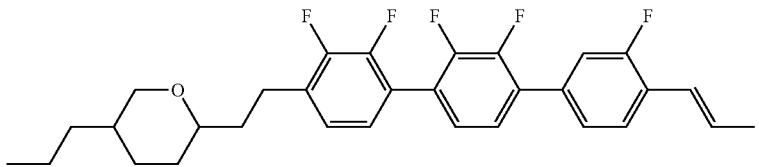 |
| 448 | 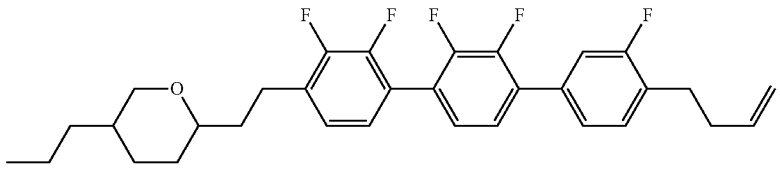 |
| 449 | 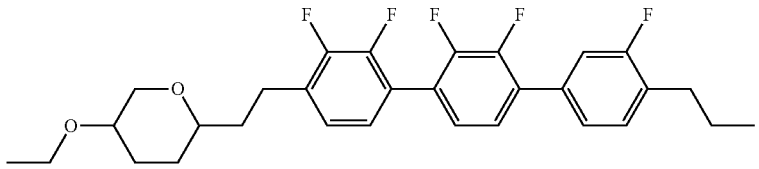 |

| No. | |
|---|---|
| 450 | 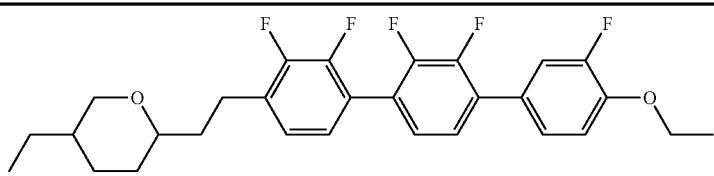 |
| 451 | 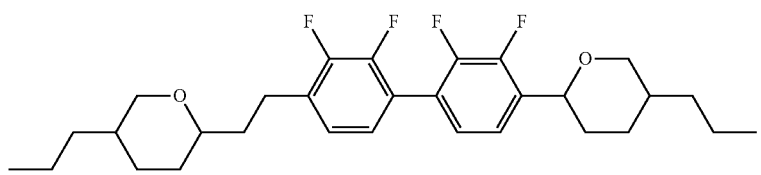 |
| 452 | 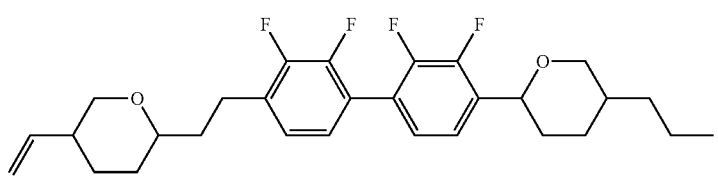 |
| 453 | 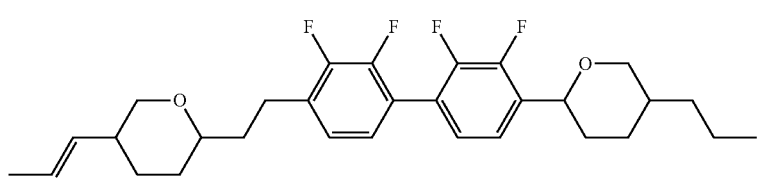 |
| 454 | 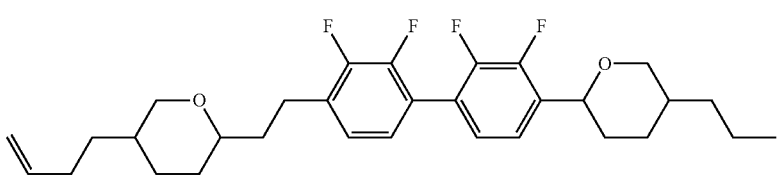 |
| 455 | 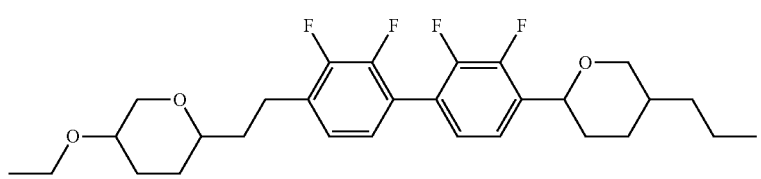 |
| 456 | 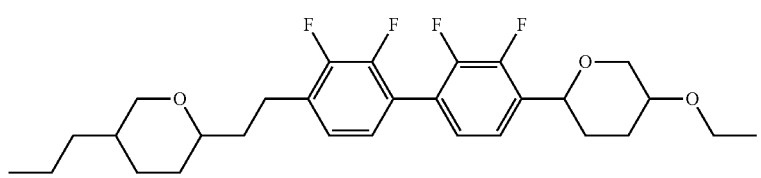 |
| 457 | 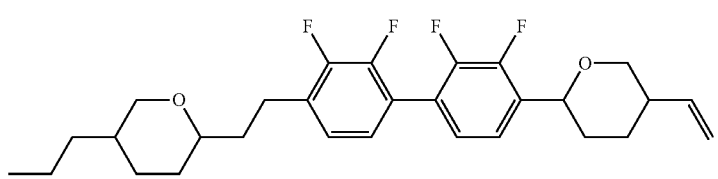 |
| 458 | 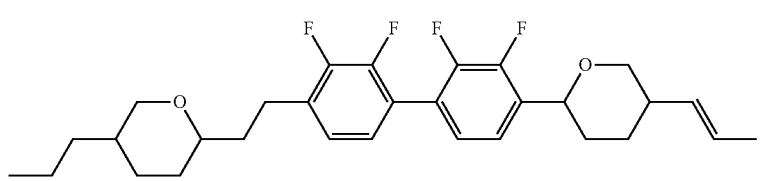 [SMILES: CCCC1CCC(CCc2ccc(-c3ccc(C4CCC(CCC)CO4)c(F)c3F)c(F)c2F)OC1] |

-continued
| No. | |
|---|---|
| 459 | 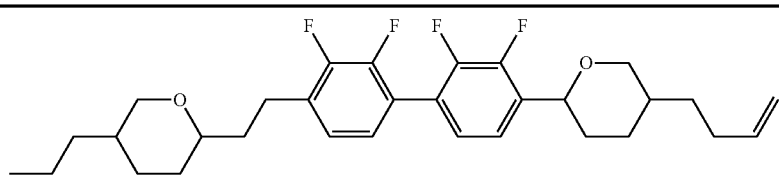 |
| 460 | 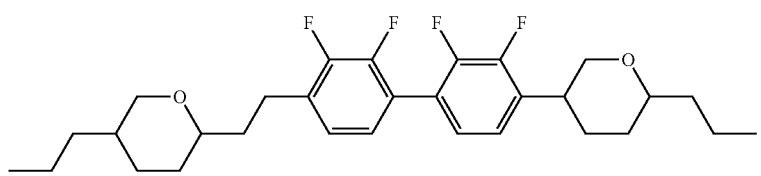 |
| 461 | 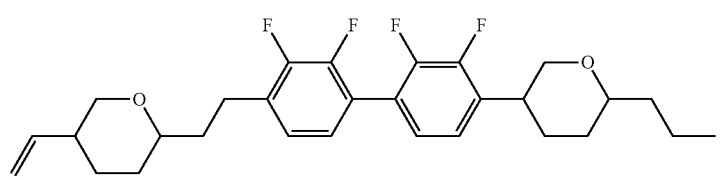 [SMILES: C=CC1CCC(CCc2ccc(-c3ccc(C4CCC(CCC)OC4)c(F)c3F)c(F)c2F)OC1] |
| 462 | 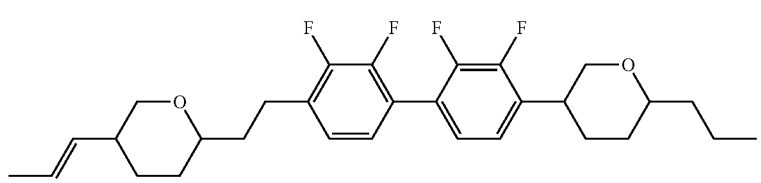 |
| 463 | 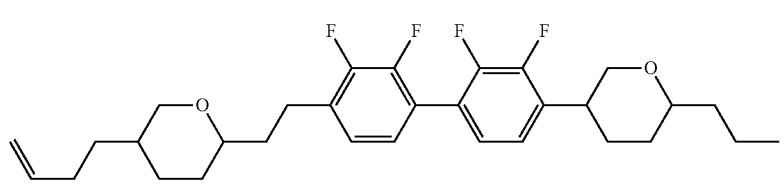 |
| 464 | 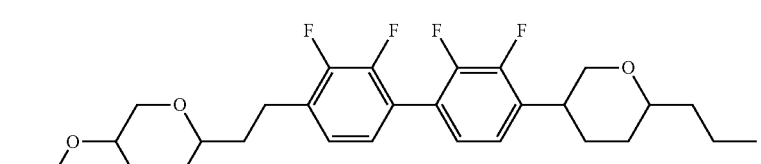 |
| 465 | 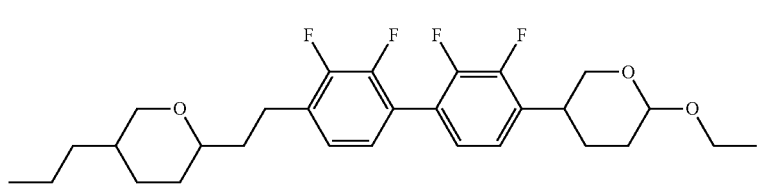 |
| 466 | 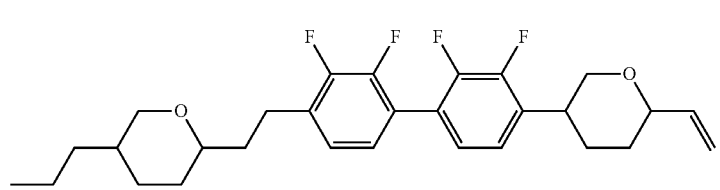 [SMILES: C=CC1CCC(c2ccc(-c3ccc(CCC4CCC(CCC)CO4)c(F)c3F)c(F)c2F)CO1] |
| 467 | 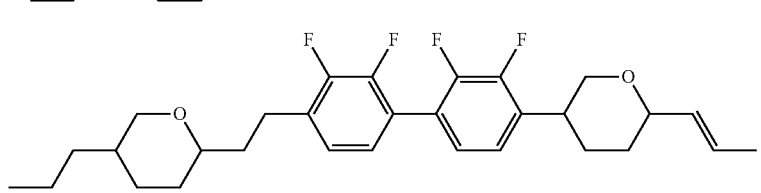 |

-continued
| No. | |
|---|---|
| 468 | 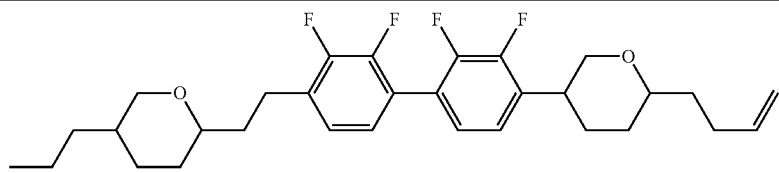 |
| 469 | 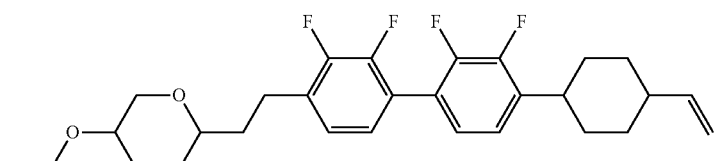 |
| 470 | 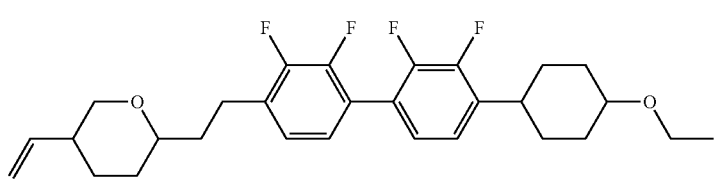 [SMILES: C=CC1CCC(CCc2ccc(-c3ccc(C4CCC(OCC)CC4)c(F)c3F)c(F)c2F)OC1] |
| 471 | 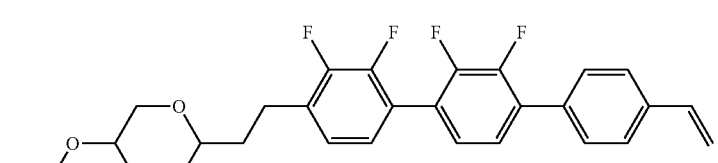 |
| 472 | 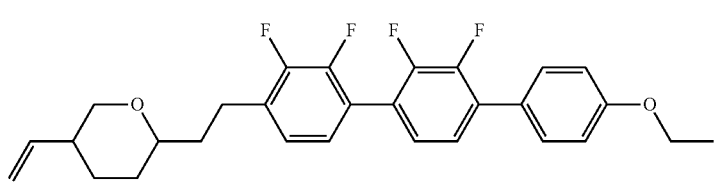 |
| 473 | 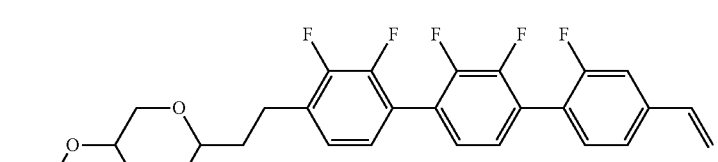 |
| 474 | 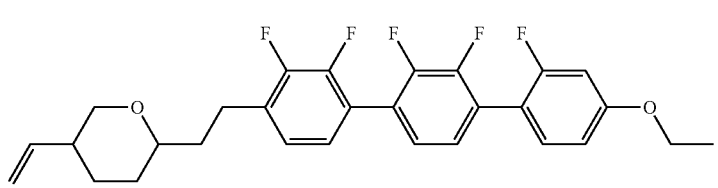 [SMILES: C=CC1CCC(CCc2ccc(-c3ccc(-c4ccc(OCC)cc4F)c(F)c3F)c(F)c2F)OC1] |
| 475 | 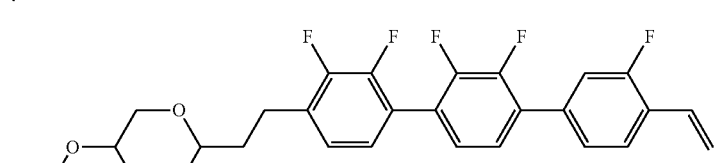 |
| 476 | 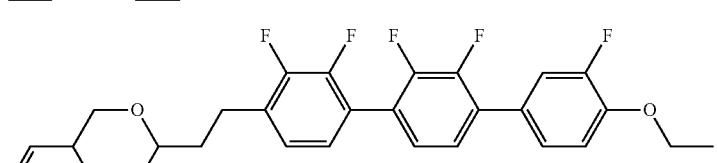 |

| No. |
|---|
| 477 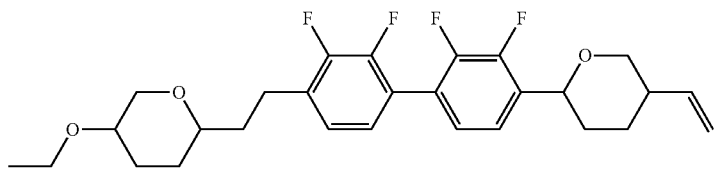 |
| 478 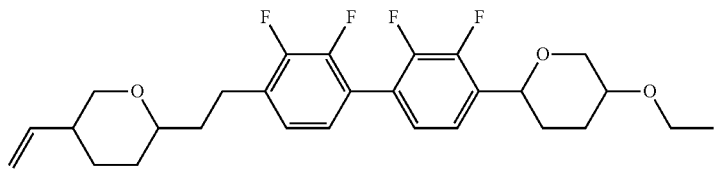 [SMILES: C=CC1CCC(CCc2ccc(-c3ccc(C4CCC(OCC)CO4)c(F)c3F)c(F)c2F)OC1] |
| 479 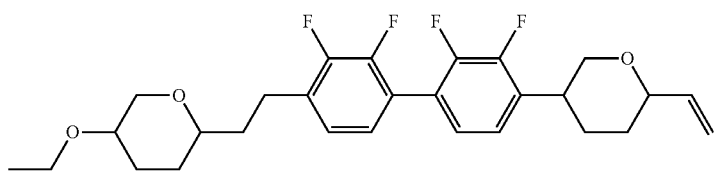 |
| 480 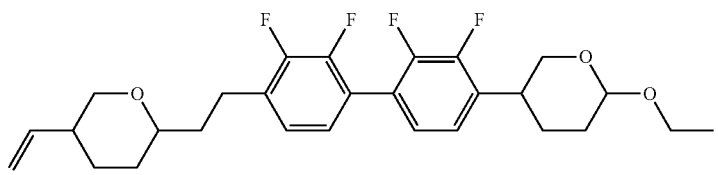 |
| 481 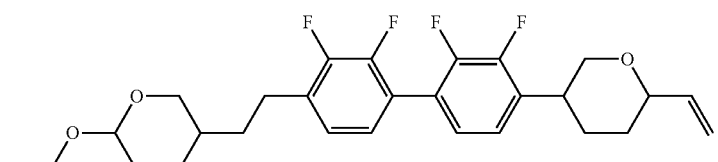 |
| 482 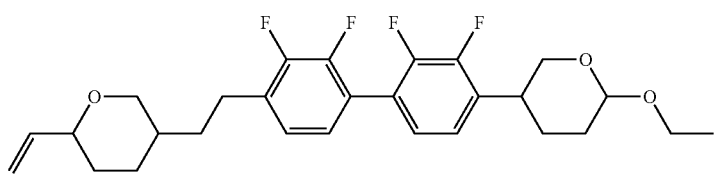 |
| 483 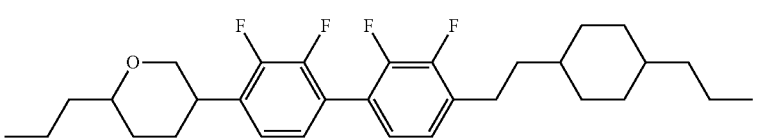 |
| 484 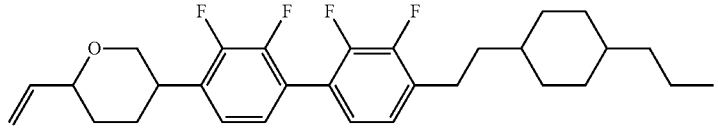 |
| 485 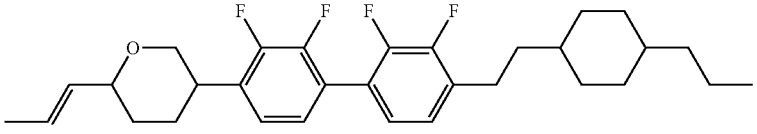 [SMILES: C/C=C/C1CCC(c2ccc(-c3ccc(CCC4CCC(CCC)CC4)c(F)c3F)c(F)c2F)CO1] |

-continued
| No. |
|---|
| 486 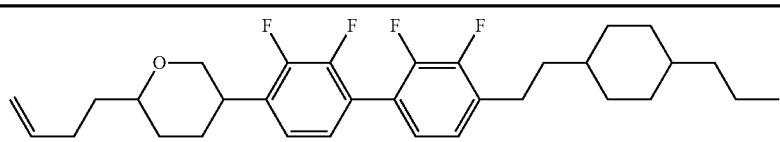 |
| 487 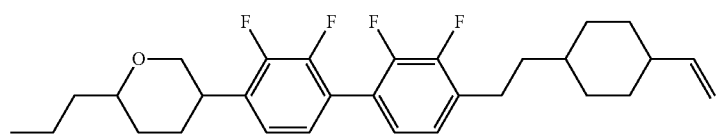 |
| 488 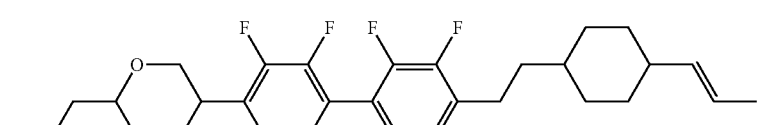 |
| 489 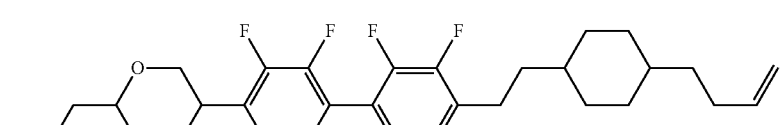 |
| 490 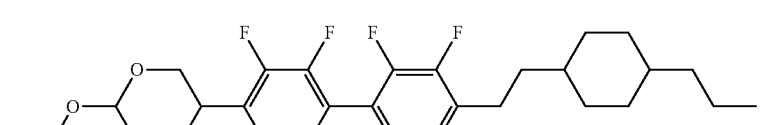 |
| 491 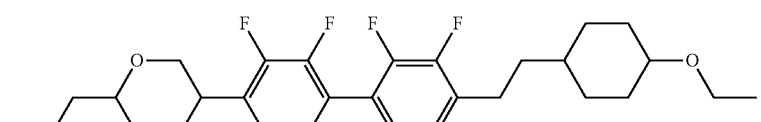 |
| 492 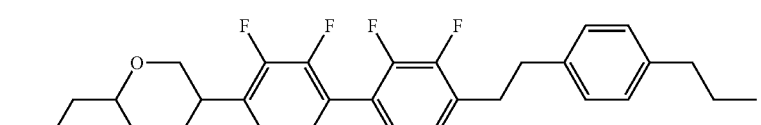 |
| 493 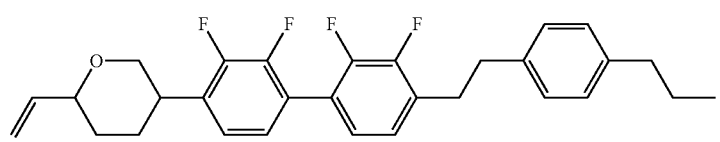 |
| 494 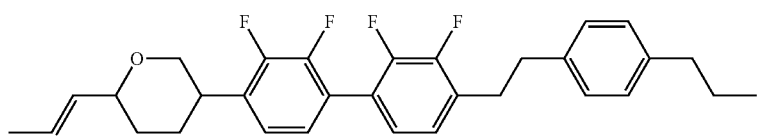 |
| 495 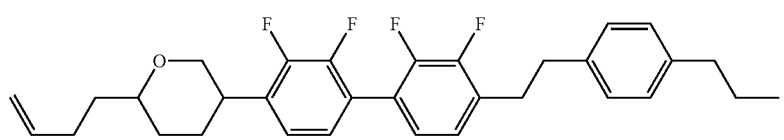 [SMILES: C=CCCC1CCC(c2ccc(-c3ccc(CCc4ccc(CCC)cc4)c(F)c3F)c(F)c2F)CO1] |
| 496 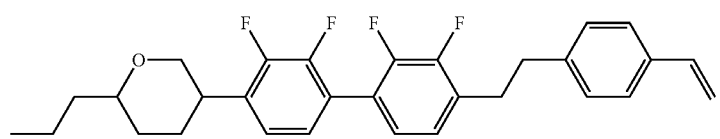 |

-continued
| No. |  |
|---|---|
| 497 | 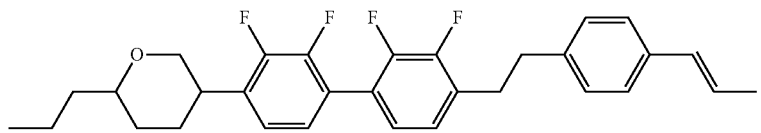 |
| 498 | 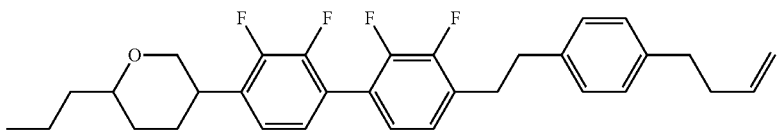 |
| 499 | 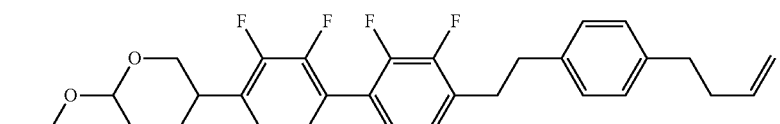 |
| 500 | 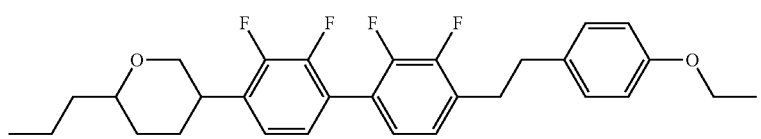 [SMILES: CCCC1CCC(c2ccc(-c3ccc(CCc4ccc(OCC)cc4)c(F)c3F)c(F)c2F)CO1] |
| 501 | 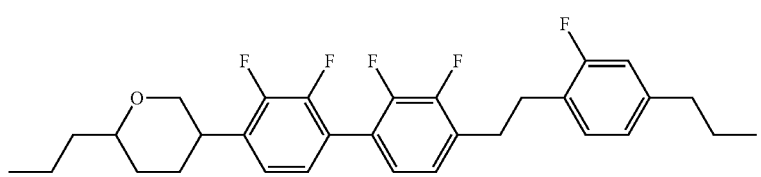 [SMILES: CCCc1ccc(CCc2ccc(-c3ccc(C4CCC(CCC)OC4)c(F)c3F)c(F)c2F)c(F)c1] |
| 502 | 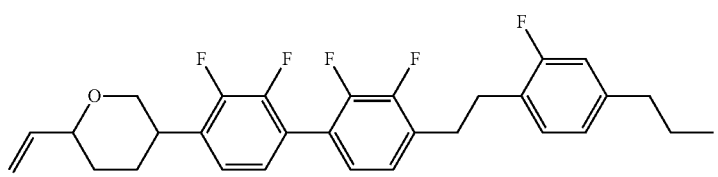 [SMILES: C=CC1CCC(c2ccc(-c3ccc(CCc4ccc(CCC)cc4F)c(F)c3F)c(F)c2F)CO1] |
| 503 | 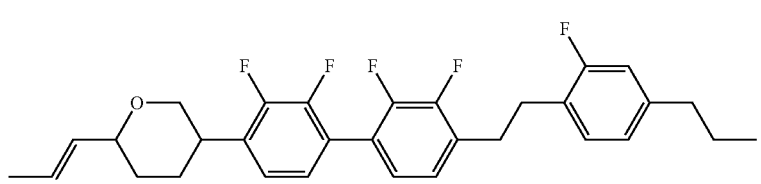 |
| 504 | 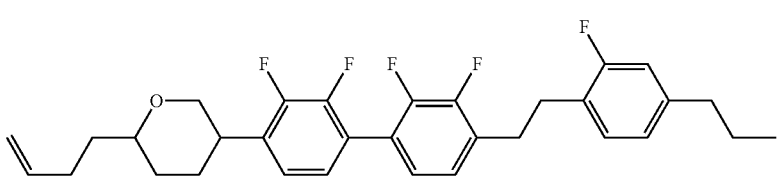 [SMILES: C=CCCC1CCC(c2ccc(-c3ccc(CCc4ccc(CCC)cc4F)c(F)c3F)c(F)c2F)CO1] |
| 505 | 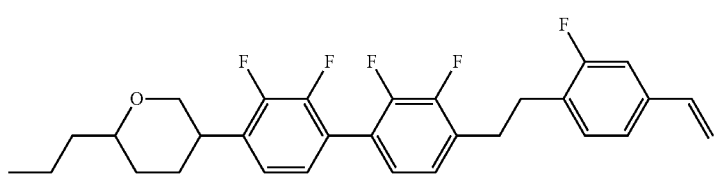 |

| No. |
|---|
| 506 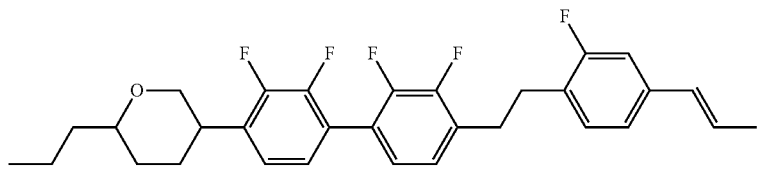 [SMILES: C/C=C/c1ccc(CCc2ccc(-c3ccc(C4CCC(CCC)OC4)c(F)c3F)c(F)c2F)c(F)c1] |
| 507 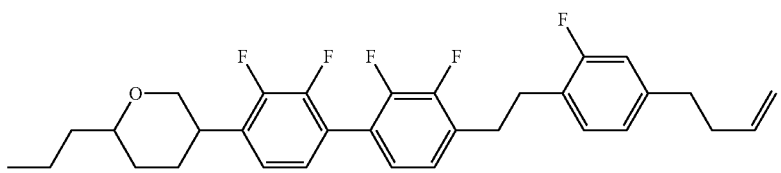 [SMILES: C=CCCc1ccc(CCc2ccc(-c3ccc(C4CCC(CCC)OC4)c(F)c3F)c(F)c2F)c(F)c1] |
| 508 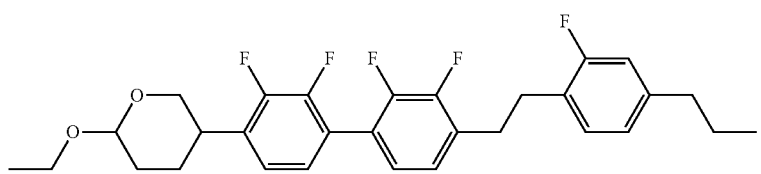 |
| 509 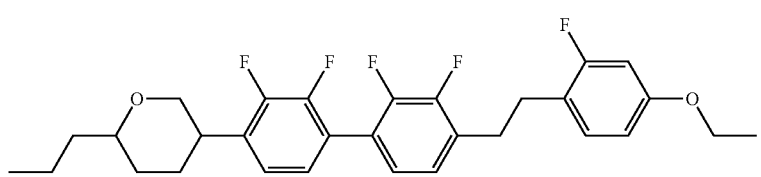 |
| 510 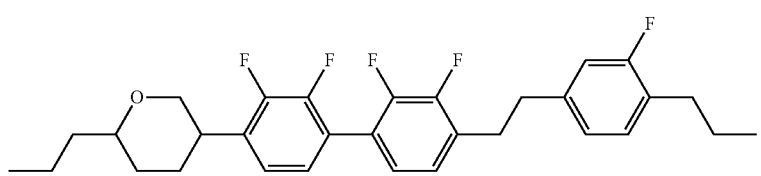 |
| 511 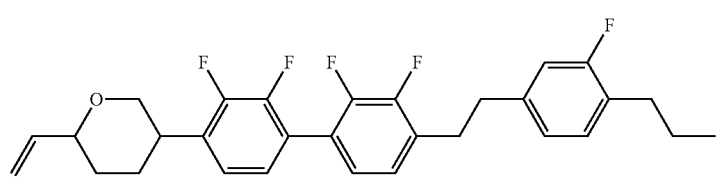 [SMILES: C=CC1CCC(c2ccc(-c3ccc(CCc4ccc(CCC)c(F)c4)c(F)c3F)c(F)c2F)CO1] |
| 512 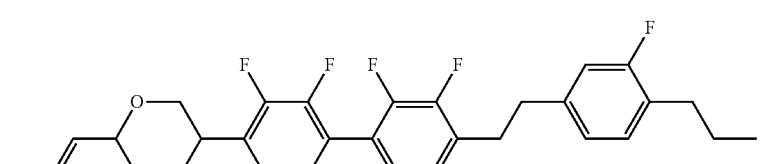 |
| 513 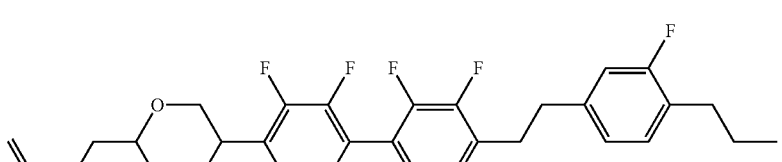 |
| 514 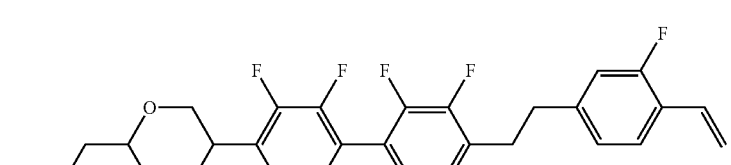 |

-continued
| No. | |
|---|---|
| 515 | 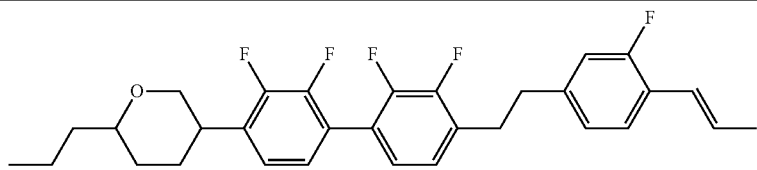 |
| 516 | 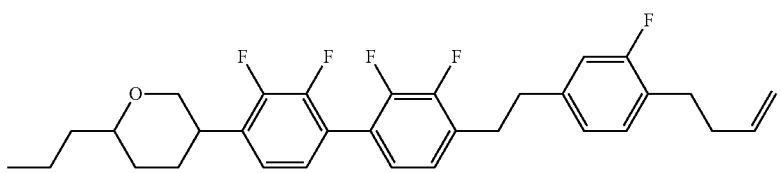 [SMILES: C=CCCc1ccc(CCc2ccc(-c3ccc(C4CCC(CCC)OC4)c(F)c3F)c(F)c2F)cc1F] |
| 517 | 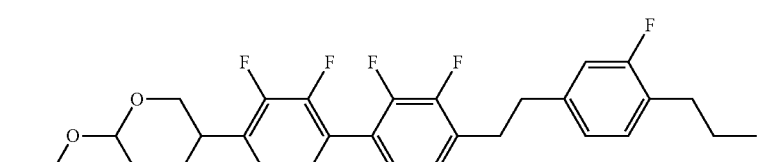 |
| 518 | 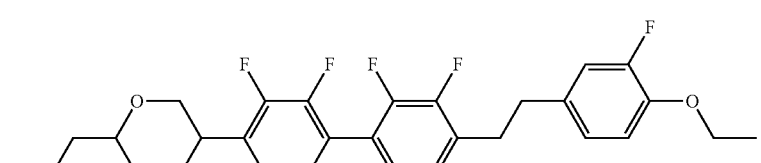 |
| 519 | 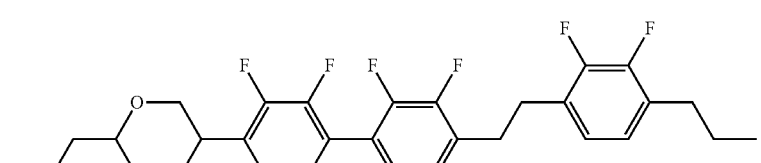 |
| 520 | 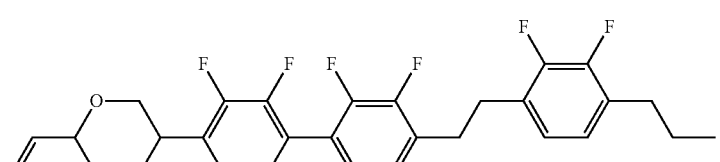 |
| 521 | 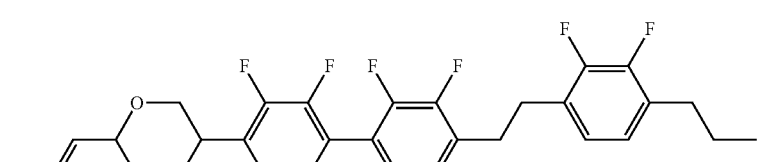 |
| 522 | 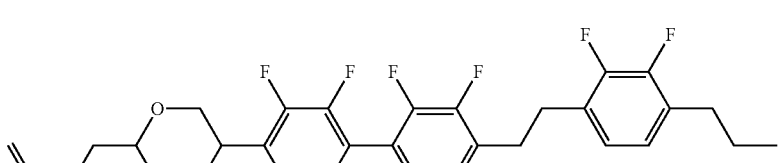 |
| 523 | 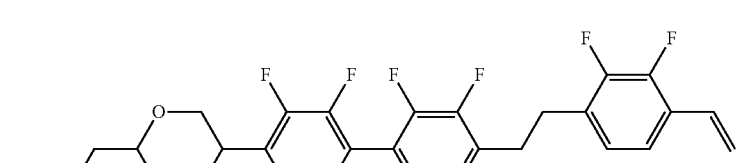 |

-continued
| No. | |
|---|---|
| 524 | 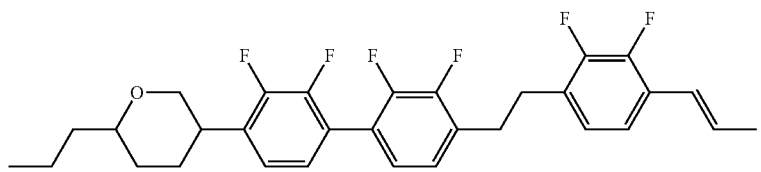 |
| 525 | 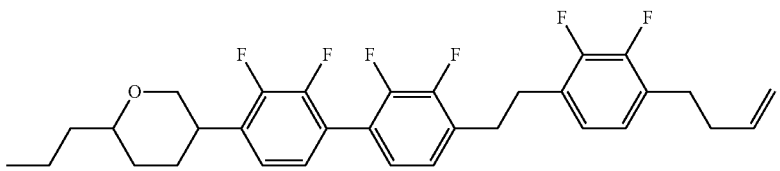 |
| 526 | 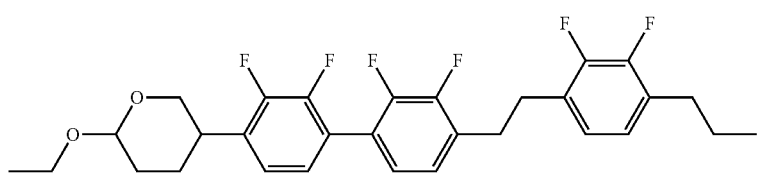 |
| 527 | 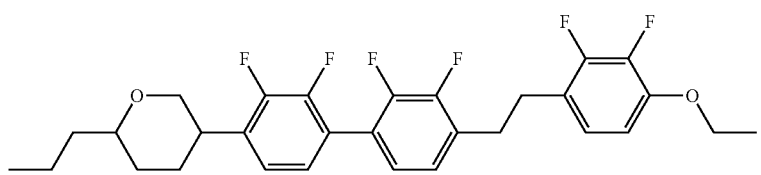 [SMILES: C/C=C/c1ccc(CCc2ccc(-c3ccc(C4CCC(CCC)OC4)c(F)c3F)c(F)c2F)c(F)c1F] |
| 528 | 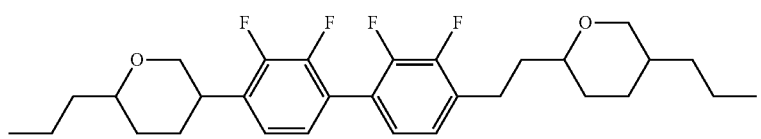 |
| 529 | 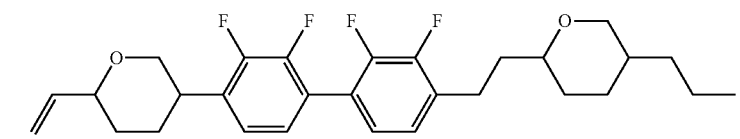 [SMILES: C=CC1CCC(c2ccc(-c3ccc(CCC4CCC(CCC)CO4)c(F)c3F)c(F)c2F)CO1] |
| 530 | 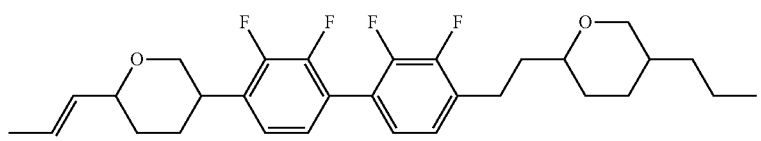 |
| 531 | 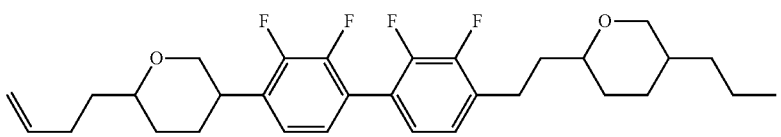 [SMILES: C=CCCC1CCC(c2ccc(-c3ccc(CCC4CCC(CCC)CO4)c(F)c3F)c(F)c2F)CO1] |
| 532 | 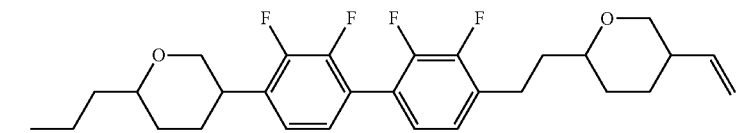 |
| 533 | 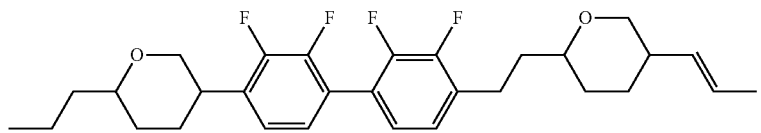 |

-continued
| No. | |
|---|---|
| 534 | 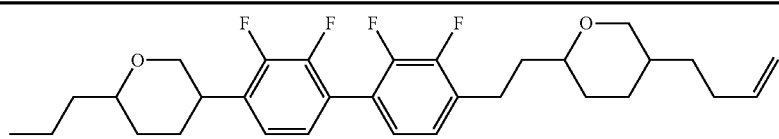 |
| 535 | 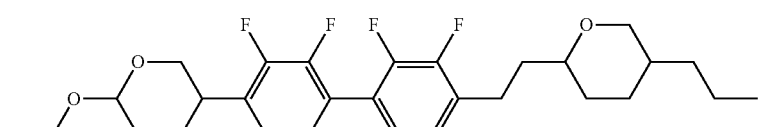 |
| 536 | 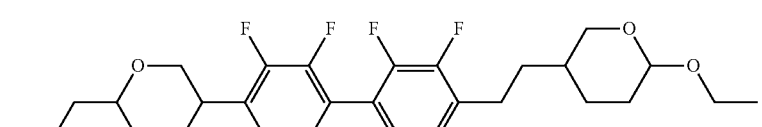 |
| 537 | 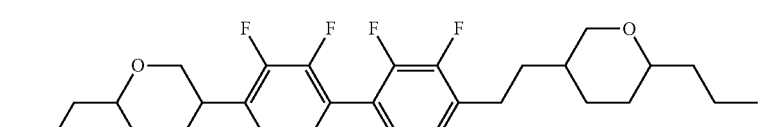 |
| 538 | 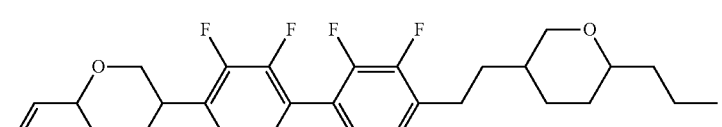 |
| 539 | 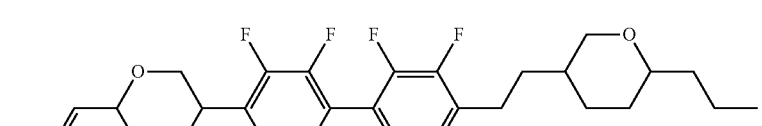 |
| 540 | 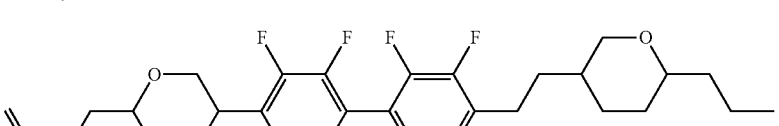 |
| 541 | 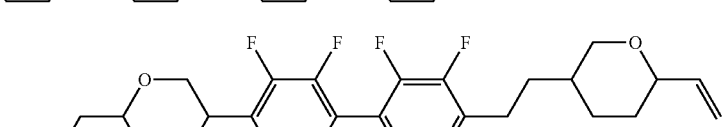 |
| 542 | 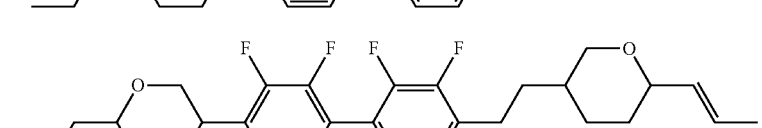 |
| 543 | 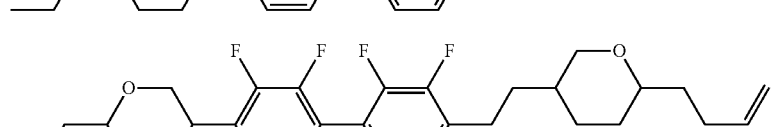 |
| 544 | 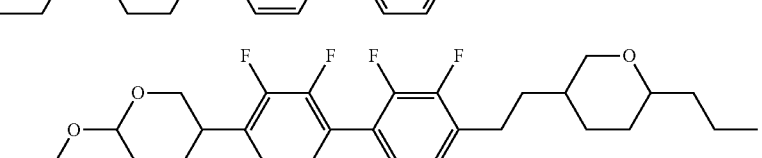 |

-continued
| No. | |
|---|---|
| 545 | 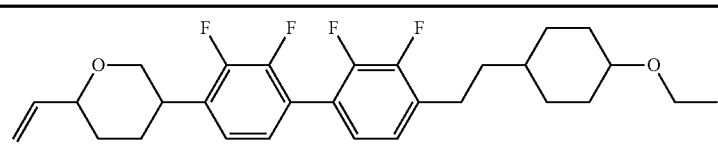 |
| 546 | 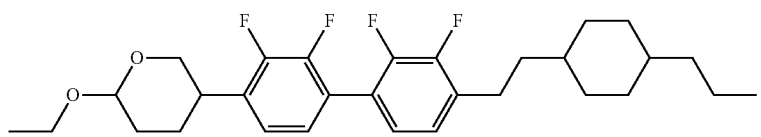 |
| 547 | 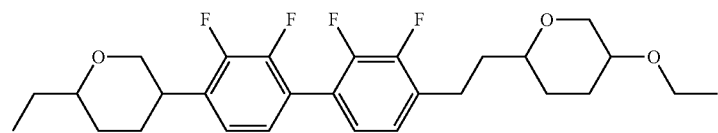 [SMILES: CCOC1CCC(CCc2ccc(-c3ccc(C4CCC(CC)OC4)c(F)c3F)c(F)c2F)OC1] |
| 548 | 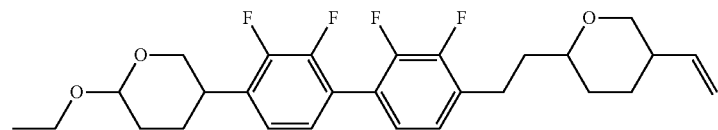 [SMILES: C=CC1CCC(CCc2ccc(-c3ccc(C4CCC(OCC)OC4)c(F)c3F)c(F)c2F)OC1] |
| 549 | 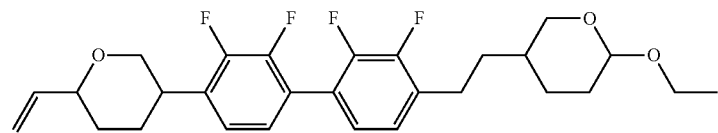 |
| 550 | 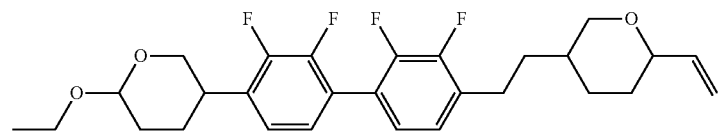 |
| 551 | 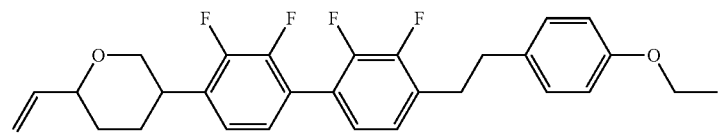 [SMILES: C=CC1CCC(c2ccc(-c3ccc(CCc4ccc(OCC)cc4)c(F)c3F)c(F)c2F)CO1] |
| 552 | 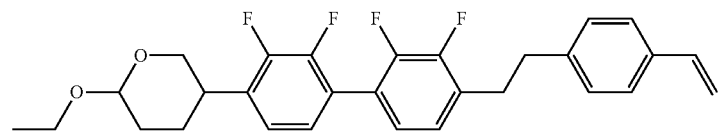 [SMILES: C=Cc1ccc(CCc2ccc(-c3ccc(C4CCC(OCC)OC4)c(F)c3F)c(F)c2F)cc1] |
| 553 | 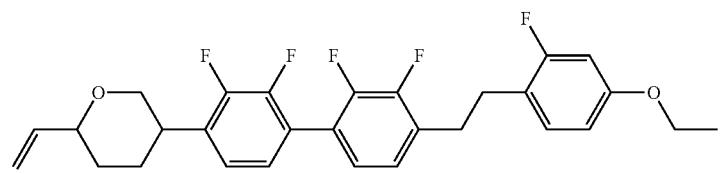 [SMILES: C=CC1CCC(c2ccc(-c3ccc(CCc4ccc(OCC)cc4F)c(F)c3F)c(F)c2F)CO1] |
| 554 | 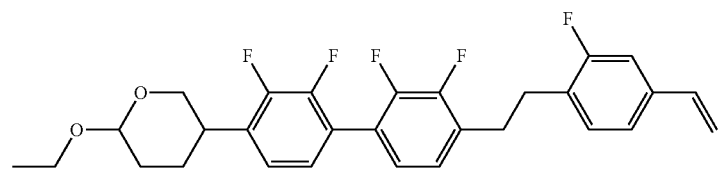 [SMILES: C=Cc1ccc(CCc2ccc(-c3ccc(C4CCC(OCC)OC4)c(F)c3F)c(F)c2F)c(F)c1] |

| No. |
|---|
| 555 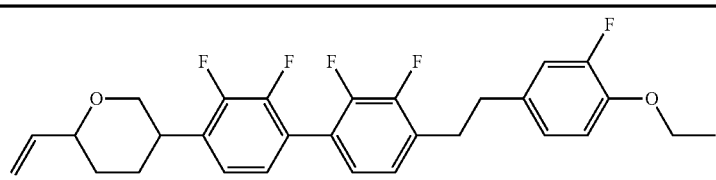 |
| 556 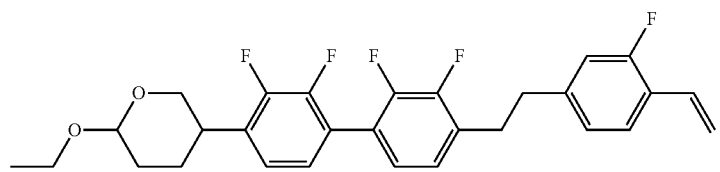 |
| 557 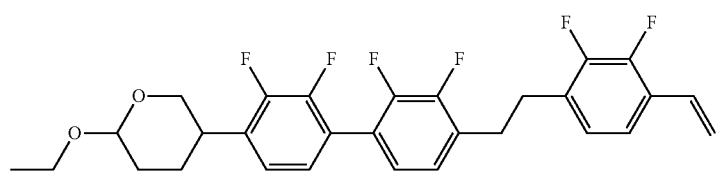 |
| 558 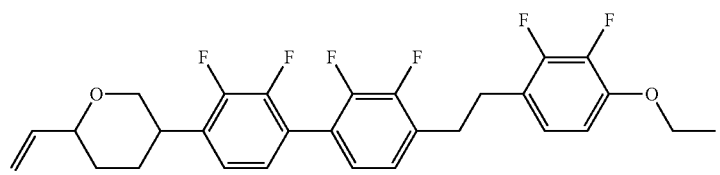 |
| 559 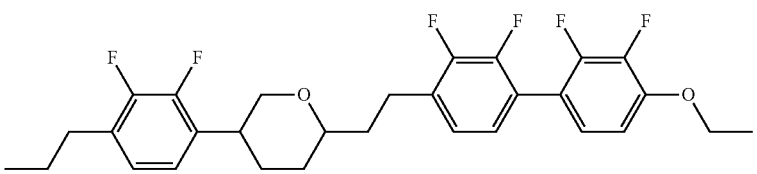 [SMILES: CCCc1ccc(C2CCC(CCc3ccc(-c4ccc(OCC)c(F)c4F)c(F)c3F)OC2)c(F)c1F] |
| 560 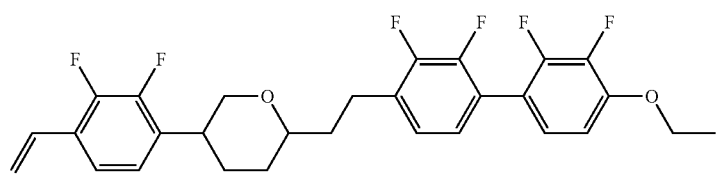 [SMILES: C=Cc1ccc(C2CCC(CCc3ccc(-c4ccc(OCC)c(F)c4F)c(F)c3F)OC2)c(F)c1F] |
| 561 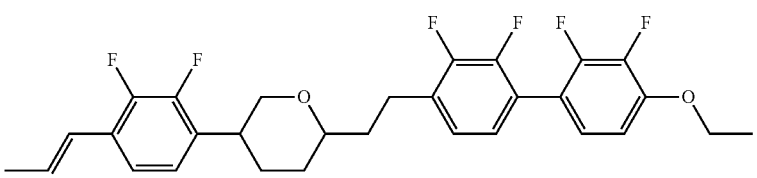 |
| 562 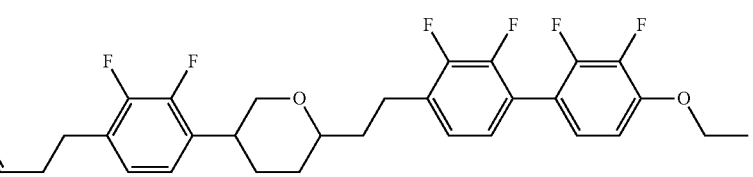 |
| 563 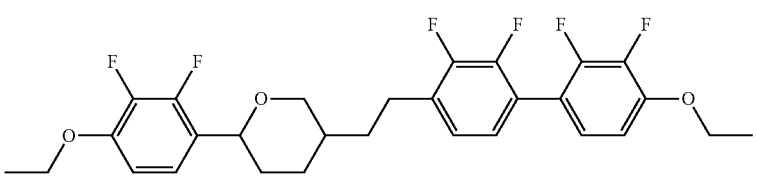 |

-continued
| No. | |
|---|---|
| 564 | 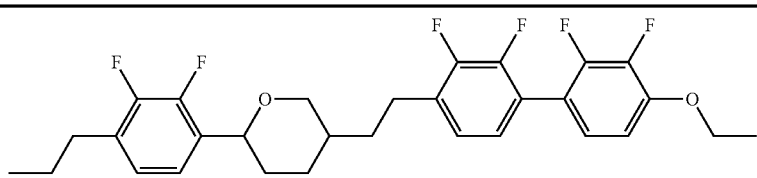 |
| 565 | 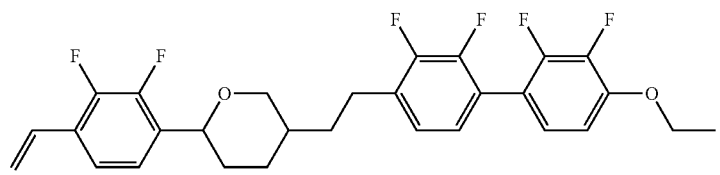 [SMILES: C=Cc1ccc(C2CCC(CCc3ccc(-c4ccc(OCC)c(F)c4F)c(F)c3F)CO2)c(F)c1F] |
| 566 | 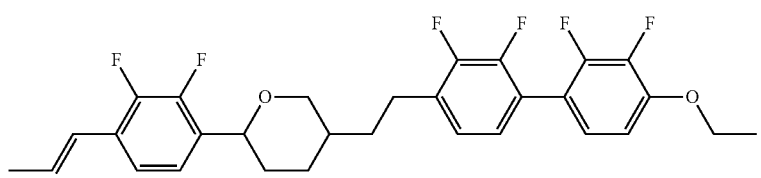 [SMILES: C/C=C/c1ccc(C2CCC(CCc3ccc(-c4ccc(OCC)c(F)c4F)c(F)c3F)CO2)c(F)c1F] |
| 567 | 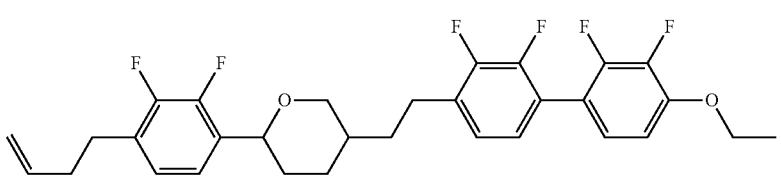 [SMILES: C=CCCc1ccc(C2CCC(CCc3ccc(-c4ccc(OCC)c(F)c4F)c(F)c3F)CO2)c(F)c1F] |
| 568 | 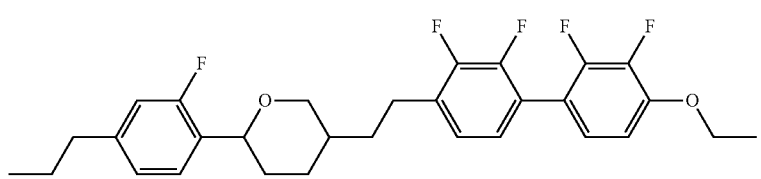 |
| 569 | 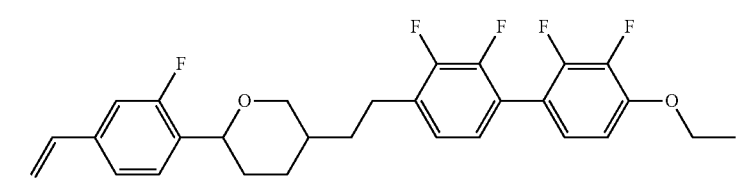 |
| 570 | 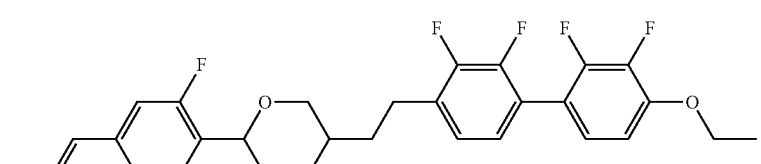 |
| 571 | 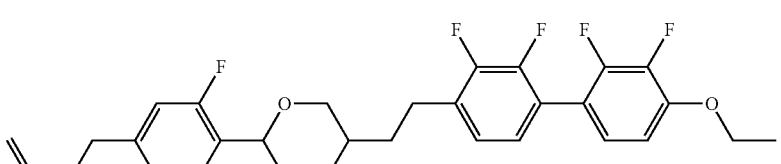 |
| 572 | 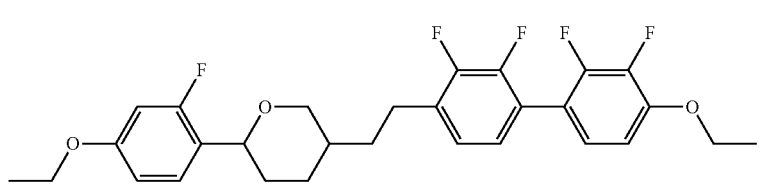 [SMILES: CCOc1ccc(C2CCC(CCc3ccc(-c4ccc(OCC)c(F)c4F)c(F)c3F)CO2)c(F)c1] |

| No. | |
|---|---|
| 573 | 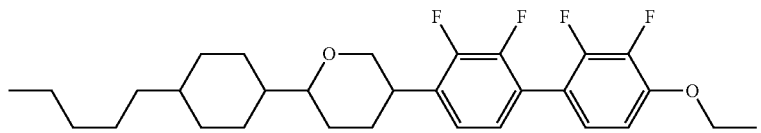 [SMILES: CCCCCC1CCC(C2CCC(c3ccc(-c4ccc(OCC)c(F)c4F)c(F)c3F)CO2)CC1] |
| 574 | 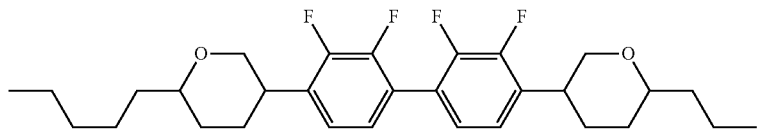 |

Comparative Example 1

The liquid crystal composition B was prepared by mixing 15% by weight of the compound (b) that had been synthesized by the synthetic method described in JP 2000-008040 A (Patent document No. 3) and 85% by weight of the mother liquid crystals A. The extrapolated values of physical properties of the liquid crystal compound (b) were calculated by measuring the physical property values of the resulting liquid crystal composition B and then by extrapolating the measured value. The extrapolated values were as follows.

Maximum temperature (NI)=121.3° C.; dielectric anisotropy (Δ∈)=−7.3; refractive index anisotropy (Δn)=0.107; viscosity (η)=61.4 mPa·s.

Comparative Example 2

The liquid crystal composition C was prepared by mixing 15% by weight of the compound, 4-(4'-ethoxy-2,2',3,3'-tetrafluorobiphenyl-4-yl)-4'-propylbi(cyclohexane) (c) that had been described in JP 2000-038585 A (Patent document No. 4) and 85% by weight of the mother liquid crystals A. The extrapolated values of physical properties of the liquid crystal compound (c) were calculated by measuring the physical property values of the resulting liquid crystal composition C and then by extrapolating the measured value. The extrapolated values were as follows.

Maximum temperature (NI)=229.3° C.; dielectric anisotropy (Δ∈)=−8.28; refractive index anisotropy (Δn)=0.162; viscosity (η)=83.5 mPa·s.

Example 7

The liquid crystal composition D was prepared by mixing 15% by weight of the compound No. 1 and 85% by weight of the mother liquid crystals A. The extrapolated values of physical properties of the compound No. 1 were calculated by measuring the physical property values of the resulting liquid crystal composition D and by extrapolating the measured value. The extrapolated values were as follows.

Maximum temperature (NI)=195.3° C.; dielectric anisotropy (Δ∈)=−9.66; refractive index anisotropy (Δn)=0.165; viscosity (η)=114.7 mPa·s It was found that the compound No. 1 of the invention was excellent in view of a large negative dielectric anisotropy (Δ∈) by comparing the compound No. 1 in Example 1 with the compound (b) in Comparative Example 1 and the compound (c) in Comparative Example 2.

Example of Liquid Crystal Compositions

Typical compositions of the invention were summarized in Examples 8 to 25. First, compounds that are a component of the composition and their amounts (% by weight) were shown. The compounds were expressed with the symbols of a left-terminal group, a bonding group, a ring structure and a right-terminal group according to the definition in Table 1.

TABLE 1

Method of Description of Compounds using Symbols
R—(A₁)—Z₁—...—$Z_n$—($A_n$)—R'

| 1) Left-terminal Group R— | Symbol |
|---|---|
| $C_nH_{2n+1}$— | n— |
| $C_nH_{2n+1}O$— | nO— |
| $C_mH_{2m+1}OC_nH_{2n}$— | mOn— |
| $CH_2=CH$— | V— |
| $C_nH_{2n+1}—CH=CH$— | nV— |
| $CH_2=CH—C_nH_{2n}$— | Vn— |
| $C_mH_{2m+1}—CH=CH—C_nH_{2n}$— | mVn— |
| $CF_2=CH$— | VFF— |
| $CF_2=CH—C_nH_{2n}$— | VFFn— |

| 2) Right-terminal Group —R' | Symbol |
|---|---|
| —$C_nH_{2n+1}$ | —n |
| —$OC_nH_{2n+1}$ | —On |
| —$CH=CH_2$ | —V |
| —$CH=CH—C_nH_{2n+1}$ | —Vn |
| —$C_nH_{2n}—CH=CH_2$ | —nV |
| —$CH=CF_2$ | —VFF |
| —$COOCH_3$ | —EMe |
| —CN | —C |
| —F | —F |
| —Cl | —CL |
| —$OCF_3$ | —OCF3 |
| —$CF_3$ | —CF3 |

| 3) Bonding Group —$Z_n$— | Symbol |
|---|---|
| —$C_nH_{2n}$— | n |
| —COO— | E |
| —CH=CH— | V |
| —$CH_2O$— | 1O |
| —$CF_2O$— | X |
| —C≡C— | T |

| 4) Ring Structure-$A_n$— | Symbol |
|---|---|
| (cyclohexane ring) | H |
| (cyclohexene ring) | Ch |

TABLE 1-continued

Method of Description of Compounds using Symbols
R—(A$_1$)—Z$_1$—...—Z$_n$—(A$_n$)—R'

| Structure | Symbol |
|---|---|
| (tetrahydropyran ring) | Dh |
| (tetrahydropyran ring) | dh |
| (dioxane ring) | G |
| (benzene ring) | B |
| (pyrimidine ring) | Py |
| (fluorobenzene) | B(2F) |
| (fluorobenzene) | B(F) |
| (difluorobenzene) | B(F,F) |
| (difluorobenzene) | B(2F,3F) |
| (fluoro-chlorobenzene) | B(2F,3CL) |
| (chloro-fluorobenzene) | B(2CL,3F) |

TABLE 1-continued

Method of Description of Compounds using Symbols
R—(A$_1$)—Z$_1$—...—Z$_n$—(A$_n$)—R'

5) Examples of Description

Example 1. 3-HDhB(2F,3F)B(2F,3F)—O2

Example 2. 3-DhB(2F,3F)B(2F,3F)B-3

Example 3. 3-HHB-3

Example 4. 5-HBB(2F,3CL)—O2

Example 8

| Compound | Code | % |
|---|---|---|
| 3-HDhB(2F,3F)B(2F,3F)-O2 | (No. 1) | 8% |
| 3-HH-5 | (12-1) | 5% |
| 3-HH-4 | (12-1) | 10% |
| 3-HH-O1 | (12-1) | 6% |
| 3-HH-O3 | (12-1) | 6% |
| 3-HB-O1 | (12-5) | 5% |
| 3-HB-O2 | (12-5) | 5% |
| 3-HB(2F,3F)-O2 | (6-1) | 10% |
| 5-HB(2F,3F)-O2 | (6-1) | 10% |
| 3-HHB(2F,3F)-O2 | (7-1) | 12% |
| 3-HHB(2F,3F)-2 | (7-1) | 4% |
| 2-HHB(2F,3F)-1 | (7-1) | 4% |
| 3-HHEH-3 | (13-13) | 5% |
| 3-HHEH-5 | (13-13) | 5% |
| 4-HHEH-3 | (13-13) | 5% |

NI = 83.6° C.; Δn = 0.078; Δε = −3.4.

Example 9

| Compound | Code | % |
|---|---|---|
| 5-HDhB(2F,3F)B(2F,3F)-O2 | (No. 573) | 3% |
| 3-DhB(2F,3F)B(2F,3F)B-3 | (No. 227) | 3% |
| 3-HB-O1 | (12-5) | 15% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 6% |
| 3-HHB(2F,3F)-O2 | (7-1) | 13% |
| 5-HHB(2F,3F)-O2 | (7-1) | 13% |
| 3-HHB-1 | (13-1) | 6% |

Example 10

| | | |
|---|---|---|
| 3-DhB(2F,3F)B(2F,3F)dh-3 | (No. 257) | 5% |
| 3-HB-O1 | (12-5) | 10% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 13% |
| 6-HEB(2F,3F)-O2 | (6-6) | 6% |

Example 11

| | | |
|---|---|---|
| 3-DhB(2F,3F)B(2F,3F)H-3 | (No. 217) | 9% |
| 3-HH-4 | (12-1) | 8% |
| 3-H2B(2F,3F)-O2 | (6-4) | 22% |
| 5-H2B(2F,3F)-O2 | (6-4) | 22% |
| 2-HHB(2F,3CL)-O2 | (7-12) | 2% |
| 3-HHB(2F,3CL)-O2 | (7-12) | 3% |
| 4-HHB(2F,3CL)-O2 | (7-12) | 2% |
| 5-HHB(2F,3CL)-O2 | (7-12) | 2% |
| 3-HBB(2F,3CL)-O2 | (7-13) | 9% |
| V-HHB-1 | (13-1) | 6% |
| 3-HHB-3 | (13-1) | 6% |
| 3-HHEBH-3 | (14-6) | 3% |
| 3-HHEBH-4 | (14-6) | 3% |
| 3-HHEBH-5 | (14-6) | 3% |

NI = 93.7° C.;
Δn = 0.100;
η = 30.3 mPa · s;
Δε = −4.1.

Example 12

| | | |
|---|---|---|
| 3-HDhB(2F,3F)B(2F,3F)-O2 | (No. 1) | 7% |
| 3-HH-4 | (12-1) | 15% |
| 3-HB-O2 | (12-5) | 12% |
| 3-H2B(2F,3F)-O2 | (6-4) | 15% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 9% |
| 3-HHB-1 | (13-1) | 3% |
| 3-HHB-3 | (13-1) | 4% |
| 3-HHB-O1 | (13-1) | 3% |

NI = 85.3° C.;
TC ≦ −20° C.;
Δn = 0.102;
η = 27.6 mPa · s;
Δε = −3.5.

The helical pitch was 61.2 micrometer when 0.25 part of the optically active compound (Op-5) was added to 100 parts of the preceding composition.

Example 13

| | | |
|---|---|---|
| 5-HDhB(2F,3F)B(2F,3F)-O2 | (No. 573) | 3% |
| 3-DhB(2F,3F)B(2F,3F)dh-3 | (No. 257) | 3% |
| 2-HH-3 | (12-1) | 5% |
| 3-HH-O1 | (12-1) | 4% |
| 3-HH-O3 | (12-1) | 5% |
| 5-HH-O1 | (12-1) | 4% |
| 3-HB(2F,3F)-O2 | (6-1) | 12% |
| 5-HB(2F,3F)-O2 | (6-1) | 11% |
| 3-HHB(2F,3F)-O2 | (7-1) | 14% |
| 5-HHB(2F,3F)-O2 | (7-1) | 15% |
| 3-HHB(2F,3F)-2 | (7-1) | 24% |

Example 14

| | | |
|---|---|---|
| 3-DhB(2F,3F)B(2F,3F)B-3 | (No. 227) | 5% |
| 3-DhB(2F,3F)B(2F,3F)H-3 | (No. 217) | 5% |
| 3-HH-5 | (12-1) | 5% |
| 3-HH-4 | (12-1) | 5% |
| 3-HH-O1 | (12-1) | 6% |
| 3-HH-O3 | (12-1) | 6% |
| 3-HB-O1 | (12-5) | 5% |
| 3-HB-O2 | (12-5) | 5% |
| 3-HB(2F,3F)-O2 | (6-1) | 10% |
| 5-HB(2F,3F)-O2 | (6-1) | 10% |
| 3-HHB(2F,3F)-O2 | (7-1) | 12% |
| 5-HHB(2F,3F)-O2 | (7-1) | 13% |
| 3-HHB(2F,3F)-2 | (7-1) | 4% |
| 2-HHB(2F,3F)-1 | (7-1) | 4% |
| 3-HHEH-3 | (13-13) | 5% |

Example 15

| | | |
|---|---|---|
| 3-DhB(2F,3F)B(2F,3F)dh-3 | (No. 257) | 6% |
| 3-DhB(2F,3F)B(2F,3F)H-3 | (No. 217) | 6% |
| 2-H2H-3 | (12-3) | 5% |
| 3-H2H-V | (12-3) | 17% |
| 3-HBBH-5 | (14-1) | 3% |
| 1O1-HBBH-4 | (14-1) | 3% |
| 5-HBB(F)B-2 | (14-5) | 3% |
| V-HB(2F,3F)-O2 | (6-1) | 7% |
| 5-HB(2F,3F)-O2 | (6-1) | 7% |
| 3-H2B(2F,3F)-O2 | (6-4) | 12% |
| 5-H2B(2F,3F)-O2 | (6-4) | 12% |
| 3-HBB(2F,3F)-O2 | (7-7) | 8% |
| 5-HBB(2F,3F)-O2 | (7-7) | 8% |
| 2-BB(2F,3F)B-3 | (8-1) | 3% |

Example 16

| | | |
|---|---|---|
| 5-HDhB(2F,3F)B(2F,3F)-O2 | (No. 573) | 5% |
| 3-DhB(2F,3F)B(2F,3F)B-3 | (No. 227) | 5% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 9% |
| 3-HB-O2 | (12-5) | 8% |
| 3-HH-4 | (12-1) | 5% |
| 3-HHB-F | (3-1) | 3% |
| 3-HHB-1 | (13-1) | 8% |
| 3-HHB-O1 | (13-1) | 4% |
| 3-HBEB-F | (3-37) | 4% |
| 3-HHEB-F | (3-10) | 6% |
| 5-HHEB-F | (3-10) | 5% |
| 3-H2BTB-2 | (13-17) | 4% |
| 3-H2BTB-3 | (13-17) | 4% |
| 3-H2BTB-4 | (13-17) | 4% |
| 3-HB(F)TB-2 | (13-18) | 5% |

Example 17

| | | |
|---|---|---|
| 3-DhB(2F,3F)B(2F,3F)H-3 | (No. 217) | 8% |
| 2-HB-C | (5-1) | 5% |
| 3-HB-C | (5-1) | 12% |
| 3-HB-O2 | (12-5) | 15% |
| 2-BTB-1 | (12-10) | 3% |
| 3-HHB-F | (3-1) | 4% |
| 3-HHB-1 | (13-1) | 8% |
| 3-HHB-O1 | (13-1) | 5% |
| 3-HHB-3 | (13-1) | 14% |
| 3-HHEB-F | (3-10) | 4% |
| 5-HHEB-F | (3-10) | 4% |
| 2-HHB(F)-F | (3-2) | 4% |
| 3-HHB(F)-F | (3-2) | 4% |
| 5-HHB(F)-F | (3-2) | 5% |
| 3-HHB(F,F)-F | (3-3) | 5% |

NI = 106.2° C.;
Δn = 0.106;
η = 23.7 mPa · s;
Δε = 3.5.

Example 18

| | | |
|---|---|---|
| 5-HDhB(2F,3F)B(2F,3F)-O2 | (No. 573) | 7% |
| 5-HB-CL | (2-2) | 16% |
| 3-HH-4 | (12-1) | 12% |
| 3-HH-5 | (12-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 8% |
| 4-HHB(F)-F | (3-2) | 7% |
| 5-HHB(F)-F | (3-2) | 7% |
| 7-HHB(F)-F | (3-2) | 7% |
| 5-HBB(F)-F | (3-23) | 4% |
| 1O1-HBBH-5 | (14-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 121.7° C.;
Δn = 0.097;
η = 26.0 mPa · s;
Δε = 2.8.

Example 19

| | | |
|---|---|---|
| 3-DhB(2F,3F)B(2F,3F)B-3 | (No. 227) | 5% |
| 3-DhB(2F,3F)B(2F,3F)H-3 | (No. 217) | 6% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 20% |
| 5-HBB(F,F)-F | (3-24) | 15% |
| 3-H2BB(F,F)-F | (3-27) | 5% |
| 5-HHBB(F,F)-F | (4-6) | 3% |
| 5-HHEBB-F | (4-17) | 3% |
| 3-HH2BB(F,F)-F | (4-15) | 2% |
| 1O1-HBBH-4 | (14-1) | 4% |
| 1O1-HBBH-5 | (14-1) | 4% |

Example 20

| | | |
|---|---|---|
| 5-HDhB(2F,3F)B(2F,3F)-O2 | (No. 573) | 12% |
| 5-HB-CL | (2-2) | 11% |
| 3-HH-4 | (12-1) | 8% |
| 3-HHB-1 | (13-1) | 5% |
| 3-HHB(F,F)-F | (3-3) | 8% |
| 3-HBB(F,F)-F | (3-24) | 13% |
| 5-HBB(F,F)-F | (3-24) | 10% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

NI = 98.1° C.;
Δn = 0.108;
η = 32.2 mPa · s;
Δε = 6.3.

Example 21

| | | |
|---|---|---|
| 3-DhB(2F,3F)B(2F,3F)B-3 | (No. 227) | 4% |
| 3-DhB(2F,3F)B(2F,3F)H-3 | (No. 217) | 4% |
| 3-HB-CL | (2-2) | 6% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 14% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-21) | 7% |
| 2-H2BB(F)-F | (3-26) | 3% |
| 3-H2BB(F)-F | (3-26) | 5% |
| 3-HBEB(F,F)-F | (3-39) | 5% |

Example 22

| | | |
|---|---|---|
| 5-HDhB(2F,3F)B(2F,3F)-O2 | (No. 573) | 8% |
| 5-HB-CL | (2-2) | 3% |
| 7-HB(F)-F | (2-3) | 7% |
| 3-HH-4 | (12-1) | 9% |
| 3-HH-EMe | (12-2) | 15% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

NI = 89.7° C.;
Δn = 0.072;
η = 28.7 mPa · s;
Δε = 5.0.

Example 23

| | | |
|---|---|---|
| 5-HDhB(2F,3F)B(2F,3F)-O2 | (No. 573) | 5% |
| 3-DhB(2F,3F)B(2F,3F)B-3 | (No. 227) | 5% |
| 3-HH-4 | (12-1) | 8% |
| 3-HHB-1 | (13-1) | 6% |
| 3-HHB(F,F)-F | (3-3) | 10% |
| 3-H2HB(F,F)-F | (3-15) | 9% |
| 3-HBB(F,F)-F | (3-24) | 15% |
| 3-BB(F,F)XB(F,F)-F | (3-97) | 25% |
| 1O1-HBBH-5 | (14-1) | 7% |
| 2-HHBB(F,F)-F | (4-6) | 3% |
| 3-HHBB(F,F)-F | (4-6) | 3% |
| 3-HH2BB(F,F)-F | (4-15) | 4% |

Example 24

| | | |
|---|---|---|
| 3-DhB(2F,3F)B(2F,3F)B-3 | (No. 227) | 3% |
| 3-DhB(2F,3F)B(2F,3F)H-3 | (No. 217) | 5% |
| 3-HB-CL | (2-2) | 13% |
| 3-HB-O2 | (12-5) | 10% |
| 3-PyB(F)-F | (2-15) | 10% |
| 5-PyB(F)-F | (2-15) | 10% |
| 3-HBB(F,F)-F | (3-24) | 7% |
| 3-PyBB-F | (3-80) | 8% |
| 3-PyBB-F | (3-80) | 7% |
| 3-PyBB-F | (3-80) | 7% |
| 5-HBB(F)B-2 | (14-5) | 10% |
| 5-HBB(F)B-3 | (14-5) | 10% |

Example 25

| | | |
|---|---|---|
| 3-HdhB(2F,3F)B(2F,3F)-O2 | (No. 43) | 3% |
| 3-Hdh2B(2F,3F)B(2F,3F)-O2 | (No. 72) | 5% |
| 2-HH-5 | (12-1) | 3% |
| 3-HH-4 | (12-1) | 10% |
| 3-HH-5 | (12-1) | 4% |
| 3-H2B(2F,3F)-O2 | (6-4) | 15% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 6% |
| 3-HHB-1 | (13-1) | 3% |
| 3-HHB-3 | (13-1) | 4% |
| 3-HHB-O1 | (13-1) | 3% |
| 3-HB-O2 | (12-5) | 12% |

NI = 83.2° C.;
Δn = 0.099;
η = 26.7 mPa · s;
Δε = −3.2.

INDUSTRIAL APPLICABILITY

The invention provides a liquid crystal compound having an excellent compatibility with other liquid crystal compounds and a large value of negative dielectric anisotropy (Δε).

The invention also provides a new liquid crystal composition having the features of desired physical properties, by including this liquid crystal compound as a component and by suitably selecting the ring, the substituent and so forth that are composing the compound, and further provides a liquid crystal display device containing this liquid crystal composition.

What is claimed is:

1. A compound represented by formula (1):

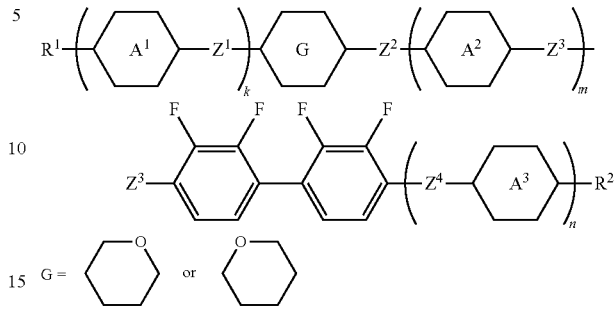

wherein
$R^1$ and $R^2$ are independently hydrogen, alkyl having 1 to 10 carbons, alkoxy having 1 to 9 carbons or alkoxyalkyl having 2 to 9 carbons and in the alkyl, alkoxy and alkoxyalkyl arbitrary hydrogen may be replaced by fluorine;

the ring $A^1$, the ring $A^2$ and the ring $A^3$ are independently 1,4-cyclohexylene, 1,4-cyclohexenylene, 1,4-phenylene, tetrahydropyran-2,5-diyl, tetrahydropyran-3,6-diyl, 2-fluoro-1,4-phenylene, 3-fluoro-1,4-phenylene or 2,3-difluoro-1,4-phenylene;

the ring G is tetrahydropyran-2,5-diyl or tetrahydropyran-3,6-diyl;

$Z^1$, $Z^2$, $Z^3$ and $Z^4$ are a single bond; and k, m and n are independently 0 or 1, and the sum of k, m and n is 1.

2. The compound according to claim 1, wherein in formula (1), $R^1$ and $R^2$ are independently alkyl having 1 to 10 carbons or alkoxy having 1 to 9 carbons.

3. A compound represented by formula (1-1):

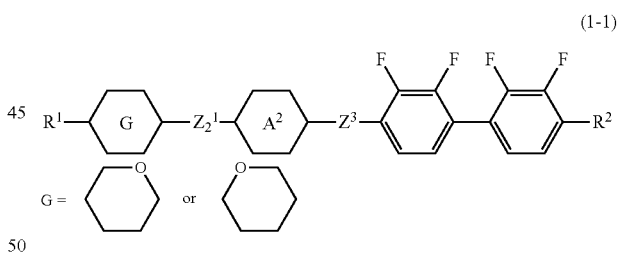

wherein
$R^1$ and $R^2$ are independently alkyl having 1 to 10 carbons or alkoxy having 1 to 9 carbons;

the ring $A^2$ is 1,4-cyclohexylene, 1,4-cyclohexenylene, 1,4-phenylene, tetrahydropyran-2,5-diyl, tetrahydropyran-3,6-diyl, 2-fluoro-1,4-phenylene, 3-fluoro-1,4-phenylene or 2,3-difluoro-1,4-phenylene;

the ring G is tetrahydropyran-2,5-diyl or tetrahydropyran-3,6-diyl; and $Z^2$ and $Z^3$ are a single bond.

4. The compound according to claim 3, wherein in formula (1-1), the ring $A^2$ is 1,4-cyclohexylene.

5. The compound according to claim 3, wherein in (1-1), $R^1$ is alkyl having 1 to 10 carbons, $R^2$ is alkoxy having 1 to 9 carbons, the ring $A^2$ is 1,4-cyclohexylene.

6. A compound represented by formula (1-2):

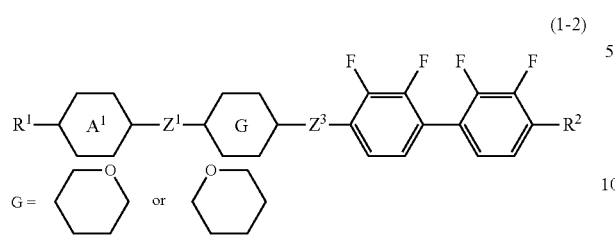

wherein
- $R^1$ and $R^2$ are independently alkyl having 1 to 10 carbons or alkoxy having 1 to 9 carbons;
- the ring $A^1$ is 1,4-cyclohexylene, 1,4-cyclohexenylene, 1,4-phenylene, tetrahydropyran-2,5-diyl, tetrahydropyran-3,6-diyl, 2-fluoro-1,4-phenylene, 3-fluoro-1,4-phenylene or 2,3-difluoro-1,4-phenylene;
- the ring G is tetrahydropyran-2,5-diyl or tetrahydropyran-3,6-diyl; and
- $Z^1$ and $Z^2$ are a single bond.

7. The compound according to claim 6, wherein in formula (1-2), the ring $A^1$ is 1,4-cyclohexylene.

8. The compound according to claim 6, wherein in formula (1-2), $R^1$ is alkyl having 1 to 10 carbons, $R^2$ is alkoxy having 1 to 9 carbons, the ring $A^1$ is 1,4-cyclohexylene.

9. A compound represented by formula (1-3):

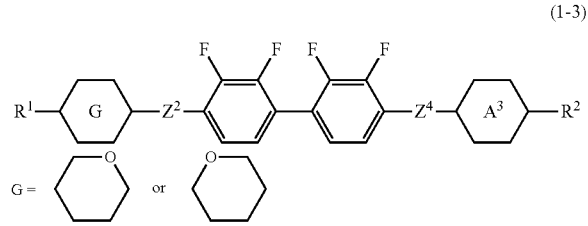

wherein
- $R^1$ and $R^2$ are independently alkyl having 1 to 10 carbons or alkoxy having 1 to 9 carbons;
- the ring $A^3$ is 1,4-cyclohexylene, 1,4-cyclohexenylene, 1,4-phenylene, tetrahydropyran-2,5-diyl, tetrahydropyran-3,6-diyl, 2-fluoro-1,4-phenylene, 3-fluoro-1,4-phenylene or 2,3-difluoro-1,4-phenylene;
- the ring G is tetrahydropyran-2,5-diyl or tetrahydropyran-3,6-diyl; and
- $Z^2$ and $Z^4$ are a single bond.

10. The compound according to claim 9, wherein in formula (1-3), the ring $A^3$ is 1,4-cyclohexylene.

11. The compound according to claim 9, wherein in formula (1-3), $R^1$ is alkyl having 1 to 10 carbons, $R^2$ is alkoxy having 1 to 9 carbons, the ring $A^3$ is 1,4-cyclohexylene.

12. A liquid crystal composition including at least two compounds and one of them is the compound according to claim 2.

13. The liquid crystal composition according to claim 12, including at least one compound selected from the group of compounds represented by formulas (2), (3) and (4):

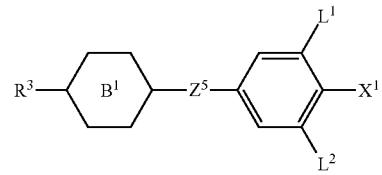

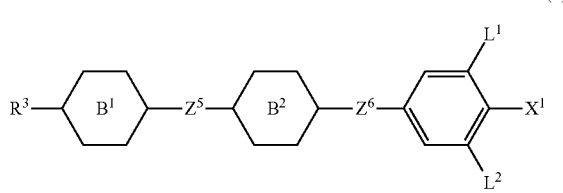

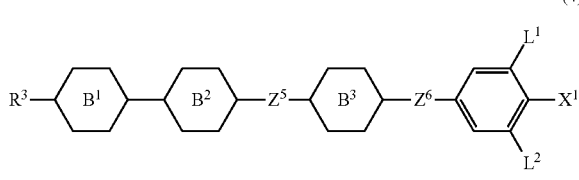

wherein
- $R^3$ is independently alkyl having 1 to 10 carbons or alkenyl having 2 to 10 carbons, and in the alkyl and alkenyl, arbitrary hydrogen may be replaced by fluorine, and arbitrary —$CH_2$— may be replaced by —O—;
- $X^1$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
- the ring $B^1$, the ring $B^2$ and the ring $B^3$ are independently 1,4-cyclohexylene, 1,3-dioxane-2,5-diyl, pyrimidine-2,5-diyl, 1-pyran-2,5-diyl or 1,4-phenylene in which arbitrary hydrogen may be replaced by fluorine;
- $Z^5$ and $Z^6$ are independently —$(CH_2)_2$—, —$(CH_2)_4$—, —COO—, —$CF_2O$—, —$OCF_2$—, CH=CH—, —C≡C—, —$CH_2O$— or a single bond; and
- $L^1$ and $L^2$ are independently hydrogen or fluorine;
- where in formula (4), the ring $B^3$ is not 1-pyran-2,5-diyl, when both the ring $B^1$ and the ring $B^2$ are 2,3-difluoro-1,4-phenylene; and the ring $B^1$ is not 1-pyran-2,5-diyl, when both the ring $B^2$ and the ring $B^3$ are 2,3-difluoro-1,4-phenylene and $Z^5$ is a single bond.

14. The liquid crystal composition according to claim 12, including at least one compound selected from the group of compounds represented by formula (5):

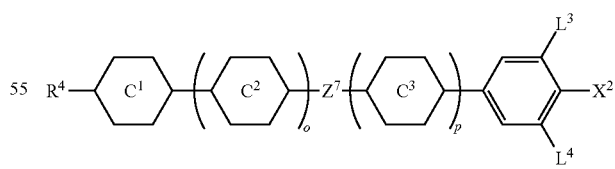

wherein
- $R^4$ is alkyl having 1 to 10 carbons or alkenyl having 2 to 10 carbons, and in the alkyl and alkenyl, arbitrary hydrogen may be replaced by fluorine, and arbitrary —$CH_2$— may be replaced by —O—;
- $X^2$ is —C≡N or —C≡C—C≡N;
- the ring $C^1$, the ring $C^2$ and the ring $C^3$ are independently 1,4-cyclohexylene, 1,4-phenylene in which arbitrary hydrogen may be replaced by fluorine, 1,3-dioxane-2,5-diyl, 1-pyran-2,5-diyl or pyrimidine-2,5-diyl;

$Z^7$ is —$(CH_2)_2$—, —COO—, —$CF_2O$—, —$OCF_2$—, —C≡C—, —$CH_2O$— or a single bond;

$L^3$ and $L^4$ are independently hydrogen or fluorine; and o is 0, 1 or 2, and p is 0 or 1.

15. The liquid crystal composition according to claim 12, including at least one compound selected from the group of compounds represented by formulas (6), (7), (8), (9), (10) and (11):

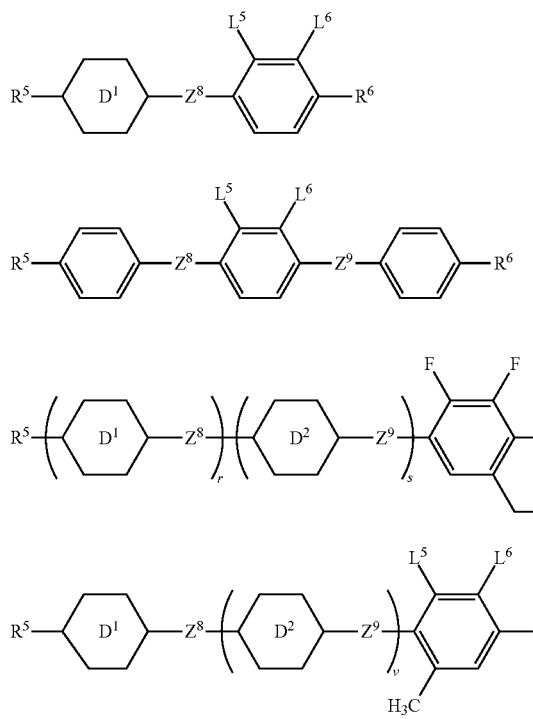
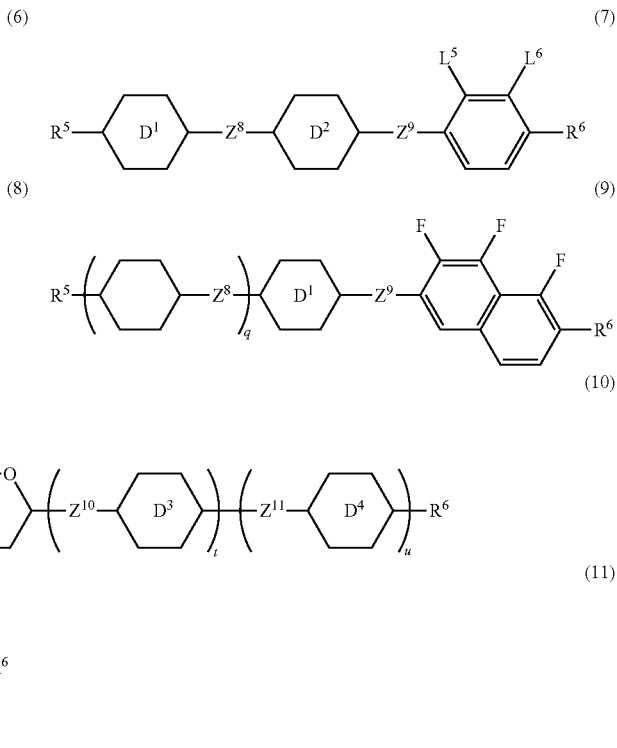

wherein $R^5$ and $R^6$ are independently alkyl having 1 to 10 carbons or alkenyl having 2 to 10 carbons, and in the alkyl and alkenyl, arbitrary hydrogen may be replaced by fluorine, and arbitrary —$CH_2$— may be replaced by —O—;

the ring $D^1$, the ring $D^2$, the ring $D^3$ and the ring $D^4$ are independently 1,4-cyclohexylene, 1,4-cyclohexenylene, 1,4-phenylene in which arbitrary hydrogen may be replaced by fluorine, 6-pyran-2,5-diyl or decahydro-2,6-naphthalene;

$Z^8$, $Z^9$, $Z^{10}$ and $Z^{11}$ are independently —$(CH_2)_2$—, —COO—, —$CH_2O$—, —$OCF_2$—, —$OCF_2(CH_2)_2$— or a single bond;

$L^5$ and $L^6$ are independently fluorine or chlorine; and q, r, s, t, u and v are independently 0 or 1, and the sum of r, s, t and u is 1 or 2.

16. The liquid crystal composition according to claim 12, including at least one compound selected from the group of compounds represented by formulas (12), (13) and (14):

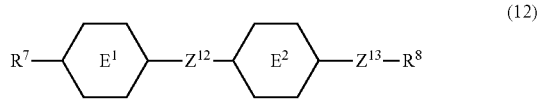

-continued

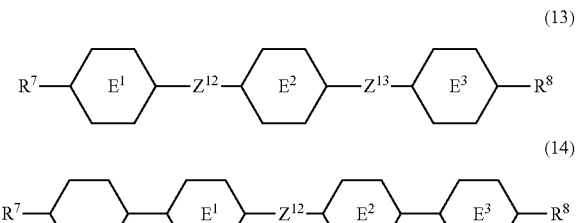

wherein $R^7$ and $R^8$ are independently alkyl having 1 to 10 carbons or alkenyl having 2 to 10 carbons, and in the alkyl and alkenyl, arbitrary —$CH_2$— may be replaced by —O—;

the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro1,4-phenylene; and $Z^{12}$ and $Z^{13}$ are independently —C≡C—, —COO—, —$(CH_2)_2$—, —CH=CH— or a single bond.

17. The liquid crystal composition according to claim 13, further including at least one compound selected from the group of compounds represented by formula (5):

(5)

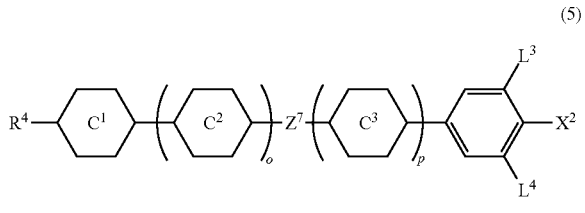

wherein
  $R^4$ is alkyl having 1 to 10 carbons or alkenyl having 2 to 10 carbons, and in the alkyl and alkenyl, arbitrary hydrogen may be replaced by fluorine, and arbitrary —$CH_2$— may be replaced by —O—;
  $X^2$ is —C≡N or —C≡C—C≡N;
  the ring $C^1$, the ring $C^2$ and the ring $C^3$ are independently 1,4-cyclohexylene, 1,4-phenylene in which arbitrary hydrogen may be replaced by fluorine, 1,3-dioxane-2,5-diyl, 1-pyran-2,5-diyl or pyrimidine-2,5-diyl;
  $Z^7$ is —$(CH_2)_2$—, —COO—, —$CF_2O$—, —$OCF_2$—, —C≡C—, —$CH_2O$— or a single bond;
  $L^3$ and $L^4$ are independently hydrogen or fluorine; and
  o is 0, 1 or 2, and p is 0 or 1.

18. The liquid crystal composition according to claim 13, further including at least one compound selected from the group of compounds represented by formulas (12), (13) and (14):

(12)

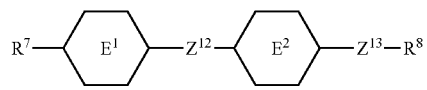

(13)

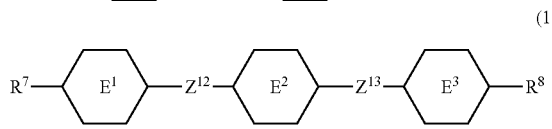

(14)

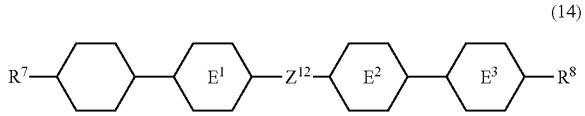

wherein
  $R^7$ and $R^8$ are independently alkyl having 1 to 10 carbons or alkenyl having 2 to 10 carbons, and in the alkyl and alkenyl, arbitrary —$CH_2$— may be replaced by —O—;
  the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro1,4-phenylene; and
  $Z^{12}$ and $Z^{13}$ are independently —C≡C—, —COO—, —$(CH_2)_2$—, —CH=CH— or a single bond.

19. The liquid crystal composition according to claim 14, further including at least one compound selected from the group of compounds represented by formulas (12), (13) and (14):

(12)

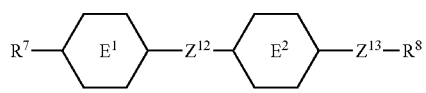

-continued (13)

(14)

wherein
  $R^7$ and $R^8$ are independently alkyl having 1 to 10 carbons or alkenyl having 2 to 10 carbons, and in the alkyl and alkenyl, arbitrary —$CH_2$— may be replaced by —O—;
  the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro1,4-phenylene; and
  $Z^{12}$ and $Z^{13}$ are independently —C≡C—, —COO—, —$(CH_2)_2$—, —CH=CH— or a single bond.

20. The liquid crystal composition according to claim 15, further including at least one compound selected from the group of compounds represented by formulas (12), (13) and (14):

(12)

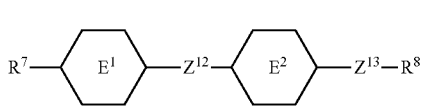

(13)

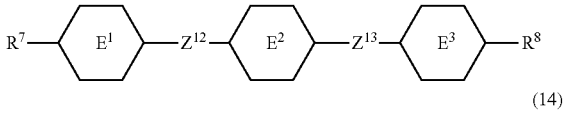

(14)

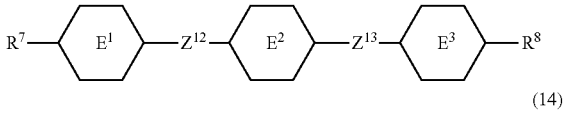

wherein
  $R^7$ and $R^8$ are independently alkyl having 1 to 10 carbons or alkenyl having 2 to 10 carbons, and in the alkyl and alkenyl, arbitrary —$CH_2$— may be replaced by —O—;
  the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro1,4-phenylene; and
  $Z^{12}$ and $Z^{13}$ are independently —C≡C—, —COO—, —$(CH_2)_2$—, —CH=CH— or a single bond.

21. The liquid crystal composition according to claim 12, further including at least one optically active compound and/or one polymerizable compound.

22. The liquid crystal composition according to claim 12, further including at least one antioxidant and/or one ultraviolet light absorber.

23. A liquid crystal display device containing the liquid crystal composition according to claim 12.

* * * * *